(12) United States Patent
Wilt et al.

(10) Patent No.: US 11,052,181 B2
(45) Date of Patent: Jul. 6, 2021

(54) CASSETTE SYSTEM INTEGRATED APPARATUS

(71) Applicant: DEKA Products Limited Partnership, Manchester, NH (US)

(72) Inventors: Michael J. Wilt, Windham, NH (US); Kevin L. Grant, Litchfield, NH (US); James D. Dale, Milton, FL (US); Jason A. Demers, Manchester, NH (US); Brian D. Tracey, Litchfield, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 17/067,605

(22) Filed: Oct. 9, 2020

(65) Prior Publication Data

US 2021/0093770 A1 Apr. 1, 2021

Related U.S. Application Data

(60) Continuation of application No. 15/619,961, filed on Jun. 12, 2017, now Pat. No. 10,799,628, which is a
(Continued)

(51) Int. Cl.
*A61M 1/16* (2006.01)
*F04B 43/06* (2006.01)
(Continued)

(52) U.S. Cl.
CPC ............ *A61M 1/1656* (2013.01); *A61M 1/14* (2013.01); *A61M 1/16* (2013.01); *A61M 1/1601* (2014.02);
(Continued)

(58) Field of Classification Search
CPC ........ A61M 1/14; A61M 1/16; A61M 1/1601; A61M 1/1639; A61M 1/1656;
(Continued)

(56) References Cited

U.S. PATENT DOCUMENTS 4,267,040 A 5/1981 Schal
4,386,634 A 6/1983 Stasz et al.
(Continued)

FOREIGN PATENT DOCUMENTS

CA 1323312 C 10/1993
CA 2704411 A1 5/2009
(Continued)

OTHER PUBLICATIONS

First Examination Report for AU Application No. 2018200039 filed Jan. 3, 2018, which First Examination Report is dated Mar. 25, 2019, and claims pending as of Mar. 25, 2019.
(Continued)

*Primary Examiner* — John Kim
(74) *Attorney, Agent, or Firm* — Wolf, Greenfield & Sacks, P.C.

(57) ABSTRACT

A cassette integrated system. The cassette integrated system includes a mixing cassette, a balancing cassette, a middle cassette fluidly connected to the mixing cassette and the balancing cassette and at least one pod. The mixing cassette is fluidly connected to the middle cassette by at least one fluid line and the middle cassette is fluidly connected to the balancing cassette by at least one fluid line. The at least one pod is connected to at least two of the cassettes wherein the pod is located in an area between the cassettes.

7 Claims, 205 Drawing Sheets

Related U.S. Application Data continuation of application No. 14/673,822, filed on Mar. 30, 2015, now Pat. No. 9,677,554, which is a continuation of application No. 13/619,343, filed on Sep. 14, 2012, now Pat. No. 8,992,189, which is a continuation of application No. 13/280,274, filed on Oct. 24, 2011, now Pat. No. 8,499,780, which is a division of application No. 12/038,648, filed on Feb. 27, 2008, now Pat. No. 8,042,563, which is a continuation-in-part of application No. 11/871,803, filed on Oct. 12, 2007, now Pat. No. 7,697,022.

(60) Provisional application No. 60/921,314, filed on Apr. 2, 2007, provisional application No. 60/904,024, filed on Feb. 27, 2007.

(51) Int. Cl.
| | |
|---|---|
| *F04B 43/02* | (2006.01) |
| *F04B 43/073* | (2006.01) |
| *F04B 45/053* | (2006.01) |
| *F04B 53/10* | (2006.01) |
| *F16K 99/00* | (2006.01) |
| *A61M 60/268* | (2021.01) |
| *A61M 1/14* | (2006.01) |
| *A61M 60/43* | (2021.01) |
| *A61M 60/113* | (2021.01) |

(52) U.S. Cl.
CPC .......... *A61M 1/166* (2014.02); *A61M 1/1639* (2014.02); *A61M 1/1658* (2013.01); *A61M 60/268* (2021.01); *A61M 60/43* (2021.01); *F04B 43/02* (2013.01); *F04B 43/06* (2013.01); *F04B 43/073* (2013.01); *F04B 43/0733* (2013.01); *F04B 45/053* (2013.01); *F04B 45/0536* (2013.01); *F04B 53/106* (2013.01); *F04B 53/1062* (2013.01); *F16K 99/0015* (2013.01); *A61M 60/113* (2021.01); *A61M 2205/12* (2013.01); *A61M 2205/3317* (2013.01); *A61M 2205/3324* (2013.01); *A61M 2205/3331* (2013.01); *A61M 2205/3368* (2013.01); *Y10T 137/0329* (2015.04); *Y10T 137/2521* (2015.04); *Y10T 137/2931* (2015.04); *Y10T 137/7879* (2015.04); *Y10T 137/85978* (2015.04); *Y10T 137/86139* (2015.04)

(58) Field of Classification Search
CPC .. A61M 1/1658; A61M 1/166; A61M 60/113; A61M 60/268; A61M 60/43; A61M 2205/12; A61M 2205/3317; A61M 2205/3331; A61M 2205/3324; A61M 2205/3368; F04B 45/053; F04B 45/0536; F04B 43/02; F04B 43/06; F04B 43/073; F04B 43/0733; F04B 53/106; F04B 53/1062; F16K 99/0015; Y10T 137/0329; Y10T 137/2521; Y10T 137/2931; Y10T 137/7879; Y10T 137/85978; Y10T 137/86139
See application file for complete search history.

(56) References Cited

U.S. PATENT DOCUMENTS

| | | |
|---|---|---|
| 4,623,334 A | 11/1986 | Riddell |
| 4,770,769 A | 9/1988 | Schael |
| 4,971,700 A | 11/1990 | Tsuji et al. |
| 4,997,570 A | 3/1991 | Polaschegg |
| 5,178,182 A | 1/1993 | Kamen |
| 5,247,434 A | 9/1993 | Peterson et al. |
| 5,275,724 A | 1/1994 | Bucchianeri et al. |
| 5,306,242 A | 4/1994 | Joyce et al. |
| 5,350,357 A | 9/1994 | Kamen et al. |
| 5,421,823 A | 6/1995 | Kamen et al. |
| 5,470,483 A | 11/1995 | Bene et al. |
| 5,486,286 A | 1/1996 | Peterson et al. |
| 5,542,919 A | 8/1996 | Simon et al. |
| 5,628,908 A | 5/1997 | Kamen et al. |
| 5,744,027 A | 4/1998 | Connell et al. |
| 5,808,181 A | 9/1998 | Wamsiedler et al. |
| 5,836,908 A | 11/1998 | Beden et al. |
| 5,938,634 A | 8/1999 | Packard |
| 6,042,784 A | 3/2000 | Wamsiedler et al. |
| 6,044,691 A | 4/2000 | Kenley et al. |
| 6,146,523 A | 11/2000 | Kenley et al. |
| 6,261,065 B1 | 7/2001 | Nayak et al. |
| 6,284,131 B1 | 9/2001 | Hogard et al. |
| 6,491,656 B1 | 12/2002 | Morris |
| 6,638,478 B1 | 10/2003 | Treu et al. |
| 6,752,599 B2 | 6/2004 | Park |
| 6,852,090 B2 | 2/2005 | Burbank et al. |
| 7,083,719 B2 | 8/2006 | Bowman, Jr. et al. |
| 7,300,413 B2 | 11/2007 | Burbank et al. |
| 7,473,238 B2 | 1/2009 | Brugger et al. |
| 7,500,962 B2 | 3/2009 | Childers et al. |
| 7,699,806 B2 | 4/2010 | Ware et al. |
| 7,794,141 B2 | 9/2010 | Perry et al. |
| 7,867,214 B2 | 1/2011 | Childers et al. |
| 7,892,331 B2 | 2/2011 | Childers et al. |
| 7,935,074 B2 | 5/2011 | Plahey et al. |
| 7,967,022 B2 | 6/2011 | Grant et al. |
| 8,029,454 B2 | 10/2011 | Kelly et al. |
| 8,042,563 B2 | 10/2011 | Wilt et al. |
| 8,246,826 B2 | 8/2012 | Wilt et al. |
| 8,273,049 B2 | 9/2012 | Demers et al. |
| 8,292,594 B2 | 10/2012 | Tracey et al. |
| 8,317,492 B2 | 11/2012 | Demers et al. |
| 8,357,298 B2 | 1/2013 | Demers et al. |
| 8,393,690 B2 | 3/2013 | Grant et al. |
| 8,409,441 B2 | 4/2013 | Wilt |
| 8,425,471 B2 | 4/2013 | Grant et al. |
| 8,459,292 B2 | 6/2013 | Wilt et al. |
| 8,469,331 B2 | 6/2013 | Burbank et al. |
| 8,491,184 B2 | 7/2013 | Kamen et al. |
| 8,499,780 B2 | 8/2013 | Wilt et al. |
| 8,512,553 B2 | 8/2013 | Cicchello et al. |
| 8,545,698 B2 | 10/2013 | Wilt et al. |
| 8,562,834 B2 | 10/2013 | Kamen et al. |
| 8,721,879 B2 | 5/2014 | van der Merwe et al. |
| 8,721,884 B2 | 5/2014 | Wilt et al. |
| 8,771,508 B2 | 7/2014 | Grant et al. |
| 8,858,787 B2 | 10/2014 | Muller et al. |
| 8,863,772 B2 | 10/2014 | Dale et al. |
| 8,870,549 B2 | 10/2014 | Tracey et al. |
| 8,888,470 B2 | 11/2014 | Demers et al. |
| 8,926,294 B2 | 1/2015 | Demers et al. |
| 8,968,232 B2 | 3/2015 | Kamen et al. |
| 8,985,133 B2 | 3/2015 | Grant et al. |
| 8,992,075 B2 | 3/2015 | Kamen et al. |
| 8,992,189 B2 | 3/2015 | Wilt et al. |
| 9,028,691 B2 | 5/2015 | Grant et al. |
| 9,072,831 B2 | 7/2015 | Kelly et al. |
| 9,115,708 B2 | 8/2015 | van der Merwe et al. |
| 9,272,082 B2 | 3/2016 | Demers et al. |
| 9,302,037 B2 | 4/2016 | Wilt et al. |
| 9,302,039 B2 | 4/2016 | Kelly et al. |
| 9,364,655 B2 | 6/2016 | Grant et al. |
| 9,517,295 B2 | 12/2016 | Wilt et al. |
| 9,535,021 B2 | 1/2017 | Kamen et al. |
| 9,539,379 B2 | 1/2017 | Grant et al. |
| 9,550,018 B2 | 1/2017 | Demers et al. |
| 9,555,179 B2 | 1/2017 | Wilt et al. |
| 9,597,442 B2 | 3/2017 | Wilt |
| 9,603,985 B2 | 3/2017 | Wilt et al. |
| 9,649,418 B2 | 5/2017 | Demers et al. |
| 9,677,554 B2 | 6/2017 | Wilt et al. |
| 9,700,660 B2 | 7/2017 | Demers et al. |
| 9,700,711 B2 | 7/2017 | Grant et al. |

(56) References Cited

U.S. PATENT DOCUMENTS

| | | |
|---|---|---|
| 9,717,834 B2 | 8/2017 | Wilt et al. |
| 9,724,458 B2 | 8/2017 | Grant et al. |
| 9,795,728 B2 | 10/2017 | Grant et al. |
| 9,951,768 B2 | 4/2018 | Grant et al. |
| 9,987,407 B2 | 6/2018 | Grant et al. |
| 9,999,717 B2 | 6/2018 | van der Merwe et al. |
| 10,060,867 B2 | 8/2018 | Kamen et al. |
| 10,077,766 B2 | 9/2018 | Demers et al. |
| 10,098,998 B2 | 10/2018 | Wilt |
| 10,201,650 B2 | 2/2019 | Wilt et al. |
| 10,302,075 B2 | 5/2019 | Tracey et al. |
| 10,415,559 B2 | 9/2019 | Demers et al. |
| 10,441,697 B2 | 10/2019 | Kamen et al. |
| 10,443,591 B2 | 10/2019 | Wilt et al. |
| 10,449,280 B2 | 10/2019 | Wilt et al. |
| 10,463,774 B2 | 11/2019 | Ballantyne et al. |
| 10,500,327 B2 | 12/2019 | Grant et al. |
| 10,537,671 B2 | 1/2020 | Wilt et al. |
| 10,576,194 B2 | 3/2020 | Distler et al. |
| 10,682,450 B2 | 6/2020 | Wilt et al. |
| 10,697,913 B2 | 6/2020 | Kamen et al. |
| 10,780,210 B2 | 9/2020 | Grant et al. |
| 10,780,213 B2 | 9/2020 | Grant et al. |
| 10,799,628 B2 | 10/2020 | Wilt et al. |
| 10,850,089 B2 | 12/2020 | Grant et al. |
| 10,851,769 B2 | 12/2020 | Demers et al. |
| 10,871,157 B2 | 12/2020 | Tracey et al. |
| 2002/0182090 A1 | 12/2002 | Gray |
| 2004/0136843 A1 | 7/2004 | Jahn et al. |
| 2004/0211718 A1 | 10/2004 | Deguchi et al. |
| 2004/0245161 A1 | 12/2004 | Treu et al. |
| 2005/0045540 A1 | 3/2005 | Connell et al. |
| 2005/0069425 A1 | 3/2005 | Gray et al. |
| 2005/0095141 A1 | 5/2005 | Lanigan et al. |
| 2005/0242034 A1 | 11/2005 | Connell et al. |
| 2007/0112297 A1 | 5/2007 | Plahey et al. |
| 2007/0278155 A1 | 12/2007 | Lo et al. |
| 2008/0058697 A1 | 3/2008 | Kamen et al. |
| 2008/0138223 A1 | 6/2008 | Lanigan et al. |
| 2008/0190848 A1 | 8/2008 | Oklejas |
| 2008/0253911 A1 | 10/2008 | Demers et al. |
| 2009/0107335 A1 | 4/2009 | Wilt et al. |
| 2009/0107902 A1 | 4/2009 | Childers et al. |
| 2010/0056975 A1 | 3/2010 | Dale et al. |
| 2010/0133153 A1 | 6/2010 | Beden et al. |
| 2011/0005992 A1 | 1/2011 | Kelly et al. |
| 2011/0009797 A1 | 1/2011 | Kelly et al. |
| 2011/0105877 A1 | 5/2011 | Wilt et al. |
| 2011/0303588 A1 | 12/2011 | Kelly et al. |
| 2011/0303598 A1 | 12/2011 | Lo et al. |
| 2013/0022483 A1 | 1/2013 | Wilt et al. |
| 2013/0304020 A1 | 11/2013 | Wilt et al. |
| 2014/0112828 A1 | 4/2014 | Grant et al. |
| 2014/0153356 A1 | 6/2014 | Giant et al. |
| 2014/0199193 A1 | 7/2014 | Wilt et al. |
| 2014/0322053 A1 | 10/2014 | van der Merwe et al. |
| 2015/0125319 A1 | 5/2015 | Demers et al. |
| 2015/0196699 A9 | 7/2015 | Wilt et al. |
| 2016/0030657 A1 | 2/2016 | Kelly et al. |
| 2016/0175506 A1 | 6/2016 | Wilt et al. |
| 2017/0143886 A1 | 5/2017 | Wilt et al. |
| 2018/0296746 A1 | 10/2018 | van der Merwe et al. |
| 2018/0372084 A1 | 12/2018 | Grant et al. |
| 2019/0160220 A1 | 5/2019 | Wilt et al. |
| 2020/0054809 A1 | 2/2020 | Kamen et al. |
| 2020/0086035 A1 | 3/2020 | Wilt et al. |
| 2020/0139031 A1 | 5/2020 | Wilt et al. |
| 2020/0171226 A1 | 6/2020 | Wilt et al. |
| 2020/0191132 A1 | 6/2020 | Demers et al. |
| 2020/0215252 A1 | 7/2020 | Distler et al. |
| 2020/0222609 A1 | 7/2020 | Ballantyne et al. |
| 2020/0282124 A1 | 9/2020 | Grant et al. |
| 2020/0376185 A1 | 12/2020 | Wilt et al. |
| 2020/0376186 A1 | 12/2020 | Wilt et al. |

FOREIGN PATENT DOCUMENTS

| | | |
|---|---|---|
| DE | 3328744 A1 | 2/1985 |
| EP | 1 356 836 A2 | 10/2003 |
| JP | H07-100199 A | 4/1995 |
| JP | 3865150 B2 | 1/2007 |
| WO | WO 01/37895 A2 | 5/2001 |
| WO | WO 03/099353 A2 | 12/2003 |
| WO | WO 2006/120415 A1 | 11/2006 |

OTHER PUBLICATIONS

Office Action for AU Application No. 2008221370 filed Febraury 27, 2008, which Office Action is dated Jun. 5, 2012, and claims as pending for AU Application No. 2008221370 as of Jun. 5, 2012.

Office Action for AU Application No. 2013204505 filed Apr. 12, 2013, which Office Action is dated Jun. 12, 2014 and claims as pending for AU Application No. 2013204505 as of Jun. 12, 2014.

Office Action for CN Application No. 200880013768.5 filed Feb. 27, 2008, published as CN 101801432 on Aug. 11, 2010, which Office Action is dated Nov. 23, 2011, and claims as pending for CN Application No. 200880013768.5 as of Nov. 23, 2011.

Examination Report for EP Application No. 08730871.4 filed Feb. 27, 2008, published as EP 2131887 on Dec. 16, 2009, which Examination Report is dated Feb. 9, 2012, and claims as pending for EP Application No. 08730848.2 as of Feb. 9, 2012.

Response to Examination Report dated Feb. 9, 2012 for EP Application No. 08730871.4 filed Feb. 27, 2008, which Response is dated Dec. 5, 2012, and claims as pending for EP Application No. 08730871.4 as of Dec. 5, 2012.

Extended European Search Report for EP Application No. 14155798.3 filed Feb. 27, 2008, which Search Report is dated Apr. 22, 2014, and claims as pending for EP Application No. 14155798.3 as of Apr. 22, 2014.

Office Action for EP Application No. 14155798.3 filed Feb. 27, 2008, which Office Action is dated Sep. 29, 2015, and claims as pending for EP Application No. 14155798.3 as of Sep. 29, 2015.

Office Action for JP Application No. 2009-552957 filed Feb. 27, 2008, which Office Action is dated Nov. 20, 2012, and claims as pending for JP Application No. 2009-552957 as of Nov. 20, 2012.

Office Action for JP Application No. 2014-193586 filed Sep. 24, 2014, which Office Action is dated Sep. 1, 2015, and claims as pending for JP Application No. 2014-193586 as of Sep. 1, 2015.

Office Action for JP Application No. 2017-022161 filed Feb. 9, 2017, which Office Action is dated Dec. 5, 2017, and claims as pending for JP Application No. 2017-022161 as of Dec. 5, 2017.

Appeal Decision for JP Application No. 2017-022161 filed Feb. 27, 2008, which Appeal Decision is dated Apr. 14, 2020, and claims as pending for JP Application No. 2017-022161 as of Apr. 14, 2020.

Office Action for MX Application No. MX/A/2009/009217 filed Feb. 27, 2008, unpublished as of Jul. 16, 2013, which Office Action issued Jul. 16, 2013, and claims as pending for MX Application No. MX/A/2009/009217 as of Jul. 16, 2013.

Office Action for U.S. Appl. No. 12/038,648, filed Feb. 27, 2008, published as US 2008-0216898 on Sep. 11, 2008, which Office Action is dated Oct. 1, 2010, and claims as pending for U.S. Appl. No. 12/038,648 as of Oct. 1, 2010.

Ex Parte Quayle Action for U.S. Appl. No. 12/038,648, filed Feb. 27, 2008, published as 2008-0216898, on Sep. 11, 2008, which Office Action is dated Mar. 29, 2011, and claims as pending for U.S. Appl. No. 12/038,648 as of Mar. 29, 2011.

Notice of Allowance for U.S. Appl. No. 12/038,648, filed Feb. 27, 2008, published as US 2008-0216898 on Sep. 11, 2008, which Notice of Allowance is dated Jun. 13, 2011, and claims as allowed for U.S. Appl. No. 12/038,648 as of Jun. 13, 2011.

Office Action for U.S. Appl. No. 13/280,274, filed Oct. 24, 2011, published as US 2012-0106289 on May 3, 2012, which Office Action is dated Aug. 30, 2012, and claims as pending for U.S. Appl. No. 13/280,274 as of Aug. 30, 2012.

Invitation to Pay Additional Fees for Application No. PCT/US2008/055168 dated Aug. 5, 2008.

International Search Report and Written Opinion for Application No. PCT/US2008/055168 dated Nov. 10, 2008.

(56) References Cited

OTHER PUBLICATIONS

International Preliminary Report on Patentability for Application No. PCT/US2008/055168 dated Sep. 11, 2009.
Mineshima et al., Efficacy of internal filtration enhanced hemodialysis. Artificial Organs. 1999;28(1):127-33.

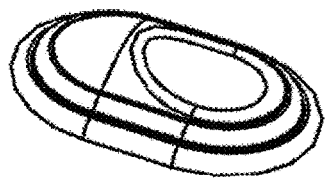
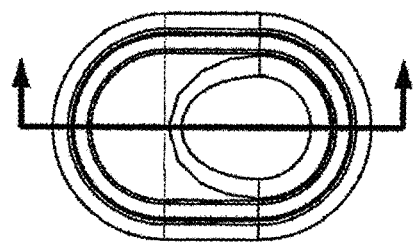
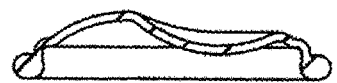
FIG. 2G

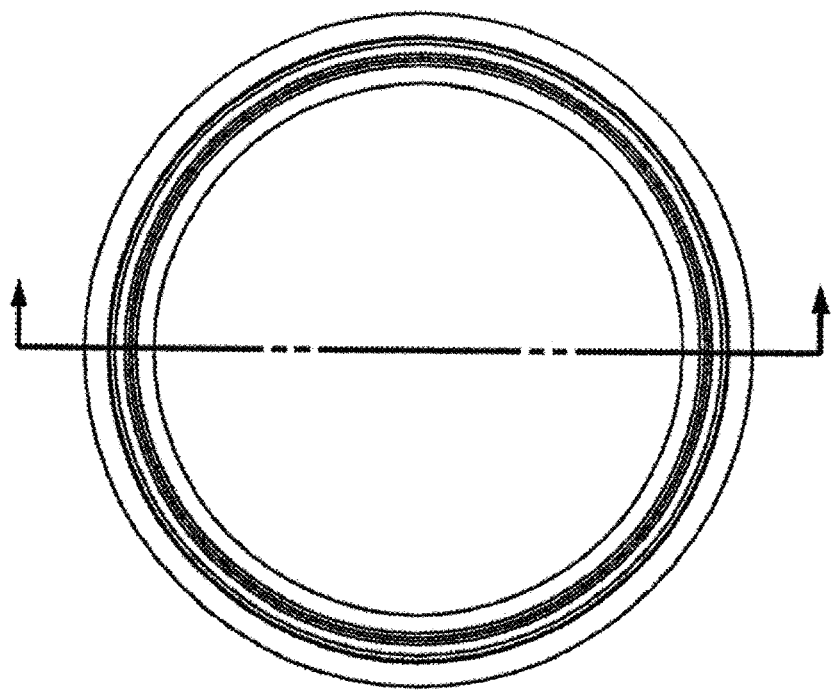
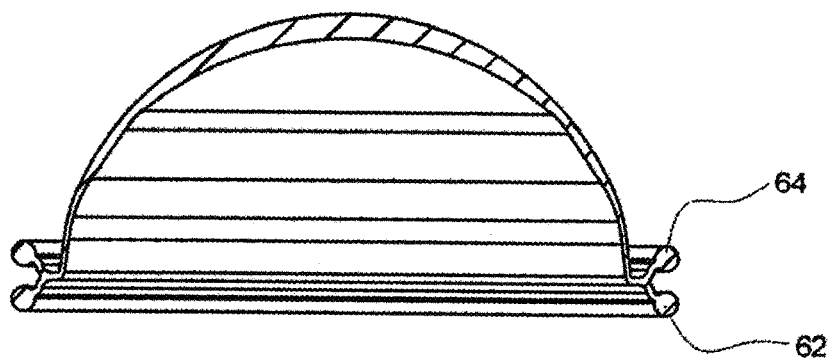
FIG. 6G

1100

1200

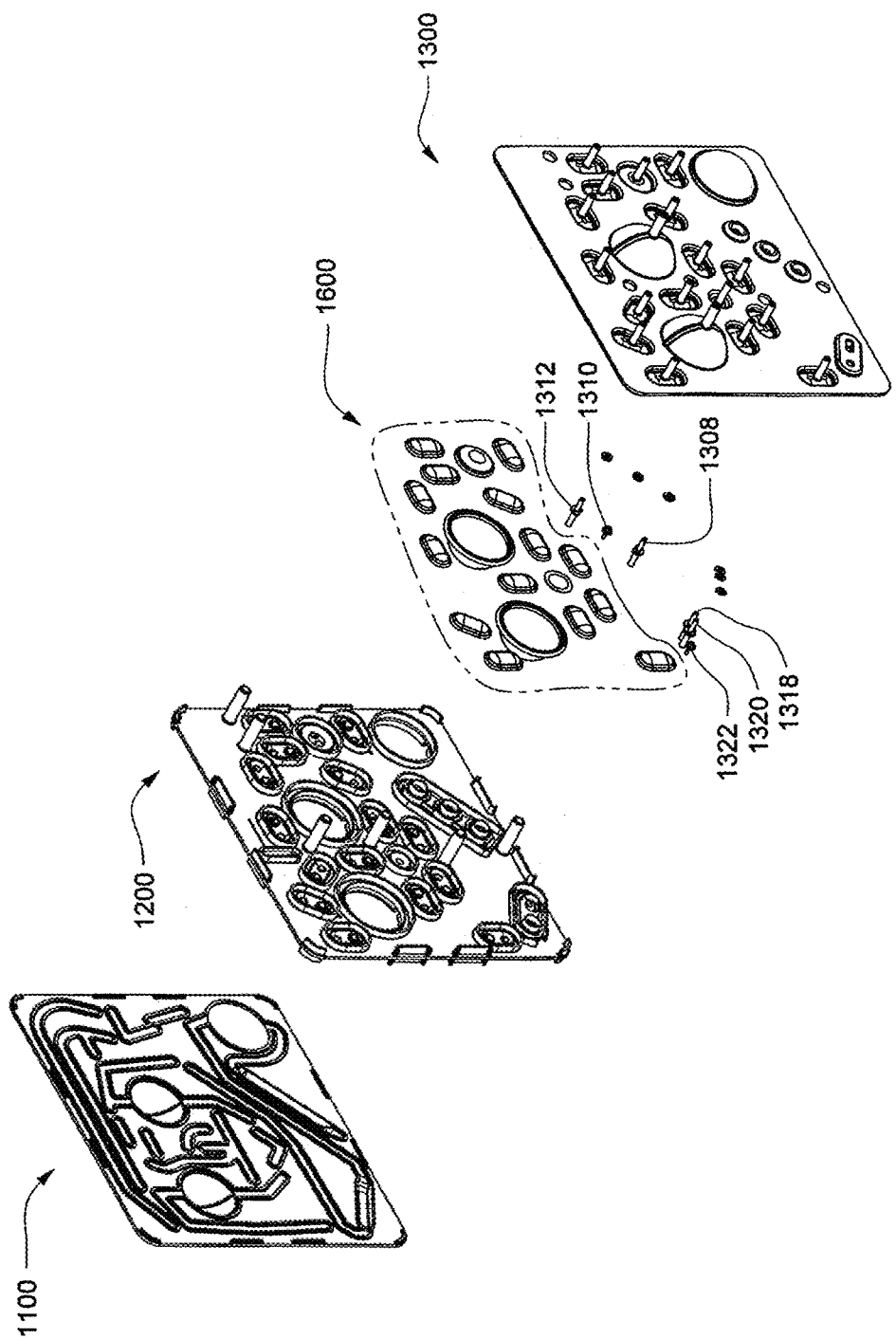

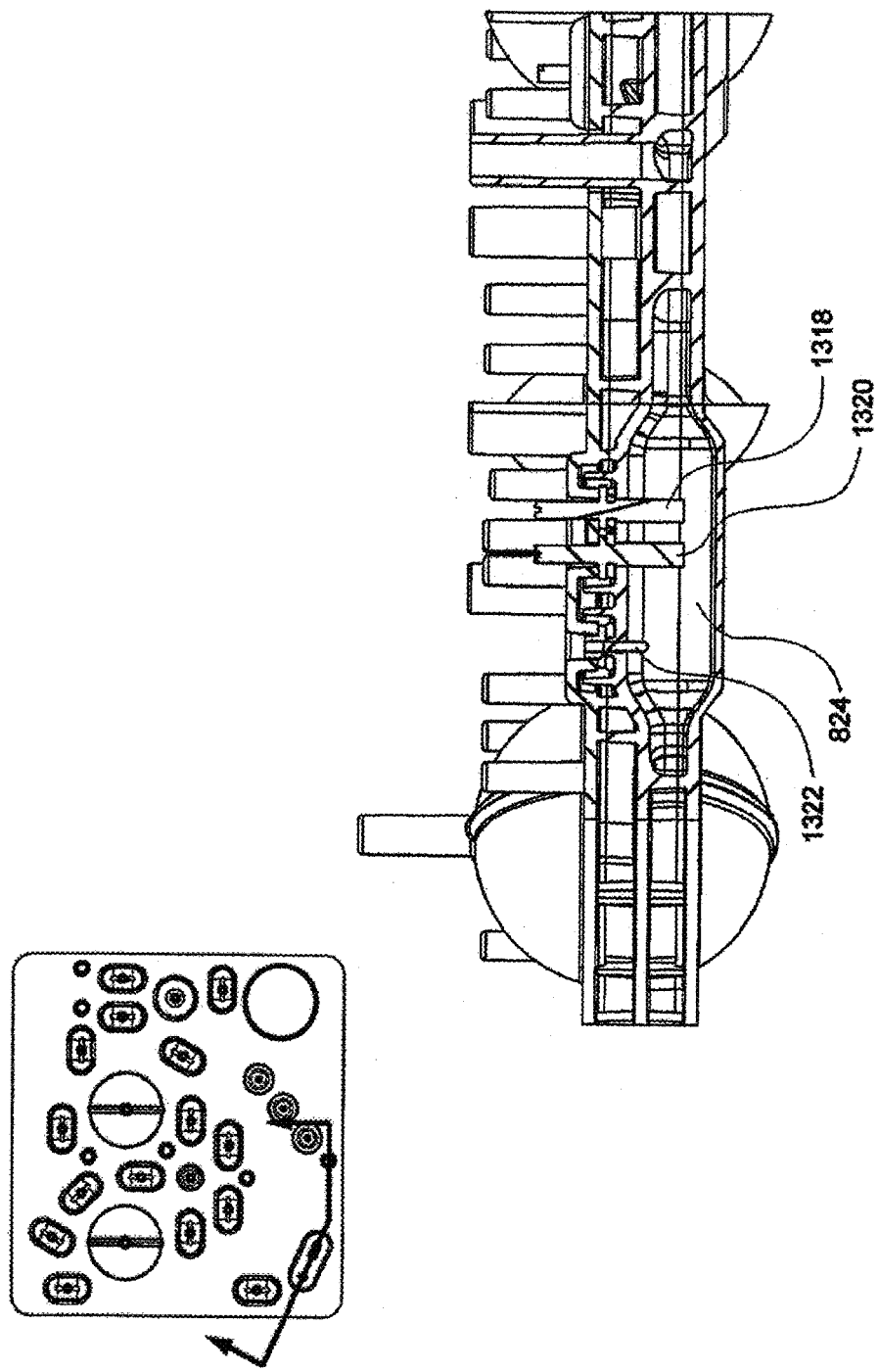

1600

1700

1800

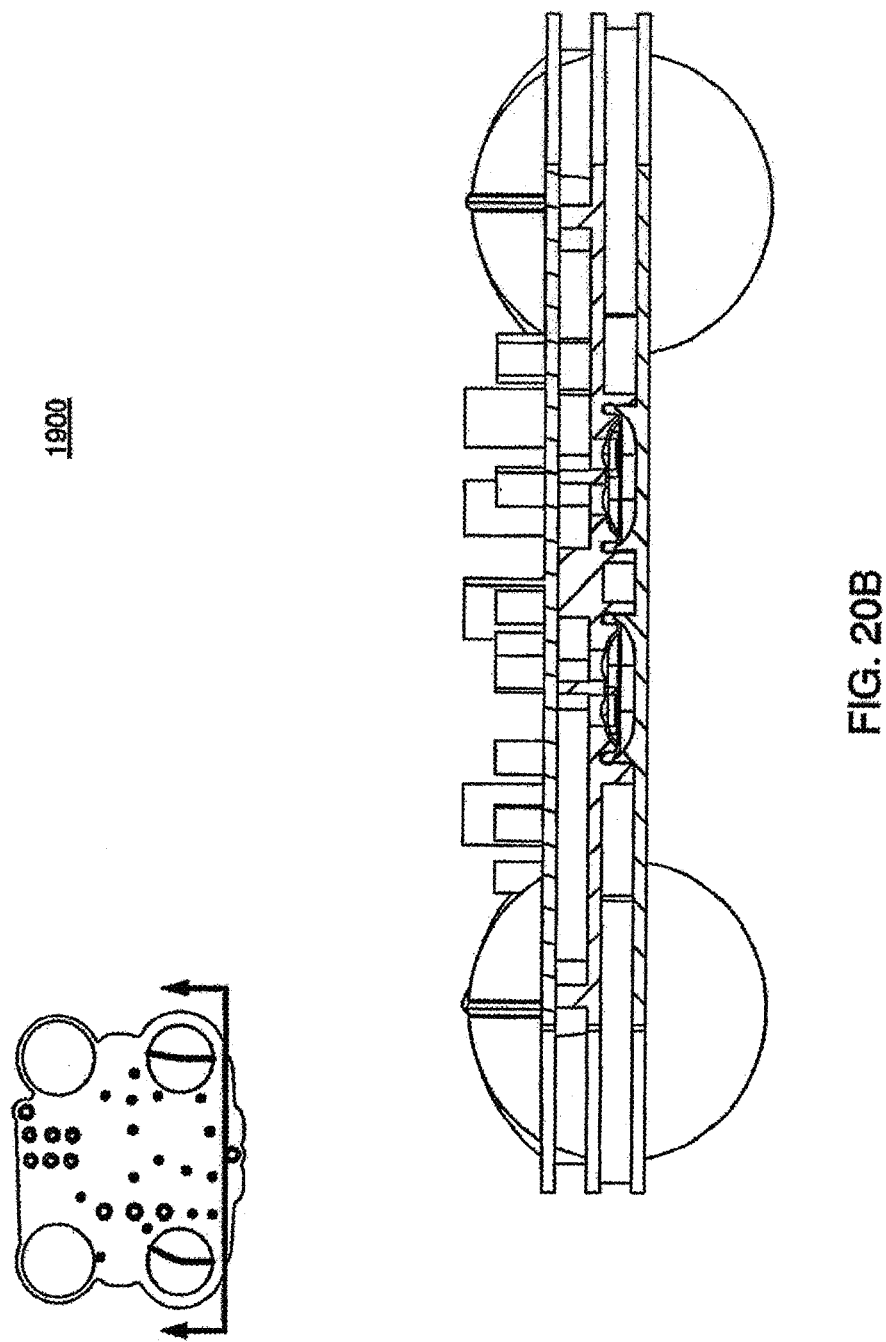

31000

31100

31100

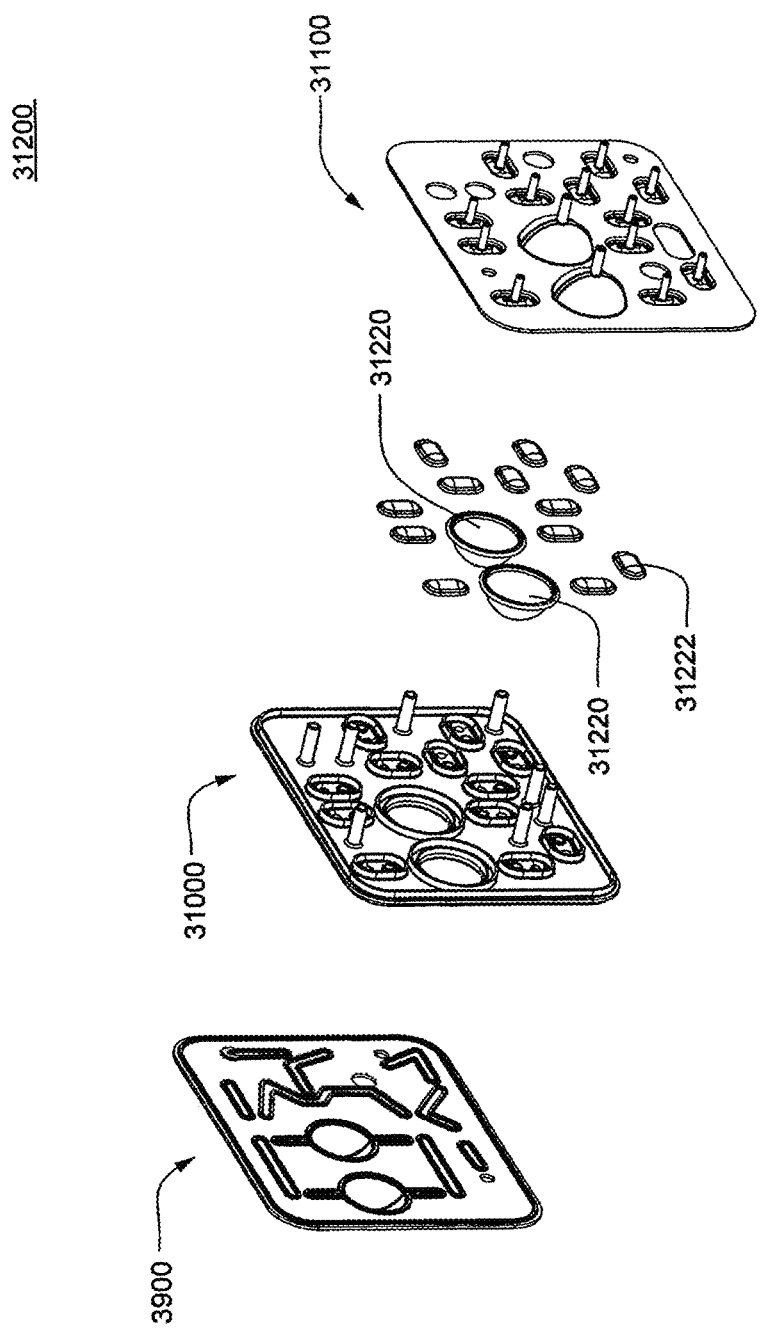

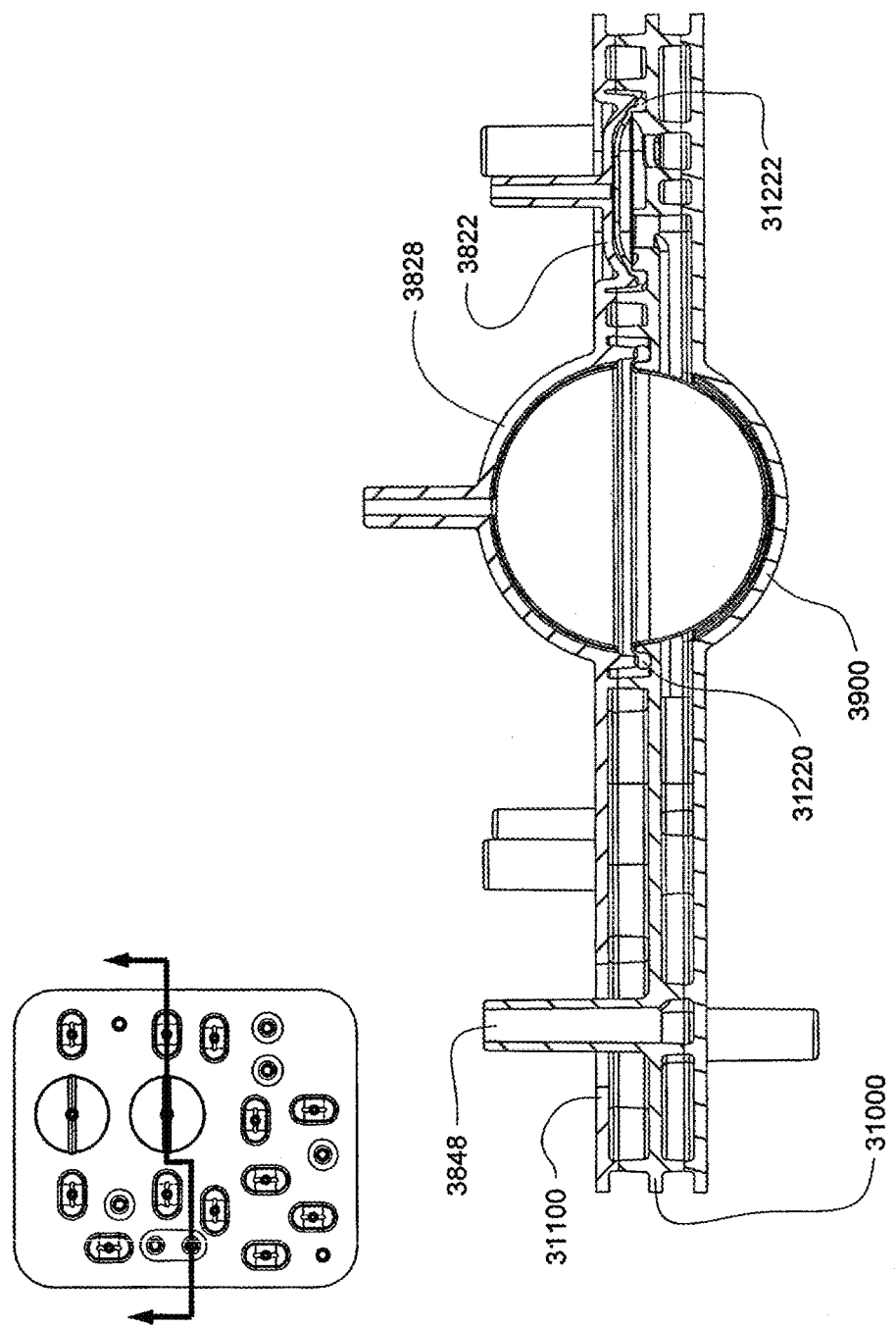

31400

31500

31600

31600

31700

31800

31800

31800

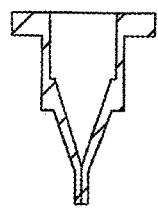
FIG. 35B
FIG. 35A
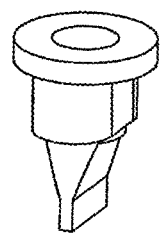 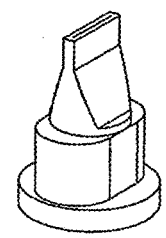
FIG. 35C          FIG. 35D

41100

41400

41400

41500

41500

41500

41600

41600

41600

41600

41600

41700

41800

41900

42000

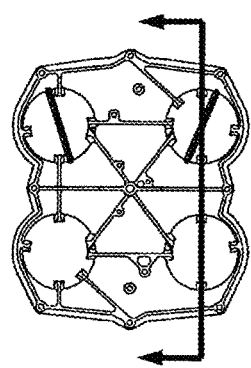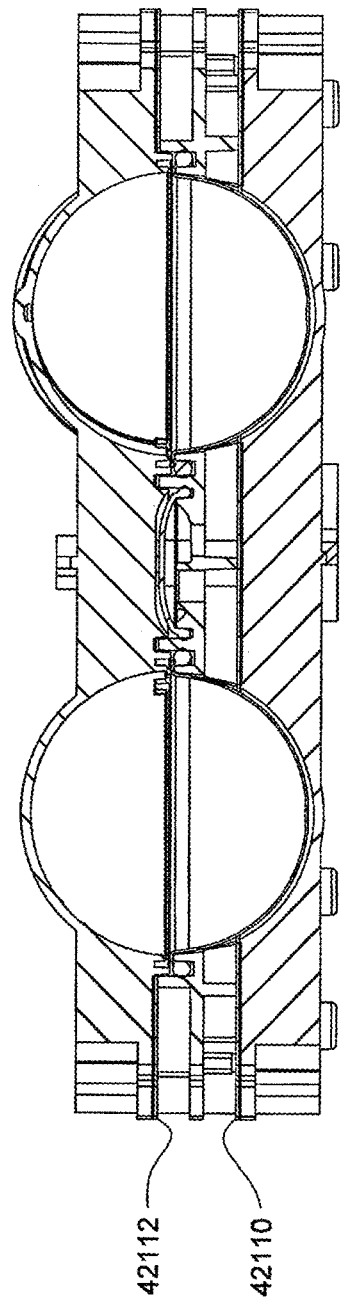
FIG. 52A

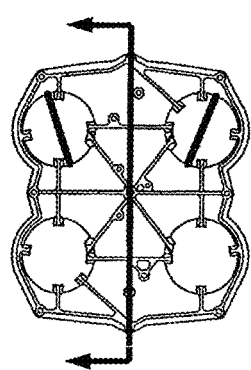
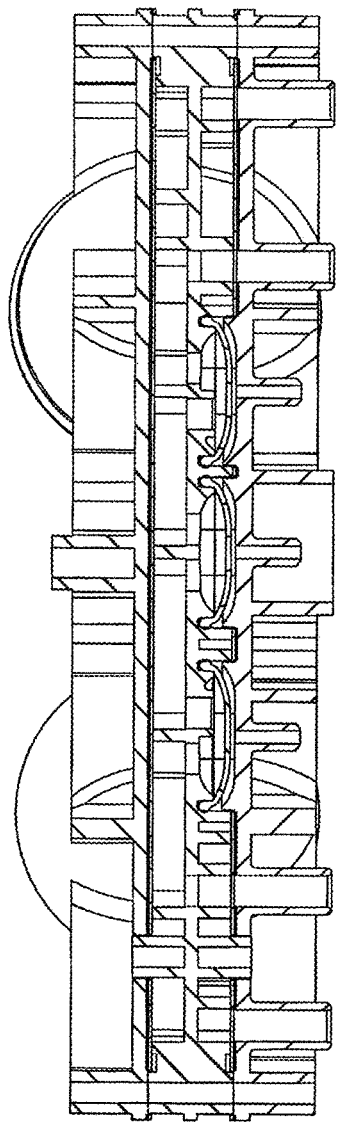
FIG. 52B

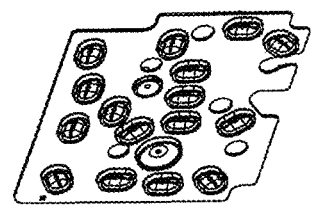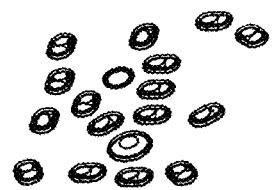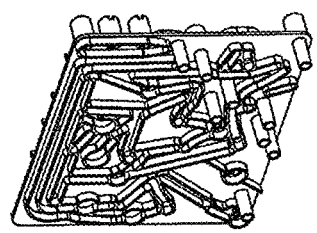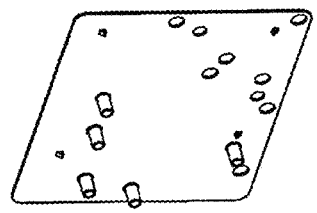
FIG. 53A

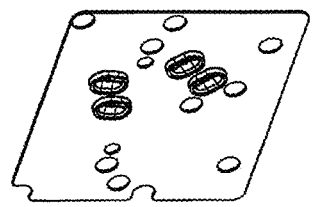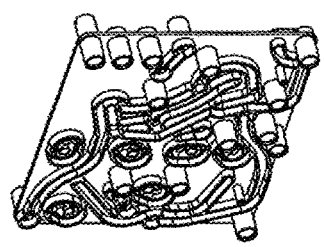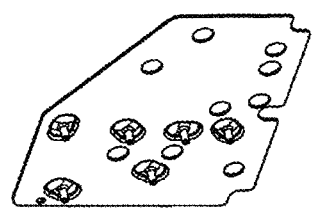
FIG. 54A

CASSETTE SYSTEM INTEGRATED APPARATUS

CROSS-REFERENCE TO RELATED APPLICATIONS

This application is a Continuation of U.S. patent application Ser. No. 15/619,961, filed on Jun. 12, 2017, and issued as U.S. Pat. No. 10,799,628 on Oct. 13, 2020, which is a Continuation of U.S. patent application Ser. No. 14/673,822, filed on Mar. 30, 2015, and issued as U.S. Pat. No. 9,677,554 on Jun. 13, 2017, which is a Continuation of U.S. patent application Ser. No. 13/619,343, filed on Sep. 14, 2012, and issued as U.S. Pat. No. 8,992,189 on Mar. 31, 2015, which is a Continuation of U.S. patent application Ser. No. 13/280,274, filed on Oct. 24, 2011 and issued as U.S. Pat. No. 8,499,780 on Aug. 6, 2013, which is a Divisional of U.S. patent application Ser. No. 12/038,648, filed on Feb. 27, 2008 and issued as U.S. Pat. No. 8,042,563 on Oct. 25, 2011, which is a Continuation in Part of U.S. patent application Ser. No. 11/871,803, filed Oct. 12, 2007 and issued as U.S. Pat. No. 7,967,022 on Jun. 28, 2011, which claims priority from the following United States Provisional Patent Applications:

U.S. Provisional Patent Application No. 60/904,024 entitled Hemodialysis System and Methods filed on Feb. 27, 2007; and U.S. Provisional Patent Application No. 60/921,314 entitled Sensor Apparatus filed on Apr. 2, 2007. All of the above mentioned U.S. Patent Applications are hereby incorporated by reference in their entireties.

TECHNICAL FIELD

The present invention relates to a cassette system integrated apparatus for pumping fluid.

SUMMARY OF THE INVENTION

In accordance with one aspect of the cassette integrated system, the cassette integrated system includes a mixing cassette, a balancing cassette, a middle cassette fluidly connected to the mixing cassette and the balancing cassette and at least one pod. The mixing cassette is fluidly connected to the middle cassette by at least one fluid line and the middle cassette is fluidly connected to the balancing cassette by at least one fluid line. The at least one pod is connected to at least two of the cassettes wherein the pod is located in an area between the cassettes.

Various embodiments of this aspect of the cassette include one or more of the following. Where the housing includes a top plate, a midplate and a bottom plate. Where the pod includes a curved rigid chamber wall having at least one fluid inlet and at least one fluid outlet. Where the mixing cassette, middle cassette and said balancing cassette further include at least one valve. In some embodiments the valve is a membrane valve. Where at least one of the fluid lines connecting the cassettes is a rigid hollow cylindrical structure.

In accordance with one aspect of the cassette integrated system, the cassette integrated system includes a mixing cassette, a middle cassette and a balancing cassette. The mixing cassette includes a mixing cassette housing including at least one fluid inlet line and at least one fluid outlet line. The mixing cassette also includes at least one reciprocating pressure displacement membrane pump fluidly connected to the housing. The pressure pump pumps at least one fluid from the fluid inlet line to at least one of the fluid outlet line. The mixing cassette also includes at least one mixing chamber fluidly connected to the housing. The mixing chamber is fluidly connected to the fluid outlet line. The middle cassette includes a housing having at least one fluid port and at least one air vent port, the air vent port vents a fluid source outside the middle cassette housing. The middle cassette also includes at least one reciprocating pressure displacement membrane pump fluidly connected to the housing. The pump pumps a fluid. The balancing cassette includes a housing including at least two inlet fluid lines and at least two outlet fluid lines. Also, at least one balancing pod fluidly connected to the balancing cassette housing and in fluid connection with the fluid paths. The balancing pod balances the flow of a first fluid and the flow of a second fluid such that the volume of the first fluid equals the volume of the second fluid. The balancing pod includes a membrane wherein the membrane forms two balancing chambers. The balancing cassette also includes at least one reciprocating pressure displacement membrane pump fluidly connected to the balancing cassette housing. The pressure pump pumps a fluid from the fluid inlet line to the fluid outlet line. The mixing cassette is fluidly connected to the middle cassette by at least one fluid line, and the middle cassette is fluidly connected to the balancing pod by at least one fluid line. The reciprocating pressure displacement membrane pumps, mixing chamber and balancing pod are connected to the housings such that the reciprocating pressure displacement membrane pumps, mixing chamber and balancing pod are located in areas between the cassettes.

Various embodiments of this aspect of the cassette include one or more of the following. Where the cassette housings include a top plate, a midplate and a bottom plate. Where the reciprocating pressure displacement pump includes a curved rigid chamber wall and a flexible membrane attached to the rigid chamber wall. The flexible membrane and the rigid chamber wall define a pumping chamber. Also, in some embodiments, the balancing pod includes a curved rigid chamber wall and a flexible membrane attached to the rigid chamber wall. The flexible membrane and the rigid chamber wall define two balancing chambers. Where the mixing chamber includes a curved rigid chamber wall having at least one fluid inlet and at least one fluid outlet. Where the mixing cassette, middle cassette and the balancing cassette further include at least one valve. Some embodiments of the valve include where the valve is a membrane valve. Some embodiments include where the membrane valve is a volcano valve.

Some embodiments include where the at least one of the fluid lines connecting the cassettes is a rigid hollow cylindrical structure. Some embodiments include where at least one of the fluid lines connecting the cassettes contain a check valve within the cylindrical structure. Some embodiments of the system include where the mixing cassette further includes at least one metering membrane pump within the mixing cassette housing. The mixing chamber fluidly connects to the fluid outlet line. Some embodiments of the system include where the balancing cassette further includes at least one metering pump within the housing and fluidly connected to a fluid line. The metering pump pumps a predetermined volume of a fluid such that the fluid bypasses the balancing chambers and wherein the metering pump is a membrane pump.

In accordance with one aspect of the cassette integrated system, the cassette integrated system includes a mixing cassette, a middle cassette and a balancing cassette. The mixing cassette includes a mixing cassette housing including at least one fluid inlet line and at least one fluid outlet line. Also, at least one reciprocating pressure displacement membrane pump fluidly connected to the housing. The pressure pump pumps at least one fluid from the fluid inlet line to at least one of the fluid outlet line. The mixing cassette also includes at least one mixing chamber fluidly connected to the housing. The mixing chamber is fluidly connected to the fluid outlet line. A plurality of membrane valves and a plurality of fluid lines are also included. The valves control the flow of fluid in the fluid lines. The mixing cassette also includes at least one metering membrane pump within the mixing cassette housing. The mixing chamber is fluidly connected to the fluid outlet line.

The middle cassette includes a middle cassette housing having at least one fluid port and at least one air vent port. The air vent port vents a fluid source outside the housing. Also includes are a plurality of fluid lines within the middle cassette housing and a plurality of membrane valves. The valves control the flow of fluid in the fluid. At least one reciprocating pressure displacement membrane pump fluidly connected to the housing is also included. The pump pumps a fluid.

The balancing cassette includes a balancing cassette housing including at least one inlet fluid line and at least one outlet fluid line. A plurality of membrane valves and a plurality of fluid paths are also included. The valves control the flow of fluid in the fluid paths. At least one balancing pod fluidly connected to the balancing cassette housing and in fluid connection with the fluid paths is also included. The balancing pod balances the flow of a first fluid and the flow of a second fluid such that the volume of the first fluid equals the volume of the second fluid. The balancing pod includes a membrane which forms two balancing chambers. The balancing cassette also includes at least one reciprocating pressure displacement membrane pump fluidly connected to the balancing cassette housing. The pressure pump pumps a fluid from the fluid inlet line to the fluid outlet line. Also, at least one metering pump within said housing and fluidly connected to a fluid line, wherein said metering pump is included. The metering pump pumps a predetermined volume of a fluid such that the fluid bypasses the balancing chambers. The metering pump is a membrane pump.

The mixing cassette is fluidly connected to the middle cassette by at least one fluid line. Also, the middle cassette is fluidly connected to the balancing pod by at least one fluid line. The reciprocating pressure displacement membrane pumps, mixing chamber and balancing pod are connected to the housings such that they are located in areas between said cassettes.

Various embodiments of this aspect of the cassette include where at least one of the fluid lines connecting the cassettes is a rigid hollow cylindrical structure.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein:

FIG. 2G shows pictorial, top and cross sectional views of one embodiment of the valving membrane;

FIG. 6G is a cross sectional view of a double ring membrane with a variable surface;

FIGS. 14C and 14E are exploded views of the assembled exemplary embodiment of the cassette;

FIGS. 15A-15C show cross sectional views of the exemplary embodiment of the assembled cassette;

FIGS. 20A-20B show cross sectional view of the exemplary embodiment of the assembled cassette.

FIG. 26D is an exploded view of the assembled exemplary embodiment of the cassette;

FIG. 27 shows a cross sectional view of the exemplary embodiment of the assembled cassette;

FIGS. 28C and 28D are isometric and front views of an alternate embodiment of the inner top plate of the cassette;

FIGS. 35A-35B show cross sectional views of one embodiment of the check valve; and FIGS. 35C-35D show pictorial views of one embodiment of the check valve.

FIGS. 40A-41B are isometric bottom views of the exemplary embodiment of bottom plate of the exemplary embodiment of the cassette;

FIG. 49E shows a side view of the alternate embodiment of the midplate;

FIGS. 50A-50B show isometric and top views of an alternate embodiment of the bottom plate according to an alternate embodiment of the cassette;

FIGS. 50C-50D show isometric and bottom views of an alternate embodiment of the bottom plate according to an alternate embodiment of the cassette;

FIG. 50E shows a side view of the alternate embodiment of the bottom plate;

FIG. 51A is a top view of an assembled alternate embodiment of the cassette;

FIG. 51B is a bottom view of an assembled alternate embodiment of the cassette;

FIG. 51C is an exploded view of the assembled alternate embodiment of the cassette;

FIG. 51D is an exploded view of the assembled alternate embodiment of the cassette;

FIG. 52A shows a cross sectional view of the exemplary embodiment of the assembled cassette;

FIG. 52B shows a cross sectional view of the exemplary embodiment of the assembled cassette.

FIG. 53A is an exploded view of the exemplary embodiment of the mixing cassette of the cassette system;

FIG. 53B is an exploded view of the exemplary embodiment of the mixing cassette of the cassette system;

Figure 54B:
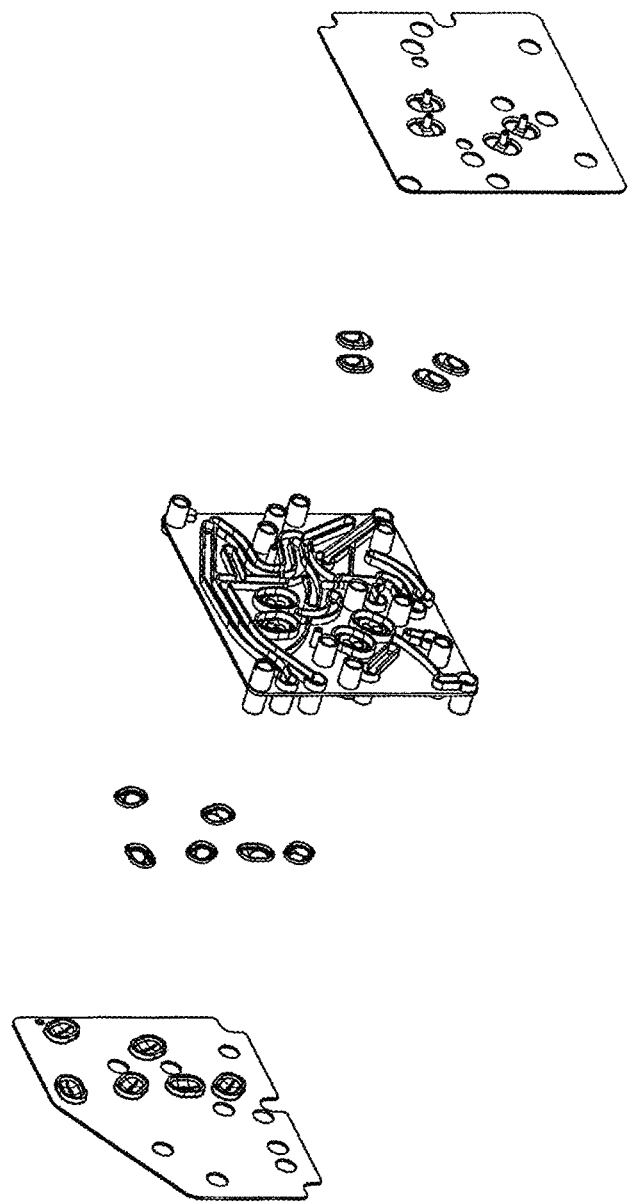
Figure 55A:
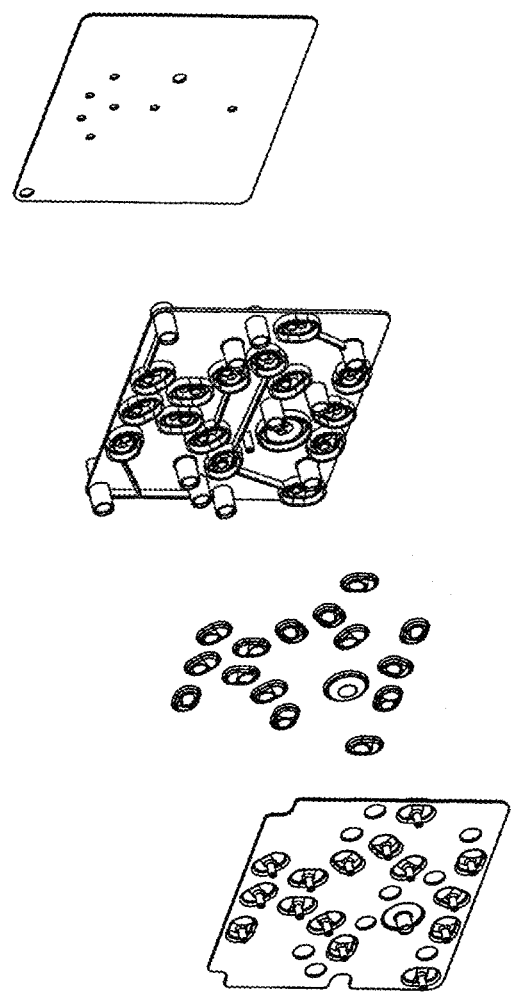
Figure 55B:
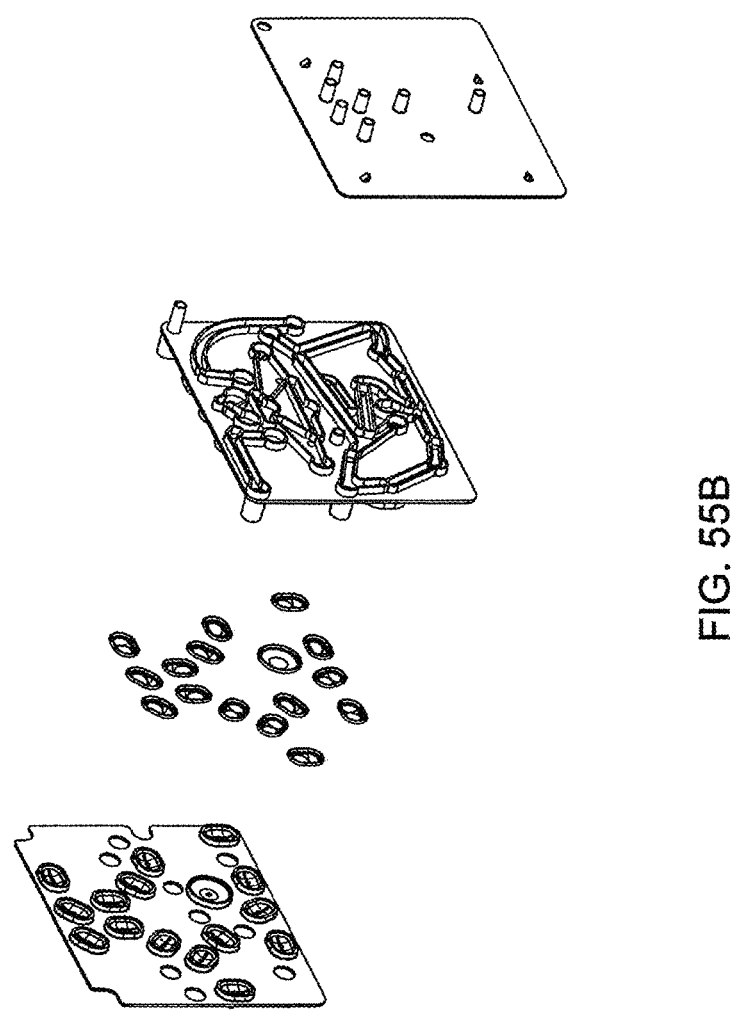
Figure 56A:
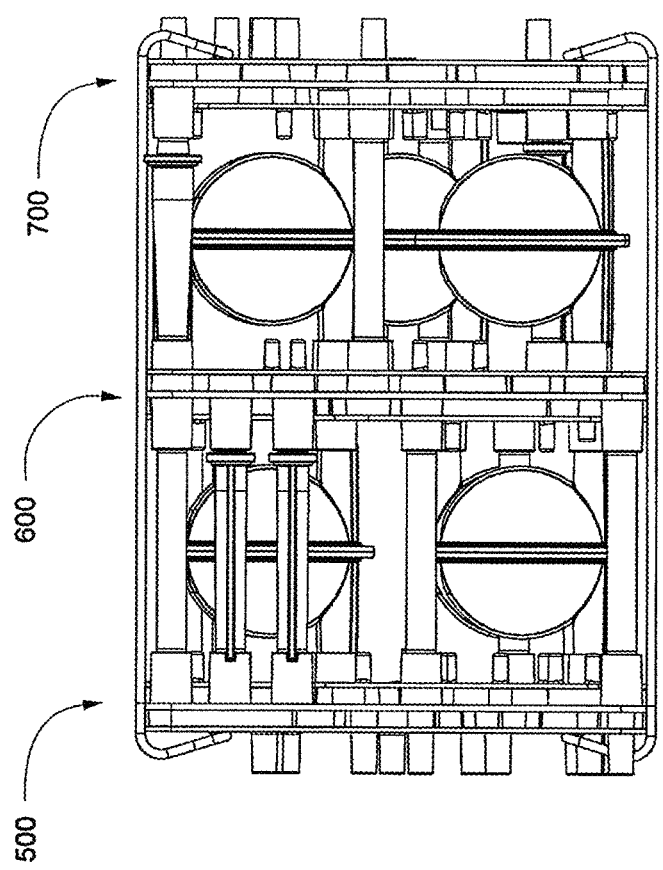
Figure 56B:
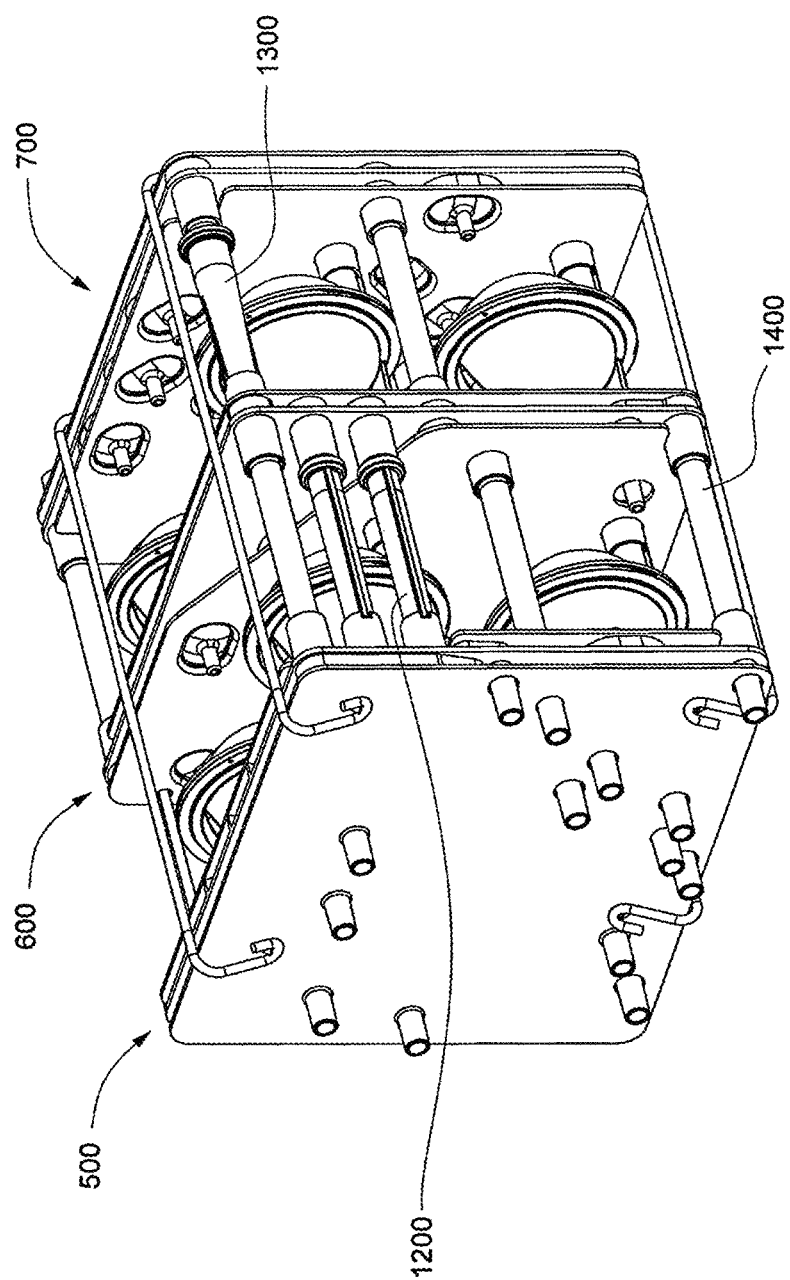
Figure 56C:
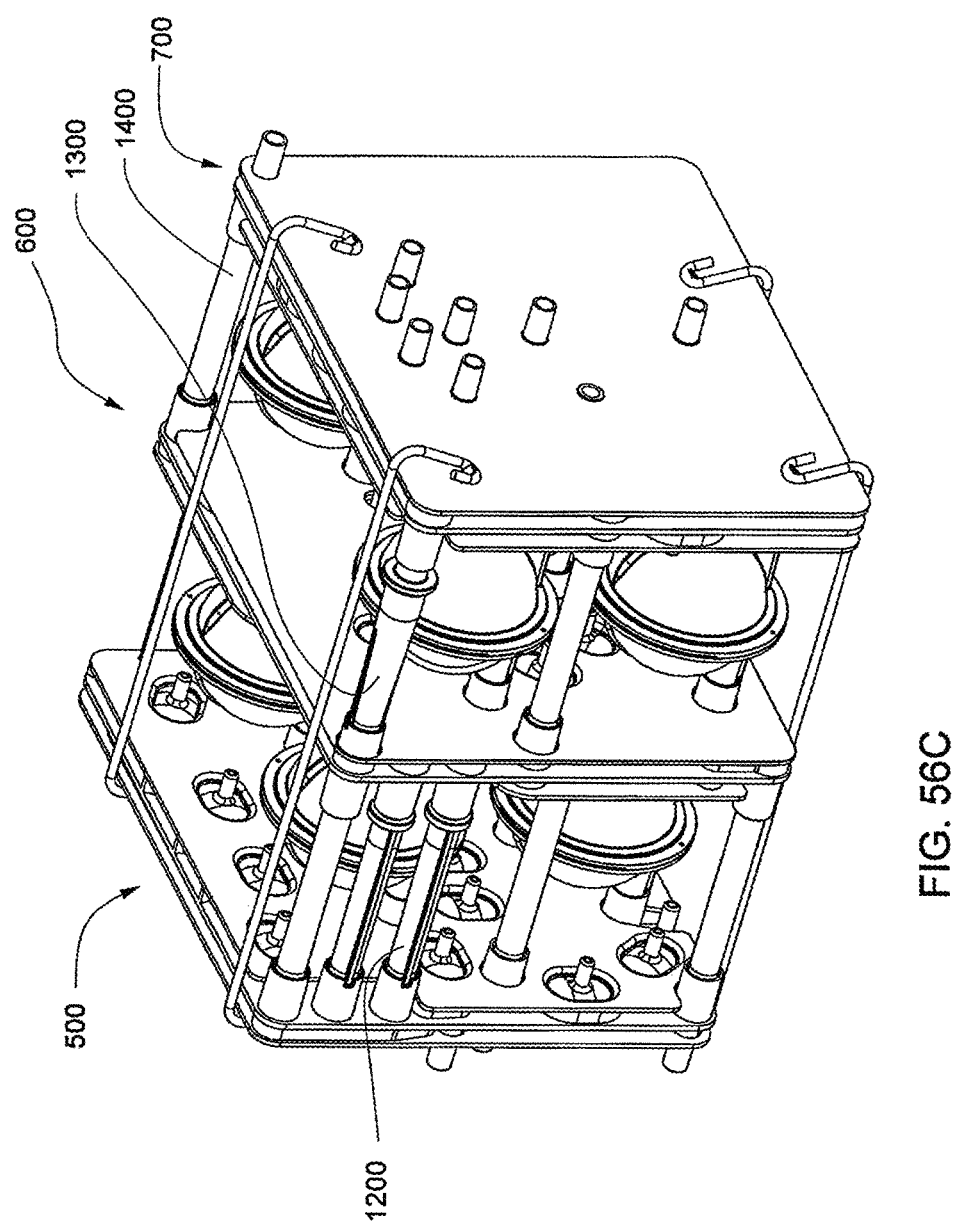
Figure 56D:
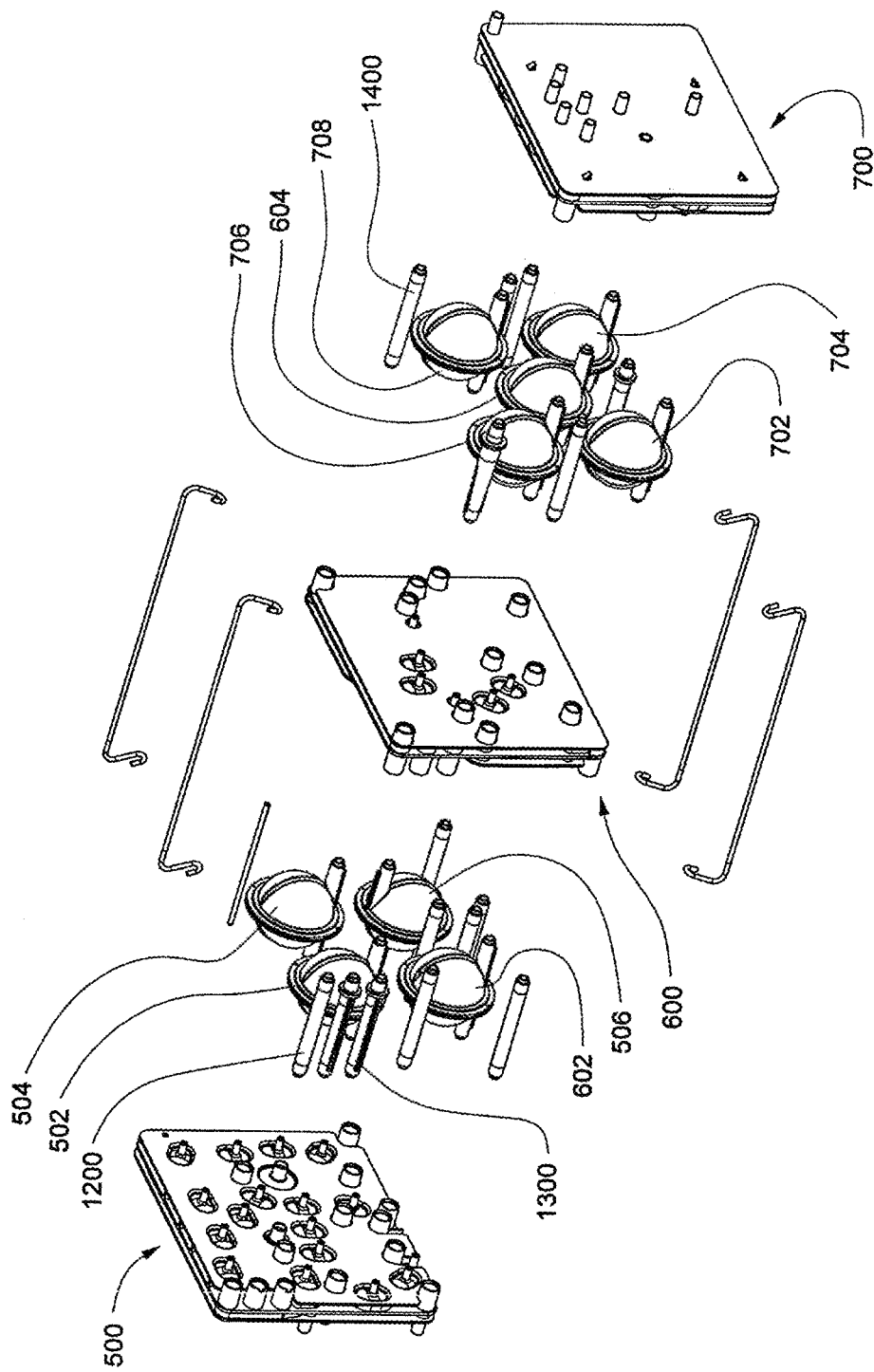
Figure 56E:
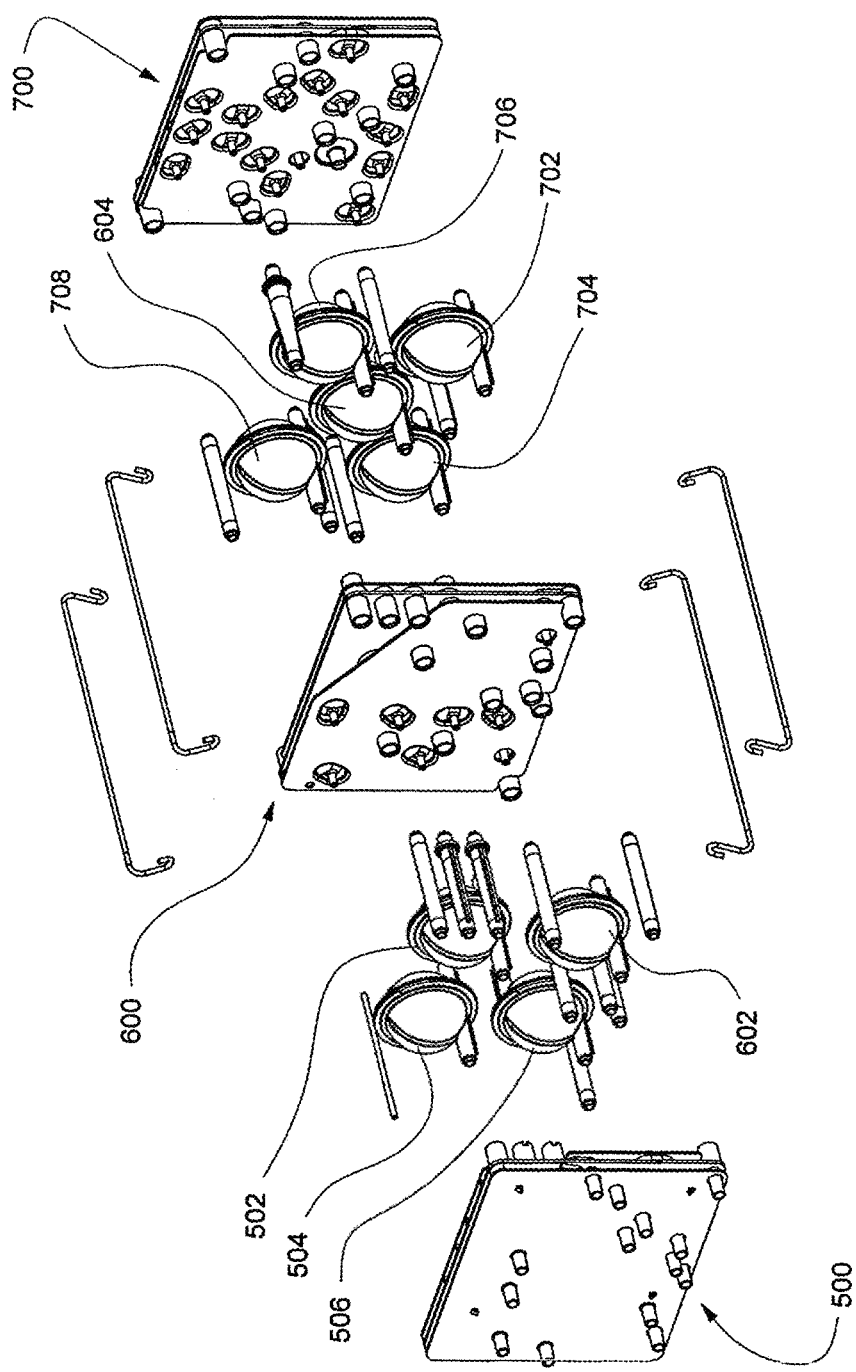
Figure 57A:
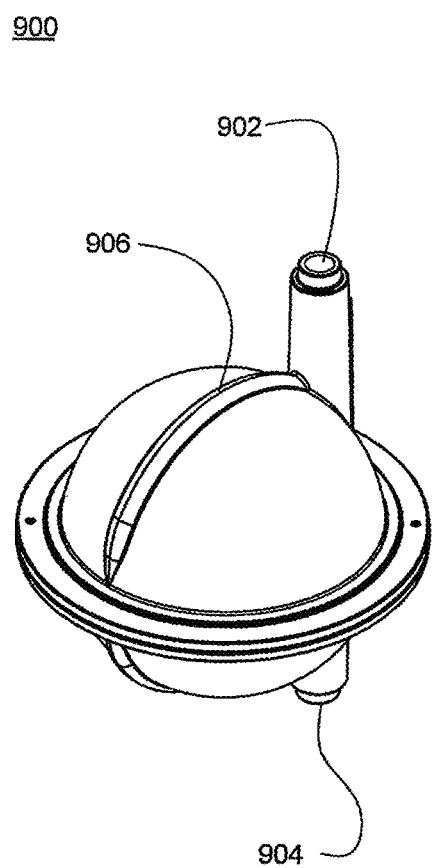
Figure 57B:
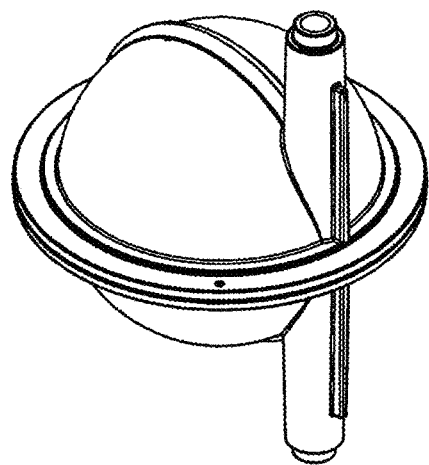
Figure 57C:
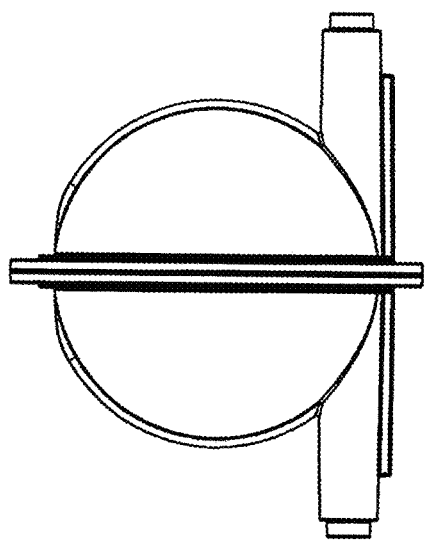
Figure 57D:
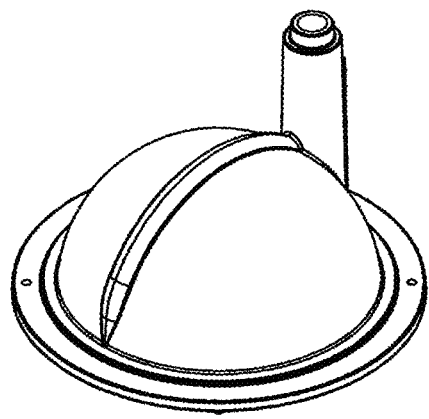
Figure 57E:
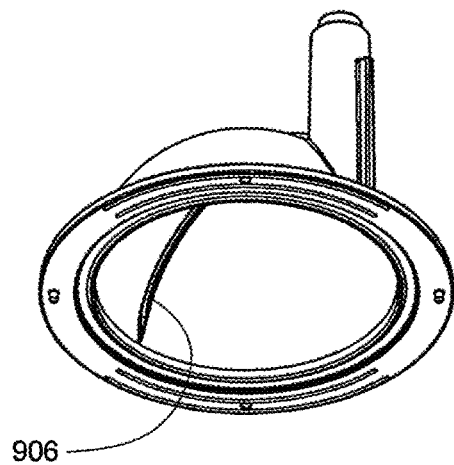
Figure 58A:
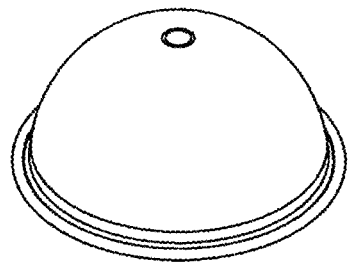
Figure 58B:
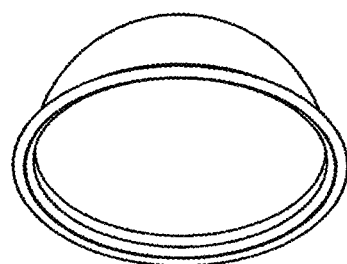
Figure 59:
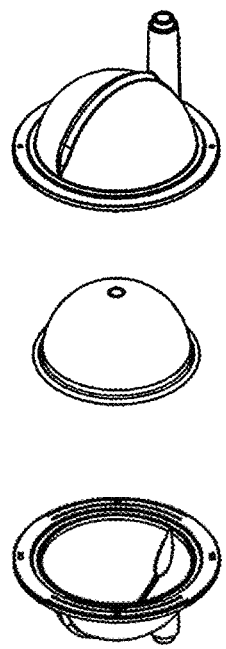
Figure 60:
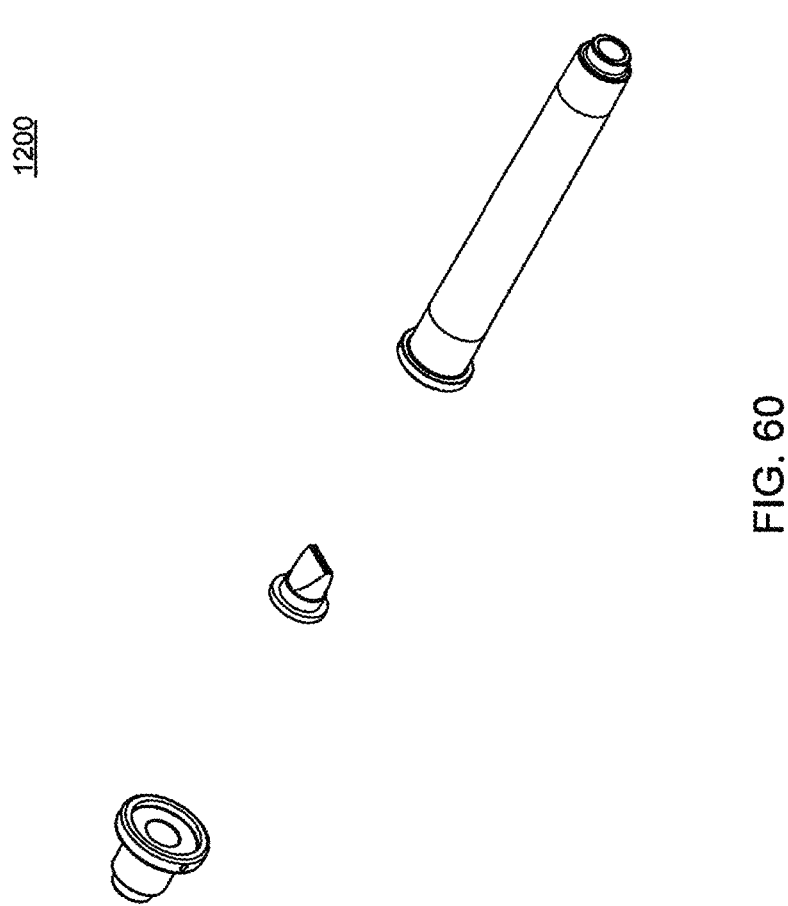
Figure 61:
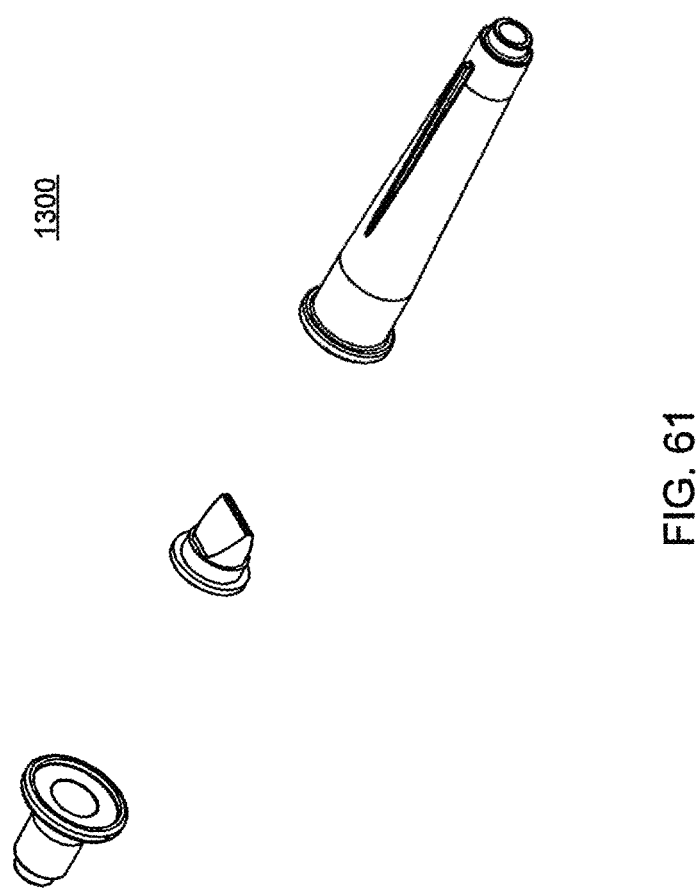
Figure 62:
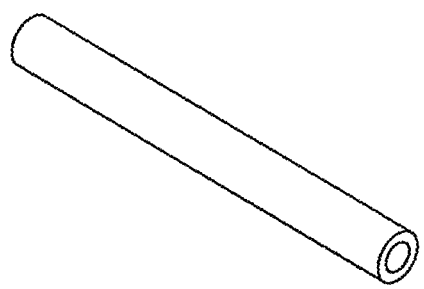
Figure 63A:
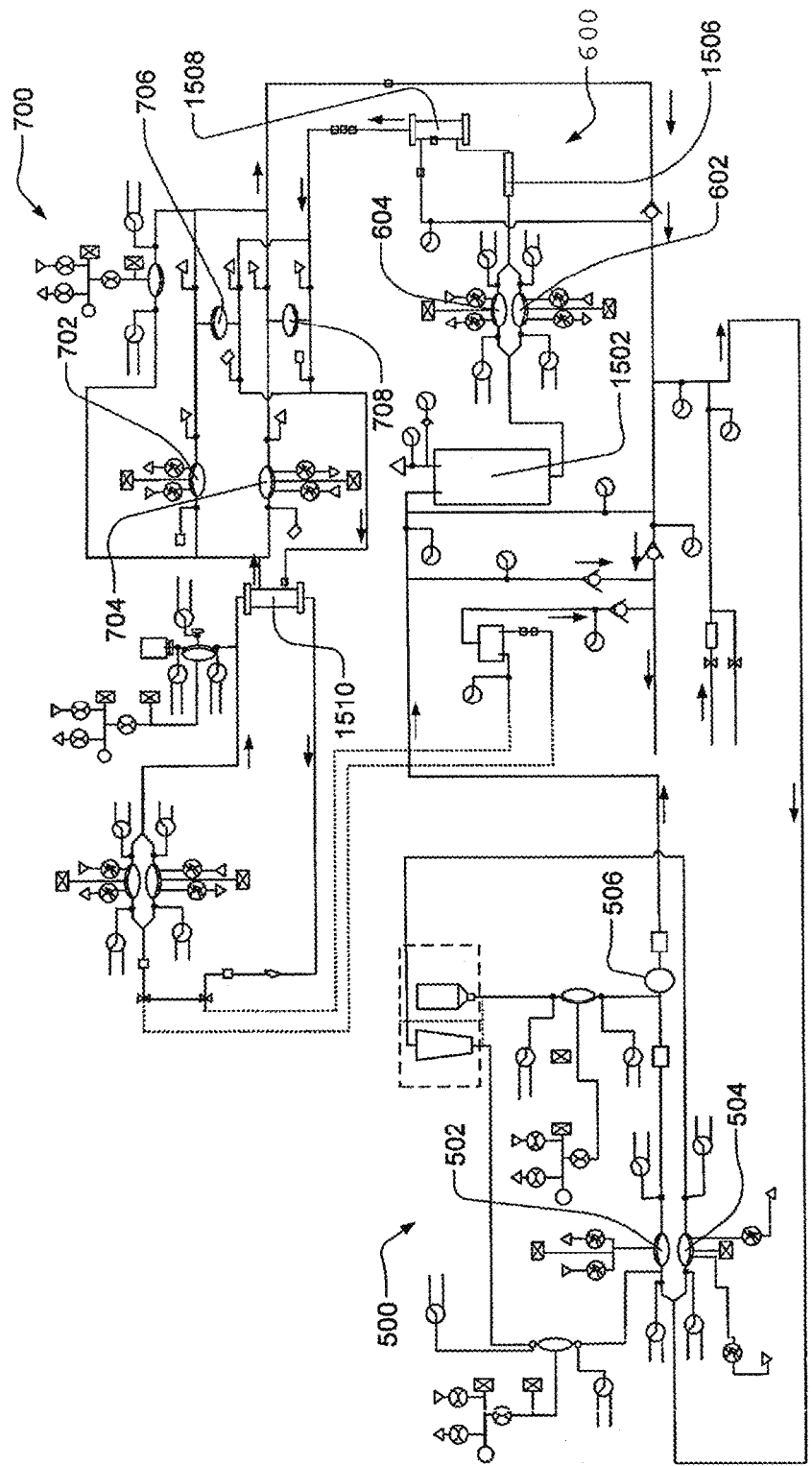
Figure 63B:
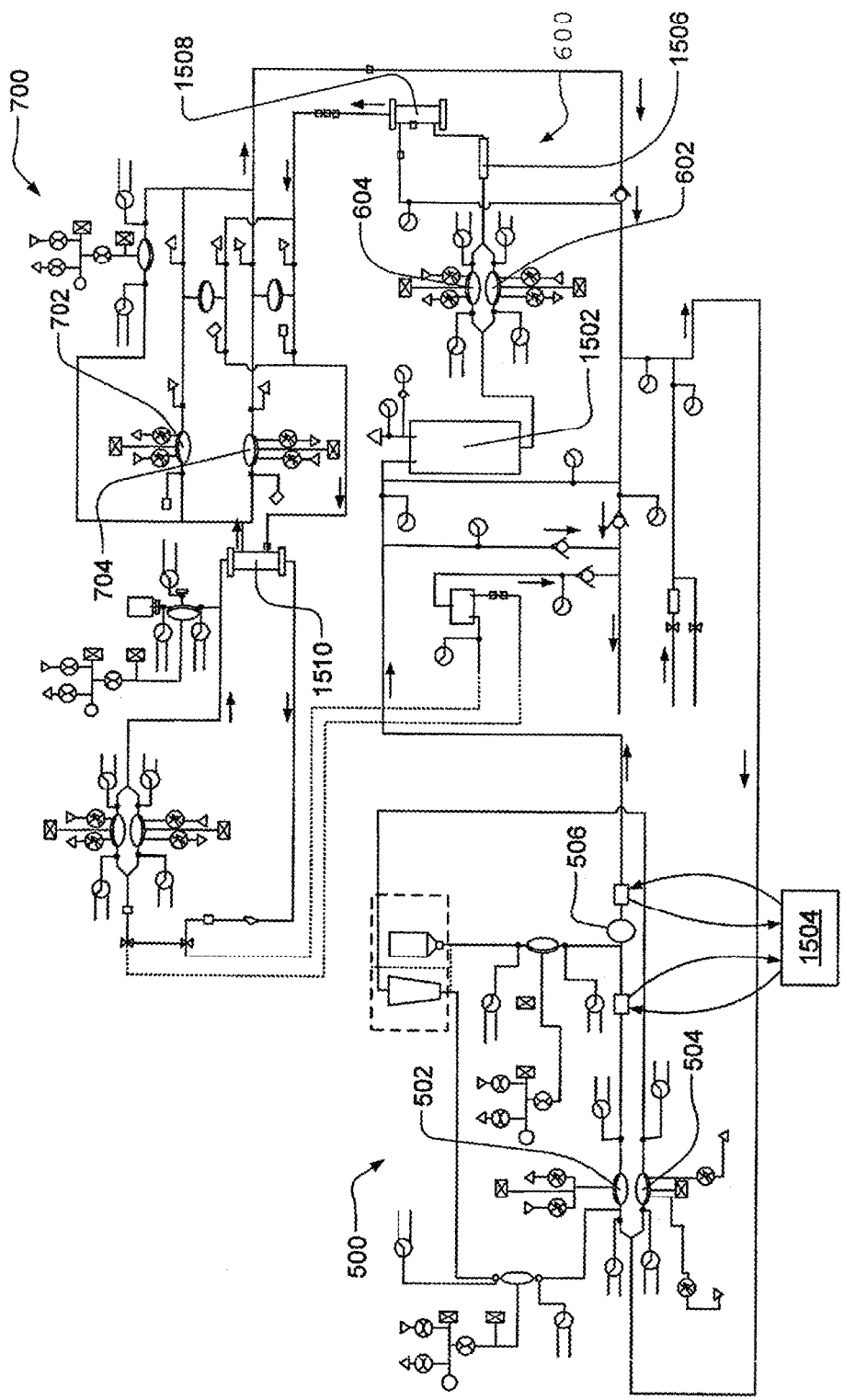
Figure 64C:
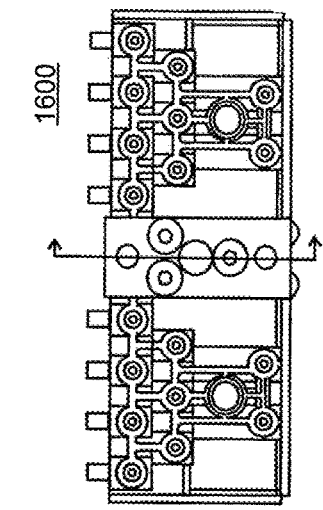
Figure 64F:
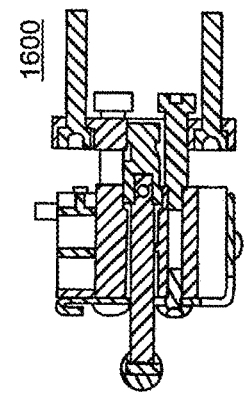
Figure 64B:
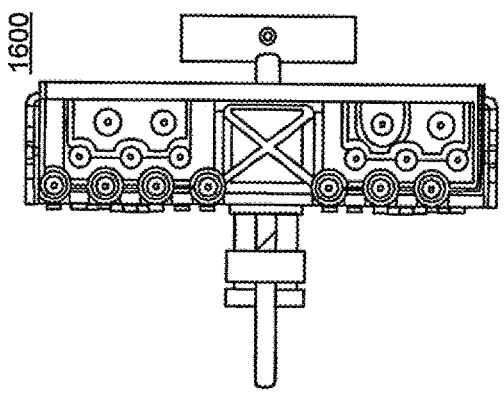
Figure 64E:
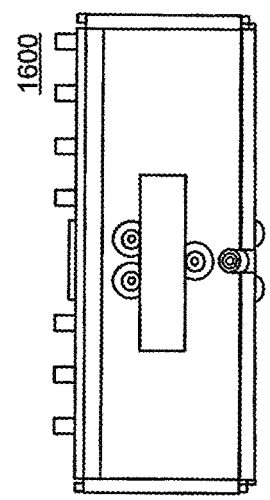
Figure 64A:
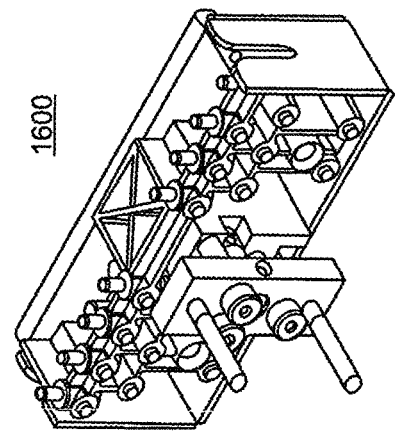
Figure 64D:
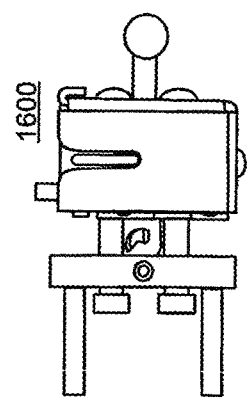

FIG. 54A is an exploded view of the exemplary embodiment of the middle cassette of the cassette system;

FIG. 54B is an exploded view of the exemplary embodiment of the middle cassette of the cassette system;

FIG. 55A is an exploded view of the exemplary embodiment of the balancing cassette of the cassette system;

FIG. 55B is an exploded view of the exemplary embodiment of the balancing cassette of the cassette system;

FIG. 56A is a front view of the assembled exemplary embodiment of the cassette system;

FIG. 56B is an isometric view of the assembled exemplary embodiment of the cassette system;

FIG. 56C is an isometric view of the assembled exemplary embodiment of the cassette system;

FIG. 56D is an exploded view of the assembled exemplary embodiment of the cassette system;

FIG. 56E is an exploded view of the assembled exemplary embodiment of the cassette system;

FIG. 57A is an isometric view of an exemplary embodiment of the pod of the cassette system;

FIG. 57B is an isometric view of an exemplary embodiment of the pod of the cassette system;

FIG. 57C is a side view of an exemplary embodiment of the pod of the cassette system;

FIG. 57D is an isometric view of an exemplary embodiment of one half of the pod of the cassette system;

FIG. 57E is an isometric view of an exemplary embodiment of one half of the pod of the cassette system;

FIG. 58A is a pictorial view of the exemplary embodiment of the pod membrane of the cassette system;

FIG. 58B is a pictorial view of the exemplary embodiment of the pod membrane of the cassette system;

FIG. 59 is an exploded view of an exemplary embodiment of the pod of the cassette system;

FIG. 60 is an exploded view of one embodiment of a check valve fluid line in the cassette system;

FIG. 61 is an exploded view of one embodiment of a check valve fluid line in the cassette system;

FIG. 62 is an isometric view of an exemplary embodiment of a fluid line in the cassette system;

FIG. 63A is one embodiment of the fluid flow-path schematic of the cassette system integrated;

FIG. 63B is one embodiment of the fluid flow-path schematic of the cassette system integrated; and FIGS. 64A-F are various views of one embodiment of the block for connecting the pneumatic tubes to the manifold according to one embodiment of the present system.

DETAILED DESCRIPTION OF SPECIFIC EMBODIMENTS

1. Pumping Cassette 1.1 Cassette

Figure 21:
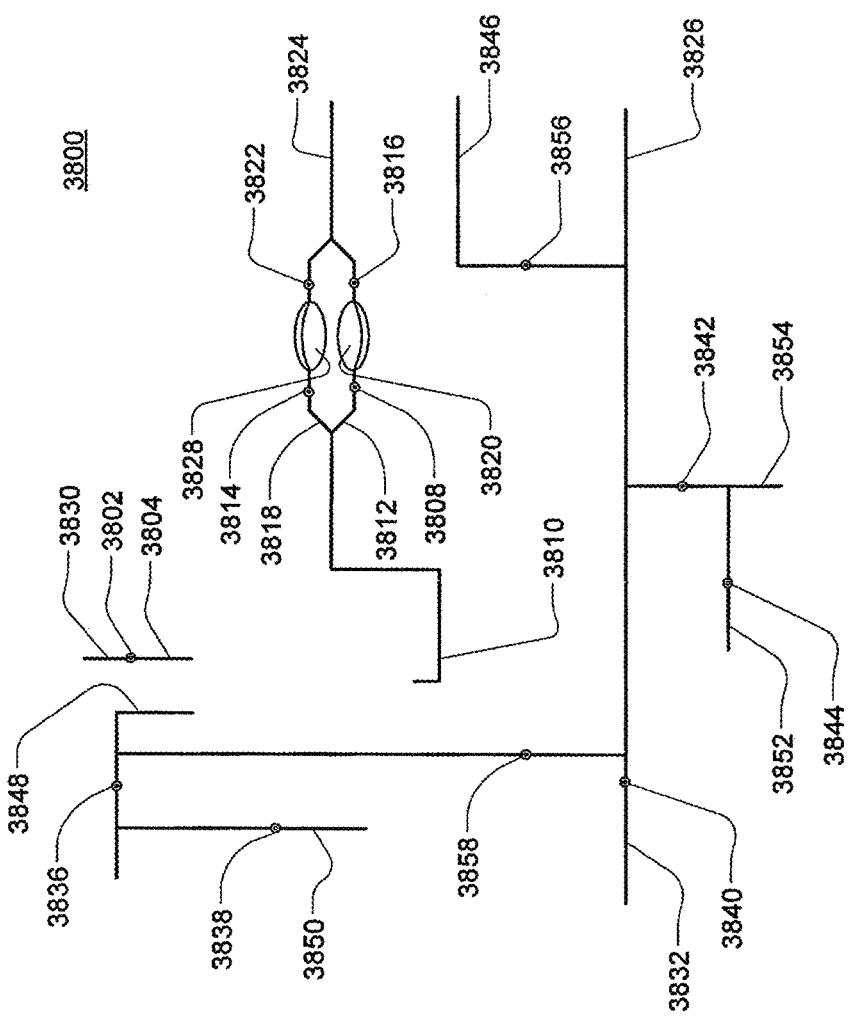
FIG. 21 is one embodiment of the fluid flow-path schematic of the cassette.
Figure 22:
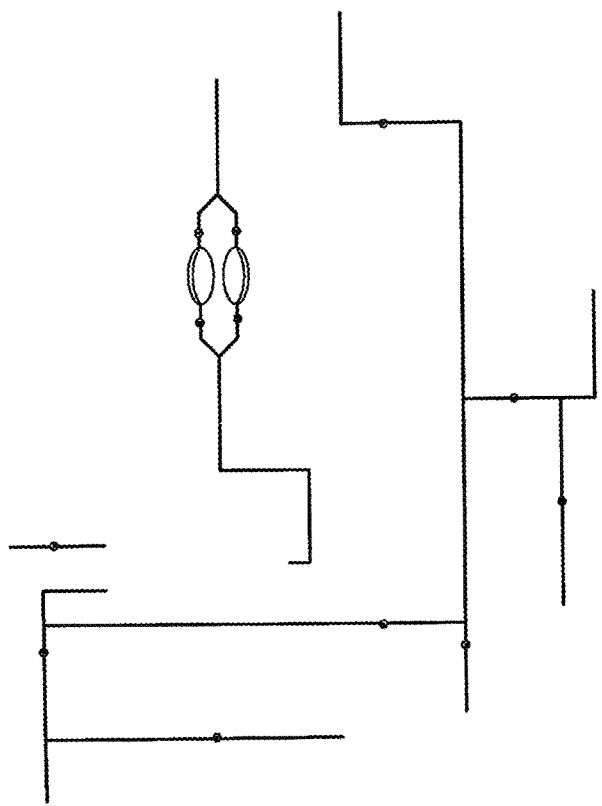
FIG. 22 is an alternate embodiment the fluid flow-path schematic of the cassette.

The pumping cassette includes various features, namely, pod pumps, fluid lines and in some embodiment, valves. The cassette embodiments shown and described in this description include exemplary and some alternate embodiments. However, any variety of cassettes having a similar functionality is contemplated. As well, although the cassette embodiments described herein are implementations of the fluid schematics as shown in FIGS. 21 and 22, in other embodiments, the cassette may have varying fluid paths and/or valve placement and/or pod pump placements and numbers and thus, is still within the scope of the invention.

In the exemplary embodiment, the cassette includes a top plate, a midplate and a bottom plate. There are a variety of embodiments for each plate. In general, the top plate includes pump chambers and fluid lines, the midplate includes complementary fluid lines, metering pumps and valves and the bottom plate includes actuation chambers (and in some embodiments, the top plate and the bottom plate include complementary portions of a balancing chamber).

In general, the membranes are located between the midplate and the bottom plate, however, with respect to balancing chambers, a portion of a membrane is located between the midplate and the top plate. Some embodiments include where the membrane is attached to the cassette, either overmolded, captured, bonded, press fit, welded in or any other process or method for attachment, however, in the exemplary embodiments, the membranes are separate from the top plate, midplate and bottom plate until the plates are assembled.

The cassettes may be constructed of a variety of materials. Generally, in the various embodiment, the materials used are solid and non flexible. In the preferred embodiment, the plates are constructed of polysulfone, but in other embodiments, the cassettes are constructed of any other solid material and in exemplary embodiment, of any thermoplastic or thermoset.

In the exemplary embodiment, the cassettes are formed by placing the membranes in their correct locations, assembling the plates in order and connecting the plates. In one embodiment, the plates are connected using a laser welding technique. However, in other embodiments, the plates may be glued, mechanically fastened, strapped together, ultrasonically welded or any other mode of attaching the plates together.

In practice, the cassette may be used to pump any type of fluid from any source to any location. The types of fluid include nutritive, nonnutritive, inorganic chemicals, organic chemicals, bodily fluids or any other type of fluid. Additionally, fluid in some embodiments include a gas, thus, in some embodiments, the cassette is used to pump a gas.

The cassette serves to pump and direct the fluid from and to the desired locations. In some embodiments, outside pumps pump the fluid into the cassette and the cassette pumps the fluid out. However, in some embodiments, the pod pumps serve to pull the fluid into the cassette and pump the fluid out of the cassette.

As discussed above, depending on the valve locations, control of the fluid paths is imparted. Thus, the valves being in different locations or additional valves are alternate embodiments of this cassette. Additionally, the fluid lines and paths shown in the figures described above are mere examples of fluid lines and paths. Other embodiments may have more, less and/or different fluid paths. In still other embodiments, valves are not present in the cassette.

The number of pod pumps described above may also vary depending on the embodiment. For example, although the exemplary and alternate embodiments shown and described above include two pod pumps, in other embodiments, the cassette includes one. In still other embodiments, the cassette includes more than two pod pumps. The pod pumps can be single pumps or work in tandem to provide a more continuous flow. Either or both may be used in various embodiments of the cassette.

The various fluid inlets and fluid outlets are fluid ports. In practice, depending on the valve arrangement and control, a fluid inlet can be a fluid outlet. Thus, the designation of the fluid port as a fluid inlet or a fluid outlet is only for description purposes. The various embodiments have interchangeable fluid ports. The fluid ports are provided to impart particular fluid paths onto the cassette. These fluid ports are not necessarily all used all of the time; instead, the variety of fluid ports provides flexibility of use of the cassette in practice.

1.2 Exemplary Pressure Pod Pump Embodiments

Figure 1A:
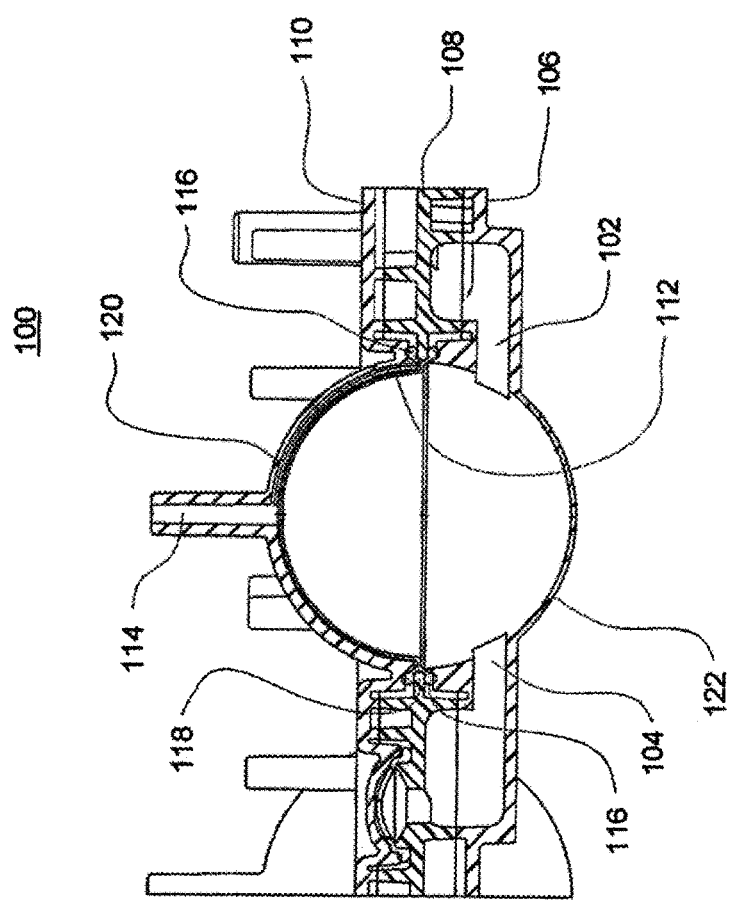
FIG. 1A is a sectional view of one embodiment of a pod-pump that is incorporated into embodiments of cassette.

FIG. 1A is a sectional view of an exemplary pod pump 100 that is incorporated into a fluid control or pump cassette (see also FIGS. 3 and 4), in accordance with an exemplary embodiment of the cassette. In this embodiment, the pod pump is formed from three rigid pieces, namely a "top" plate 106, a midplate 108, and a "bottom" plate 110 (it should be noted that the terms "top" and "bottom" are relative and are used here for convenience with reference to the orientation shown in FIG. 1A). The top and bottom plates 106 and 110 include generally hemispheroid portions that when assembled together define a hemispheroid chamber, which is a pod pump 100.

A membrane 112 separates the central cavity of the pod pump into two chambers. In one embodiment, these chambers are: the pumping chamber that receives the fluid to be pumped and an actuation chamber for receiving the control gas that pneumatically actuates the pump. An inlet 102 allows fluid to enter the pumping chamber, and an outlet 104 allows fluid to exit the pumping chamber. The inlet 102 and the outlet 104 may be formed between midplate 108 and the top plate 106. Pneumatic pressure is provided through a pneumatic port 114 to either force, with positive gas pressure, the membrane 112 against one wall of the pod pump cavity to minimize the pumping chamber's volume, or to draw, with negative gas pressure, the membrane 112 towards the other wall of the pod pump 100 cavity to maximize the pumping chamber's volume.

The membrane 112 is provided with a thickened rim 116, which is held tightly by a protrusion 118 in the midplate 108. Thus, in manufacturing, the membrane 112 can be placed in and held by the groove 108 before the bottom plate 110 is connected (in the exemplary embodiment) to the midplate 108.

Figure 1B:
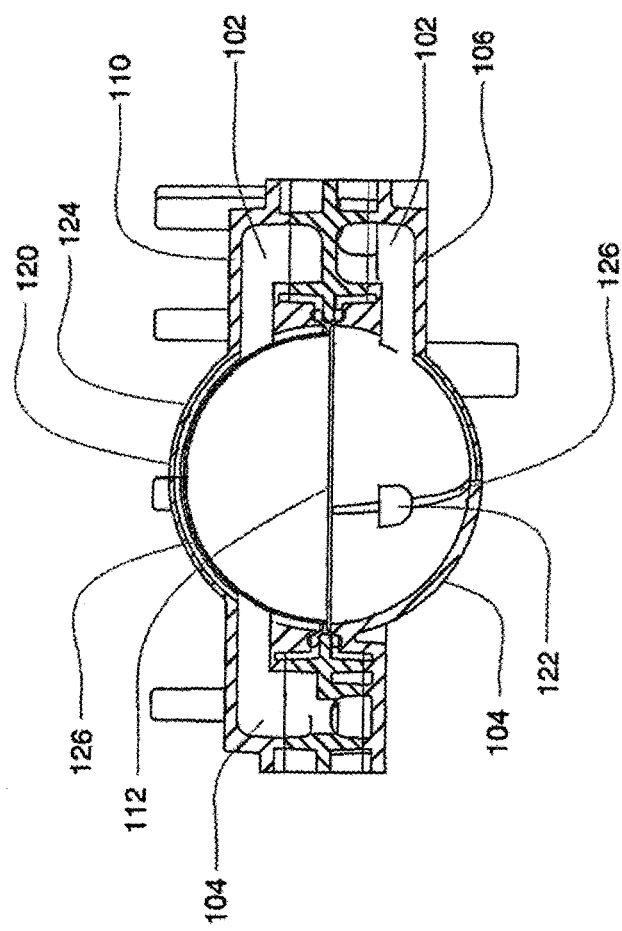
FIG. 1B is a sectional view of an exemplary embodiment of a pod pump that is incorporated into embodiments of the cassette.

Although not shown in FIGS. 1A and 1B, in some embodiments of the pod pump, on the fluid side, a groove is present on the chamber wall. The groove acts to prevent folds in the membrane from trapping fluid in the chamber when emptying.

Referring first to FIG. 1A a cross sectional view of a reciprocating positive-displacement pump 100 in a cassette is shown. The pod pump 100 includes a flexible membrane 112 (also referred to as the "pump diaphragm" or "membrane") mounted where the pumping chamber (also referred to as a "liquid chamber" or "liquid pumping chamber") wall 122 and the actuation chamber (also referred to as the "pneumatic chamber") wall 120 meet. The membrane 112 effectively divides that interior cavity into a variable-volume pumping chamber (defined by the rigid interior surface of the pumping chamber wall 122 and a surface of the membrane 112) and a complementary variable-volume actuation chamber (defined by the rigid interior surface of the actuation chamber wall 120 and a surface of the membrane 112). The top portion 106 includes a fluid inlet 102 and a fluid outlet 104, both of which are in fluid communication with the pumping/liquid chamber. The bottom portion 110 includes an actuation or pneumatic interface 114 in fluid communication with the actuation chamber. As discussed in greater detail below, the membrane 112 can be urged to move back and forth within the cavity by alternately applying negative or vent to atmosphere and positive pneumatic pressure at the pneumatic interface 114. As the membrane 112 reciprocates back and forth, the sum of the volumes of the pumping and actuation chambers remains constant.

During typical fluid pumping operations, the application of negative or vent to atmosphere pneumatic pressure to the actuation or pneumatic interface 114 tends to withdraw the membrane 112 toward the actuation chamber wall 120 so as to expand the pumping/liquid chamber and draw fluid into the pumping chamber through the inlet 102, while the application of positive pneumatic pressure tends to push the membrane 112 toward the pumping chamber wall 122 so as to collapse the pumping chamber and expel fluid in the pumping chamber through the outlet 104. During such pumping operations, the interior surfaces of the pumping chamber wall 122 and the actuation chamber wall 120 limit movement of the membrane 112 as it reciprocates back and forth. In the embodiment shown in FIG. 1A, the interior surfaces of the pumping chamber wall 122 and the actuation chamber wall 120 are rigid, smooth, and hemispherical. In lieu of a rigid actuation chamber wall 120, an alternative rigid limit structure—for example, a portion of a bezel used for providing pneumatic pressure and/or a set of ribs—may be used to limit the movement of the membrane as the pumping chamber approaches maximum value. Bezels and rib structures are described generally in U.S. patent application Ser. No. 10/697,450 entitled BEZEL ASSEMBLY FOR PNEUMATIC CONTROL filed on Oct. 30, 2003 and published as Publication No. US 2005/0095154, now U.S. Pat. No. 7,632,080 and related PCT Application No. PCT/US2004/035952 entitled BEZEL ASSEMBLY FOR PNEUMATIC CONTROL filed on Oct. 29, 2004 and published as Publication No. WO 2005/044435, both of which are hereby incorporated herein by reference in their entireties. Thus, the rigid limit structure—such as the rigid actuation chamber wall 120, a bezel, or a set of ribs defines the shape of the membrane 112 when the pumping chamber is at its maximum value. In a preferred embodiment, the membrane 112 (when urged against the rigid limit structure) and the rigid interior surface of the pumping chamber wall 122 define a spherical pumping chamber volume when the pumping chamber volume is at a minimum.

Thus, in the embodiment shown in FIG. 1A, movement of the membrane 112 is limited by the pumping chamber wall 122 and the actuation chamber wall 120. As long as the positive and vent to atmosphere or negative pressurizations provided through the pneumatic port 114 are strong enough, the membrane 112 will move from a position limited by the actuation chamber wall 120 to a position limited by the pumping chamber wall 122. When the membrane 112 is forced against the actuation chamber wall 120, the membrane and the pumping chamber wall 122 define the maximum volume of the pumping chamber. When the membrane is forced against the pumping chamber wall 122, the pumping chamber is at its minimum volume.

In an exemplary embodiment, the pumping chamber wall 122 and the actuation chamber wall 120 both have a hemispheroid shape so that the pumping chamber will have a spheroid shape when it is at its maximum volume. By using a pumping chamber that attains a spheroid shape—and particularly a spherical shape—at maximum volume, circulating flow may be attained throughout the pumping chamber. Such shapes accordingly tend to avoid stagnant pockets of fluid in the pumping chamber. As discussed further below, the orientations of the inlet 102 and outlet 104 also tend to have an impact on the flow of fluid through the pumping chamber and in some embodiments, reduce the likelihood of stagnant pockets of fluid forming. Additionally, compared to other volumetric shapes, the spherical shape (and spheroid shapes in general) tends to create less shear and turbulence as the fluid circulates into, through, and out of the pumping chamber.

Figure 3:
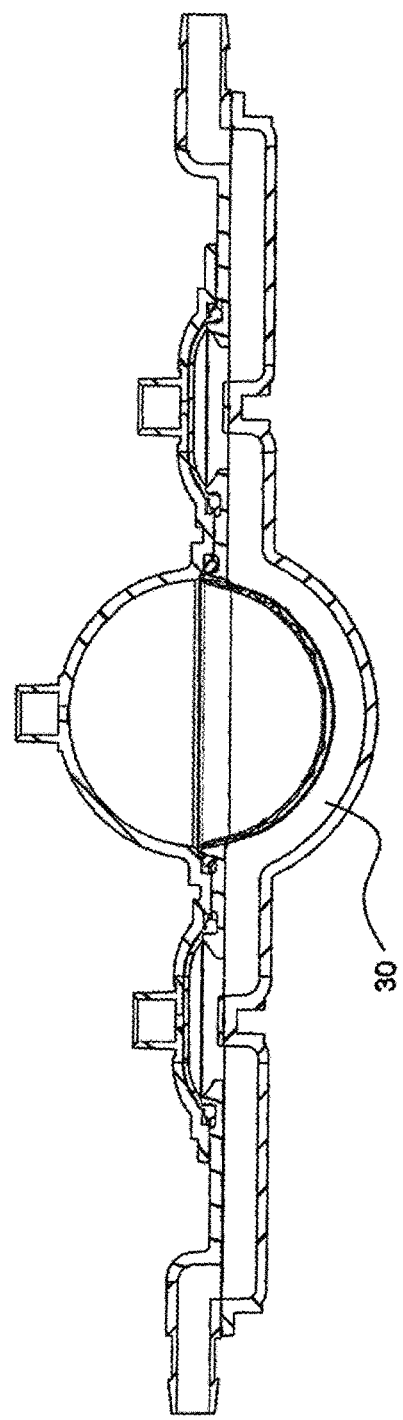
FIG. 3 is a sectional view of a pod pump within a cassette.
Figure 4:
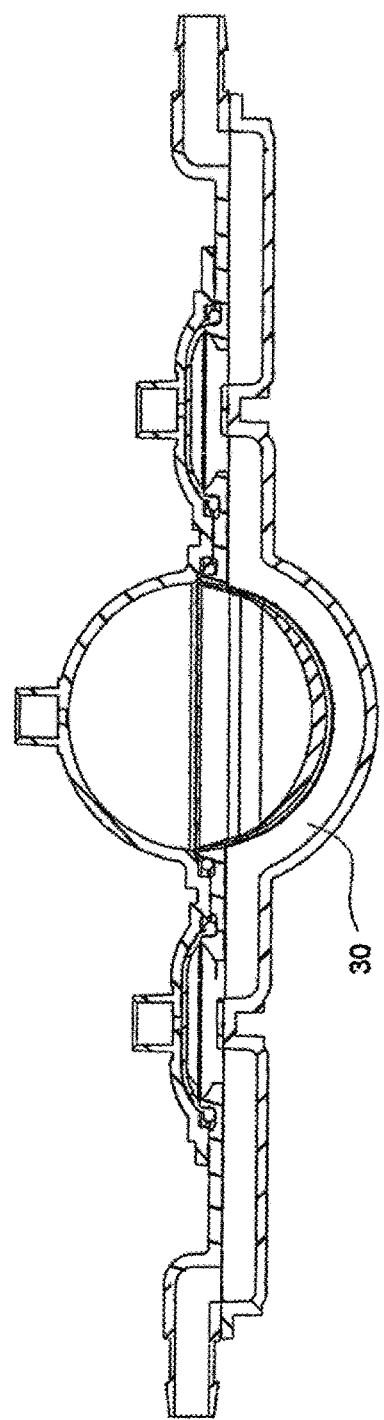
FIG. 4 is a sectional view of a pod pump within a cassette having a variable membrane.

Referring now to FIGS. 3-4, a raised flow path 30 is shown in the pumping chamber. This raised flow path 30 allows for the fluid to continue flowing through the pod pumps after the membrane reaches the end of stroke. Thus, the raised flow path 30 minimizes the chances of the membrane causing air or fluid to be trapped in the pod pump or the membrane blocking the inlet or outlet of the pod pump which would inhibit continuous flow. The raised flow path 30 is shown in the exemplary embodiment having particular dimensions, however, in alternate embodiments, as seen in FIGS. 18A-18E, the raised flow path 30 is narrower, or in still other embodiments, the raised flow path 30 can be any dimensions as the purpose is to control fluid flow so as to achieve a desired flow rate or behavior of the fluid. Thus, the dimensions shown and described here with respect to the raised flow path, the pod pumps, the valves or any other aspect are mere exemplary and alternate embodiments. Other embodiments are readily apparent.

1.3 Exemplary Balancing Pods Embodiment

Referring now to FIG. 1B, an exemplary embodiment of a balancing pod is shown. The balancing pod is constructed similar to the pod pump described above with respect to FIG. 1A. However, a balancing pod includes two fluid balancing chambers, rather than an actuation chamber and a pumping chamber, and does not include an actuation port.

Additionally, each balancing chamber includes an inlet 102 and an outlet 104. In the exemplary embodiment, a groove 126 is included on each of the balancing chamber walls 120, 122. The groove 126 is described in further detail below.

The membrane 112 provides a seal between the two chambers. The balancing chambers work to balance the flow of fluid into and out of the chambers such that both chambers maintain an equal volume rate flow. Although the inlets 102 and outlets 104 for each chamber are shown to be on the same side, in other embodiments, the inlets 102 and outlets 104 for each chamber are on different sides. Also, the inlets 102 and outlets 104 can be on either side, depending on the flow path in which the balancing pod is integrated.

In one embodiment of the balancing pod the membrane 112 includes an embodiment similar to the one described below with respect to FIG. 6A-6G. However, in alternate embodiments, the membrane 112 can be over molded or otherwise constructed such that a double-ring seal is not applicable.

1.4 Metering Pumps and Fluid Management System

The metering pump can be any pump that is capable of adding any fluid or removing any fluid. The fluids include but are not limited to pharmaceuticals, inorganic compounds or elements, organic compounds or elements, nutraceuticals, nutritional elements or compounds or solutions, or any other fluid capable of being pumped. In one embodiment, the metering pump is a membrane pump. In the exemplary embodiment, the metering pump is a smaller volume pod pump. In the exemplary embodiment, the metering pump includes an inlet and an outlet, similar to a larger pod pump (as shown in FIG. 1A for example). However, the inlet and outlet are generally much smaller than a pod pump and, in one exemplary embodiment, includes a volcano valve-like raised ring around either the inlet or outlet. Metering pumps include a membrane, and various embodiments of a metering pump membrane are shown in FIGS. 5E-5H. The metering pump, in some embodiments, pumps a volume of fluid out of the fluid line. Once the fluid is in the pod pump, a reference chamber, located outside the cassette, using the FMS, determines the volume that has been removed.

Thus, depending on the embodiment, this volume of fluid that has been removed will not then flow to the fluid outlet, the balance chambers or to a pod pump. Thus, in some embodiments, the metering pump is used to remove a volume of fluid from a fluid line. In other embodiments, the metering pump is used to remove a volume of fluid to produce other results.

FMS may be used to perform certain fluid management system measurements, such as, for example, measuring the volume of subject fluid pumped through the pump chamber during a stroke of the membrane or detecting air in the pumping chamber, e.g., using techniques described in U.S. Pat. Nos. 4,808,161; 4,826,482; 4,976,162; 5,088,515; and 5,350,357, which are hereby incorporated herein by reference in their entireties.

Metering pumps are also used in various embodiments to pump a second fluid into the fluid line. In some embodiments, the metering pump is used to pump a therapeutic or a compound into a fluid line. One embodiment uses the metering pump to pump a volume of compound into a mixing chamber in order to constitute a solution. In some of these embodiments, the metering pumps are configured for FMS volume measurement. In other embodiments, the metering pumps are not.

For FMS measurement, a small fixed reference air chamber is located outside of the cassette, for example, in the pneumatic manifold (not shown). A valve isolates the reference chamber and a second pressure sensor. The stroke volume of the metering pump may be precisely computed by charging the reference chamber with air, measuring the pressure, and then opening the valve to the pumping chamber. The volume of air on the chamber side may be computed based on the fixed volume of the reference chamber and the change in pressure when the reference chamber was connected to the pump chamber.

1.5 Valves

Figure 2A:
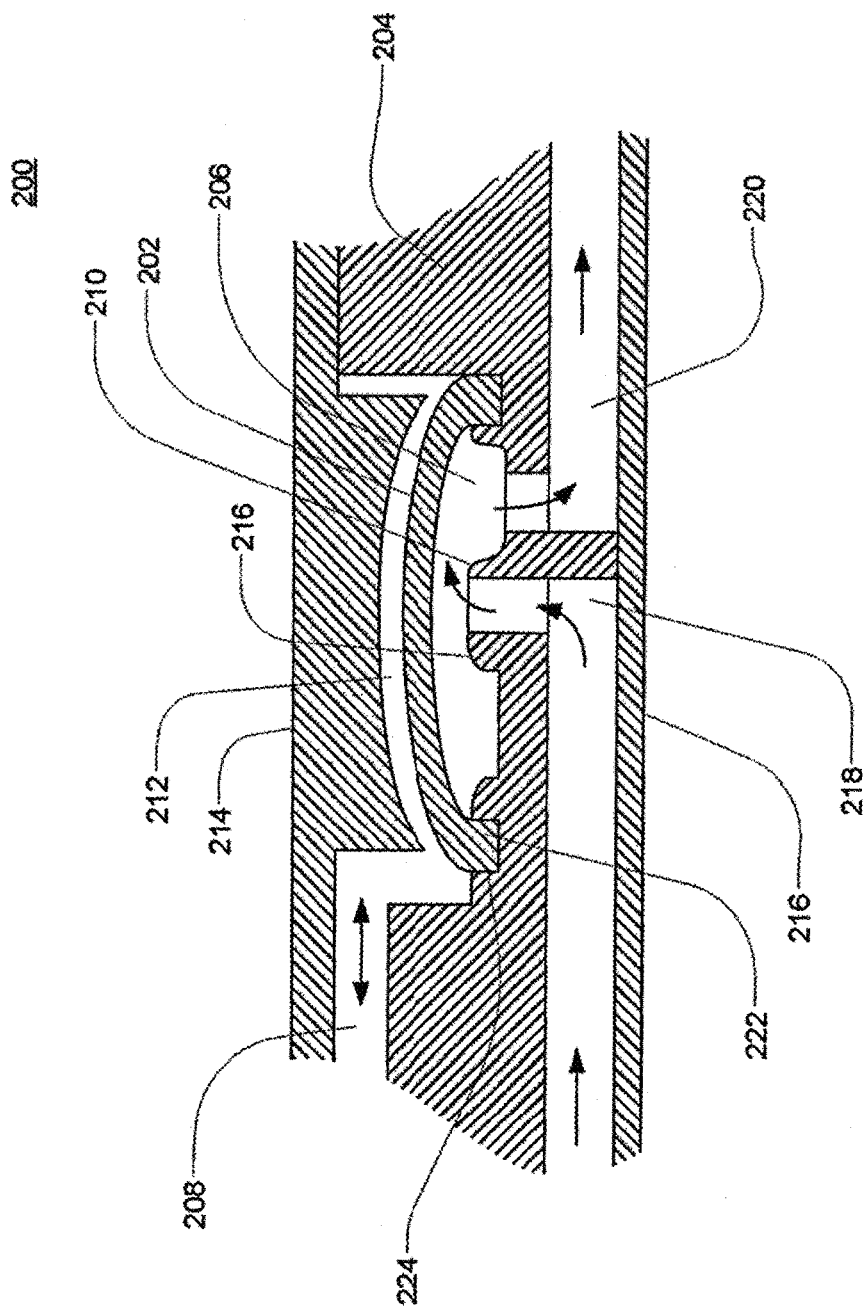
FIG. 2A is an illustrative sectional view of one embodiment of one type of pneumatically controlled valve that is incorporated into some embodiments of the cassette.
Figure 2B:
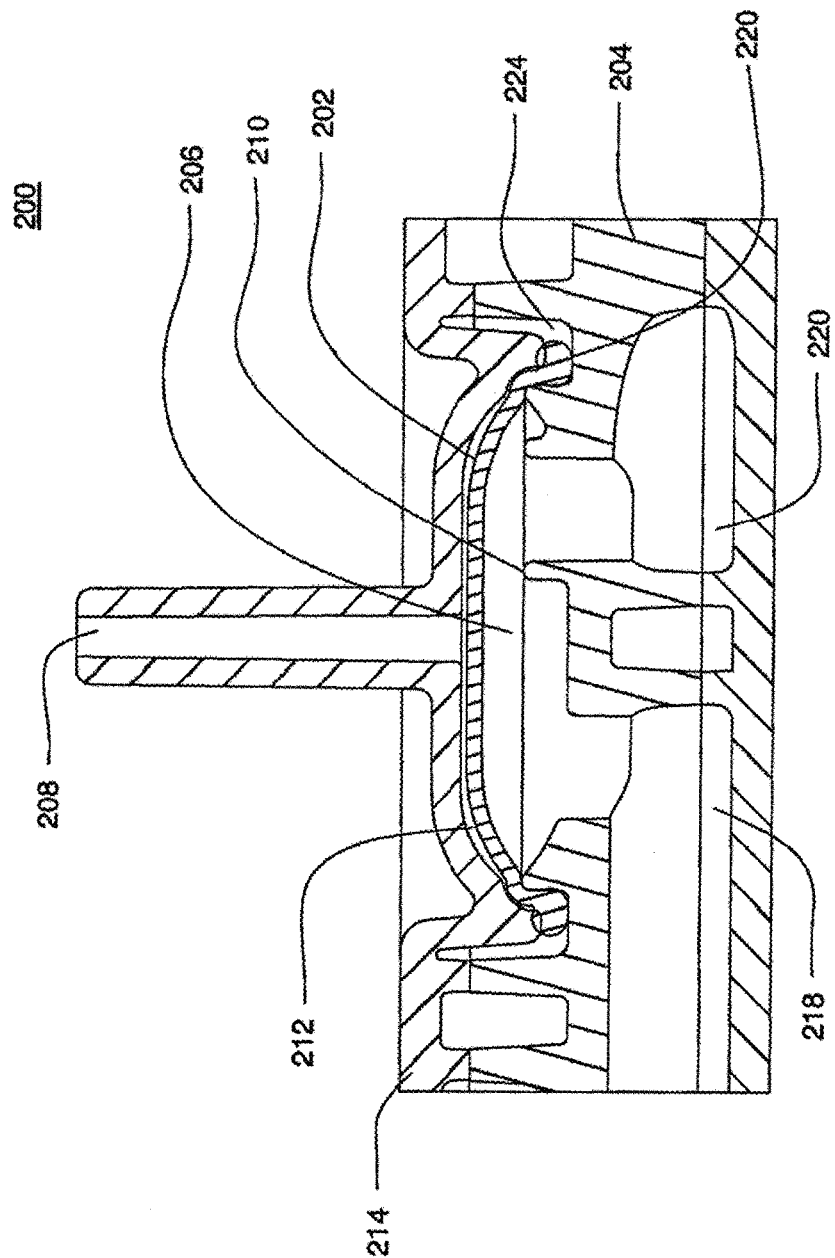
FIG. 2B is a sectional view of another embodiment of one type of pneumatically controlled valve that is incorporated into some embodiments of the cassette.
Figure 2C:
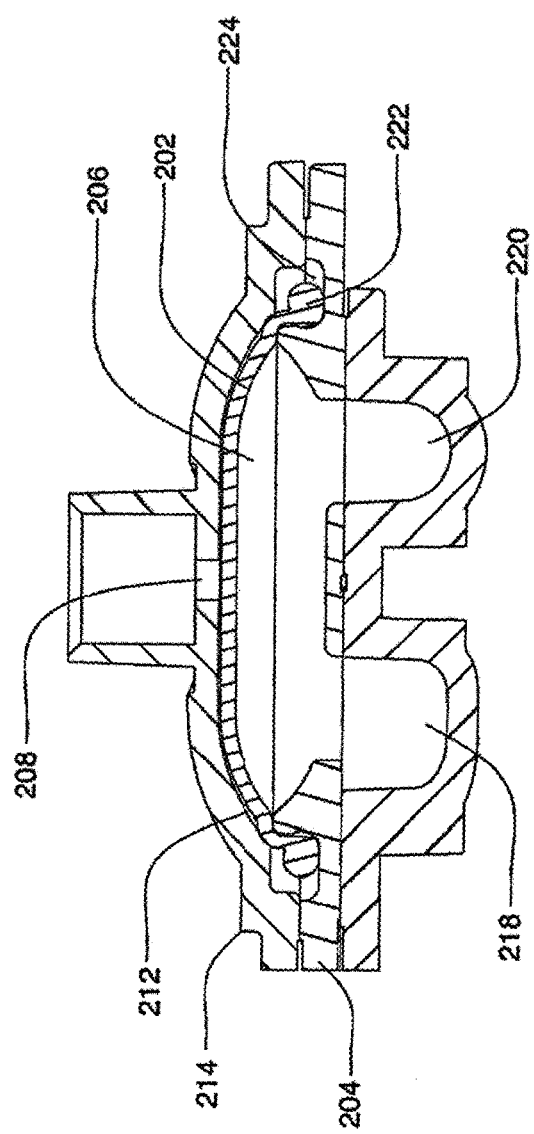
FIG. 2C is a sectional view of another embodiment of one type of pneumatically controlled valve that is incorporated into some embodiments of the cassette.

The exemplary embodiment of the cassette includes one or more valves. Valves are used to regulate flow by opening and closing fluid lines. The valves included in the various embodiments of the cassette include one or more of the following: volcano valves or smooth valves. In some embodiment of the cassette, check valves may be included. Embodiments of the volcano valve are shown in FIGS. 2A and 2B, while an embodiment of the smooth valve is shown in FIG. 2C. Additionally, FIGS. 3 and 4 show cross sections of one embodiment of a pod pump in a cassette with an inlet and an outlet valve.

Generally speaking, reciprocating positive-displacement pumps of the types just described may include, or may be used in conjunction with, various valves to control fluid flow through the pump. Thus, for example, the reciprocating positive-displacement pump or the balancing pods may include, or be used in conjunction with, an inlet valve and/or an outlet valve. The valves may be passive or active. In the exemplary embodiment of the reciprocating positive-displacement pump the membrane is urged back and forth by positive and negative pressurizations, or by positive and vent to atmosphere pressurizations, of a gas provided through the pneumatic port, which connects the actuation chamber to a pressure actuation system. The resulting reciprocating action of the membrane pulls fluid into the pumping chamber from the inlet (the outlet valve prevents liquid from being sucked back into the pumping chamber from the outlet) and then pushes the fluid out of the pumping chamber through the outlet (the inlet valve prevents fluid from being forced back from the inlet).

In the exemplary embodiments, active valves control the fluid flow through the pump(s) and the cassette. The active valves may be actuated by a controller in such a manner as to direct flow in a desired direction. Such an arrangement would generally permit the controller to cause flow in either direction through the pod pump. In a typical system, the flow would normally be in a first direction, e.g., from the inlet to the outlet. At certain other times, the flow may be directed in the opposite direction, e.g., from the outlet to the inlet. Such reversal of flow may be employed, for example, during priming of the pump, to check for an aberrant line condition (e.g., a line occlusion, blockage, disconnect, or leak), or to clear an aberrant line condition (e.g., to try to dislodge a blockage).

Pneumatic actuation of valves provides pressure control and a natural limit to the maximum pressure that may be developed in a system. In the context of a system, pneumatic actuation has the added benefit of providing the opportunity to locate all the solenoid control valves on one side of the system away from the fluid paths.

Referring now to FIGS. 2A and 2B, sectional views of two embodiments of a volcano valve are shown. The volcano valves are pneumatically controlled valves that may be used in embodiments of the cassette. A membrane 202, along with the midplate 204, defines a valving chamber 206. Pneumatic pressure is provided through a pneumatic port 208 to either force, with positive gas pressure, the membrane 202 against a valve seat 210 to close the valve, or to draw, with negative gas pressure, or in some embodiments, with vent to atmospheric pressure, the membrane away from the valve seat 210 to open the valve. A control gas chamber 212 is defined by the membrane 202, the top plate 214, and the midplate 204. The midplate 204 has an indentation formed on it, into which the membrane 202 is placed so as to form the control gas chamber 212 on one side of the membrane 202 and the valving chamber 206 on the other side.

The pneumatic port 208 is defined by a channel formed in the top plate 214. By providing pneumatic control of several valves in a cassette, valves can be ganged together so that all the valves ganged together can be opened or closed at the same time by a single source of pneumatic pressure. Channels formed on the midplate 204, corresponding with fluid paths along with the bottom plate 216, define the valve inlet 218 and the valve outlet 220. Holes formed through the midplate 204 provide communication between the inlet 218 and the valving chamber 206 and between the valving chamber 206 and the outlet 220.

The membrane 202 is provided with a thickened rim 222, which fits tightly in a groove 224 in the midplate 204. Thus, the membrane 202 can be placed in and held by the groove 224 before the top plate 214 is connected to the midplate 204. Thus, this valve design may impart benefits in manufacturing. As shown in FIGS. 2B and 2C, the top plate 214 may include additional material extending into control gas chamber 212 so as to prevent the membrane 202 from being urged too much in a direction away from the groove 224, so as to prevent the membrane's thickened rim 222 from popping out of the groove 224. The location of the pneumatic port 208 with respect to the control gas chamber 212 varies in the two embodiments shown in FIGS. 2A and 2B.

Figure 2D:
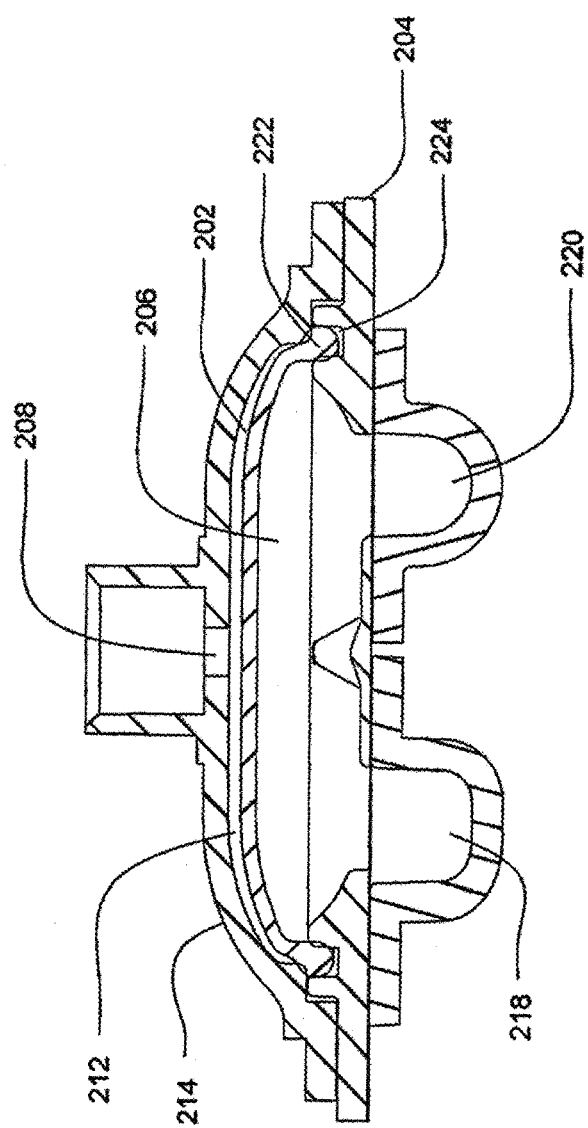
FIG. 2D is a sectional view of another embodiment of one type of pneumatically controlled valve that is incorporated into some embodiments of the cassette.
Figure 2E:
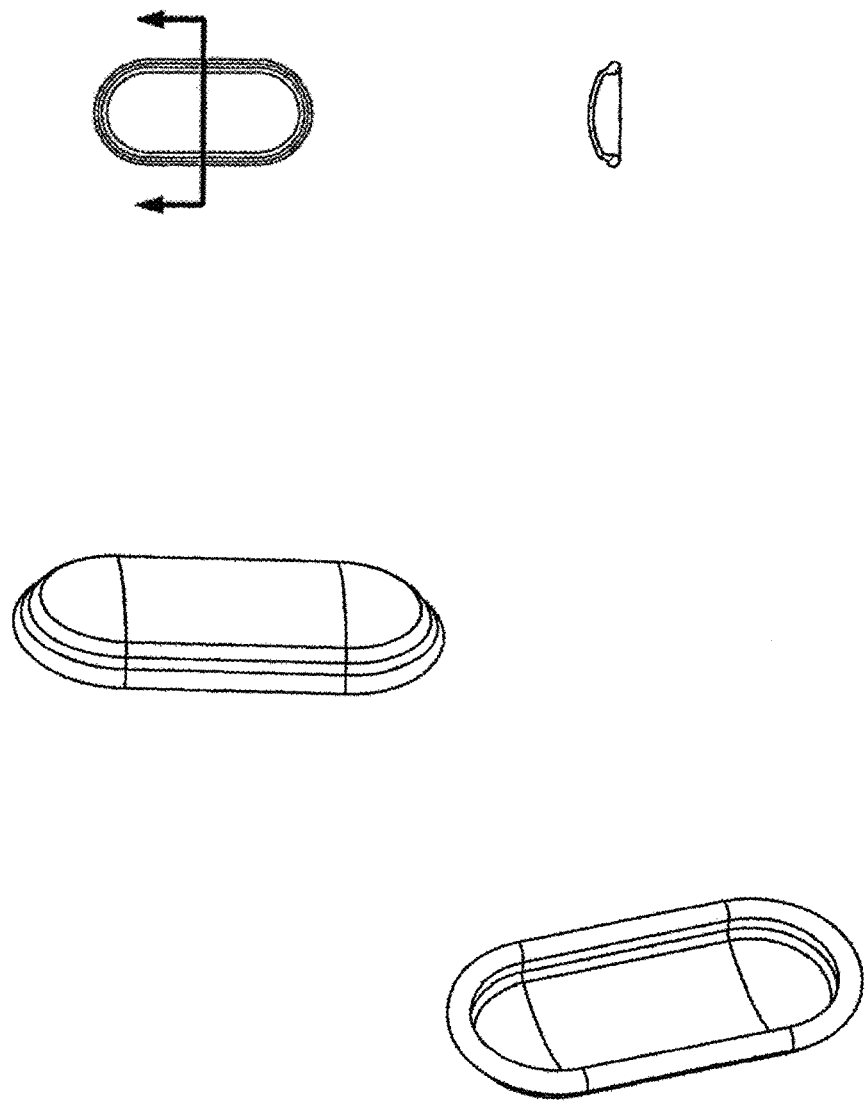
FIGS. 2E-2F are top and bottom views of embodiments of the valving membrane.
Figure 2F:
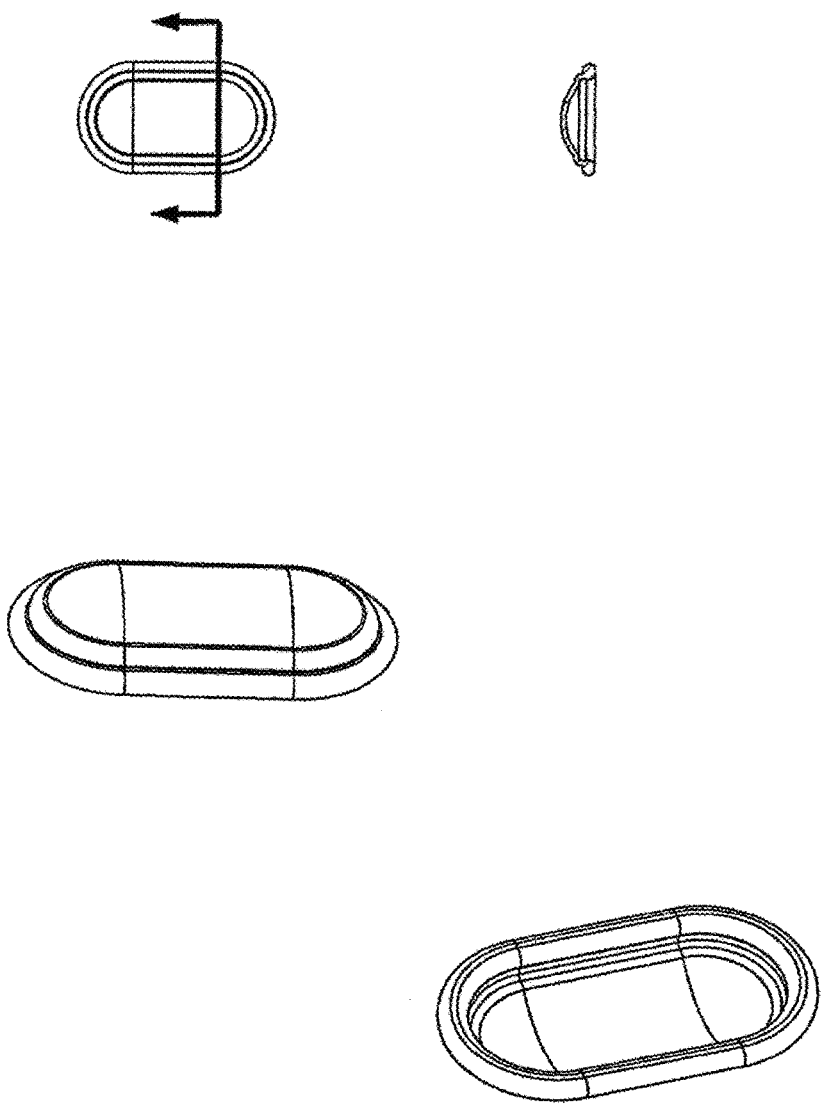

FIG. 2C shows an embodiment in which the valving chamber lacks a valve seat feature. Rather, in FIG. 2C, the valve in this embodiment does not include any volcano features and thus, the valving chamber 206, i.e., the fluid side, does not include any raised features and thus is smooth. This embodiment is used in cassettes used to pump fluid sensitive to shearing. FIG. 2D shows an embodiment in which the valving chamber has a raised area to aid in the sealing of the valving membrane. Referring now to FIGS. 2E-2G, various embodiments of the valve membrane are shown. Although some exemplary embodiments have been shown and described, in other embodiments, variations of the valve and valving membrane may be used.

1.6 Exemplary Embodiments of the Pod Membrane

In some embodiments, the membrane has a variable cross-sectional thickness, as shown in FIG. 4. Thinner, thicker or variable thickness membranes may be used to accommodate the strength, flexural and other properties of the chosen membranes materials. Thinner, thicker or variable membrane wall thickness may also be used to manage the membrane thereby encouraging it to flex more easily in some areas than in other areas, thereby aiding in the management of pumping action and flow of subject fluid in the pump chamber. In this embodiment the membrane is shown having its thickest cross-sectional area closest to its center. However in other embodiments having a membrane with a varying cross-sectional, the thickest and thinnest areas may be in any location on the membrane. Thus, for example, the thinner cross-section may be located near the center and the thicker cross-sections located closer to the perimeter of the membrane. Still other configurations are possible. Referring to FIGS. 5A-5D, one embodiment of a membrane is shown having various surface embodiments, these include smooth (FIG. 5A), rings (FIG. 5D), ribs (FIG. 5C), dimples or dots (FIG. 5B) of variable thickness and or geometry located at various locations on the actuation and or pumping side of the membrane. In one embodiment of the membrane, the membrane has a tangential slope in at least one section, but in other embodiments, the membrane is completely smooth or substantially smooth.

Figure 4A:
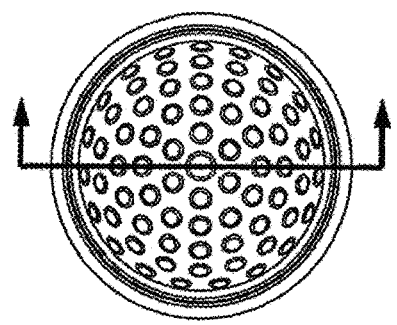
FIGS. 4A and 4B are top and section views respectively of a pod pump within a cassette having a dimpled/variable membrane.
Figure 4B:
Figure 4C:
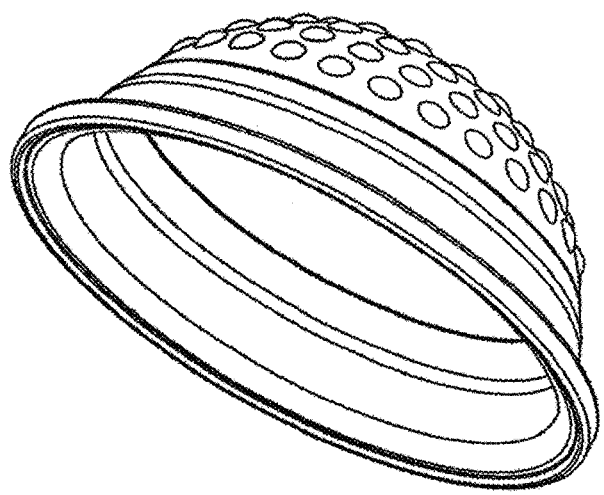
FIGS. 4C and 4D are pictorial views of a single ring membrane with a variable surface.
Figure 4D:
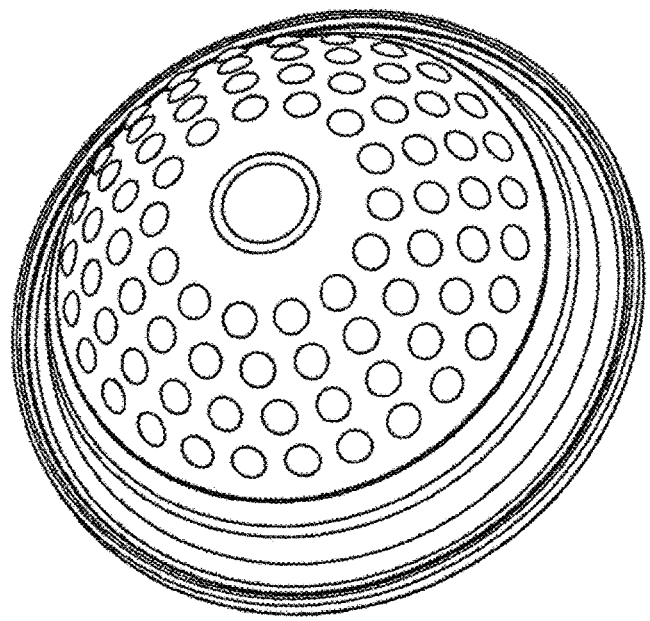

Referring now to FIGS. 4A, 4C and 4D, an alternate embodiment of the membrane is shown. In this embodiment, the membrane has a dimpled or dotted surface.

The membrane may be made of any flexible material having a desired durability and compatibility with the subject fluid. The membrane can be made from any material that may flex in response to fluid, liquid or gas pressure or vacuum applied to the actuation chamber. The membrane material may also be chosen for particular bio-compatibility, temperature compatibility or compatibility with various subject fluids that may be pumped by the membrane or introduced to the chambers to facilitate movement of the membrane. In the exemplary embodiment, the membrane is made from high elongation silicone. However, in other embodiments, the membrane is made from any elastomer or rubber, including, but not limited to, silicone, urethane, nitrile, EPDM or any other rubber, elastomer or flexible material.

The shape of the membrane is dependent on multiple variables. These variables include, but are not limited to: the shape of the chamber; the size of the chamber; the subject fluid characteristics; the volume of subject fluid pumped per stroke; and the means or mode of attachment of the membrane to the housing. The size of the membrane is dependent on multiple variables. These variables include, but are not limited to: the shape of the chamber; the size of the chamber; the subject fluid characteristics; the volume of subject fluid pumped per stroke; and the means or mode of attachment of the membrane to the housing. Thus, depending on these or other variables, the shape and size of the membrane may vary in various embodiments.

The membrane can have any thickness. However, in some embodiments, the range of thickness is between 0.002 inches to 0.125 inches. Depending on the material used for the membrane, the desired thickness may vary. In one embodiment, high elongation silicone is used in a thickness ranging from 0.015 inches to 0.050 inches. However in other embodiments, the thickness may vary.

In the exemplary embodiment, the membrane is preformed to include a substantially dome-shape in at least part of the area of the membrane. One embodiment of the dome-shaped membrane is shown in FIGS. 4E and 4F. Again, the dimensions of the dome may vary based on some or more of the variables described above. However, in other embodiments, the membrane may not include a pre-formed dome shape.

In the exemplary embodiment, the membrane dome is formed using liquid injection molding. However, in other embodiments, the dome may be formed by using compression molding. In alternate embodiments, the membrane is substantially flat. In other embodiments, the dome size, width or height may vary.

In various embodiments, the membrane may be held in place by various means and methods. In one embodiment, the membrane is clamped between the portions of the cassette, and in some of these embodiments, the rim of the cassette may include features to grab the membrane. In others of this embodiment, the membrane is clamped to the cassette using at least one bolt or another device. In another embodiment, the membrane is over-molded with a piece of plastic and then the plastic is welded or otherwise attached to the cassette. In another embodiment, the membrane is pinched between the mid plate described with respect to FIGS. 1A and 1B and the bottom plate. Although some embodiments for attachment of the membrane to the cassette are described, any method or means for attaching the membrane to the cassette can be used. The membrane, in one alternate embodiment, is attached directly to one portion of the cassette. In some embodiments, the membrane is thicker at the edge, where the membrane is pinched by the plates, than in other areas of the membrane. In some embodiments, this thicker area is a gasket, in some embodiments an O-ring, ring or any other shaped gasket. Referring again to 6A-6D, one embodiment of the membrane is shown with two gaskets 62, 64. In some of these embodiments, the gasket(s) 62, 64 provides the attachment point of the membrane to the cassette. In other embodiments, the membrane includes more than two gaskets. Membranes with one gasket are also included in some embodiments (see FIGS. 4A-4D).

In some embodiments of the gasket, the gasket is contiguous with the membrane. However, in other embodiments, the gasket is a separate part of the membrane. In some embodiments, the gasket is made from the same material as the membrane. However, in other embodiments, the gasket is made of a material different from the membrane. In some embodiments, the gasket is formed by over-molding a ring around the membrane. The gasket can be any shape ring or seal desired so as to complement the pod pump housing embodiment. In some embodiments, the gasket is a compression type gasket.

1.7 Mixing Pods

Some embodiments of the cassette include a mixing pod. A mixing pod includes a chamber for mixing. In some embodiments, the mixing pod is a flexible structure, and in some embodiments, at least a section of the mixing pod is a flexible structure. The mixing pod can include a seal, such as an o-ring, or a membrane. The mixing pod can be any shape desired. In the exemplary embodiment, the mixing pod is similar to a pod pump except it does not include a membrane and does not include an actuation port. Some embodiments of this embodiment of the mixing pod include an o-ring seal to seal the mixing pod chamber. Thus, in the exemplary embodiment, the mixing pod is a spherical hollow pod with a fluid inlet and a fluid outlet. As with the pod pumps, the chamber size can be any size desired.

2. Pressure Pump Actuation System

Figure 7:
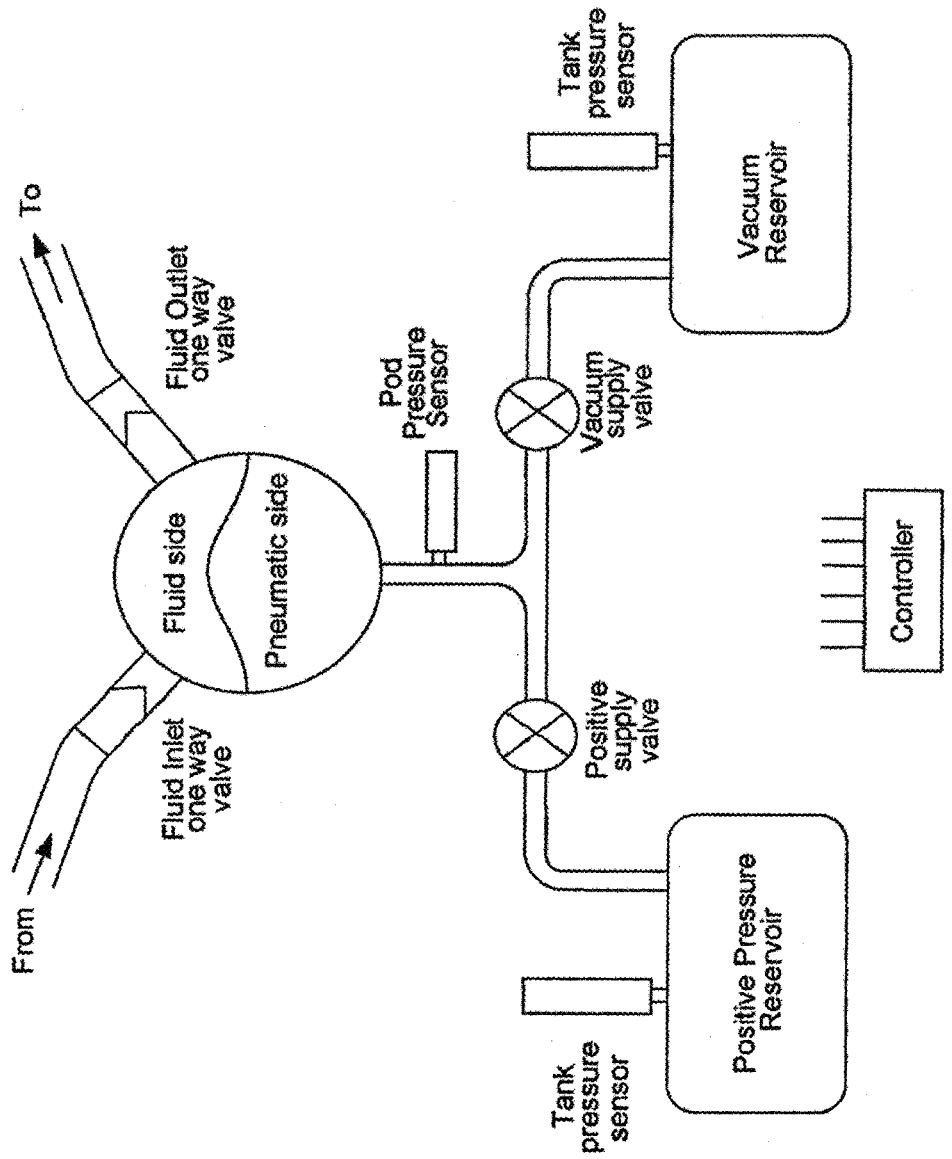
FIG. 7 is a schematic showing a pressure actuation system that may be used to actuate a pod pump.

FIG. 7 is a schematic showing an embodiment of a pressure actuation system that may be used to actuate a pod pump with both positive and negative pressure, such as the pod pump shown in FIG. 1A. The pressure actuation system is capable of intermittently or alternately providing positive and negative pressurizations to the gas in the actuation chamber of the pod pump. However, in some embodiments, FIG. 7 does not apply in these embodiments, actuation of the pod pump is accomplished by applying positive pressure and vent to atmosphere (again, not shown in FIG. 7). The pod pump—including the flexible membrane, the inlet, the outlet, the pneumatic port, the pumping chamber, the actuation chamber, and possibly including an inlet check valve and an outlet check valve or other valves—is part of a larger disposable system. The pneumatic actuation system—including an actuation-chamber pressure transducer, a positive-supply valve, a negative-supply valve, a positive-pressure gas reservoir, a negative-pressure gas reservoir, a positive-pressure-reservoir pressure transducer, a negative-pressure-reservoir pressure transducer, as well as an electronic controller including, in some embodiments—a user interface console (such as a touch-panel screen)—may be part of a base unit.

The positive-pressure reservoir provides to the actuation chamber the positive pressurization of a control gas to urge the membrane towards a position where the pumping chamber is at its minimum volume (i.e., the position where the membrane is against the rigid pumping-chamber wall). The negative-pressure reservoir provides to the actuation chamber the negative pressurization of the control gas to urge the membrane in the opposite direction, towards a position where the pumping chamber is at its maximum volume (i.e., the position where the membrane is against the rigid actuation-chamber wall).

A valving mechanism is used to control fluid communication between each of these reservoirs and the actuation chamber. As shown in FIG. 7, a separate valve is used for each of the reservoirs; a positive-supply valve controls fluid communication between the positive-pressure reservoir and the actuation chamber, and a negative-supply valve controls fluid communication between the negative-pressure reservoir and the actuation chamber. These two valves are controlled by the controller. Alternatively, a single three-way valve may be used in lieu of the two separate valves. The valves may be binary on-off valves or variable-restriction valves.

The controller also receives pressure information from the three pressure transducers: an actuation-chamber pressure transducer, a positive-pressure-reservoir pressure transducer, and a negative-pressure-reservoir pressure transducer. As their names suggest, these transducers respectively measure the pressure in the actuation chamber, the positive-pressure reservoir, and the negative-pressure reservoir. The actuation-chamber-pressure transducer is located in a base unit but is in fluid communication with the actuation chamber through the pod pump pneumatic port. The controller monitors the pressure in the two reservoirs to ensure they are properly pressurized (either positively or negatively). In one exemplary embodiment, the positive-pressure reservoir may be maintained at around 750 mmHG, while the negative-pressure reservoir may be maintained at around −450 mmHG.

Still referring to FIG. 7, a compressor-type pump or pumps (not shown) may be used to maintain the desired pressures in these reservoirs. For example, two independent compressors may be used to respectively service the reservoirs. Pressure in the reservoirs may be managed using a simple bang-bang control technique in which the compressor servicing the positive-pressure reservoir is turned on if the pressure in the reservoir falls below a predetermined threshold and the compressor servicing the negative-pressure reservoir is turned on if the pressure in the reservoir is above a predetermined threshold. The amount of hysteresis may be the same for both reservoirs or may be different. Tighter control of the pressure in the reservoirs can be achieved by reducing the size of the hysteresis band, although this will generally result in higher cycling frequencies of the compressors. If very tight control of the reservoir pressures is required or otherwise desirable for a particular application, the bang-bang technique could be replaced with a PID control technique and could use PWM signals on the compressors.

The pressure provided by the positive-pressure reservoir is preferably strong enough—under normal conditions—to urge the membrane all the way against the rigid pumping-chamber wall. Similarly, the negative pressure (i.e., the vacuum) provided by the negative-pressure reservoir is preferably strong enough—under normal conditions—to urge the membrane all the way against the actuation-chamber wall. In a further preferred embodiment, however, these positive and negative pressures provided by the reservoirs are within safe enough limits that even with either the positive-supply valve or the negative-supply valve open all the way, the positive or negative pressure applied against the membrane is not so strong as to damage the pod pump or create unsafe fluid pressures (e.g., that may harm a patient receiving pumped blood or other fluid).

It will be appreciated that other types of actuation systems may be used to move the membrane back and forth instead of the two-reservoir pneumatic actuation system shown in FIG. 7, although a two-reservoir pneumatic actuation system is generally preferred. For example, alternative pneumatic actuation systems may include either a single positive-pressure reservoir or a single negative-pressure reservoir along with a single supply valve and a single tank pressure sensor, particularly in combination with a resilient membrane. Such pneumatic actuation systems may intermittently provide either a positive gas pressure or a negative gas pressure to the actuation chamber of the pod pump. In embodiments having a single positive-pressure reservoir, the pump may be operated by intermittently providing positive gas pressure to the actuation chamber, causing the membrane to move toward the pumping chamber wall and expel the contents of the pumping chamber, and releasing the gas pressure, causing the membrane to return to its relaxed position and draw fluid into the pumping chamber. In embodiments having a single negative-pressure reservoir, the pump may be operated by intermittently providing negative gas pressure to the actuation chamber, causing the membrane to move toward the actuation chamber wall and draw fluid into the pumping chamber, and releasing the gas pressure, causing the membrane to return to its relaxed position and expel fluid from the pumping chamber.

3. Fluid Handling

As shown and described with respect to FIGS. 2A-2D, a fluid valve in the exemplary embodiment consists of a small chamber with a flexible membrane or membrane across the center dividing the chamber into a fluid half and a pneumatic half. The fluid valve, in the exemplary embodiment, has 3 entry/exit ports, two on the fluid half of the chamber and one the pneumatic half of the chamber. The port on the pneumatic half of the chamber can supply either positive pressure or vacuum (or rather than vacuum, in some embodiments, there is a vent to atmosphere) to the chamber. When a vacuum is applied to the pneumatic portion of the chamber, the membrane is pulled towards the pneumatic side of the chamber, clearing the fluid path and allowing fluid to flow into and out of the fluid side of the chamber. When positive pressure is applied to the pneumatic portion of the chamber, the membrane is pushed towards the fluid side of the chamber, blocking the fluid path and preventing fluid flow. In the volcano valve embodiment (as shown in FIGS. 2A-2B) on one of the fluid ports, that port seals off first when closing the valve and the remainder of any fluid in the valve is expelled through the port without the volcano feature. Additionally, in one embodiment of the valves, shown in FIG. 2D, the raised feature between the two ports allows for the membrane to seal the two ports from each other earlier in the actuation stroke (i.e., before the membrane seals the ports directly).

Referring again to FIG. 7, pressure valves are used to operate the pumps located at different points in the flow path. This architecture supports pressure control by using two variable-orifice valves and a pressure sensor at each pump chamber which requires pressure control. In one embodiment, one valve is connected to a high-pressure source and the other valve is connected to a low-pressure sink. A high-speed control loop monitors the pressure sensor and controls the valve positions to maintain the necessary pressure in the pump chamber.

Pressure sensors are used to monitor pressure in the pneumatic portion of the chambers themselves. By alternating between positive pressure and vacuum on the pneumatic side of the chamber, the membrane is cycled back and forth across the total chamber volume. With each cycle, fluid is drawn through the upstream valve of the inlet fluid port when the pneumatics pull a vacuum on the pods. The fluid is then subsequently expelled through the outlet port and the downstream valve when the pneumatics deliver positive pressure to the pods.

In many embodiments pressure pumps consist of a pair of chambers. When the two chambers are run 180 degrees out of phase from one another the flow is essentially continuous.

4. Volume Measurement

These flow rates in the cassette are controlled using pressure pod pumps which can detect end-of-stroke. An outer control loop determines the correct pressure values to deliver the required flow. Pressure pumps can run an end of stroke algorithm to detect when each stroke completes. While the membrane is moving, the measured pressure in the chamber tracks a desired sinusoidal pressure. When the membrane contacts a chamber wall, the pressure becomes constant, no longer tracking the sinusoid. This change in the pressure signal is used to detect when the stroke has ended, i.e., the end-of-stroke.

The pressure pumps have a known volume. Thus, an end of stroke indicates a known volume of fluid is in the chamber. Thus, using the end-of-stroke, fluid flow may be controlled using rate equating to volume.

As described above in more detail, FMS may be used to determine the volume of fluid pumped by the metering pumps. In some embodiments, the metering pump may pump fluid without using the FMS volume measurement system, however, in the exemplary embodiments, the FMS volume measurement system is used to calculate the exact volume of fluid pumped.

5. Exemplary Embodiment of the Mixing Cassette

The terms inlet and outlet as well as first fluid, second fluid, third fluid, and the number designations given to valving paths (i.e. "first valving path") are used for description purposes only. In other embodiments, an inlet can be an outlet, as well, an indication of a first, second, third fluid does not denote that they are different fluids or are in a particular hierarchy. The denotations simply refer to separate entrance areas into the cassette and the first, second, third, etc, fluids may be different fluids or the same fluid types or composition or two or more may be the same. Likewise, the designation of the first, second, third, etc. valving paths do not have any particular meaning, but are used for clearness of description.

The designations given for the fluid inlets (which can also be fluid outlets), for example, first fluid outlet, second fluid outlet, merely indicate that a fluid may travel out of or into the cassette via that inlet/outlet. In some cases, more than one inlet/outlet on the schematic is designated with an identical name. This merely describes that all of the inlet/outlets having that designation are pumped by the same metering pump or set of pod pumps (which in alternate embodiments, can be a single pod pump).

Figure 8:
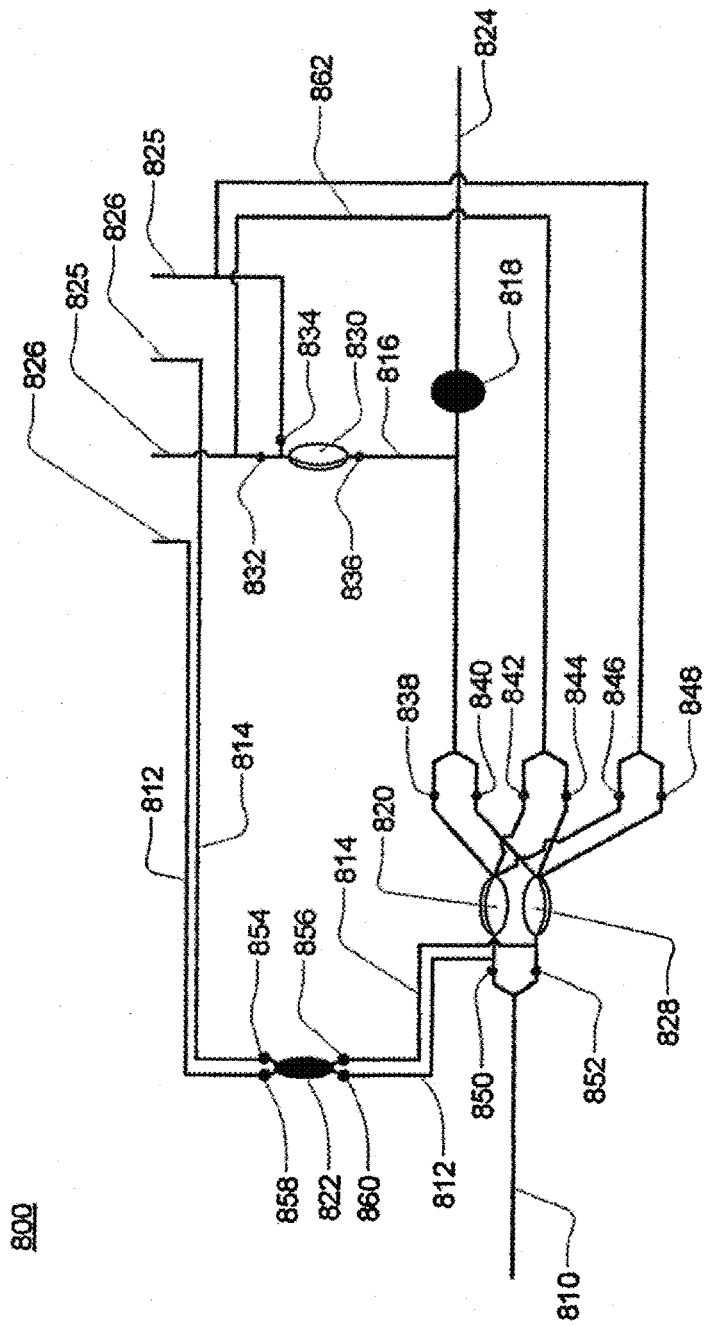
FIG. 8 is one embodiment of the fluid flow-path schematic of the cassette.

Referring now to FIG. 8, an exemplary embodiment of the fluid schematic of the cassette 800 is shown. Other schematics are readily discernable. The cassette 800 includes at least one pod pump 828, 820 and at least one mixing chamber 818. The cassette 800 also includes a first fluid inlet 810, where a first fluid enters the cassette. The first fluid includes a flow rate provided by one of the at least one pod pump 820, 828 in the cassette 800. The cassette 800 also includes a first fluid outlet 824 where fluid exits the cassette 800 having a flow rate provided by one of the at least one pod pump 820, 828. The cassette 800 includes at least one metering fluid line 812, 814, 816 that is in fluid connection with the first fluid outlet. The cassette also includes at least one second fluid inlet 826 where the second fluid enters the cassette 800. In some embodiments of the cassette 800 a third fluid inlet 825 is also included.

Metering pumps 822, 830 pump the second fluid and the third fluid into the first fluid outlet line. The second fluid and, in some embodiments, the third fluid, connected to the cassette 800 at the second fluid inlet 826 and third fluid inlet 825 respectively, are each fluidly connected to a metering pump 822, 830 and to the first fluid outlet line through a metering fluid line 812, 814, 816. The metering pumps 822, 830, described in more detail below, in the exemplary embodiment, include a volume measurement capacity such that the volume of fluid pumped by the metering pumps 822, 830 is readily discernable.

The mixing chamber 818 is connected to the first fluid outlet line 824 and includes a fluid inlet and a fluid outlet. In some embodiments, sensors are located upstream and downstream from the mixing chamber 818. The location of the sensors in the exemplary embodiment are shown and described below with respect to FIGS. 14C, 14D and FIGS. 15B and 15C.

The cassette 800 is capable of internally mixing a solution made up of at least two components. The cassette 800 also includes the capability of constituting a powder to a fluid prior to pumping the fluid into the mixing chamber. These capabilities will be described in greater detail below.

Various valves 832-860 impart the various capabilities of the cassette 800. The components of the cassette 800 may be used differently in the different embodiments based on various valving controls.

The fluid schematic of the cassette 800 shown in FIG. 8 may be embodied into various cassette apparatus. Thus, the embodiments of the cassette 800 including the fluid schematic shown in FIG. 8 are not the only cassette embodiments that may incorporate this or an alternate embodiment of this fluid schematic. Additionally, the types of valves, the ganging of the valves, the number of pumps and chambers may vary in various cassette embodiments of this fluid schematic.

Figure 10:
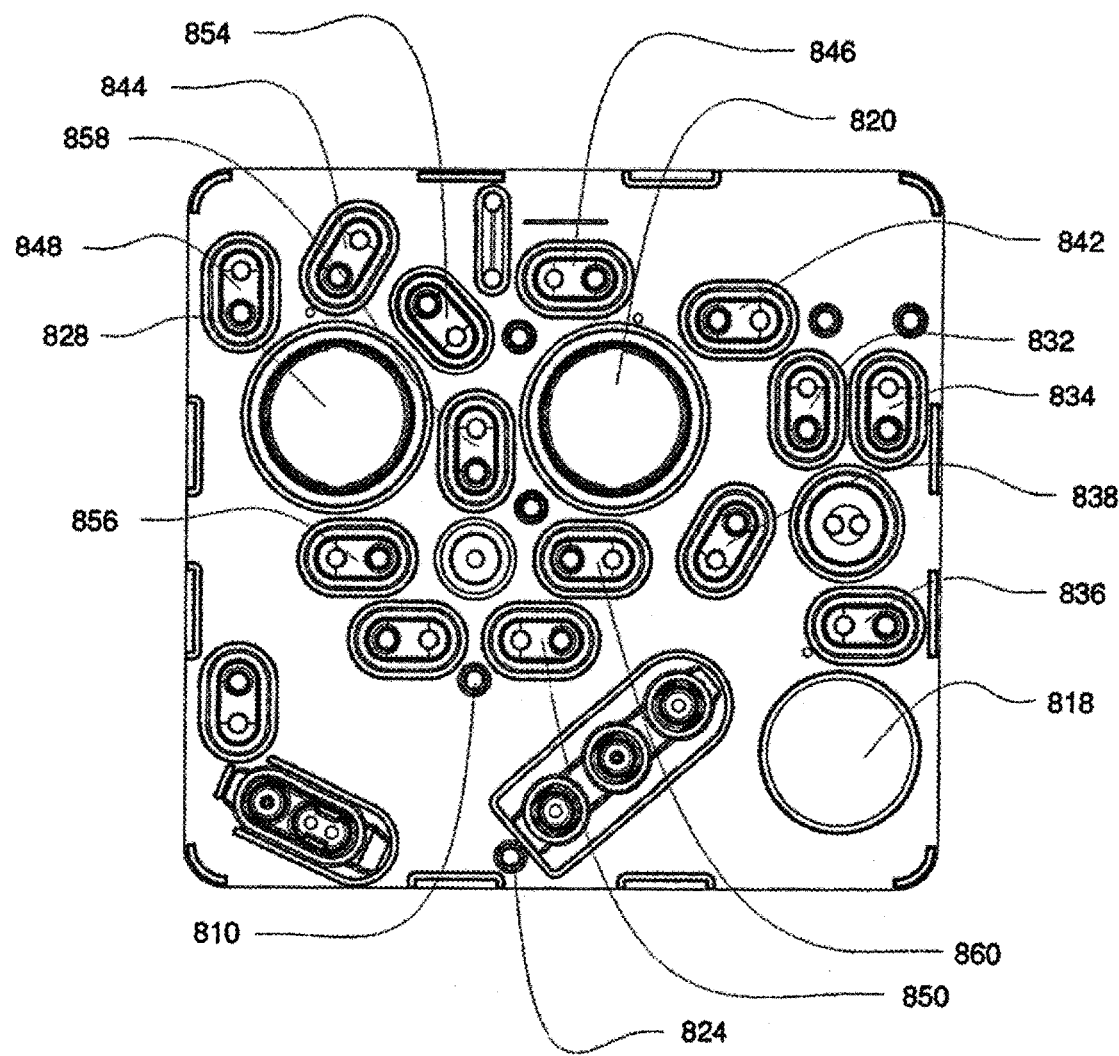
FIG. 10 is an isometric front view of the exemplary embodiment of the actuation side of the midplate of the cassette with the valves indicated corresponding to FIG. 8.
Figure 12A:
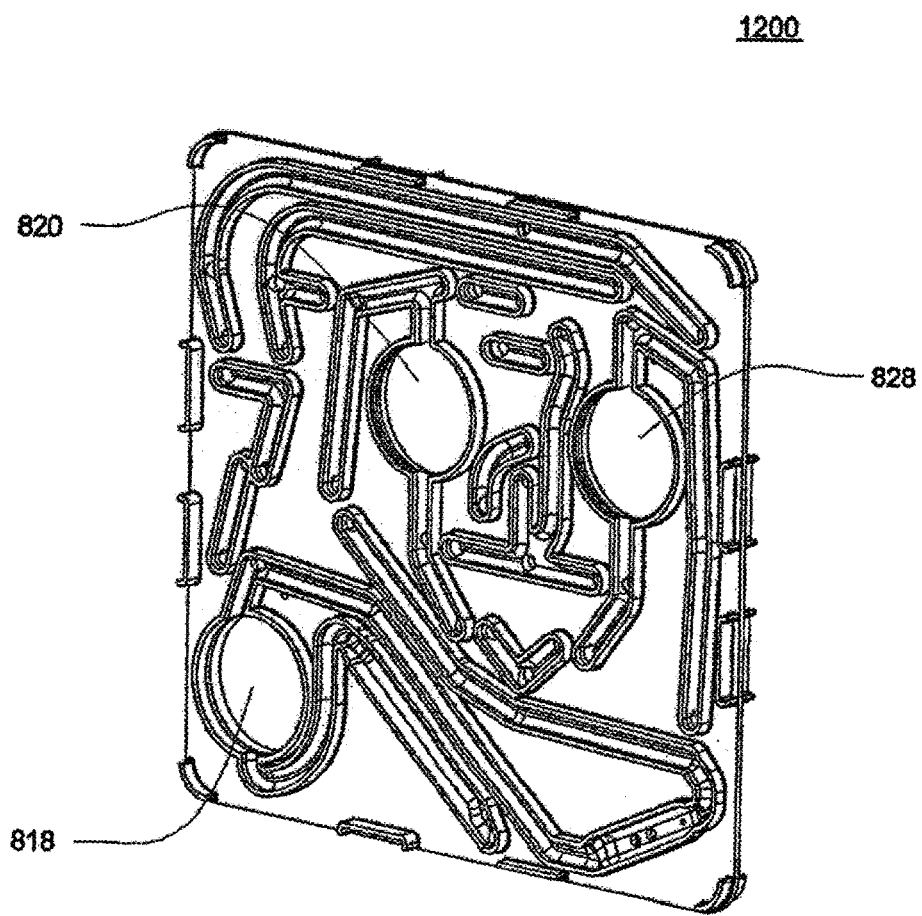
FIG. 12A is an isometric view.
Figure 12B:
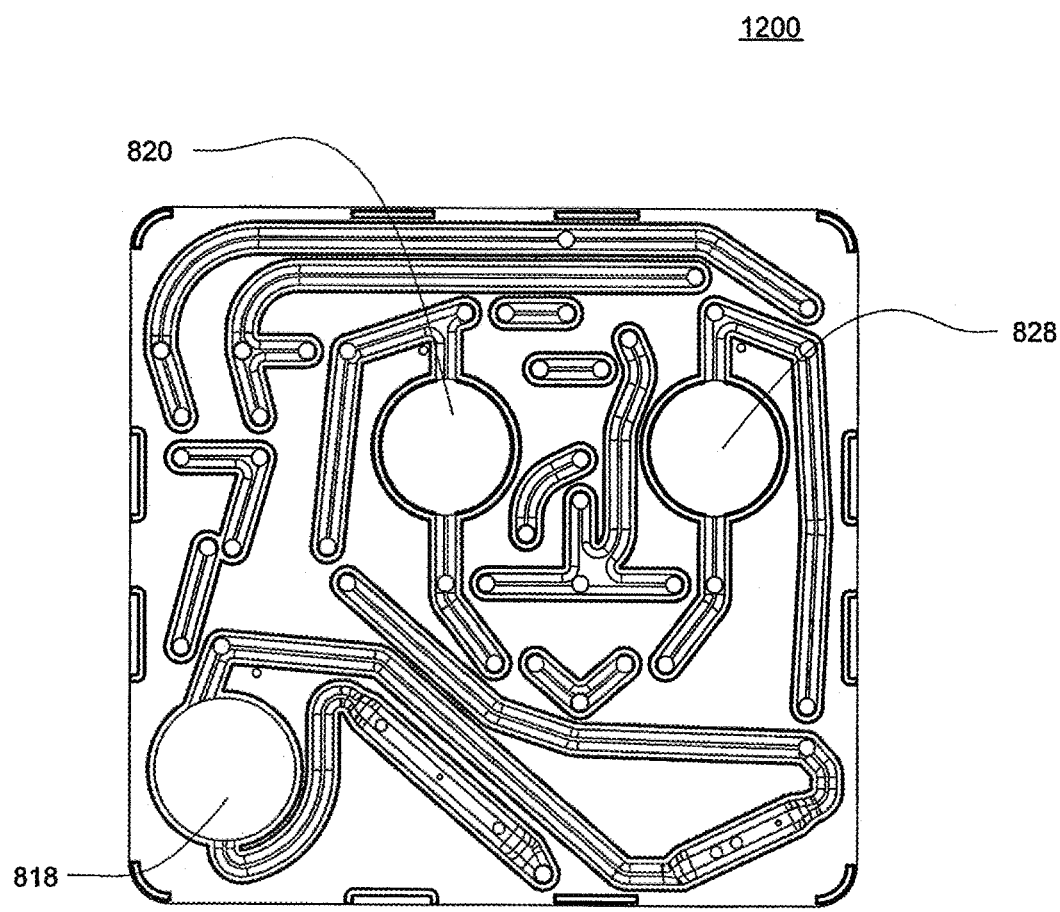
FIG. 12B is a front view of the exemplary embodiment of the fluid side of the midplate of the cassette.

Referring now to FIG. 8, a fluid flow-path schematic 800 is shown with the fluid paths indicated based on different valving flow paths. The fluid flow-path schematic 800 is described herein corresponding to the valving flow paths in one embodiment of the cassette. The exemplary embodiment of the midplate 900 of the cassette are shown in FIG. 10 with the valves indicated corresponding to the respective fluid flow-path schematic 800 in FIG. 8. For the purposes of the description, the fluid flow paths will be described based on the valving. The term "valving path" refers to a fluid path that may, in some embodiments, be available based on the control of particular valves. The corresponding fluid side structures of FIG. 10 are shown in FIG. 12A.

Referring now to FIGS. 8 and 10 the first valving path includes valves 858, 860. This valving path 858, 860 includes the metering fluid line 812, which connects to the second fluid inlet 826. As shown in these FIGS., in some embodiments of the cassette, there are two second fluid inlets 826. In practice, these two second fluid inlets 826 can be connected to the same fluid source or a different fluid source. Either way, the same fluid or a different fluid may be connected to each second fluid inlet 826. Each second fluid inlet 826 is connected to a different metering fluid line 812, 814.

The first of the two metering fluid lines connected to the second fluid inlet 826 is as follows. When valve 858 opens and valve 860 is closed and metering pump 822 is actuated, fluid is drawn from the second fluid inlet 826 and into metering fluid line 812. When valve 860 is open and valve 858 is closed and the metering pump 822 is actuated, second fluid continues on metering fluid line 812 into pod pump 820.

Referring now to the second valving path including valve 842, when valve 842 is open and pod pump 820 is actuated, fluid is pumped from pod pump 820 to one of the third fluid inlet 825. In one embodiment, this valving path is provided to send liquid into a container or source connected to third fluid inlet 825.

Referring now to the third valving path including valves 832 and 836 this valving path 832, 835 includes the metering fluid line 816, which connects to the third fluid inlet 825. As shown in these FIGS., in some embodiments of the cassette, there are two third fluid inlets 825. In practice, these two third fluid inlets 825 can be connected to the same fluid source or a different fluid source. Either way, the same fluid or a different fluid may be connected to each third fluid inlet 825. Each third fluid inlet 825 is connected to a different metering fluid line 862, 868.

When valve 832 opens and valve 836 is closed and metering pump 830 is actuated, fluid is drawn from the third fluid inlet 825 and into metering fluid line 830. When valve 836 is open and valve 832 is closed and the metering pump 830 is actuated, third fluid continues on metering fluid line 816 into first fluid outlet line 824.

Referring now to the fourth valving path, valve 846, when valve 846 is open and pod pump 820 is actuated, fluid is pumped from pod pump 820 to one of the third fluid inlet 825. In one embodiment, this valving path is provided to send liquid into a container or source connected to third fluid inlet 825.

Referring now to the fifth valving path, when valve 850 opens and pod pump 820 is actuated, fluid is pumped into the cassette 800 through the first fluid inlet 810, and into pod pump 820.

Referring now to the sixth valving path, when valve 838 is open and pod pump 820 is actuated, fluid is pumped from pod pump 820 to the mixing chamber 818 and to the first fluid outlet 824.

The seventh valving path includes valves 858, 856. This valving path 858, 856 includes the metering fluid line 812, which connects to the second fluid inlet 826. As shown in these FIGS., in some embodiments of the cassette, there are two second fluid inlets 826. In practice, these two second fluid inlets 826 can be connected the same fluid source or a different fluid source. Either way, the same fluid or a different fluid may be connected to each second fluid inlet 826. Each second fluid inlet 826 is connected to a different metering fluid line 812, 814.

When valve 858 opens and valve 856 is closed and metering pump 822 is actuated, fluid is drawn from the second fluid inlet 826 and into metering fluid line 812. When valve 856 is open and valve 858 is closed, and the metering pump is actuated, second fluid continues on metering fluid line 814 into pod pump 828.

Referring now to the eighth valving path, valve 848, when valve 848 is open and pod pump 828 is actuated, fluid is pumped from pod pump 828 to one of the third fluid inlet

825. In one embodiment, this valving path is provided to send fluid/liquid into a container or source connected to third fluid inlet 825.

Referring now to the ninth valving path including valve 844, when valve 844 is open and pod pump 828 is actuated, fluid is pumped from pod pump 828 to one of the third fluid inlet 825. In one embodiment, this valving path is provided to send liquid into a container or source connected to third fluid inlet 825.

Referring now to the tenth valving path, valve 848, when valve 848 is open and pod pump 828 is actuated, fluid is pumped from pod pump 828 to one of the third fluid inlet 825. In one embodiment, this valving path is provided to send fluid/liquid into a container or source connected to third fluid inlet 825.

The eleventh valving path including valves 854 and 856 is shown. This valving path 854, 856 includes the metering fluid line 814, which connects to the second fluid inlet 826. As shown in these FIGS., in some embodiments of the cassette, there are two second fluid inlets 826. In practice, these two second fluid inlets 826 can be connected the same fluid source or a different fluid source. Either way, the same fluid or a different fluid may be connected to each second fluid inlet 826. Each second fluid inlet 826 is connected to a different metering fluid line 812, 814.

The second of the two metering fluid lines connected to the second fluid inlet 826 is shown in FIG. 8. The twelfth valving path is as follows. When valve 854 opens and valve 856 is closed and metering pump 822 is actuated, fluid is drawn from the second fluid inlet 826 and into metering fluid line 814. When valve 856 is open and valve 854 is closed and the metering pump 822 is actuated, the second fluid continues on metering fluid line 814 into pod pump 828.

Similarly, the thirteenth valving path is seen when valve 854 opens and valve 860 is closed and metering pump 822 is actuated, fluid is drawn from the second fluid inlet 826 and into metering fluid line 814. When valve 860 is open and valve 854 is closed, and the metering pump 822 is actuated, the second fluid continues on metering fluid line 814 into pod pump 820.

Referring now to the fourteenth valving path including valve 852. When valve 852 opens and pod pump 828 is actuated, fluid is pumped into the cassette 800 through the first fluid inlet 810, and into pod pump 828.

Referring now to the fifteenth valving path, when valve 840 is open and pod pump 828 is actuated, fluid is pumped from pod pump 828 to the mixing chamber 818 and to the first fluid outlet 824. The sixteenth valving path including valve 834, when valve 834 is open and valve 836 opens, and the metering pump 830 is actuated, fluid from the third fluid inlet 825 flows on metering fluid line 862 and to metering fluid line 816.

In the exemplary fluid flow-path embodiment shown in FIG. 8, and corresponding structure of the cassette shown in FIG. 10, valves are open individually. In the exemplary embodiment, the valves are pneumatically open. Also, in the exemplary embodiment, the fluid valves are volcano valves, as described in more detail in this specification.

Referring now to FIGS. 11A-11D, the top plate 1100 of exemplary embodiment of the cassette is shown. In the exemplary embodiment, the pod pumps 820, 828 and the mixing chambers 818 on the top plate 1100, are formed in a similar fashion. In the exemplary embodiment, the pod pumps 820, 828 and mixing chamber 818, when assembled with the bottom plate, have a total volume of capacity of 38 ml. However, in other embodiments, the mixing chamber can have any size volume desired.

Figure 11A:
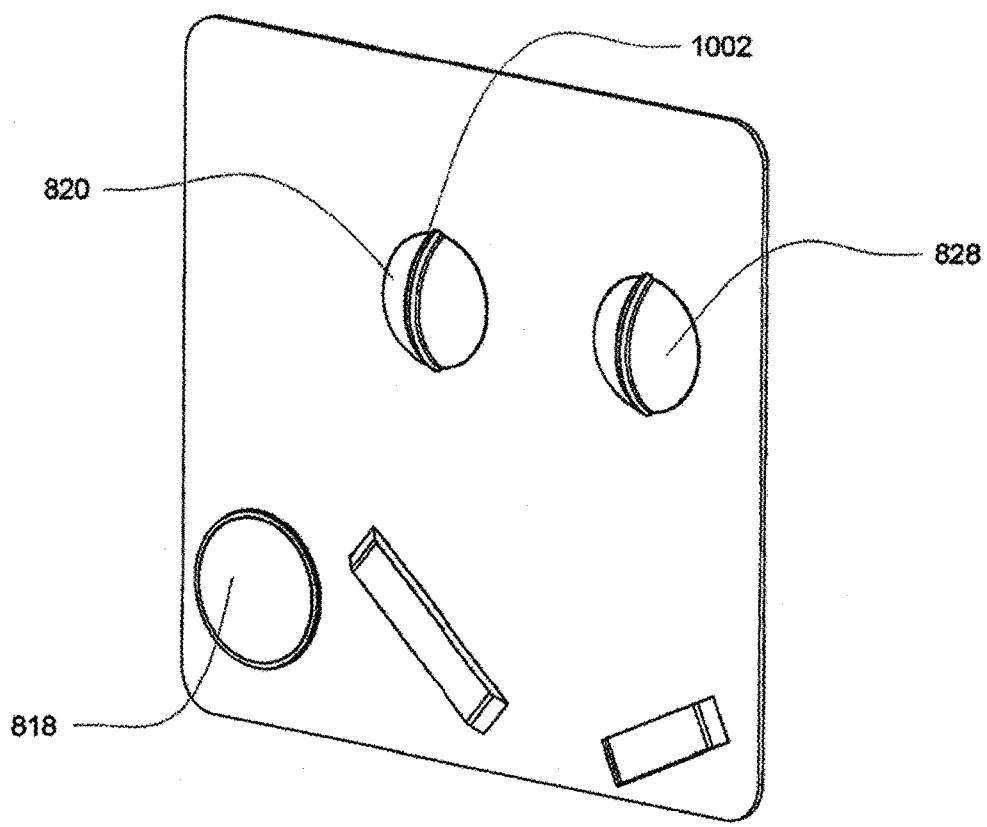
FIG. 11A is an isometric view.
Figure 11B:
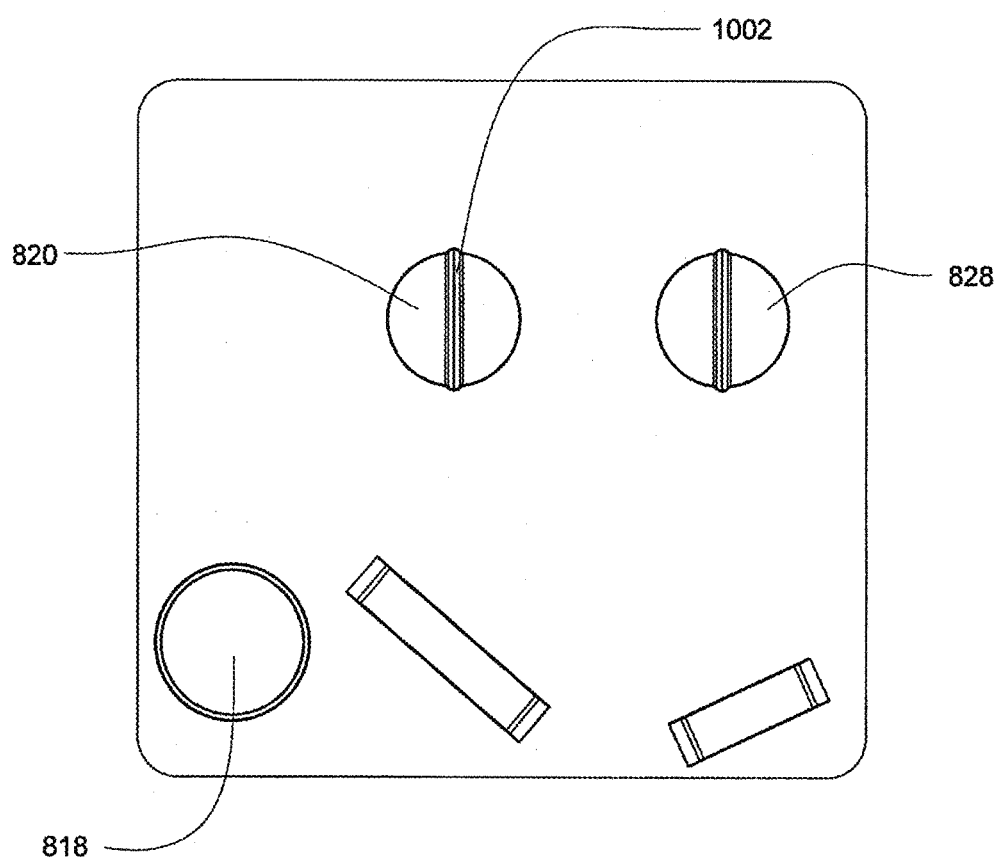
FIG. 11B is a front view of the exemplary embodiment of the outer top plate of the cassette.
Figure 11C:
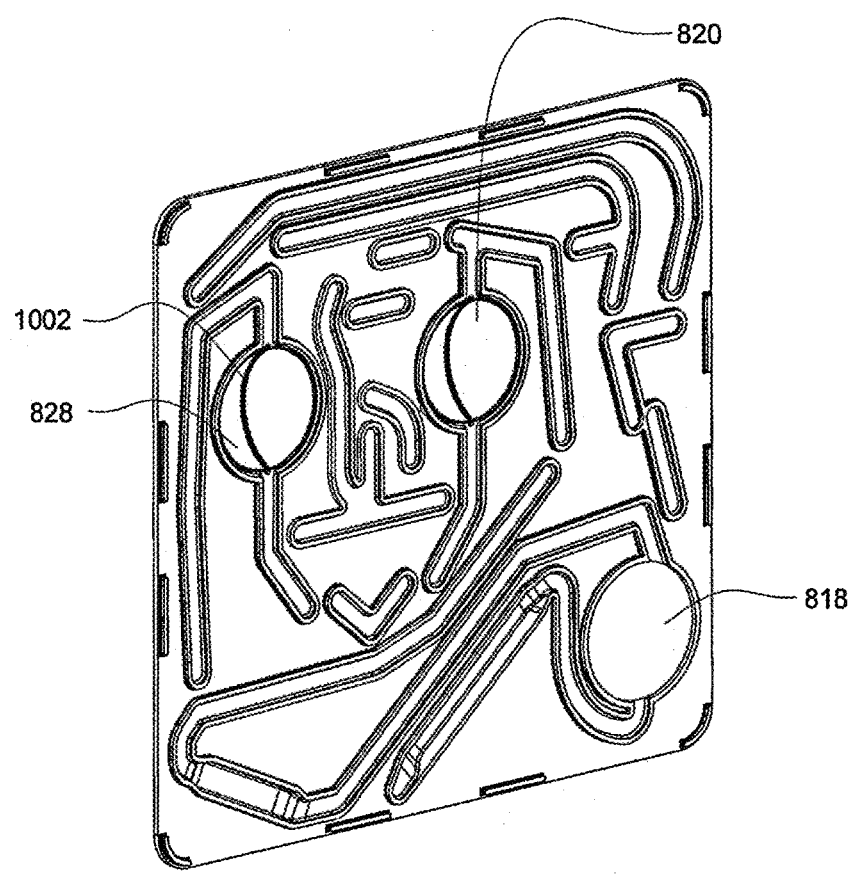
FIG. 11C is an isometric view.
Figure 11D:
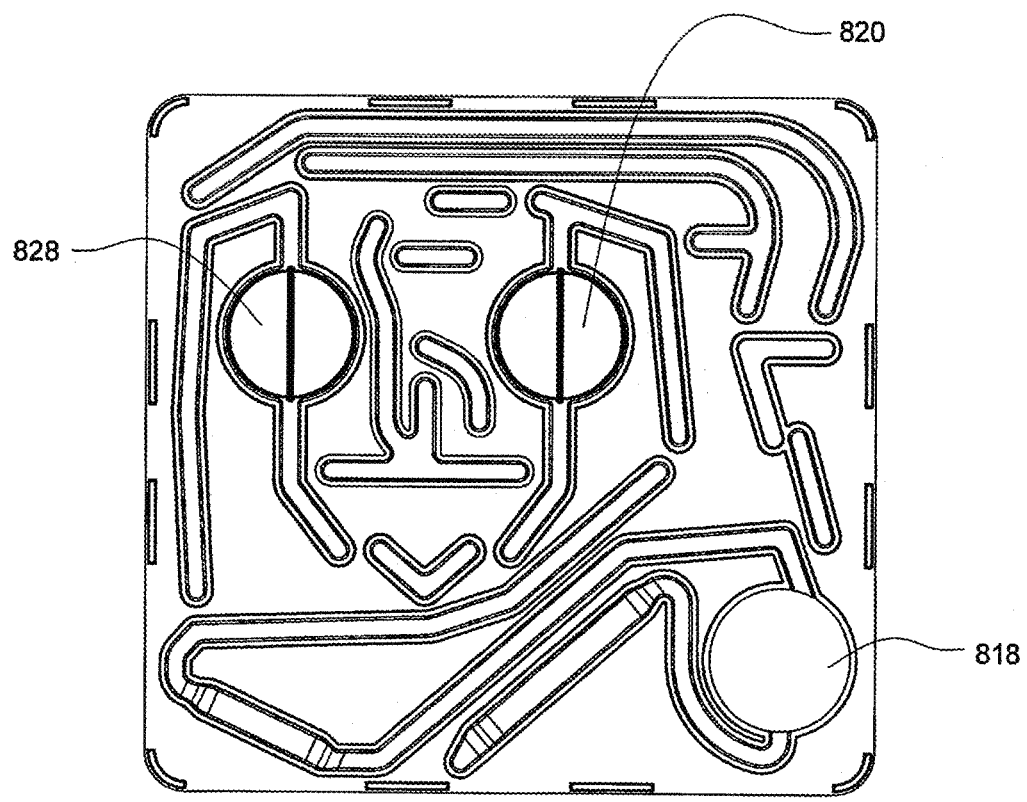
FIG. 11D is a front view of the exemplary embodiment of the inner top plate of the cassette.
Figure 12C:
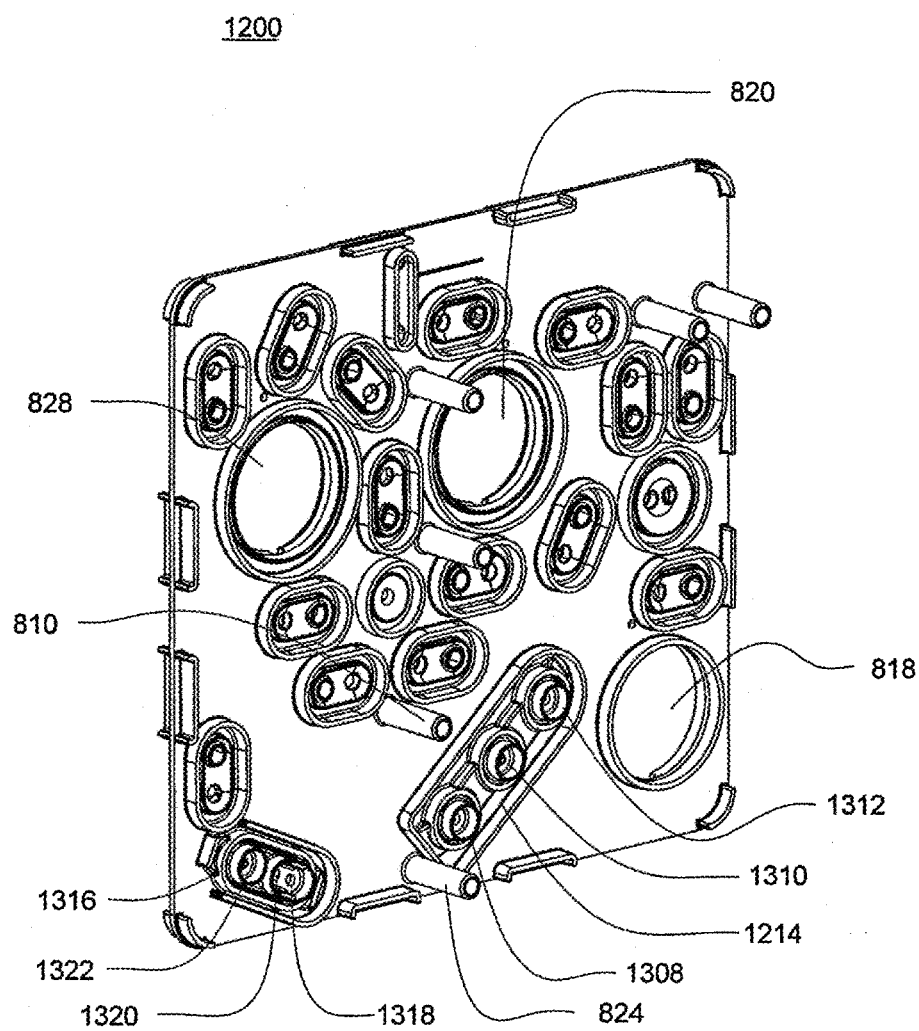
FIG. 12C is an isometric view.
Figure 12D:
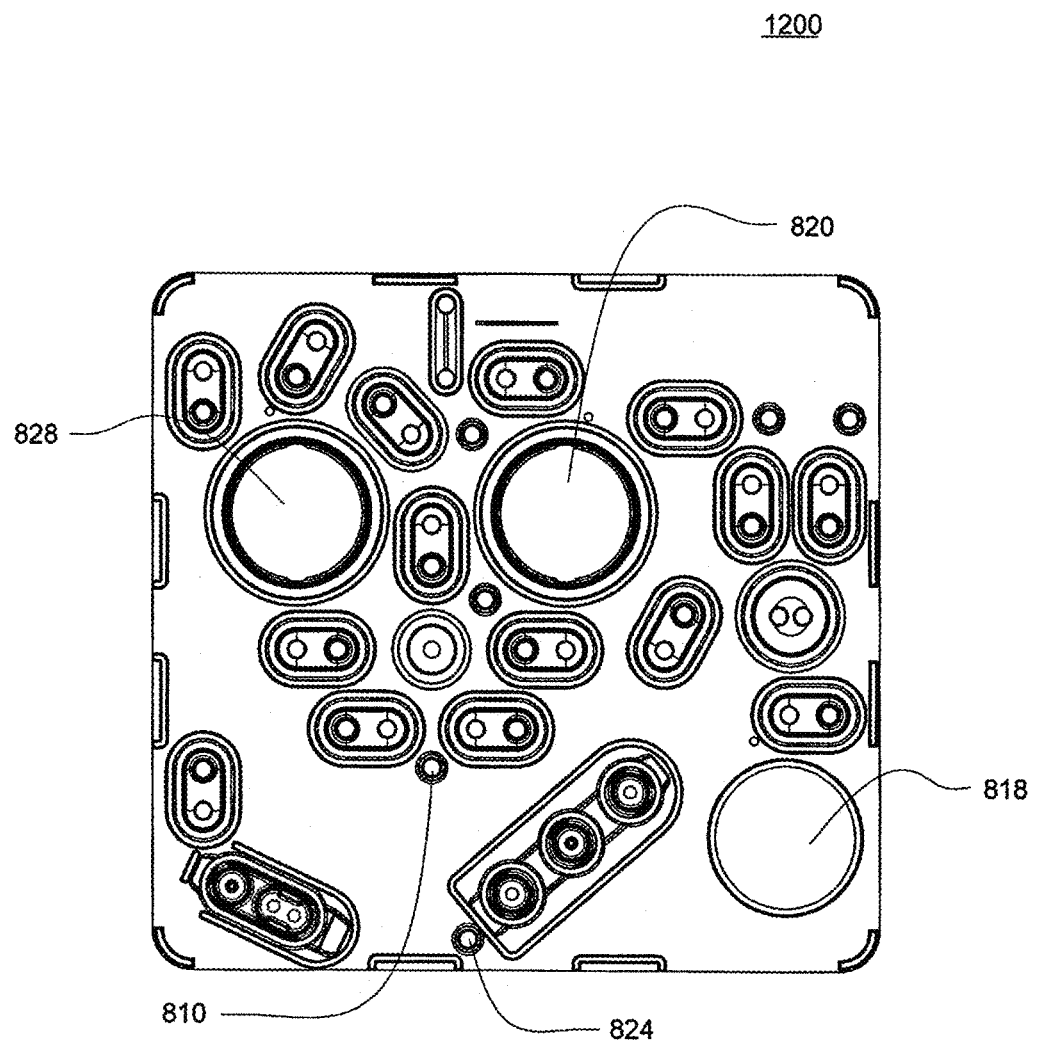
FIG. 12D is a front view of the exemplary embodiment of the air side of the midplate of the cassette.

Referring now to FIGS. 11C and 11D, the bottom view of the top plate 1100 is shown. The fluid paths are shown in this view. These fluid paths correspond to the fluid paths shown in FIGS. 12A-12D in the midplate 1200. The top plate 1100 and the top of the midplate 1200 form the liquid or fluid side of the cassette for the pod pumps 820, 828 and for one side of the mixing chamber 818. Thus, most of the liquid flow paths are on the top 1100 and midplates 1200. Referring to FIGS. 12C and 12D, the first fluid inlet 810 and the first fluid outlet 824 are shown.

Still referring to FIGS. 11A-11D, the pod pumps 820, 828 include a groove 1002 (in alternate embodiments, this is a groove). The groove 1002 is shown having a particular size and shape, however, in other embodiments, the size and shape of the groove 1002 can be any size or shape desirable. The size and shape shown in FIGS. 11A-11D is the exemplary embodiment. In all embodiments of the groove 1002, the groove 1002 forms a path between the fluid inlet side and the fluid outlet side of the pod pumps 820, 828. In alternate embodiments, the groove 1002 is a groove in the inner pumping chamber wall of the pod pump.

The groove 1002 provides a fluid path whereby when the membrane is at the end-of-stroke there is still a fluid path between the inlet and outlet such that the pockets of fluid or air do not get trapped in the pod pump. The groove 1002 is included in both the liquid/fluid and air/actuation sides of the pod pumps 820, 828. In some embodiments, the groove 1002 may also be included in the mixing chamber 818 (see FIGS. 13A-13D with respect to the actuation/air side of the pod pumps 820, 828 and the opposite side of the mixing chamber 818. In alternate embodiments, the groove 1002 is either not included or on only one side of the pod pumps 820, 828.

Figure 11E:
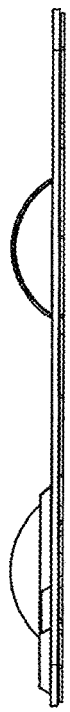
FIG. 11E is a side view of the exemplary embodiment of the top plate of the cassette.

In an alternate embodiment of the cassette, the liquid/fluid side of the pod pumps 820, 828 may include a feature (not shown) whereby the inlet and outlet flow paths are continuous and a rigid outer ring (not shown) is molded about the circumference of the pumping chamber is also continuous. This feature allows for the seal, formed with the membrane (not shown) to be maintained. Referring to FIG. 11E, the side view of the exemplary embodiment of the top plate 1100 is shown.

Referring now to FIGS. 12A-12D, the exemplary embodiment of the midplate 1200 is shown. The midplate 1200 is also shown in FIGS. 9A-9F and 10A-10F, where these figures correspond with FIGS. 12A-12D. Thus, FIGS. 9A-9F and 10A-10F indicate the locations of the various valves and valving paths. The locations of the membranes (not shown) for the respective pod pumps 820, 828 as well as the location of the mixing chamber 818 are shown.

Referring now to FIG. 12C, in the exemplary embodiment of the cassette, sensor elements are incorporated into the cassette so as to discern various properties of the fluid being pumped. In one embodiment, three sensor elements are included. However, in the exemplary embodiment, six sensor elements (two sets of three) are included. The sensor elements are located in the sensor cell 1314, 1316. In this embodiment, a sensor cell 1314, 1316 is included as an area on the cassette for sensor(s) elements. In the exemplary embodiment, the three sensor elements of the two sensor cells 1314, 1316 are housed in respective sensor elements housings 1308, 1310, 1312 and 1318, 1320, 1322. In the exemplary embodiment, two of the sensor elements housings 1308, 1312 and 1318, 1320 accommodate a conductivity sensor elements and the third sensor elements housing 1310, 1322 accommodates a temperature sensor elements. The conductivity sensor elements and temperature sensor elements can be any conductivity or temperature sensor elements in the art. In one embodiment, the conductivity sensors are graphite posts. In other embodiments, the conductivity sensor elements are posts made from stainless steel, titanium, platinum or any other metal coated to be corrosion resistant and still be electrically conductive. The conductivity sensor elements will include an electrical lead that transmits the probe information to a controller or other device. In one embodiment, the temperature sensor is a thermister potted in a stainless steel probe. However, in alternate embodiments, a combination temperature and conductivity sensor elements is used similar to the one described in co-pending U.S. patent application entitled Sensor Apparatus Systems, Devices and Methods filed Oct. 12, 2007 (U.S. application Ser. No. 11/871,821).

In alternate embodiments, there are either no sensors in the cassette or only a temperature sensor, only one or more conductivity sensors or one or more of another type of sensor.

Figure 12E:
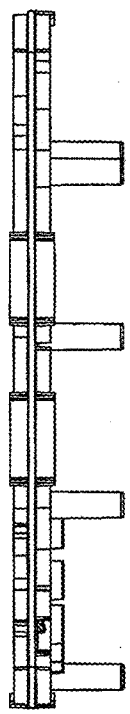
FIG. 12E is a side view of the exemplary embodiment of the midplate of the cassette.

Referring now to FIG. 12E, the side view of the exemplary embodiment of the midplate 1200 is shown.

Figure 13A:
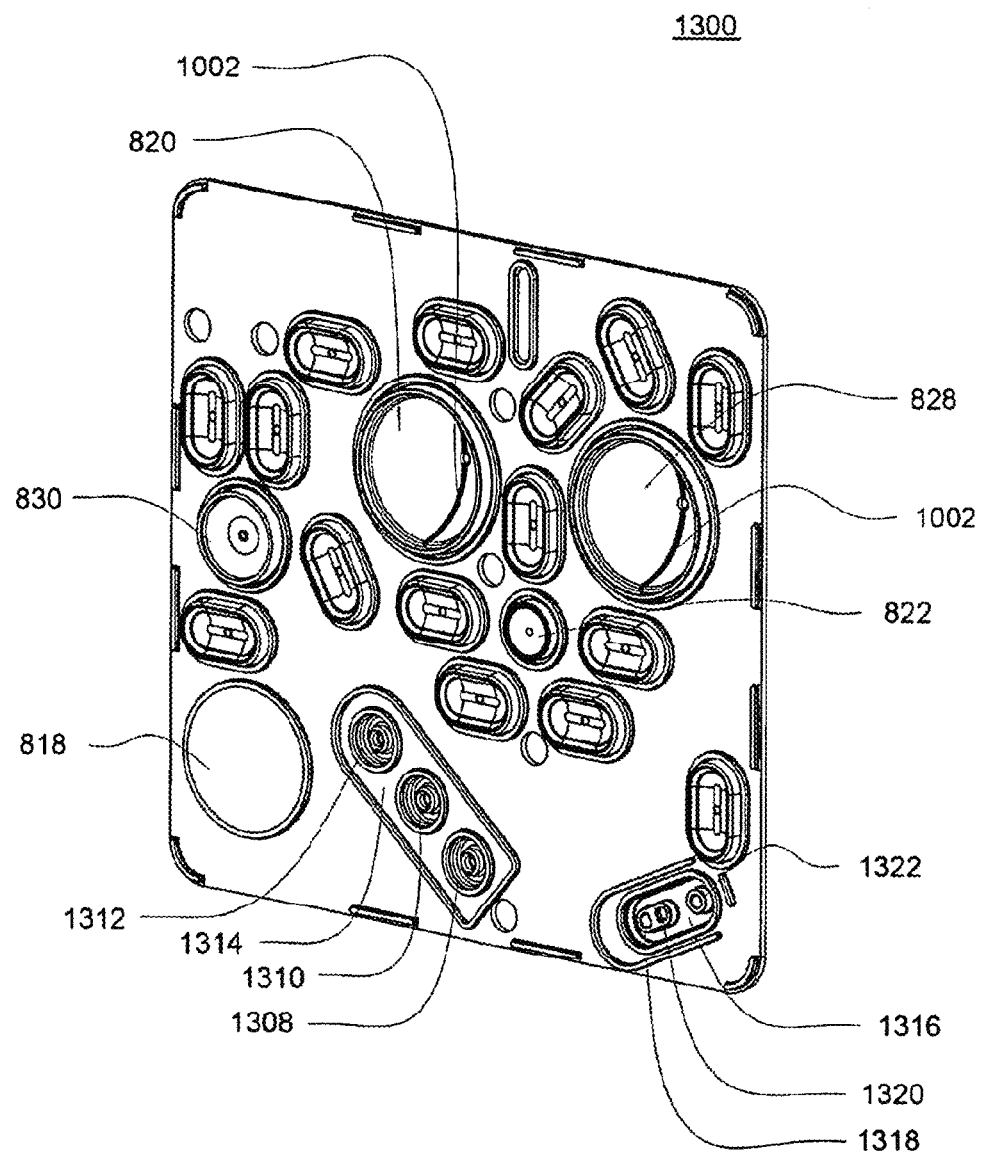
FIG. 13A is an isometric view.
Figure 13B:
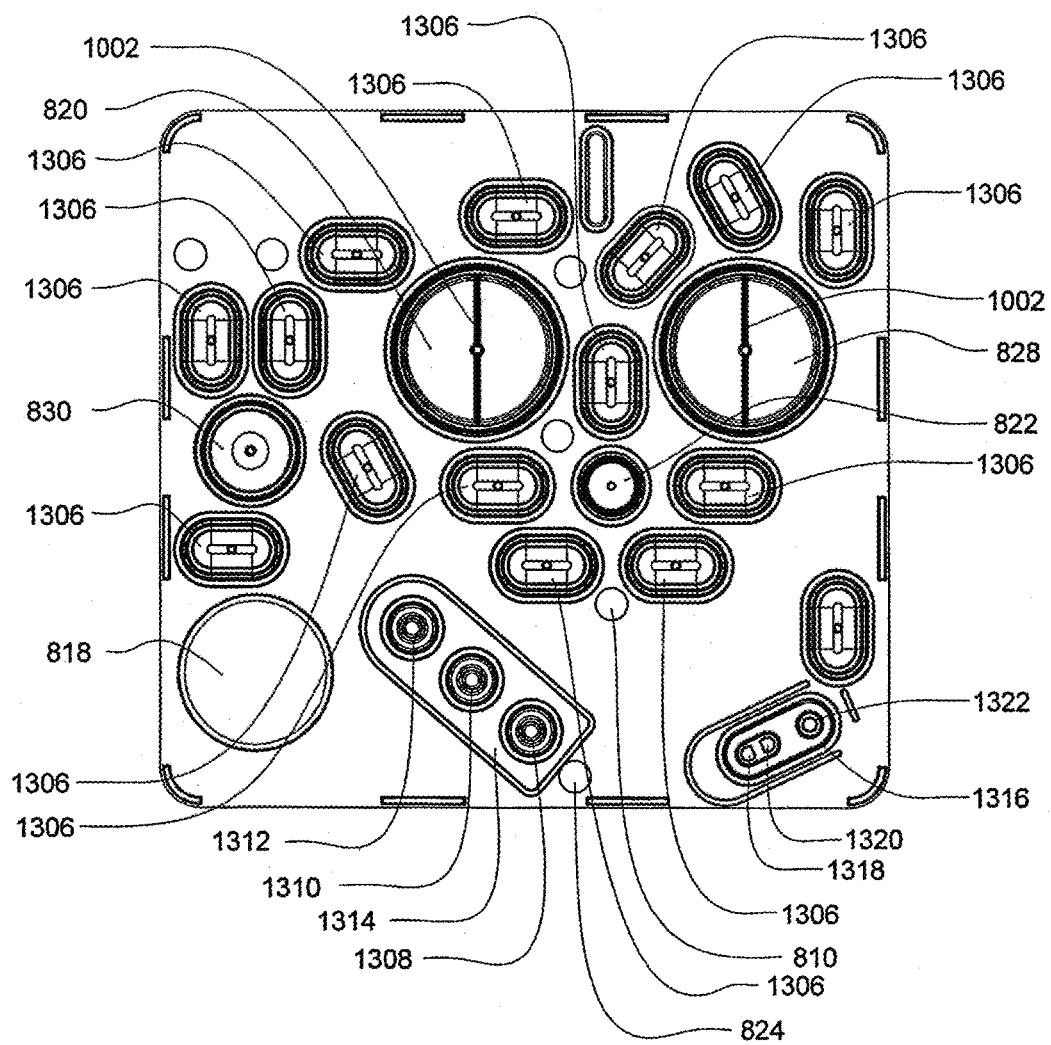
FIG. 13B is a front view of the exemplary embodiment of the inner side of the bottom plate of the cassette.

Referring now to FIGS. 13A-13D, the bottom plate 1300 is shown. Referring first to FIGS. 13A and 13B, the inner or inside surface of the bottom plate 1300 is shown. The inner or inside surface is the side that contacts the bottom surface of the midplate (not shown, see FIG. 9B). The bottom plate 1300 attaches to the air or actuation lines (not shown). The corresponding entrance holes for the air that actuates the pod pumps 820, 828 and valves (not shown, see FIGS. 10A-10F) in the midplate 1300 can be seen. Holes 810, 824 correspond to the first fluid inlet and first fluid outlet shown in FIGS. 12C and 12D, 810, 824 respectively. The corresponding halves of the pod pumps 820, 828 and mixing chamber 818 are also shown, as are the grooves 1002 for the fluid paths. The actuation holes in the pumps are also shown. Unlike the top plate, the bottom plate 1300 corresponding halves of the pod pumps 820, 828 and mixing chamber 818 make apparent the difference between the pod pumps 820, 828 and mixing chamber 818. The pod pumps 820, 828 include an air/actuation path on the bottom plate 1300, while the mixing chamber 818 has identical construction to the half in the top plate. The mixing chamber 818 mixes liquid and therefore, does not include a membrane (not shown) nor an air/actuation path. The sensor cell 1314, 1316 with the three sensor element housings 1308, 1310, 1312 and 1318, 1320, 1322 are also shown.

Figure 13C:
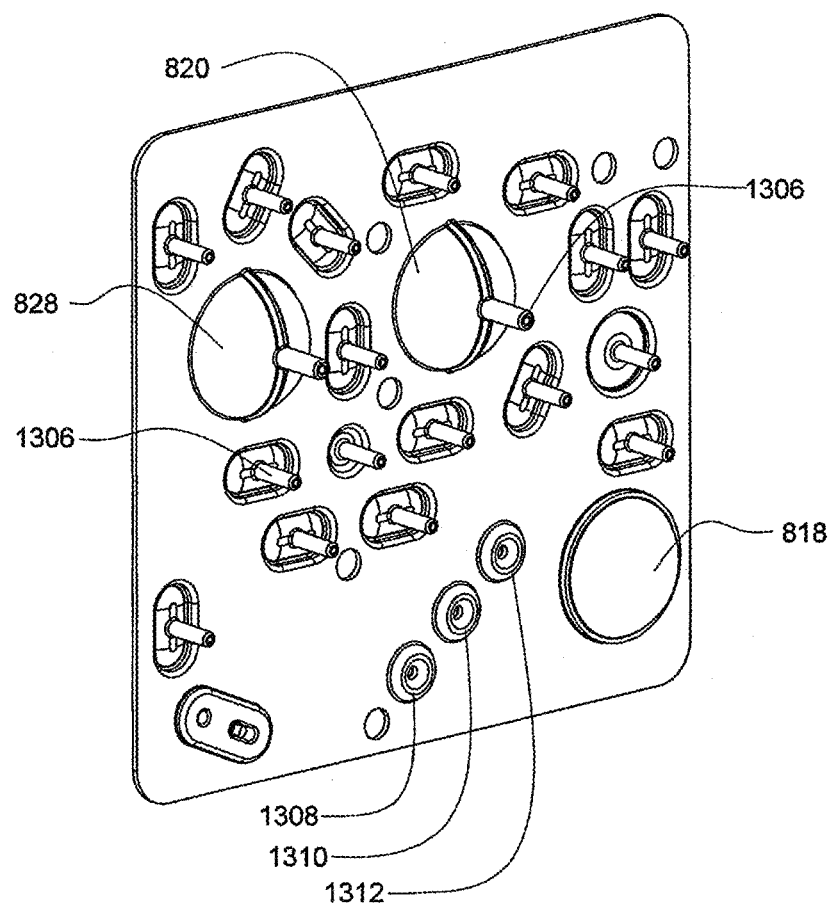
FIG. 13C is an isometric view.
Figure 13D:
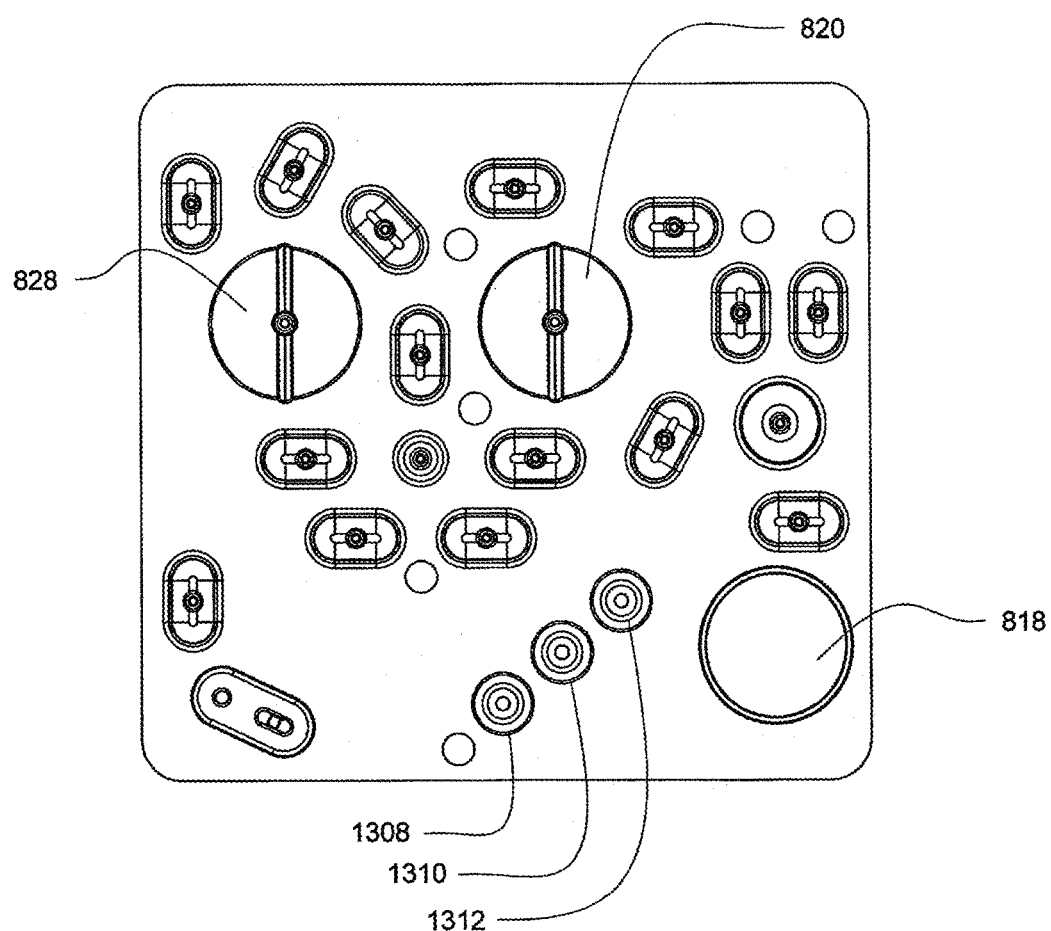
FIG. 13D is a front view of the exemplary embodiment of the outer side of the bottom plate of the cassette.
Figure 13E:
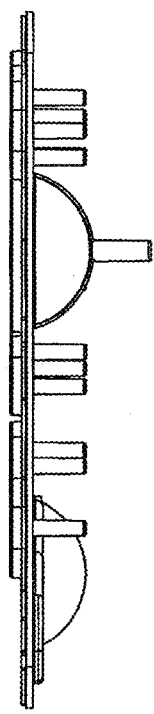
FIG. 13E is a side view of the exemplary embodiment of the midplate of the cassette.

Referring now to FIGS. 13C and 13D, the actuation ports 1306 are shown on the outside or outer bottom plate 1300. An actuation source is connected to these actuation ports 1306. Again, the mixing chamber 818 does not have an actuation port as it is not actuated by air. Referring to FIG. 13E, a side view of the exemplary embodiment of the bottom plate 1300 is shown.

5.1 Membranes

Figure 5A:
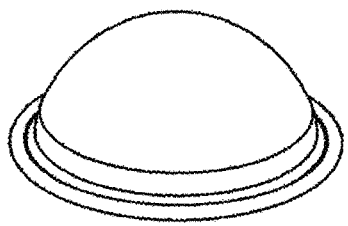
FIGS. 5A-5D are side views of various embodiments of variable membranes.
Figure 5B:
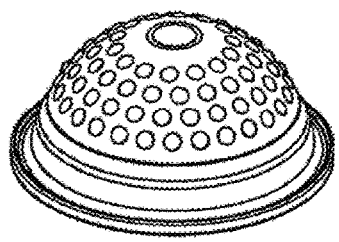
Figure 5C:
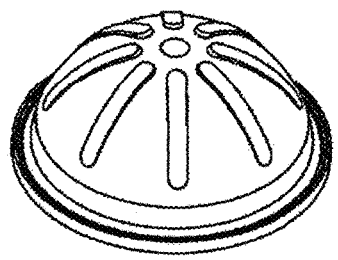
Figure 5D:
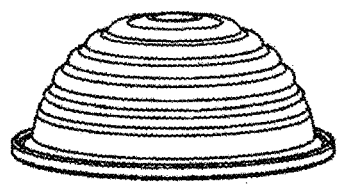

In the exemplary embodiment, the membrane is a gasket o-ring membrane as shown in FIG. 5A. However, in some embodiments, a gasket o-ring membranes having texture, including, but not limited to, the various embodiments in FIG. 4D, or 5B-5D may be used. In still other embodiments, the membranes shown in FIGS. 6A-6G may also be used.

Figure 14A:
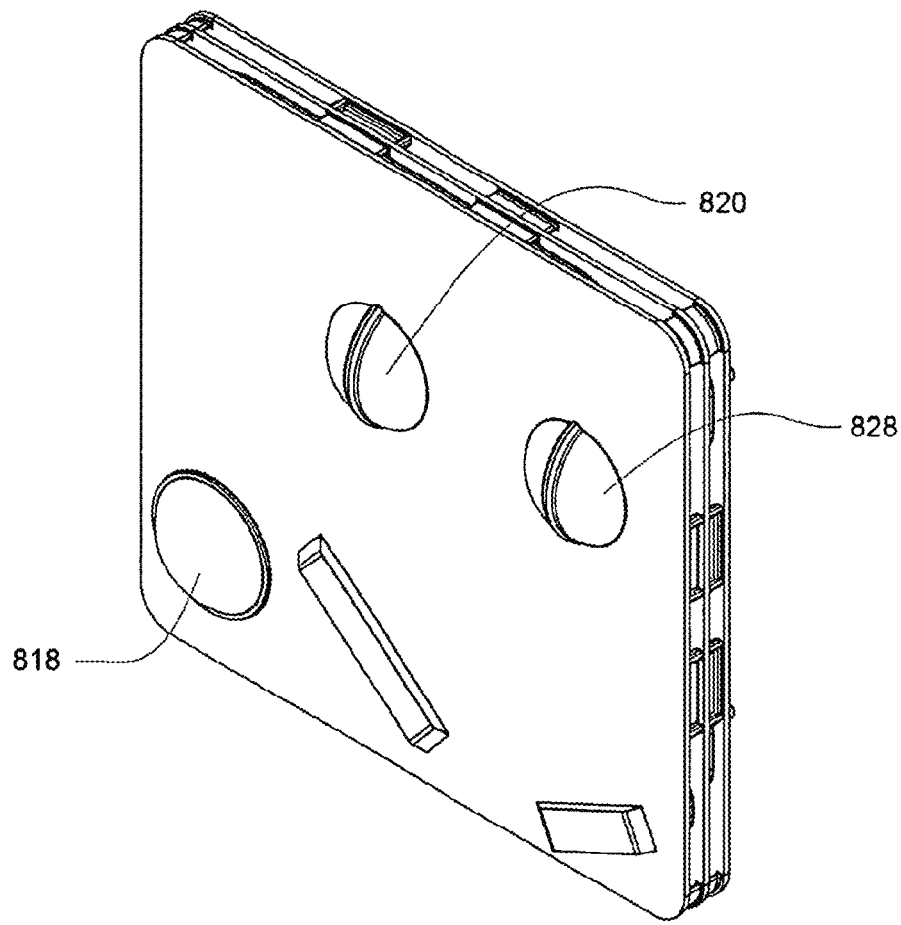
FIG. 14A is a top view of the assembled exemplary embodiment of the cassette.
Figure 14B:
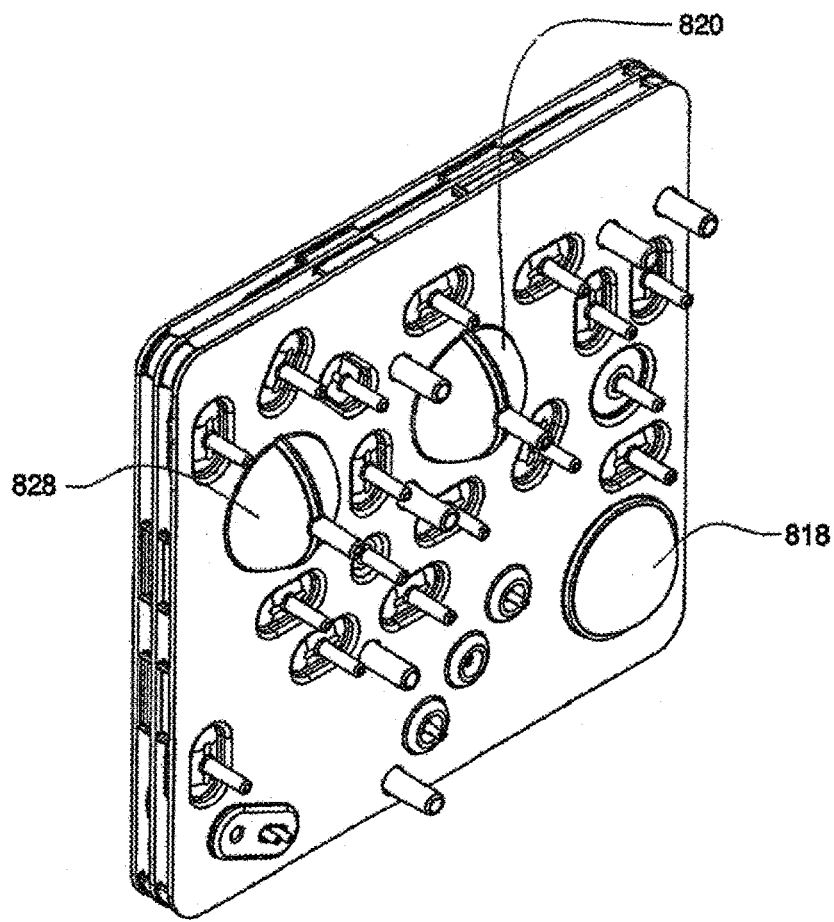
FIG. 14B is a bottom view of the assembled exemplary embodiment of the cassette.
Figure 14C:
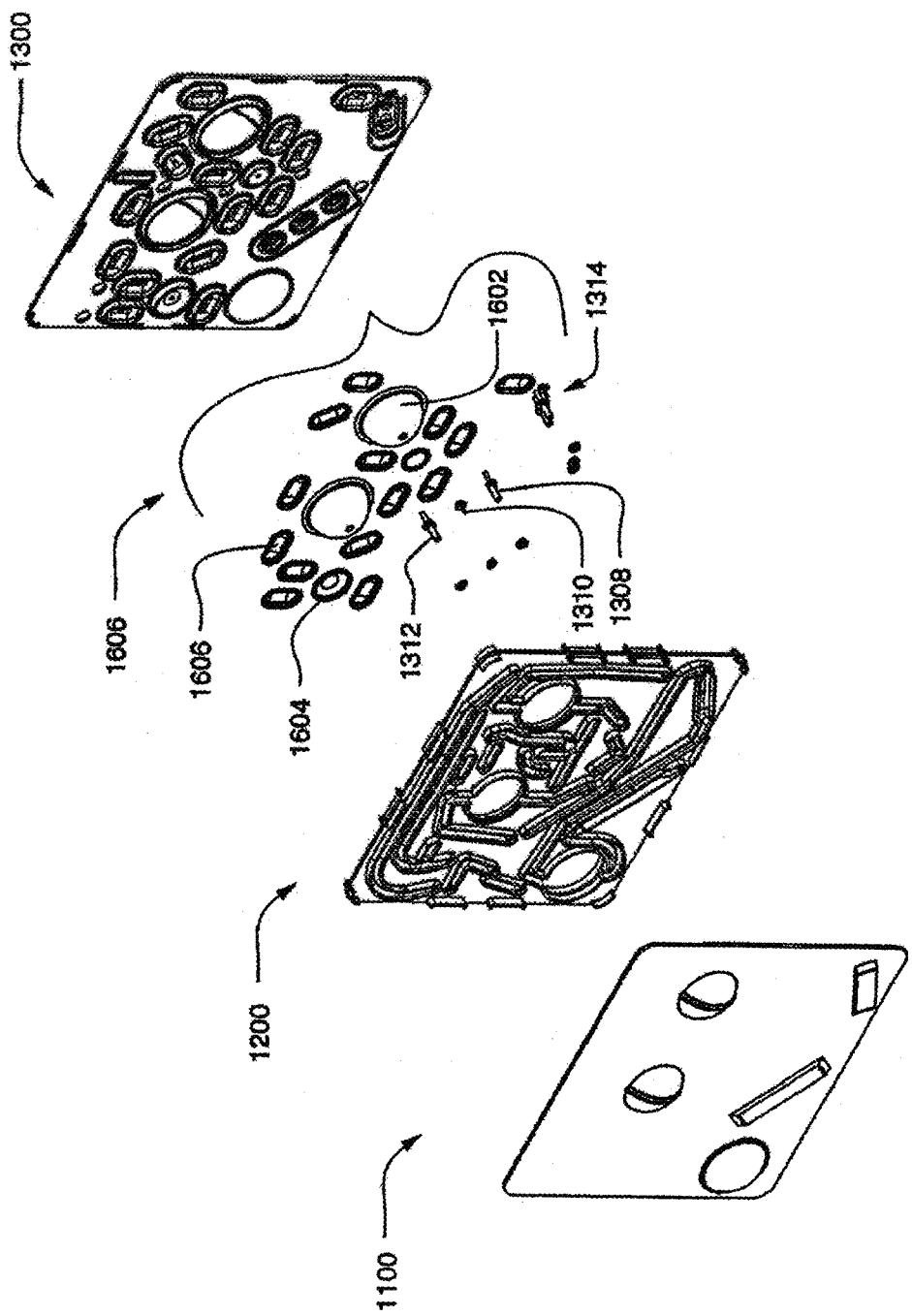
Figure 14D:
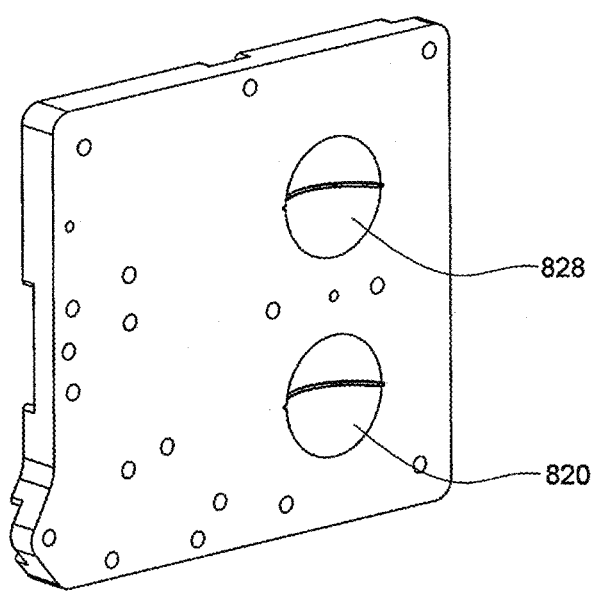
FIGS. 14D and 28C are isometric views of an alternate embodiment of the outer top plate of the cassette.

Referring next to FIGS. 14A and 14B, the assembled exemplary embodiment of the cassette 1400 is shown. FIGS. 14C and 14E are an exploded view of the exemplary embodiment of the cassette 1400. The membranes 1600 are shown. As can be seen from FIGS. 14C and 14E, there is one membrane 1602 for each of the pods pumps. In the exemplary embodiment, the membrane for the pod pumps is identical. In alternate embodiments, any membrane may be used, and one pod pump could use one embodiment of the membrane while the second pod pump can use a different embodiment of the membrane (or each pod pump can use the same membrane).

The various embodiments of the membrane used in the metering pumps 1604, in the preferred embodiment, are shown in more detail in FIGS. 5E-5H. The various embodiments of the membrane used in the valves 1222 is shown in more detail in FIGS. 2E-2G. However, in alternate embodiments, the metering pump membrane as well as the valve membranes may contain textures for example, but not limited to, the textures shown on the pod pump membranes shown in FIGS. 5A-5D.

One embodiment of the conductivity sensor elements 1314, 1316 and the temperature sensor element 1310, which make up the sensor cell 1322, are also shown in FIGS. 14C and 14E. Still referring to FIGS. 14C and 14E, the sensor elements are housed in sensor blocks (shown as 1314, 1316 in FIGS. 12C and 13A and B) which include areas on the bottom plate 1300 and the midplate 1200. O-rings seal the sensor housings from the fluid lines located on the upper side of the midplate 1200 and the inner side of the top plate 1100. However, in other embodiments, an o-ring is molded into the sensor block or any other method of sealing can be used.

5.2 Cross Sectional Views

Figure 15A:
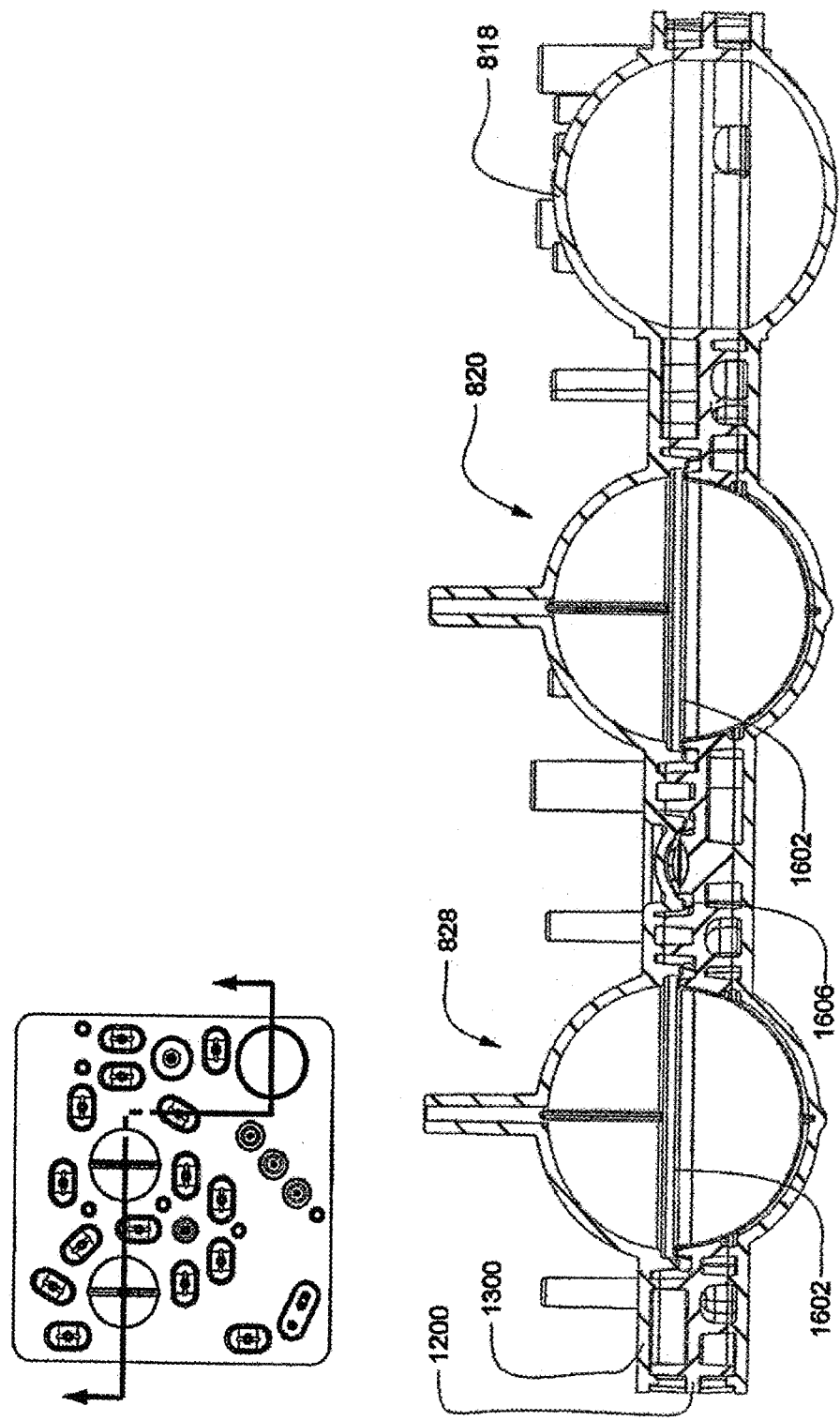
Figure 15B:
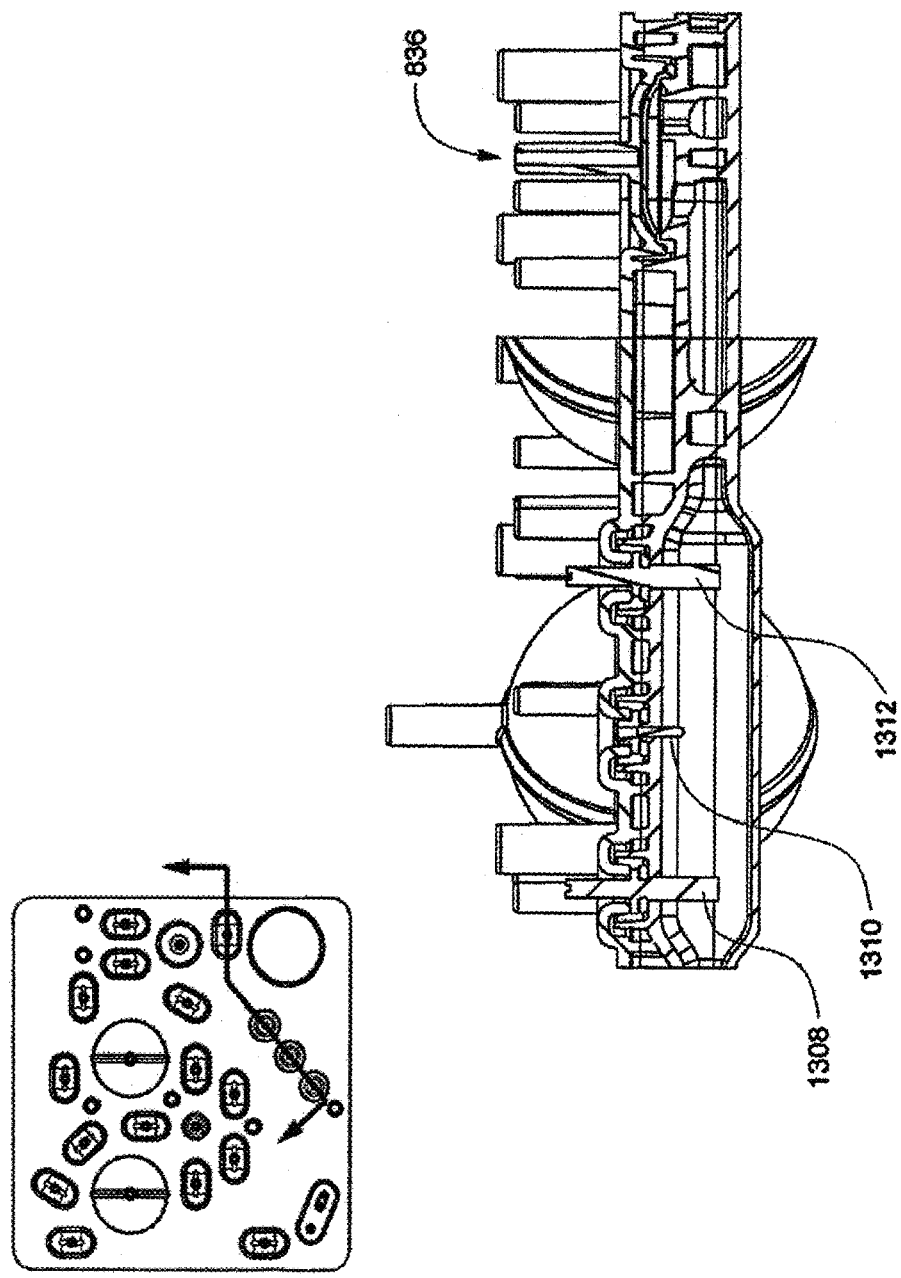
Figure 16A:
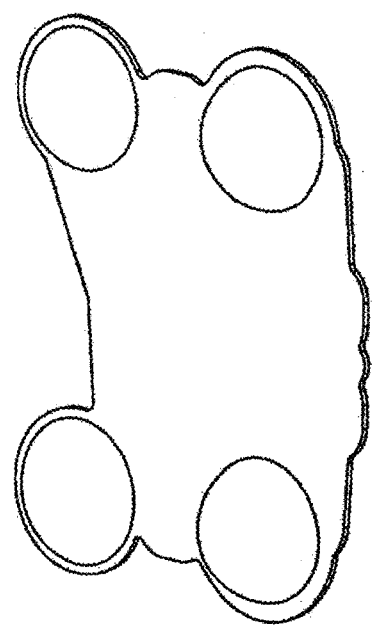
FIG. 16A shows an isometric view.
Figure 16B:
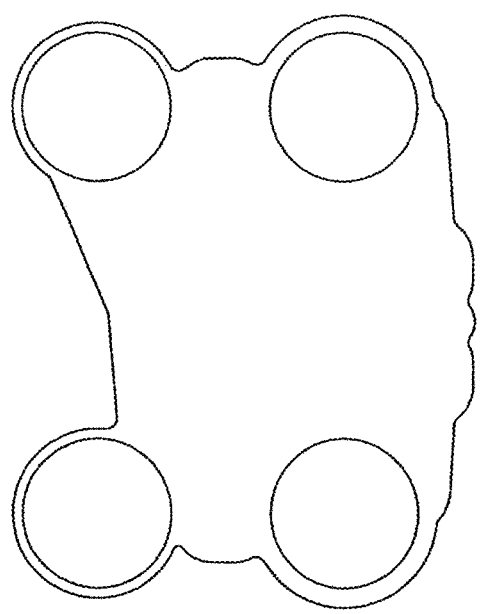
FIG. 16B shows a top view of an alternate embodiment of the top plate according to an alternate embodiment of the cassette.
Figure 16C:
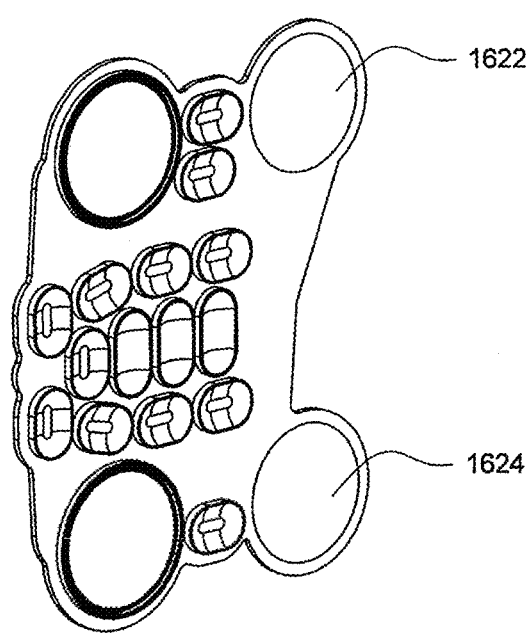
FIGS. 16C and 16D show bottom views of an alternate embodiment of the top plate according to an alternate embodiment of the cassette.
Figure 16D:
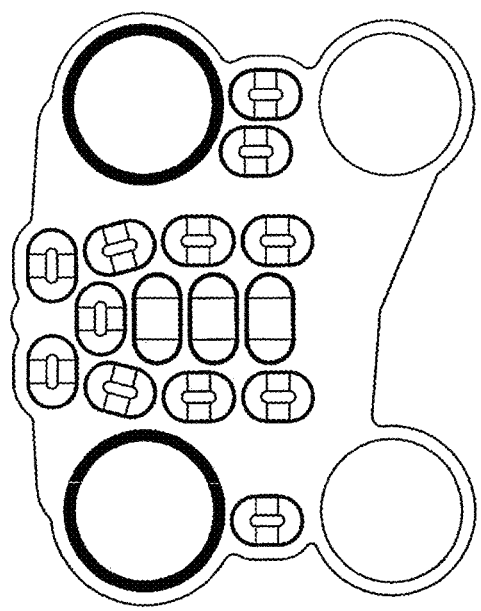
Figure 16E:
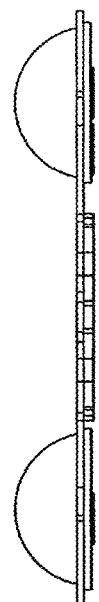
FIG. 16E shows a side view of the alternate embodiment of the top plate.
Figure 17A:
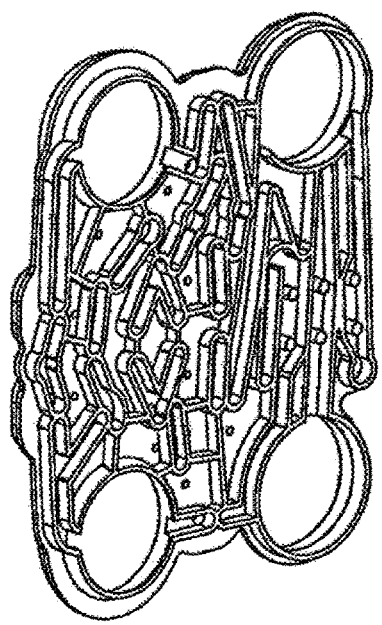
FIG. 17A shows an isometric view.
Figure 17B:
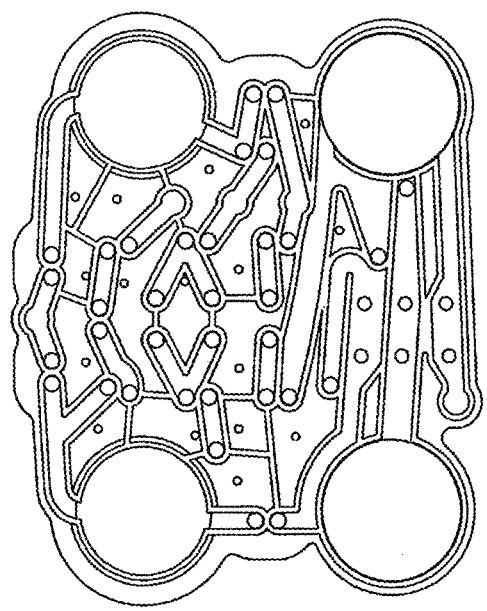
FIG. 17B shows a top view of an alternate embodiment of the midplate according to an alternate embodiment of the cassette.
Figure 17C:
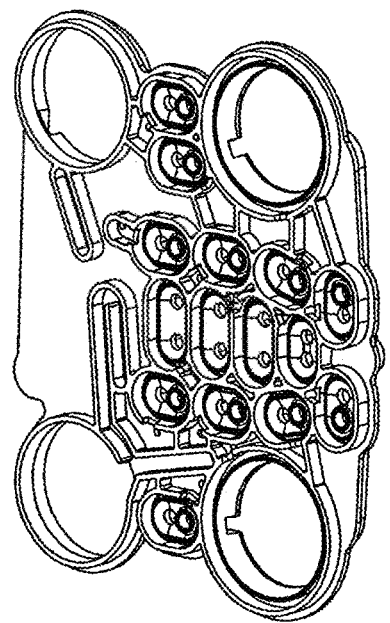
FIG. 17C shows an isometric view.
Figure 17D:
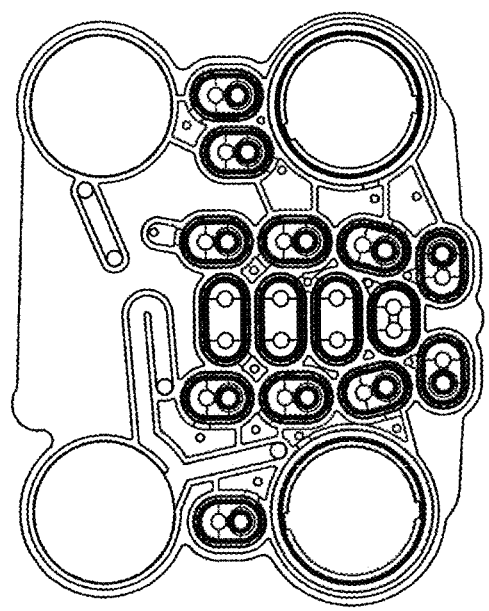
FIG. 17D shows a bottom view of an alternate embodiment of the midplate according to an alternate embodiment of the cassette.
Figure 17E:
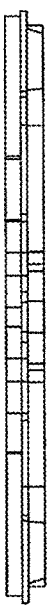
FIG. 17E shows a side view of the alternate embodiment of the midplate.
Figure 18A:
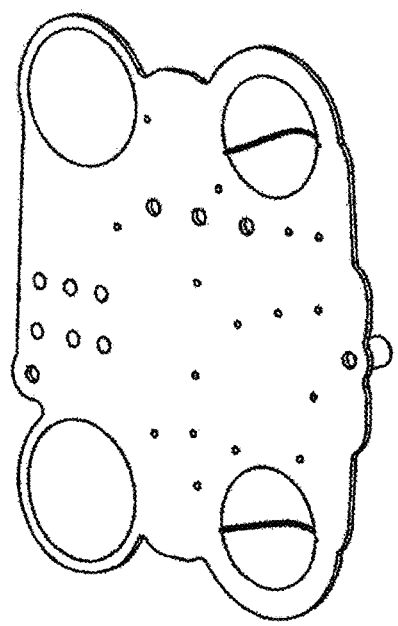
FIG. 18A shows an isometric view.
Figure 18B:
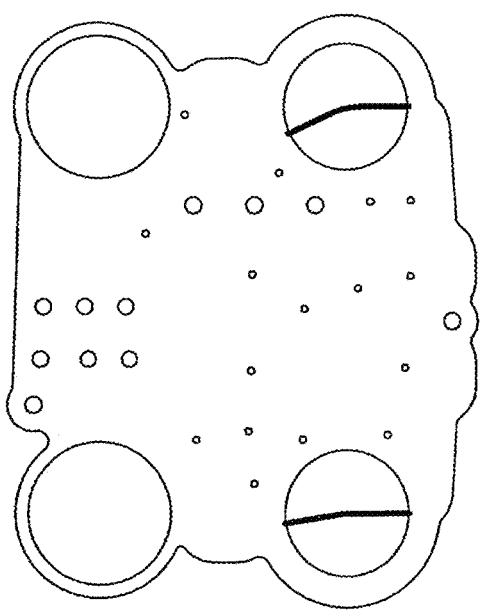
FIG. 18B shows a top view of an alternate embodiment of the bottom plate according to an alternate embodiment of the cassette.
Figure 18C:
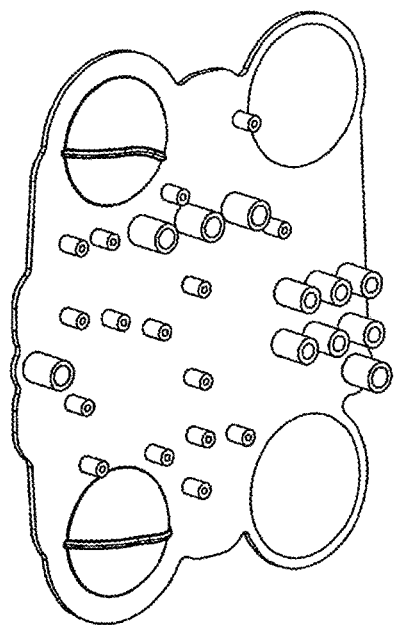
FIG. 18C shows an isometric view.
Figure 18D:
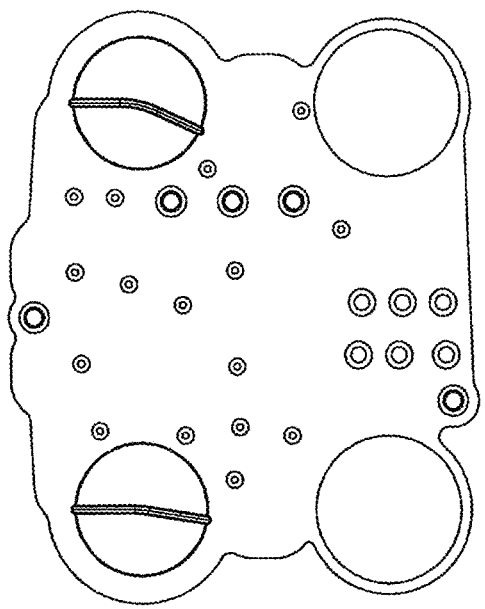
FIG. 18D shows a bottom views of an alternate embodiment of the bottom according to an alternate embodiment of the cassette.
Figure 18E:
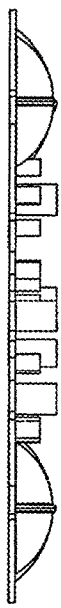
FIG. 18E shows a side view of the alternate embodiment of the bottom plate.

Referring now to FIGS. 15A-15C, various cross sectional views of the assembled cassette are shown. Referring first to FIG. 15A, the membranes 1602 are shown in a pod pumps 820, 828. As can be seen from the cross section, the o-ring of the membrane 1602 is sandwiched by the midplate 1200 and the bottom plate 1300. A valve membrane 1606 can also be seen. As discussed above, each valve includes a membrane.

Referring now to FIG. 15B, the two conductivity sensors 1308, 1312 and the temperature sensor 1310 are shown. As can be seen from the cross section, the sensors 1308, 1310, 1312 are in the fluid line 824. Thus, the sensors 1308, 1310, 1312 are in fluid connection with the fluid line and can determine sensor data of the fluid exiting fluid outlet one 824. Still referring to FIG. 15B, a valve 836 cross section is shown. As shown in this figure, in the exemplary embodiment, the valves are volcano valves similar to the embodiment shown and described above with respect to FIG. 2B. However, as discussed above, in alternate embodiment, other valves are used including, but not limited to, those described and shown above with respect to FIGS. 2A, 2C and 2D.

Referring now to FIG. 15C, the two conductivity sensor elements 1318, 1320 and the temperature sensor element 1322 are shown. As can be seen from the cross section, the sensor elements 1318, 1320, 1322 are in the fluid line 824. Thus, the sensor elements 1318, 1320, 1322 are in fluid connection with the fluid line and can be used to determine sensor data of the fluid entering the mixing chamber (not shown in this figure). Thus, in the exemplary embodiment, the sensor elements 1318, 1320, 1322 are used to collect data regarding fluid being pumped into the mixing chamber. Referring back to FIG. 12C, sensor elements 1308, 1310, 1312 are used to collect data regarding fluid being pumped from the mixing chamber and to the fluid outlet. However, in alternate embodiments, no sensors are or only one set, or only one type of sensor element (i.e., either temperature or conductivity sensor element) is used. Any type of sensor may be used and additionally, any embodiment of a temperature, a conductivity sensor element or a combined temperature/conductivity sensor element.

As described above, the exemplary embodiment is one cassette embodiment that incorporates the exemplary fluid flow-path schematic shown in FIG. 8. However, there are alternate embodiments of the cassette that incorporate many of the same features of the exemplary embodiment, but in a different structural design and with slightly different flow paths. One of these alternate embodiments is the embodiment shown in FIGS. 16A-20B.

Figure 9:
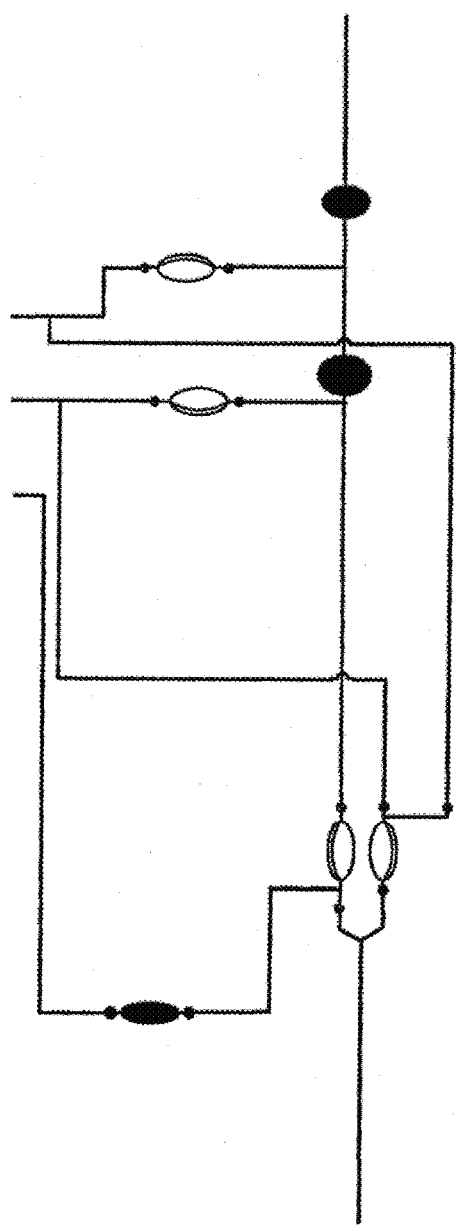
FIG. 9 is an alternate embodiment fluid flow-path schematic for an alternate embodiment of the cassette.

Referring now to FIGS. 16A-16E, views of an alternate embodiment of the top plate 1600 are shown. The features of the top plate 1600 are alternate embodiments of corresponding features in the exemplary embodiment. This alternate embodiment includes two mixing chambers 1622, 1624 and three metering pumps. Thus, this embodiment represents the flexibility in the cassette design. In various embodiments, the cassette can mix any number of fluids, as well, can meter them separately or together. FIG. 9 shows a fluid flow-path schematic of the cassette shown in FIGS. 16A-20B.

Referring now to FIGS. 17A-17E, views of an alternate embodiment of the midplate 1700 are shown. FIGS. 18A-18E show views of an alternate embodiment of the bottom plate 1800.

Figure 19A:
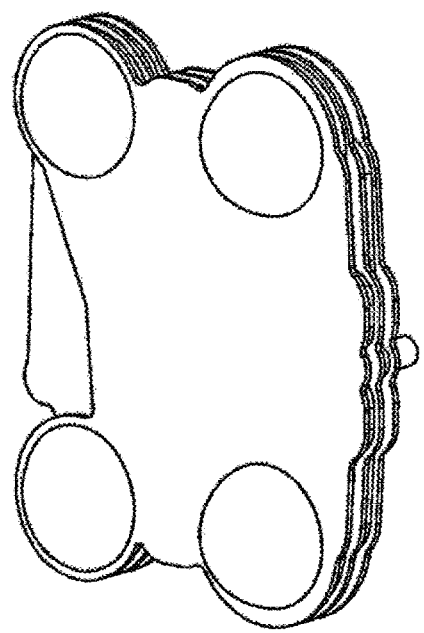
FIG. 19A is a top view of an assembled alternate embodiment of the cassette.
Figure 19B:
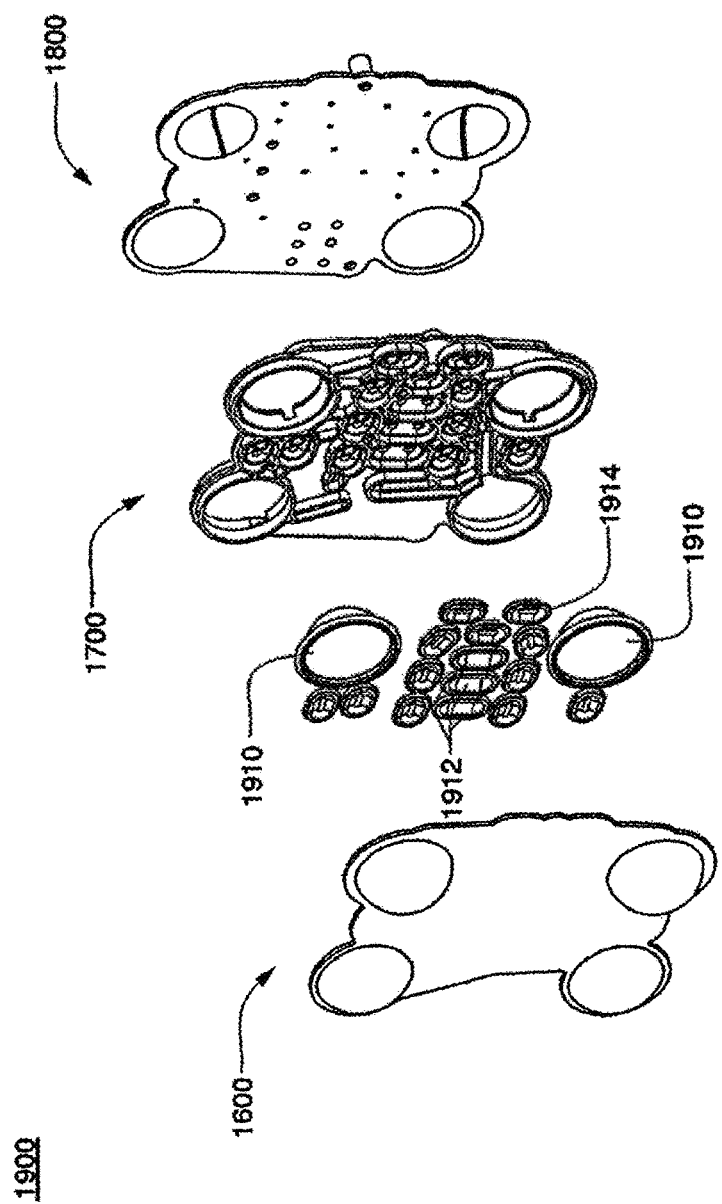
FIG. 19B is an exploded view of the assembled alternate embodiment of the cassette.
Figure 19C:
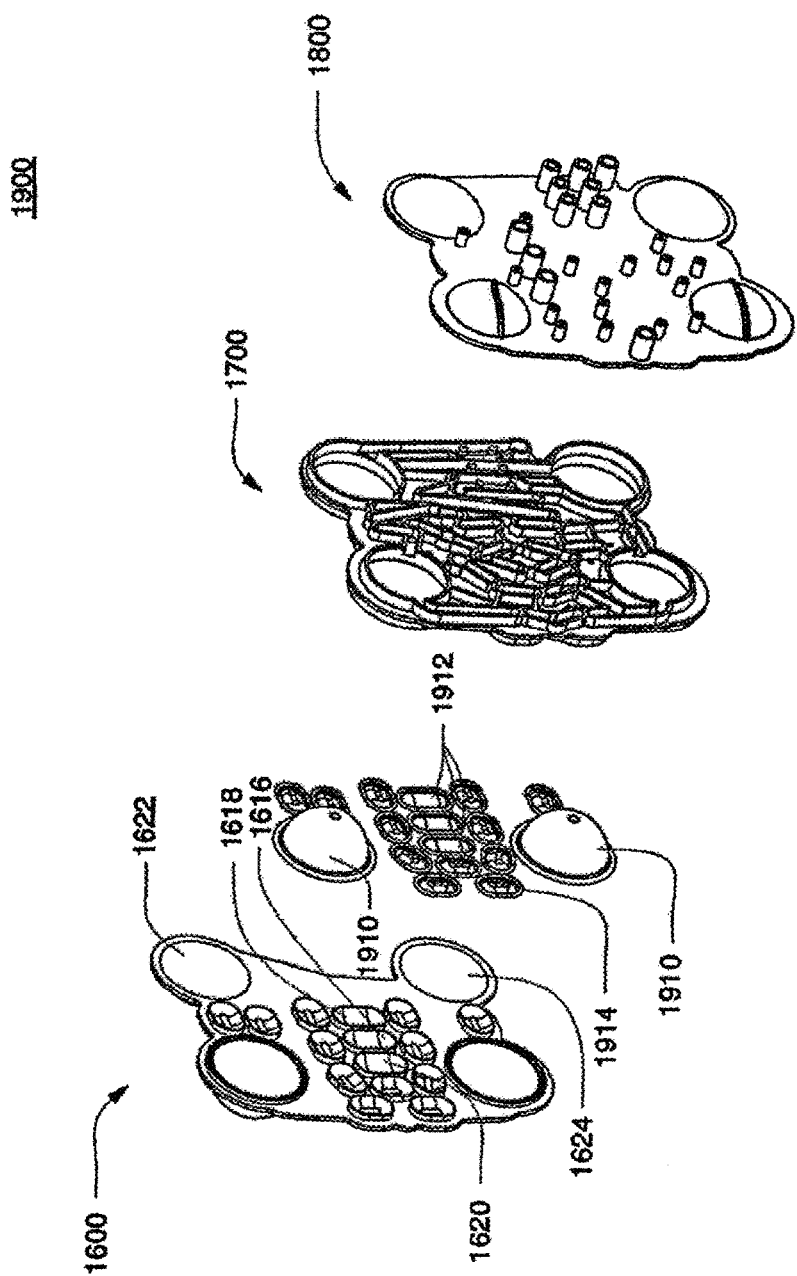
FIG. 19C is an exploded view of the assembled alternate embodiment of the cassette.
Figure 20A:
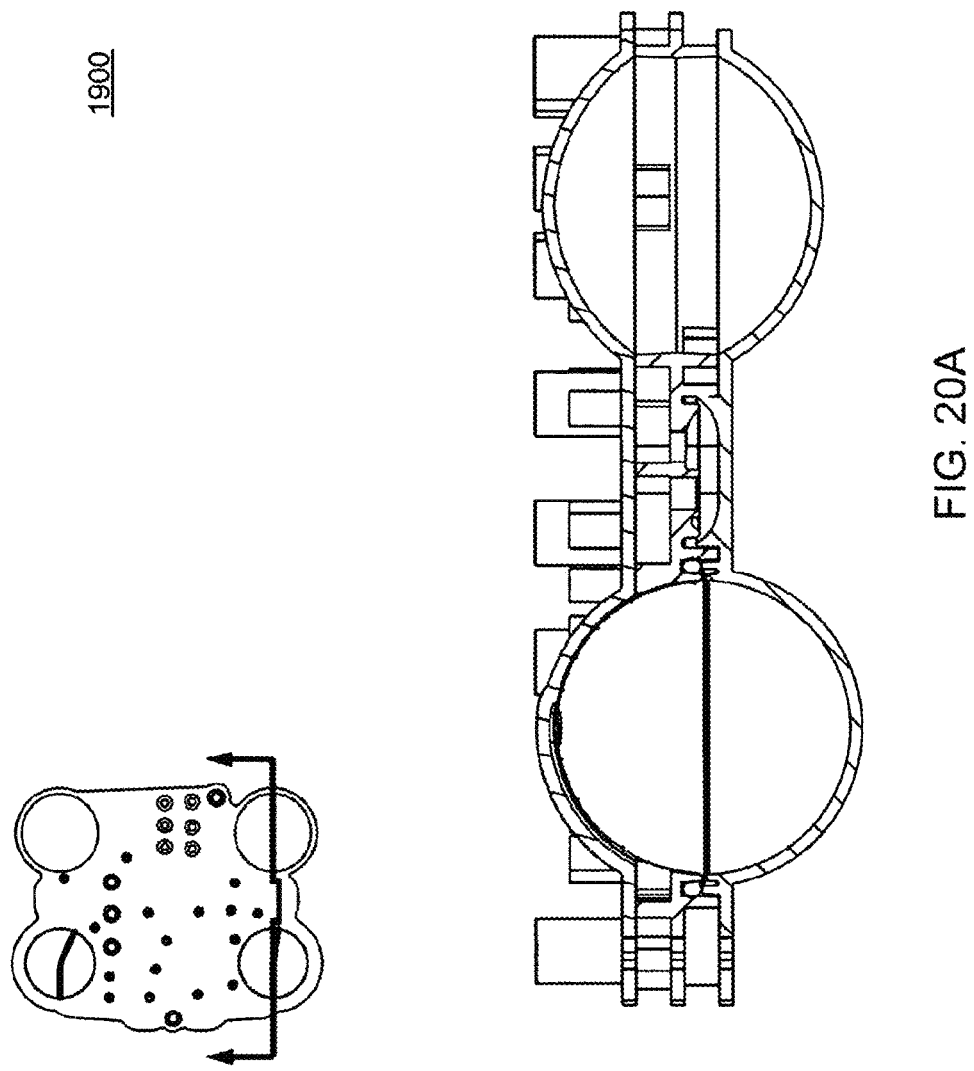

Referring now to FIG. 19A, an assembled alternate embodiment of the cassette 1900 is shown. FIGS. 19C-19D show exploded views of the cassette 1900 where the pod pump membranes 1910, valve membranes 1914 and metering pump membranes 1912 are shown. The three metering pumps 1616, 1618, 1620 can be seen as well as the respective membranes 1912. In this embodiment, three fluids can be metered and controlled volumes of each can be mixed together in the mixing chambers 1622, 1624. FIGS. 20A and 20B show a cross sectional view of the assembled cassette 1900.

As this alternate embodiment shows, there are many variations of the pumping cassette and the general fluid schematic shown in FIG. 8. Thus, additional mixing chambers and metering pumps can add additional capability to the pumping cassette to mix more than two fluids together.

5.3 Exemplary Embodiments of the Mixing Cassette

In practice, the cassette may be used to pump any type of fluid from any source to any location. The types of fluid include nutritive, nonnutritive, inorganic chemicals, organic chemicals, bodily fluids or any other type of fluid. Additionally, fluid in some embodiments includes a gas, thus, in some embodiments; the cassette is used to pump a gas.

The cassette serves to pump and direct the fluid from and to the desired locations. In some embodiments, outside pumps pump the fluid into the cassette and the cassette pumps the fluid out. However, in some embodiments, the pod pumps serve to pull the fluid into the cassette and pump the fluid out of the cassette.

As discussed above, depending on the valve locations, control of the fluid paths is imparted. Thus, the valves being in different locations or additional valves are alternate embodiments of this cassette. Additionally, the fluid lines and paths shown in the figures described above are mere examples of fluid lines and paths. Other embodiments may have more, less and/or different fluid paths. In still other embodiments, valves are not present in the cassette.

The number of pod pumps described above may also vary depending on the embodiment. For example, although the exemplary and alternate embodiments shown and described above include two pod pumps, in other embodiments, the cassette includes one. In still other embodiments, the cassette includes more than two pod pumps. The pod pumps can be single pumps or work in tandem to provide a more continuous flow. Either or both may be used in various embodiments of the cassette.

The various ports are provided to impart particular fluid paths onto the cassette. These ports are not necessarily all used all of the time, instead, the variety of ports provide flexibility of use of the cassette in practice.

The pumping cassette can be used in a myriad of applications. However, in one exemplary embodiment, the pumping cassette is used to mix a solution that includes at least two ingredients/compounds. In the exemplary embodiment, three ingredients are mixed. However, in other embodiments, less than three or more than three can be mixed by adding metering pumps, mixing chambers, inlets/outlets, valves and fluid lines. These variations to the cassette design are readily discernable.

As used herein, the terms "source ingredient" or "sources of ingredients" refers to ingredients other than the fluid pumped into the cassette from the first fluid inlet. These source ingredients are contained in a container, or provided by a source, connected to the cassette.

In the exemplary embodiment, the pumping cassette includes the ability to connect four sources of ingredients to the cassette in addition to the fluid inlet line. In the exemplary embodiment, the fluid inlet is connected to a water source. However, in other embodiments, the fluid inlet line is connected to a container of a liquid/fluid solution or to another source of fluid/liquid.

In the exemplary embodiment, the four additional sources of ingredients can be four of the same source ingredients, or two of one source ingredient and two of another. Using two of each source ingredient, or four of one source ingredient, pumping and mixing can be done in a continuous manner without having to replace the sources. However, depending on the source, the number of redundant sources of each ingredient will vary. For example, the source could be a connection to a very large container, a smaller container or a seemingly "endless" source. Thus, depending on the volume being pumped and the size of the source, the number of containers of a source ingredient may vary.

One of the fluid paths described above with respect to FIG. 8 includes a path where the pod pumps pump liquid into the cassette and to two of the source ingredients sources or containers. This available functionality of the cassette allows two of the source ingredients to be, at least initially, powder that is constituted with the fluid/liquid from the fluid inlet line. As well, there is a valving path for both pod pumps that can accomplish pumping fluid to the ingredient sources. Thus, in one embodiment, the valves are controlled for a period of time such that continuous pumping of fluid into the fluid inlet and to two source ingredient containers is accomplished. This same valving path can be instituted to the other two source ingredient containers or to one of the other two source ingredient containers in addition to or in lieu of the valving path shown in FIG. 8. In other embodiments, fluid inlet liquid is pumped to only one source ingredient container.

Additionally, in some embodiments, fluid is pumped into the fluid inlet and to the source ingredients where the source ingredients are fluid. This embodiment may be used in situations where the fluid inlet fluid is a source ingredient that needs to be mixed with one of the source ingredients prior to pumping. This functionality can be designed into any embodiment of the pumping cassette. However, in some embodiments, this valving path is not included.

In the exemplary embodiment, the metering pumps allow for the pumping of the source ingredients in known volumes.

Thus, careful pumping allows for mixing a solution requiring exact concentrations of the various ingredients. A single metering pump could pump multiple source ingredients. However, as an ingredient is pumped, small amounts of that ingredient may be present in the metering fluid line and thus, could contaminate the ingredient and thus, provide for an incorrect assessment of the volume of that second ingredient being pumped. Therefore, in the exemplary embodiment, at least one metering pump is provided for each source ingredient, and thus, a single metering pump is provided for two sources of source ingredients where those two sources contain identical source ingredients.

In the exemplary embodiment, for each source ingredient, a metering pump is provided. Thus, in embodiments where more than two source ingredients are present, additional metering pumps may be included for each additional source ingredient in the pumping cassette. In the exemplary embodiment, a single metering pump is connected to two source ingredients because in the exemplary embodiment, these two source ingredients are the same. However, in alternate embodiments, one metering pump can pump more than one source ingredient and be connected to more than one source ingredient even if they are not the same.

Sensors or sensor elements may be included in the fluid lines to determine the concentration, temperature or other characteristic of the fluid being pumped. Thus, in embodiments where the source ingredient container included a powder, water having been pumped by the cassette to the source ingredient container to constitute the powder into solution, a sensor could be used to ensure the correct concentration of the source ingredient. Further, sensor elements may be included in the fluid outlet line downstream from the mixing chamber to determine characteristics of the mixed solution prior to the mixed solution exiting the cassette through the fluid outlet. Additionally, a downstream valve can be provided to ensure badly mixed solution is not pumped outside the cassette through the fluid outlet. Discussion of the exemplary embodiment of the sensor elements is included above.

One example of the pumping cassette in use is as a mixing cassette as part of a hemodialysis system. The mixing cassette would be used to mix dialysate to feed a dialysate reservoir outside the cassette. Thus, the cassette would be connected to two containers of each citric acid and NaCl/bicarbonate. Two metering pumps are present in the cassette, one dedicated to the citric acid and the other to the NaCl/Bicarbonate. Thus, one metering pump works with two source ingredient containers.

In the exemplary embodiment, the NaCl/Bicarbonate is a powder and requires the addition of water to create the fluid source ingredient solution. Thus, water is pumped into the first fluid inlet and into the source containers of NaCl/Bicarbonate. Both pod pumps can pump out of phase to rapidly and continuously provide the necessary water to the source containers of NaCl/Bicarbonate.

To mix the dialysate, the citric acid is pumped by a metering pump into a pod pump and then towards the mixing chamber. Water is pumped into the pod pumps as well, resulting in a desired concentration of citric acid. Sensor elements are located upstream from the mixing chamber to determine if the citric acid is in the proper concentration and also, the pod pumps can pump additional water towards the mixing chamber if necessary to achieve the proper concentration.

The NaCl/Bicarbonate is pumped by the second metering pump and into the fluid outlet line upstream from the mixing chamber. The citric acid and fluid NaCl/Bicarbonate will enter the mixing chamber. The two source ingredients will then mix and be pumped out the fluid outlet.

In some embodiments, sensor elements are located downstream from the mixing chamber. These sensor elements can ensure the concentration of the finished solution is proper. Also, in some embodiments, a valve may be located downstream from the fluid outlet. In situations where the sensor data shows the mixing has not been successful or as desired, this valve can block the dialysate from flowing into the reservoir located outside the cassette.

In alternate embodiments of the cassette, addition metering pumps can be includes to remove fluid from the fluid lines. Also, additional pod pumps may be included for additional pumping features. In alternate embodiments of this dialysate mixing process, three metering pumps and two mixing chambers are used (as shown in FIG. 9). The citric acid, salt, and bicarbonate are each pumped separately in this embodiment. One mixing chamber is similar to the one described above, and the second mixing chamber is used to mix the salt and bicarbonate prior to flowing to the other mixing chamber, where the mixing between the citric acid, NaCl/Bicarbonate will be accomplished.

Various embodiments of the cassette for mixing various solutions are readily discernable. The fluid lines, valving, metering pumps, mixing chambers, pod pumps and inlet/outlets are modular elements that can be mixed and matched to impart the desired mixing functionality onto the cassette.

In various embodiments of the cassette, the valve architecture varies in order to alter the fluid flow-path. Additionally, the sizes of the pod pumps, metering pump and mixing chambers may also vary, as well as the number of valves, pod pumps, metering pumps, sensors, mixing chambers and source ingredient containers connected to the cassette. Although in this embodiment, the valves are volcano valves, in other embodiments, the valves are not volcano valves and in some embodiments are smooth surface valves.

6. Exemplary Embodiment of the Middle Cassette

Referring now to FIG. 21, an exemplary embodiment of the fluid schematic of the pumping cassette 3800 is shown. Other schematics are readily discernable and one alternate embodiment of the schematic is shown in FIG. 21. Still referring to FIG. 21, the cassette 3800 includes at least one pod pump 3820, 3828 and at least one vent 3830. The cassette 3800 also includes at least one fluid port. In the schematic, a plurality of ports 3804, 3810, 3824, 3826, 3830, 3832, 3846, 3848, 3850, 3852, 3854 are shown. However, in alternate embodiments, the number of ports and/or locations can be different. The plurality of port options presents a number of possible pumping schematics for any type of fluid for any function.

The cassette additionally includes at least one pod pump 3820, 3828 to pump fluid through at least one port and into and/or out of the cassette. The exemplary embodiment includes two pod pumps 3820, 3828. However, in alternate embodiments, one or more pod pumps are included in the cassette. In the exemplary embodiment, two pod pumps 3820, 3828 may provide for continuous or steady flow. The vent 3830 provides a vent to atmosphere for a fluid reservoir fluidly connected to, but outside of, the cassette.

The fluid schematic of the cassette 3800 shown in FIG. 21 may be embodied into various cassette apparatus. Thus, the various embodiments of the cassette 3800 that include a fluid flow path represented by the fluid schematic shown in FIG. 21 are not the only cassette embodiments that may incorporate this or an alternate embodiment of this fluid schematic. Additionally, the types of valves, the order of actuation of the valves, and the number of pumps may vary in various cassette embodiments of this fluid schematic. Also, additional features may be present in embodiments of the pumping cassette that are not represented in the schematic or on the cassette embodiments shown and described herein.

Still referring to FIG. 21, in one scenario, fluid enters the cassette through a port 3810 and is pumped to either a first pump fluid path 3812 or a second pump fluid path 3818. In one embodiment, pump inlet valves 3808, 3814 alternately open and close, and the valve 3808, 3814 that is open at any given time allows the fluid to flow into its respective fluid path 3812, 3818 and into the respective pod pump 3820, 3828. The respective pump inlet valve 3808, 3814 then closes, and the corresponding pump outlet valve 3816, 3822 opens. The fluid is pumped out of the pod pump 3820, 3828 and though first fluid outlet 3824. However, in other embodiments, both valves 3808, 3814 open and close at the same time. In some embodiments, no valves are in the cassette.

A vent 3830 provides a location for a reservoir or other container or fluid source to vent to atmosphere. In some embodiments, the source of the first fluid is connected to the vent 3830. A valve 3802 controls the venting pathway.

Although in one scenario, fluid is pumped into port 3810, in other embodiments, fluid is pumped into the cassette through any of the ports 3804, 3824, 3826, 3830, 3832, 3846, 3848, 3850, 3852, 3854 and then out of the cassette through any of the ports 3804, 3810, 3824, 3826, 3830, 3832, 3846, 3848, 3850, 3852, 3854. Additionally, the pod pumps 3820, 3828 in various embodiments pump fluid in the opposite direction than described above.

In general, the cassette 3800 provides pumping power to pump fluid as well as fluid flow paths between ports and around the cassette.

In one embodiment, the one or more ports 3804, 3810, 3824, 3826, 3830, 3832, 3846, 3848, 3850, 3852, 3854 are attached to a filter or other treatment area for the fluid being pumped out of the cassette. In some embodiments, pod pumps 3820, 3828 provide enough pumping force to push the fluid through a filter or other treatment area.

In some embodiments, the pumping cassette includes additional fluid paths and one or more additional pod pumps. Additionally, the cassette in some embodiments includes additional venting paths.

The various flow paths possible in the cassette, represented by one embodiment in FIG. 21, are controlled by the valves 3802, 3808, 3814, 3816, 3822, 3836, 38338, 3840, 3842, 3844, 3856. Opening and closing the valves 3802, 3808, 3814, 3816, 3822, 3836, 3838, 3840, 3842, 3844, 3856 in different orders leads to very different fluid pumping paths and options for pumping. Referring now to FIGS. 23C, 24A, 24B and 24C, the various valves and ports are shown on an exemplary embodiment of the cassette.

In some embodiments of the pumping cassette, more valves are included or additional flow paths and/or ports are included. In other embodiments, there are a smaller number of valves, flow paths and/or ports. In some embodiments of the cassette, the cassette may include one or more air traps, one or more filters, and/or one or more check valves.

The embodiments of the fluid flow-path schematic shown in FIG. 21, or alternate embodiments thereof, can be embodied into a structure. In the exemplary embodiment, the structure is a three plate cassette with actuating membranes. Alternate embodiments of the cassette are also described below.

Figure 23A:
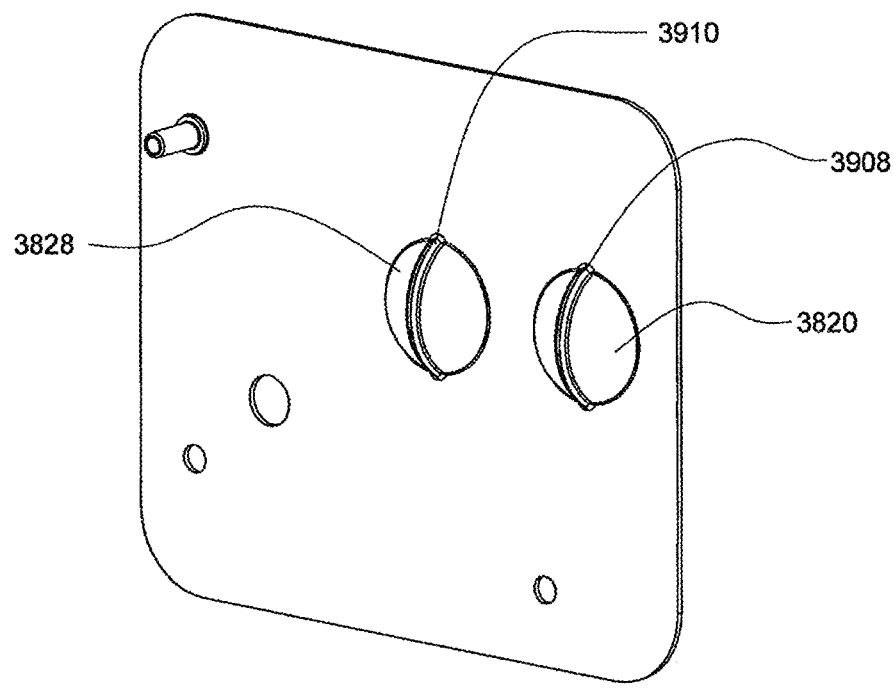
FIGS. 23A and 23B are isometric and front views of the exemplary embodiment of the outer top plate of the exemplary embodiment of the cassette.
Figure 23B:
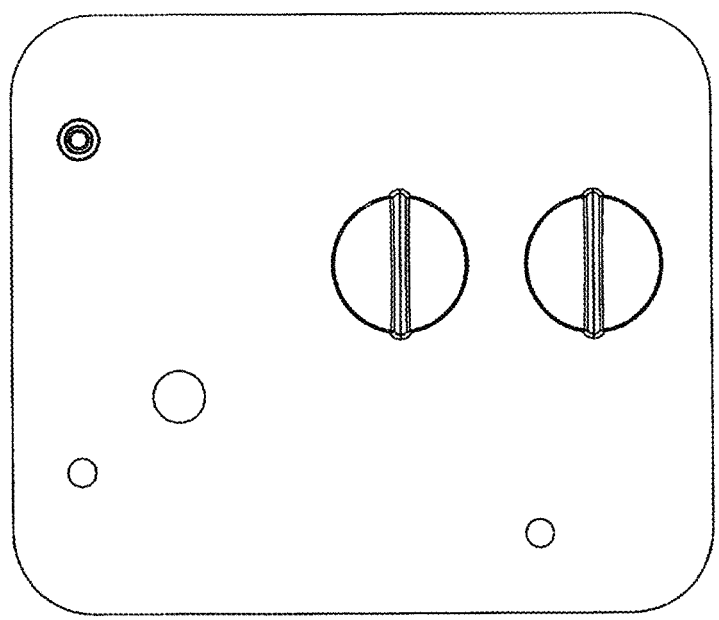

Referring now to FIGS. 23A and 23B, the outer side of the top plate 3900 of the exemplary embodiment of the cassette is shown. The top plate 3900 includes one half of the pod pumps 3820, 3828. This half is the fluid/liquid half where the source fluid will flow through. The inlet and outlet pod pump fluid paths are shown. These fluid paths lead to their respective pod pumps 3820, 3828.

The pod pumps 3820, 3828 include a raised flow path 3908, 3910. The raised flow path 3908, 3910 allows for the fluid to continue to flow through the pod pumps 3820, 3828 after the membrane (not shown) reaches the end of stroke. Thus, the raised flow path 3908, 3910 minimizes the membrane causing air or fluid to be trapped in the pod pump 3820, 3828 or the membrane blocking the inlet or outlet of the pod pump 3820, 3828, which would inhibit flow. The raised flow path 3908, 3910 is shown in the exemplary embodiment having particular dimensions. In alternate embodiments, the raised flow path 3908, 3910 is larger or narrower, or in still other embodiments, the raised flow path 3908, 3910 can be any dimension as the purpose is to control fluid flow so as to achieve a desired flow rate or behavior of the fluid. Thus, the dimensions shown and described here with respect to the raised flow path, the pod pumps, the valves, or any other aspect are mere exemplary and alternate embodiments. Other embodiments are readily apparent.

Figure 23C:
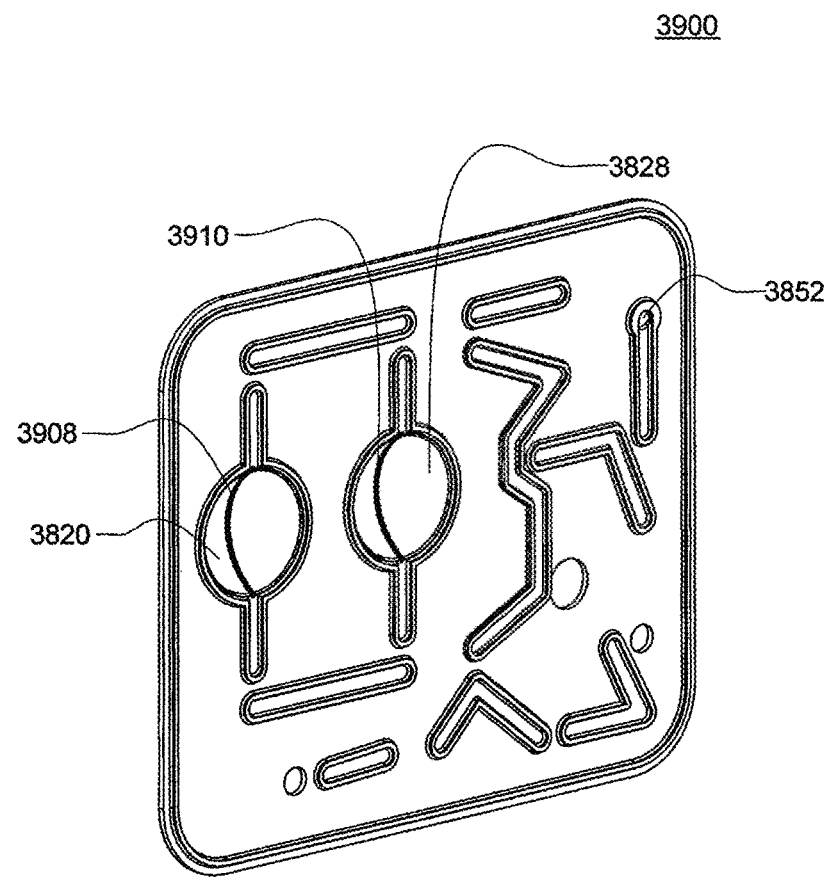
FIGS. 23C and 23D are isometric and front views of the exemplary embodiment of the inner top plate of the cassette.
Figure 23D:
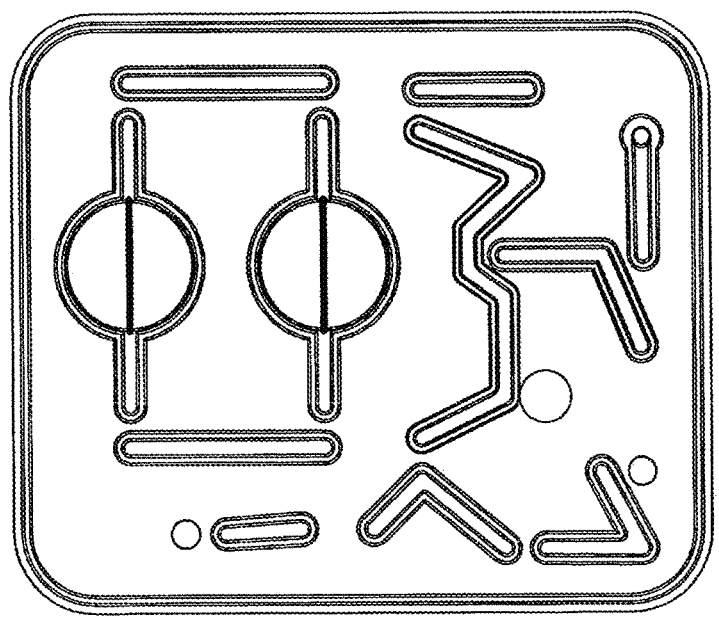
Figure 23E:
FIG. 23E is a side view of the top plate of the exemplary embodiment of the cassette.

FIGS. 23C and 23D show the inner side of the top plate 3900 of the exemplary embodiment of the cassette. FIG. 23F shows a side view of the top plate 3900.

Figure 24A:
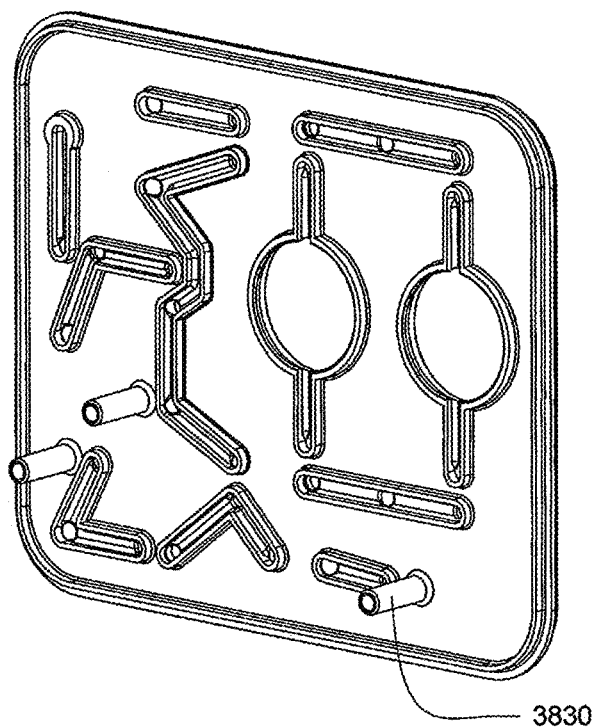
FIGS. 24A and 24B are isometric and front views of the exemplary embodiment of the liquid side of the midplate of the cassette.
Figure 24B:
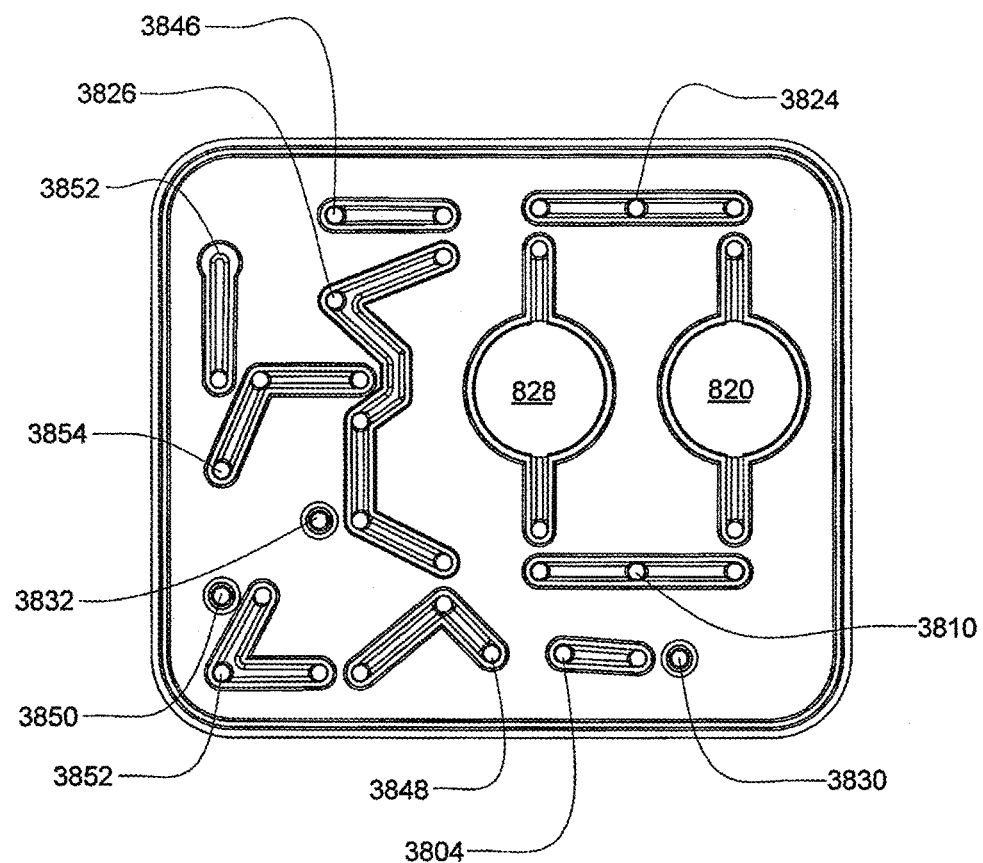

Referring now to FIGS. 24A and 24B, the fluid/liquid side of the midplate 31000 is shown. The areas complementary to the fluid paths on the inner top plate shown in FIGS. 23C and 23D are shown. These areas are slightly raised tracks that present a surface finish that is conducive to laser welding, which is one mode of manufacturing in the exemplary embodiment. Other modes of manufacturing the cassette are discussed above. Referring to FIGS. 24A and 24B, the ports of the exemplary embodiment of the cassette are labeled corresponding to the schematic shown and described above with respect to FIG. 21. One port is not labeled, port 3852. This port is best seen in FIG. 23C.

Figure 24C:
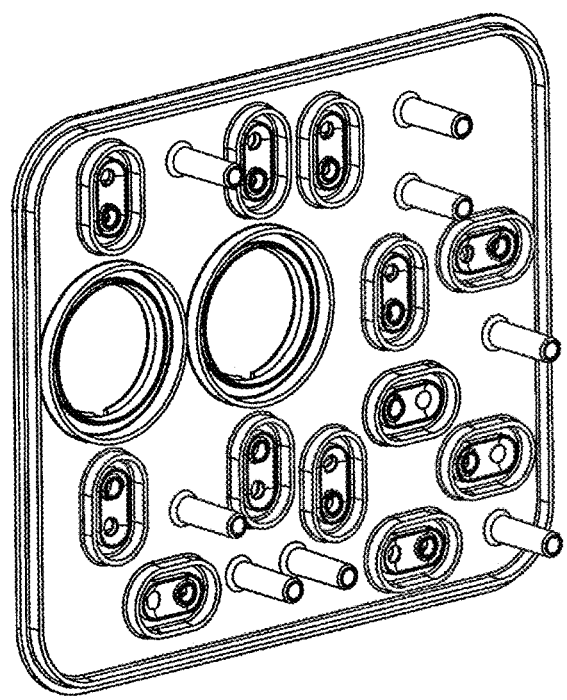
FIGS. 24C and 24D are isometric and front views of the exemplary embodiment of the air side of the midplate of the cassette.
Figure 24D:
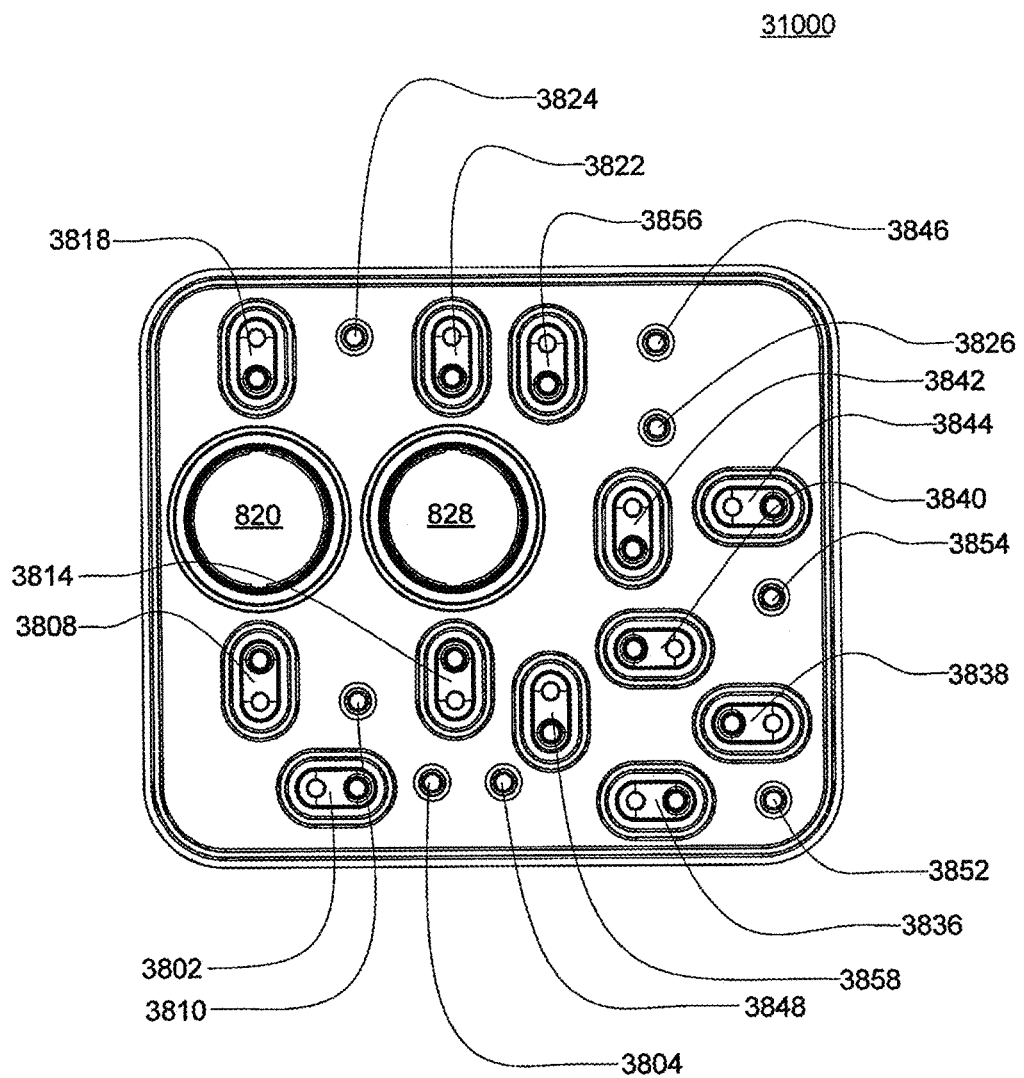
Figure 24E:
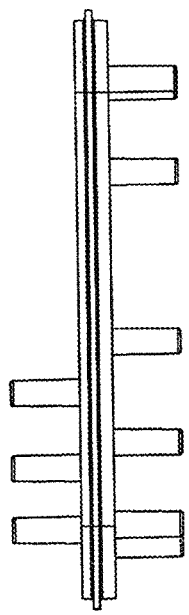
FIG. 24E is a side view of the midplate according to the exemplary embodiment of the cassette.

Referring next to FIGS. 24C and 24D, the air side, or side facing the bottom plate (not shown, shown in FIGS. 25A-25E) of the midplate 31000 is shown according to the exemplary embodiment. The air side of the valve holes 3802, 3808, 3814, 3816, 3822, 3836, 3838, 3840, 3842, 3844, 3856 correspond to the holes in the fluid side of the midplate 31000 (shown in FIGS. 24A and 24B). As seen in FIGS. 26C and 26D, membranes 31220 complete pod pumps 3820, 3828 while membranes 31222 complete valves 3802, 3808, 3814, 3816, 3822, 3836, 38338, 3840, 3842, 3844, 3856. The valves 3802, 3808, 3814, 3816, 3822, 3836, 3838, 3840, 3842, 3844, 3856 are actuated pneumatically, and as the membrane is pulled away from the holes, liquid/fluid is allowed to flow. As the membrane is pushed toward the holes, fluid flow is inhibited. The fluid flow is directed by the opening and closing of the valves 3802, 3808, 3814, 3816, 3822, 3836, 3838, 3840, 3842, 3844, 3856. The exemplary embodiment of the valve is a volcano valve, shown in described above with respect to FIGS. 2A and 2B. One embodiment of the valve membrane 31222 is shown in FIG. 2E, alternate embodiments are shown in FIGS. 2F-2G.

Figure 25A:
FIGS. 25A and 25B are isometric and front views of the inner side of the bottom plate according to the exemplary embodiment of the cassette.
Figure 25B:
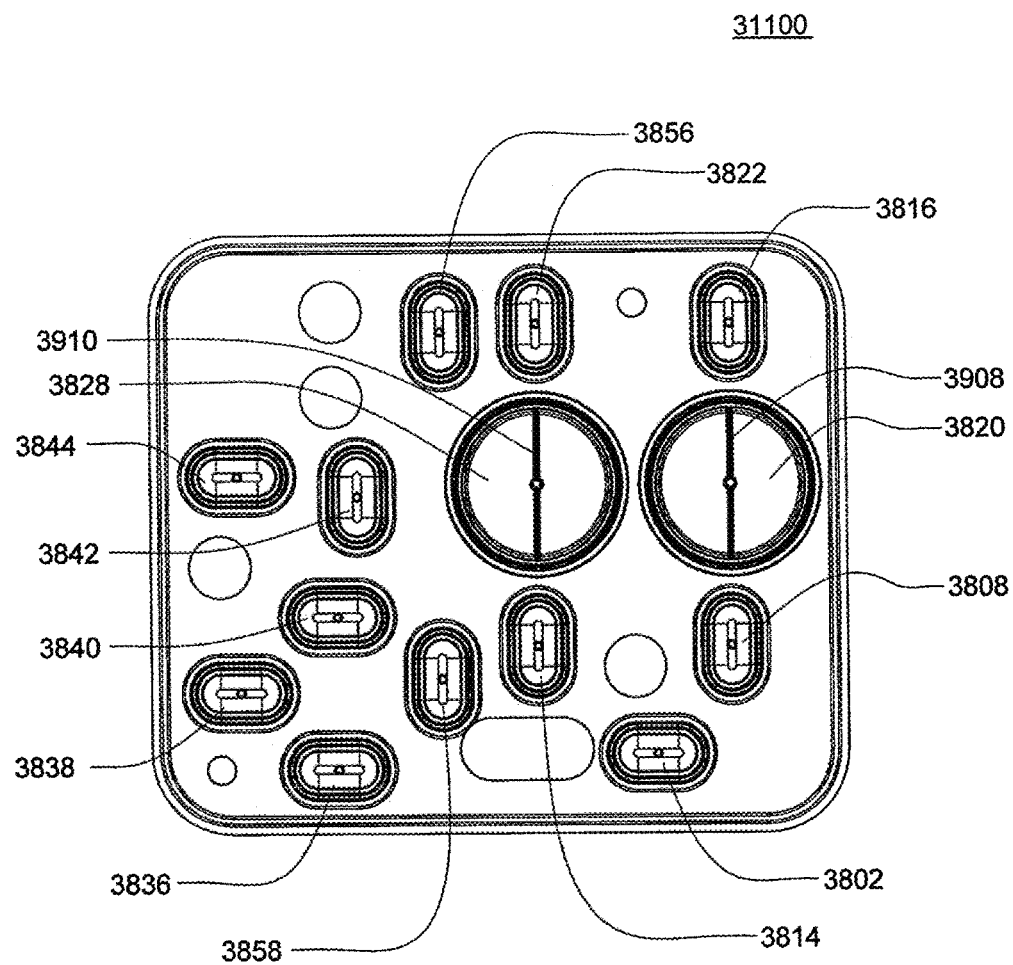
Figure 25C:
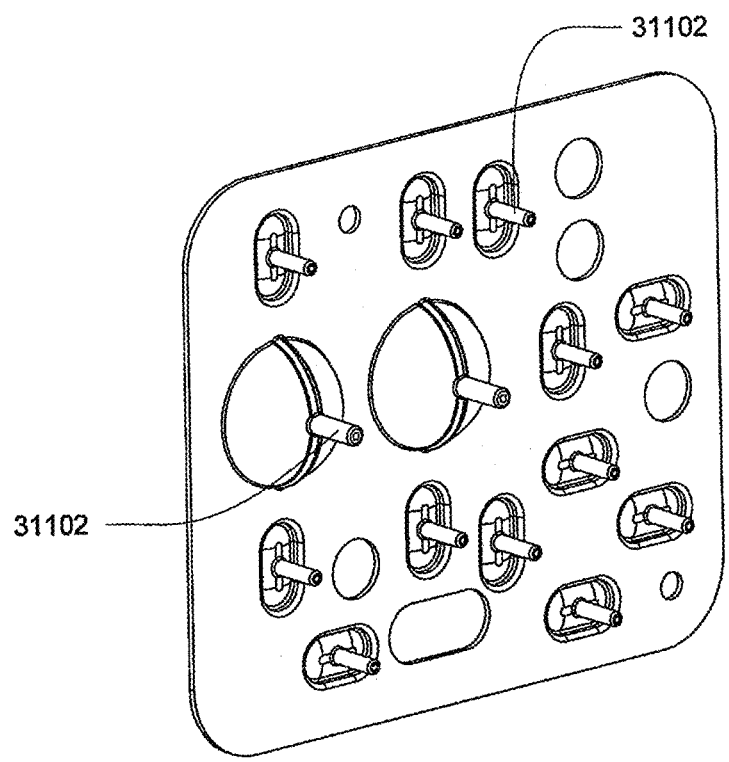
FIGS. 25C and 25D are isometric and front views of the exemplary embodiment of the outer side of the bottom plate of the cassette.
Figure 25D:
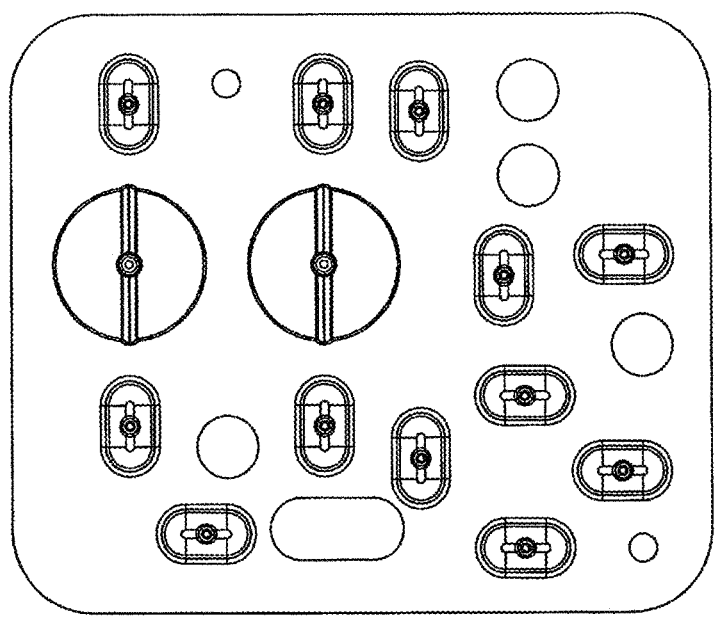
Figure 25E:
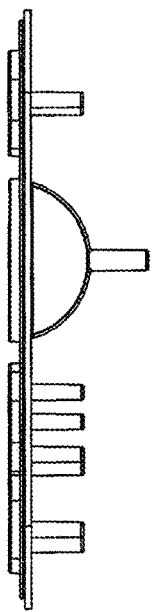
FIG. 25E is a side view of the bottom plate according to the exemplary embodiment of the cassette.

Referring next to FIGS. 25A and 25B, the inner view of the bottom plate 31100 is shown. The inside view of the pod pumps 3820, 3828, and the valves 3802, 3808, 3814, 3816, 3822, 3836, 3838, 3840, 3842, 3844, 3856 actuation/air chamber is shown. The pod pumps 3820, 3828, and the valves 3802, 3808, 3814, 3816, 3822, 3836, 3838, 3840, 3842, 3844, 3856 are actuated by a pneumatic air source. Referring now to FIGS. 25C and 25D, the outer side of the bottom plate 31100 is shown. The source of air is attached to this side of the cassette. In one embodiment, tubes connect to the tubes on the valves and pumps 1102. In some embodiments, the valves are ganged, and more than one valve is actuated by the same air line.

Figure 26A:
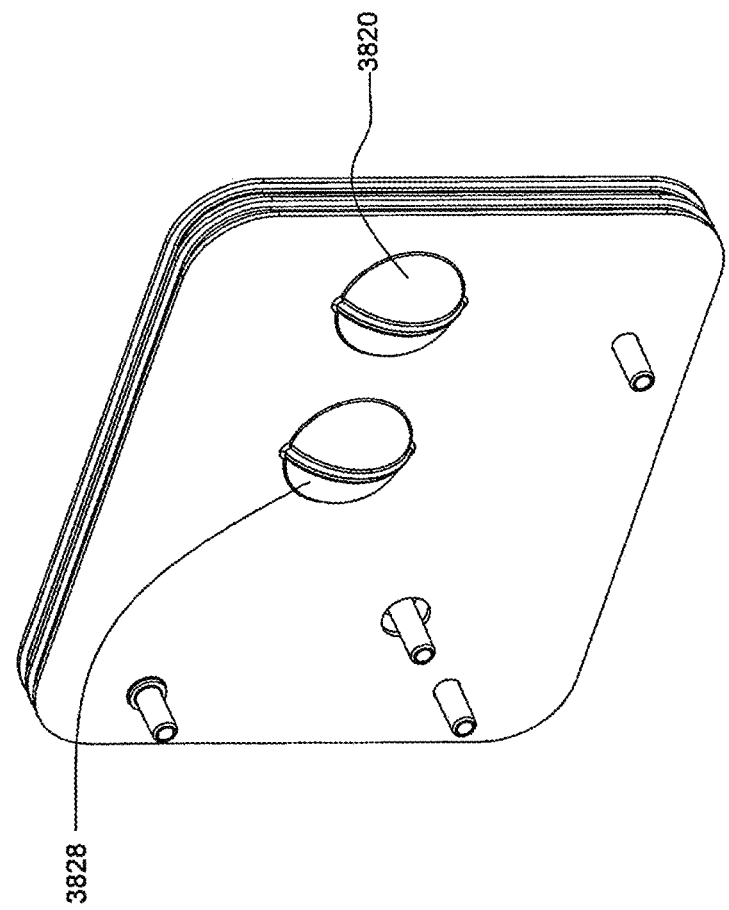
FIG. 26A is a top view of the assembled exemplary embodiment of the cassette.
Figure 26B:
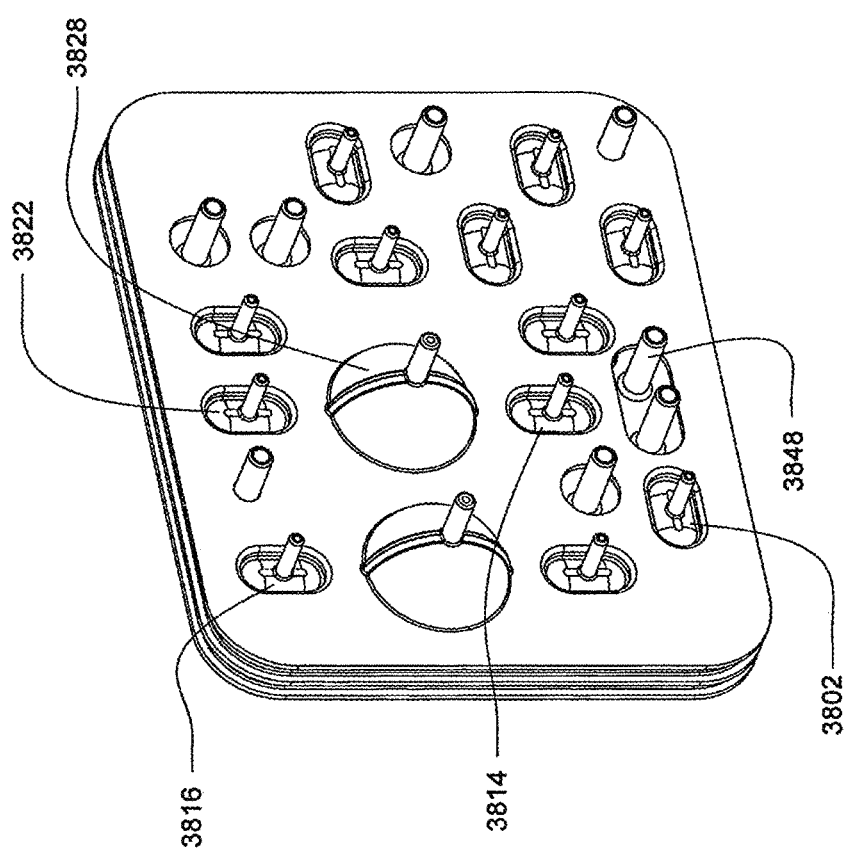
FIG. 26B is a bottom view of the assembled exemplary embodiment of the cassette.
Figure 26C:
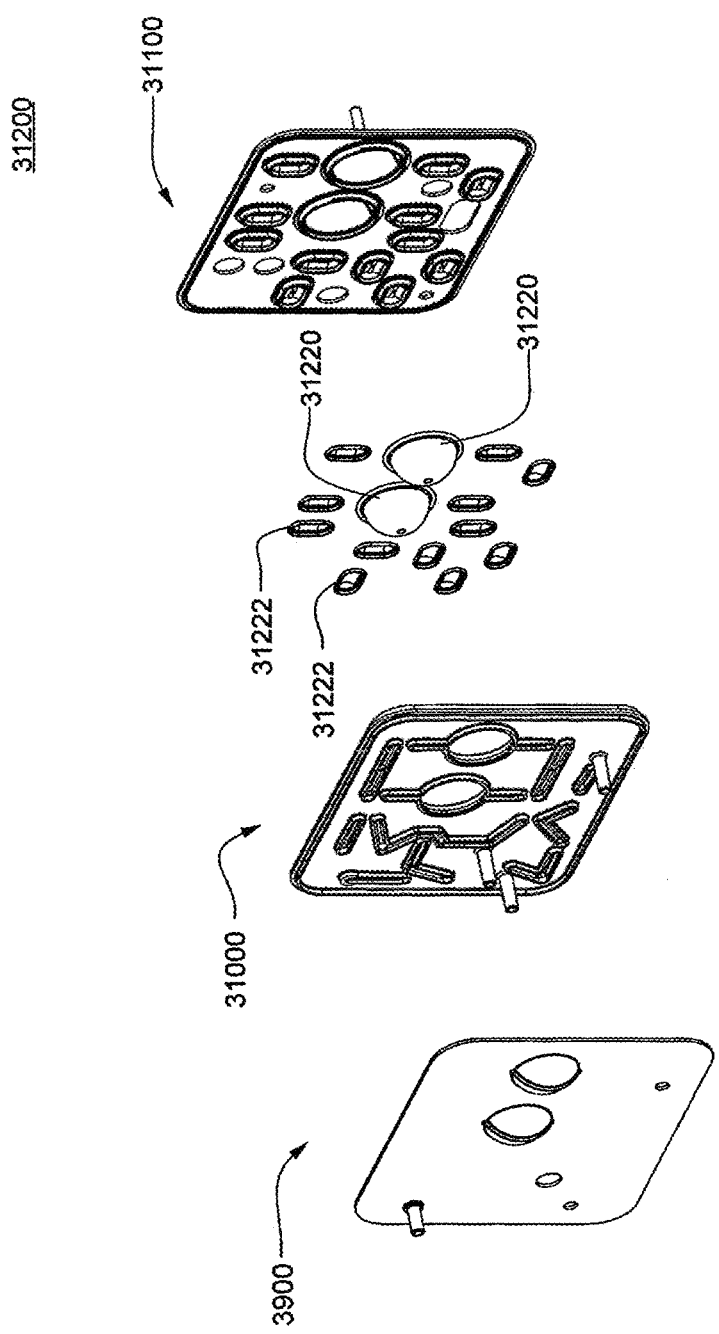
FIG. 26C is an exploded view of the assembled exemplary embodiment of the cassette.

Referring now to FIGS. 26A and 26B, an assembled cassette 31200 is shown. An exploded view of the assembled cassette 31200 shown in FIGS. 26A and 26B is shown in FIGS. 26C and 26D. In these views, the exemplary embodiment of the pod pump membranes 31220 is shown. The exemplary embodiment includes membranes shown in FIGS. 5A-5D. The gasket of the membrane provides a seal between the liquid chamber (in the top plate 3900) and the air/actuation chamber (in the bottom plate 31100). In some embodiment, including those shown in FIGS. 5B-5D, texture on the dome of the membranes 31220 provide, amongst other features, additional space for air and liquid to escape the chamber at the end of stroke. In alternate embodiments of the cassette, the membranes shown in FIGS. 6A-6G may be used. Referring to FIGS. 6A-6G, as discussed in greater detail above, these membranes include a double gasket 62, 64. The double gasket 62, 64 feature would be preferred in embodiments where both sides of the pod pump include liquid or in applications where sealing both chambers' sides is desired. In these embodiments, a rim complementary to the gasket or other feature (not shown) would be added to the inner bottom plate 31100 for the gasket 62 to seal the pod pump chamber in the bottom plate 31100.

Referring now to FIG. 27, a cross sectional view of the pod pumps 3828 in the cassette is shown. The details of the attachment of the membrane 31220 can be seen in this view. Again, in the exemplary embodiment, the membrane 31220 gasket is pinched by the midplate 31000 and the bottom plate 31100. A rim on the midplate 31000 provides a feature for the gasket to seal the pod pump 3828 chamber located in the top plate 3900.

Referring next to FIG. 27, this cross sectional view shows the valves 3834, 3836 in the assembled cassette. The membranes 31220 are shown assembled and are held in place, in the exemplary embodiment, by being sandwiched between the midplate 31000 and the bottom plate 31100.

Still referring to FIG. 27, this cross sectional view also shows a valve 3822 in the assembled cassette. The membrane 31222 is shown held in place by being sandwiched between the midplate 31000 and the bottom plate 31100.

As described above, the exemplary embodiment described above represents one cassette embodiment that incorporates the exemplary fluid flow-path schematic shown in FIG. 21. However, there are alternate embodiments of the cassette that incorporate many of the same features of the exemplary embodiment, but in a different structural design. One of these alternate embodiments is the embodiment shown in FIGS. 28A-34B. An alternate schematic is shown in FIG. 22. This schematic, although similar to the schematic shown in FIG. 21, can be viewed to show the fluid paths of the alternate embodiment shown in FIGS. 28A-34B.

Figure 28A:
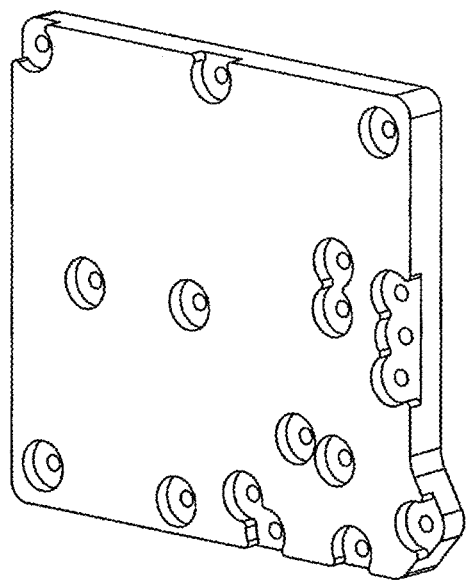
FIGS. 28A and 28B are isometric and front views of an alternate embodiment of the outer top plate of the cassette.
Figure 28B:
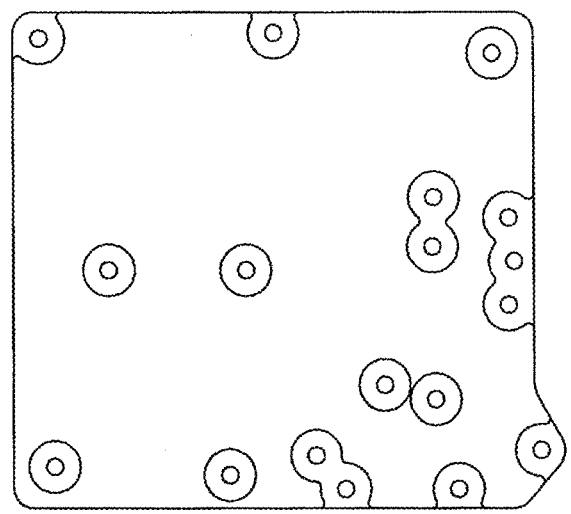
Figure 28C:
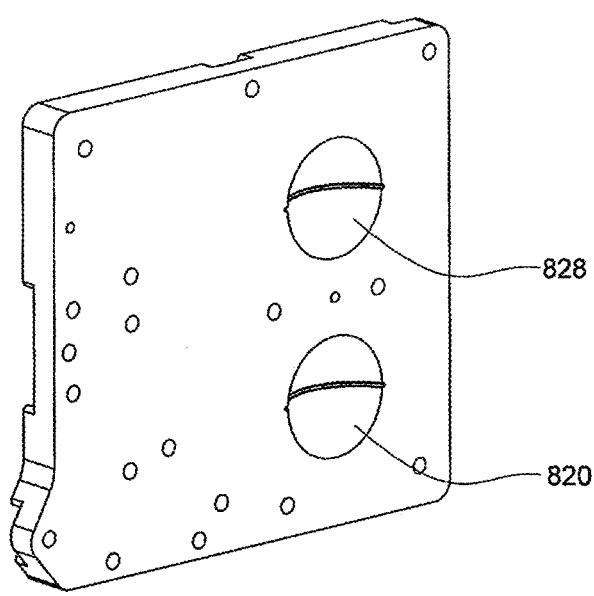
Figure 28D:
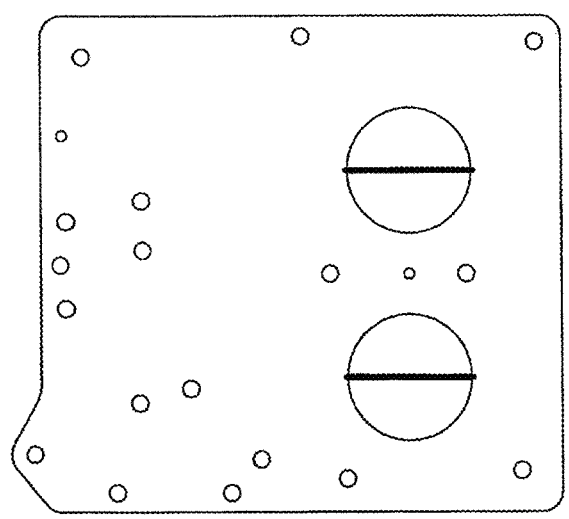
Figure 28E:
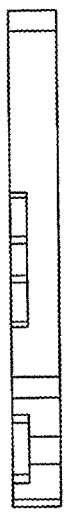
FIG. 28E is a side view of the top plate of an alternate embodiment of the cassette.

Referring now to FIGS. 28A-28E, views of an alternate embodiment of the top plate 31400 are shown. The features of the top plate 31400 are alternate embodiments of corresponding features in the exemplary embodiment. Referring to FIGS. 28C and 28D, the pod pumps 3820, 3828 are cut into the inside of the top plate 1400. And, as can be seen in FIGS. 28A and 28B, the pod pumps 3820, 3828 do not protrude on the outside top plate 31400.

Figure 29:
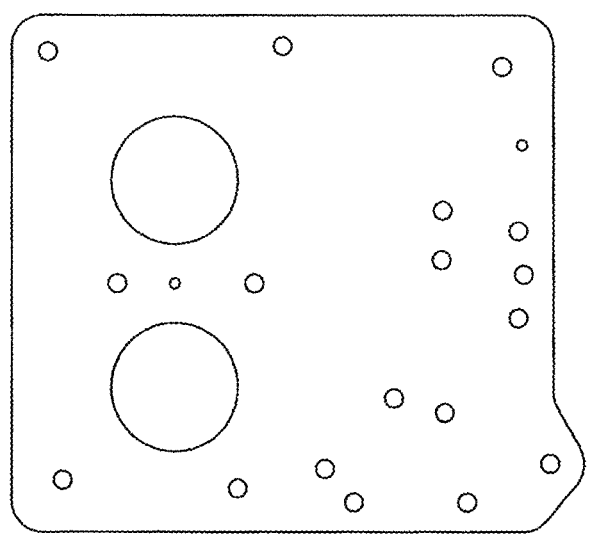
FIG. 29 is a front view of the top plate gasket according to an alternate embodiment of the cassette.
Figure 30A:
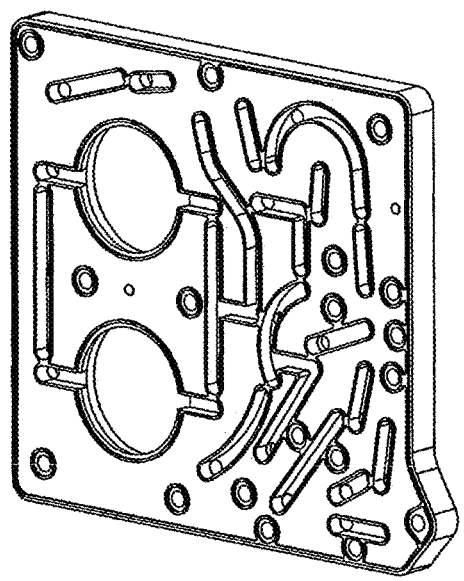
FIGS. 30A and 30B are isometric and front views of an alternate embodiment of the liquid side of the midplate of the cassette.
Figure 30B:
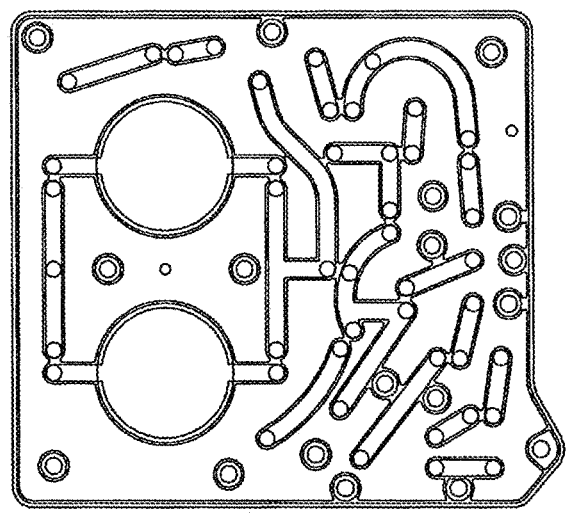
Figure 30C:
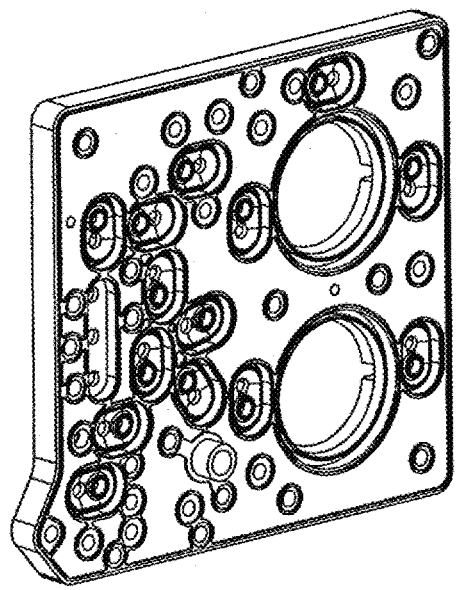
FIGS. 30C and 30D are isometric and front views of an alternate embodiment of the air side of the midplate of the cassette.
Figure 30D:
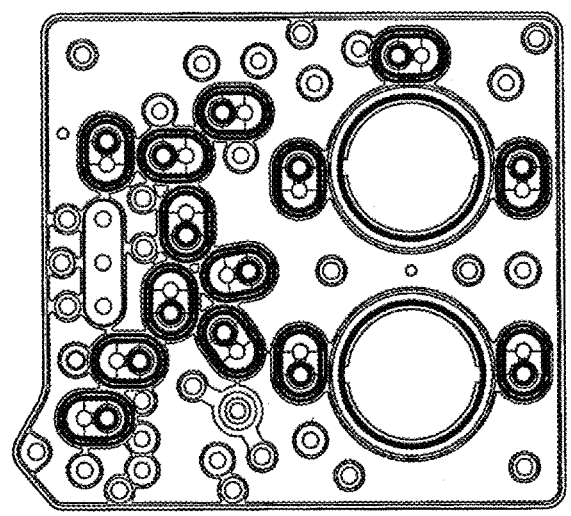
Figure 30E:
FIG. 30E is a side view of the midplate according of an alternate embodiment of the cassette.
Figure 31:
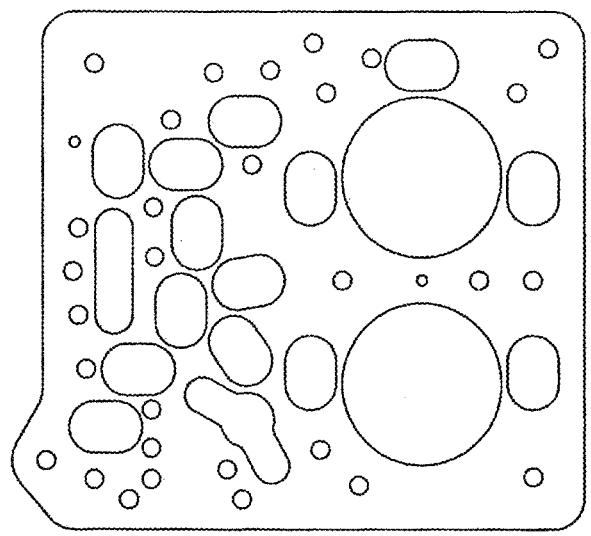
FIG. 31 is a front view of the bottom plate gasket according to an alternate embodiment of the cassette.
Figure 32A:
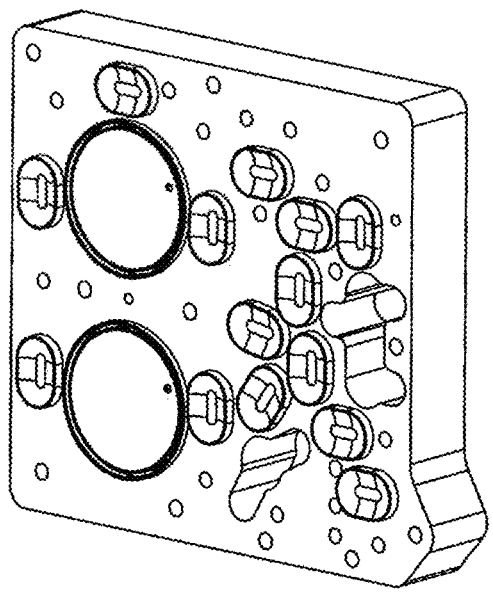
FIGS. 32A and 32B are isometric and front views of an alternate embodiment of the inner side of the bottom plate of the cassette.
Figure 32B:
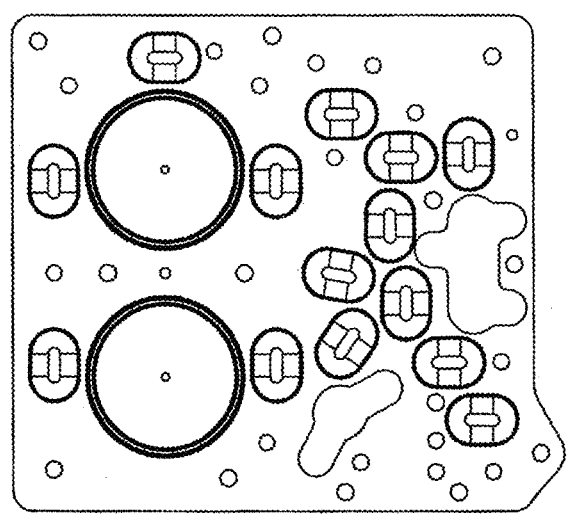
Figure 32C:
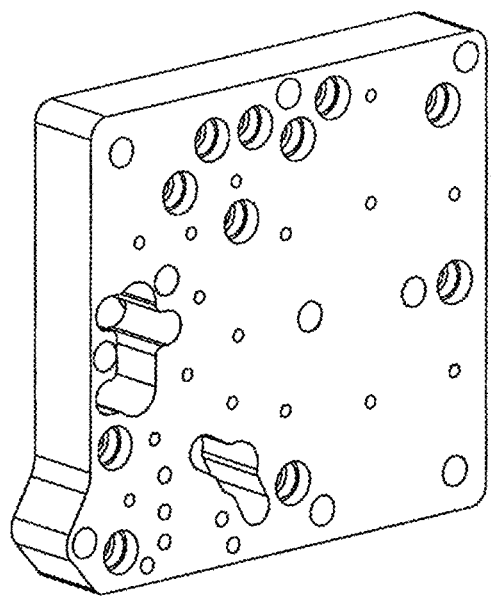
FIGS. 32C and 32D are isometric and front views of an alternate embodiment of the outer side of the bottom plate of the cassette.
Figure 32D:
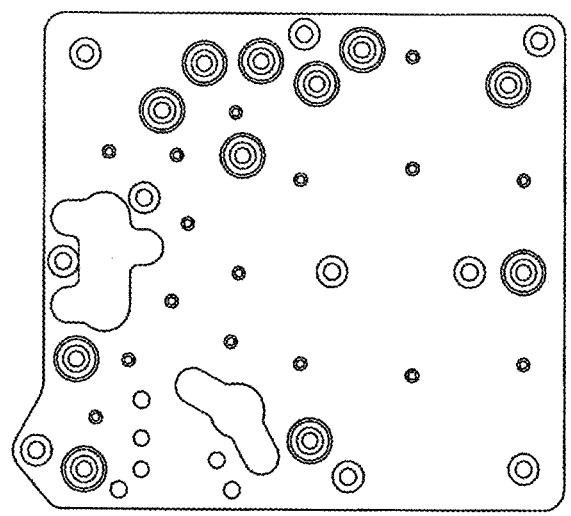
Figure 32E:
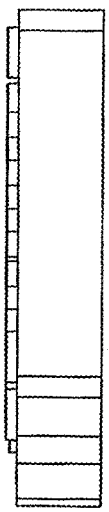
FIG. 32E is a side view of the bottom plate according to an alternate embodiment of the cassette.
Figure 33A:
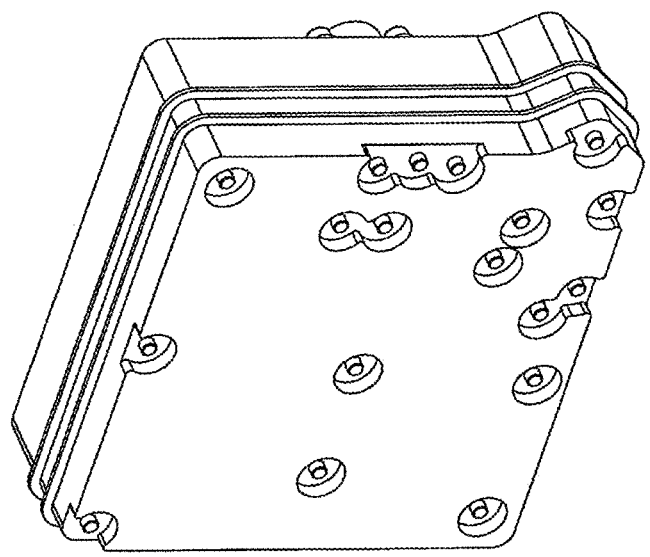
FIG. 33A is a top view of the assembled alternate embodiment of the cassette.
Figure 33B:
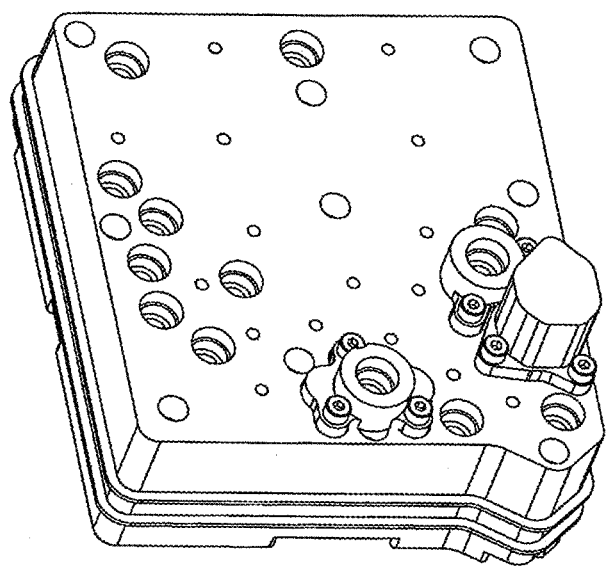
FIG. 33B is a bottom view of the assembled alternate embodiment of the cassette.

In this embodiment, when the cassette is assembled, as shown in FIGS. 33A-33B, the plates 31400, 31600, 31800 are sealed from each other using gaskets shown in FIGS. 29 and 31 as 31500 and 31700 respectively. Referring now to the exploded view of the cassette in FIGS. 33C and 33D, the pod pump membranes 31220 and valving membranes 31222 are shown. Additionally, in some embodiments, a check valve housing cell 31114 is additionally included.

Figure 33C:
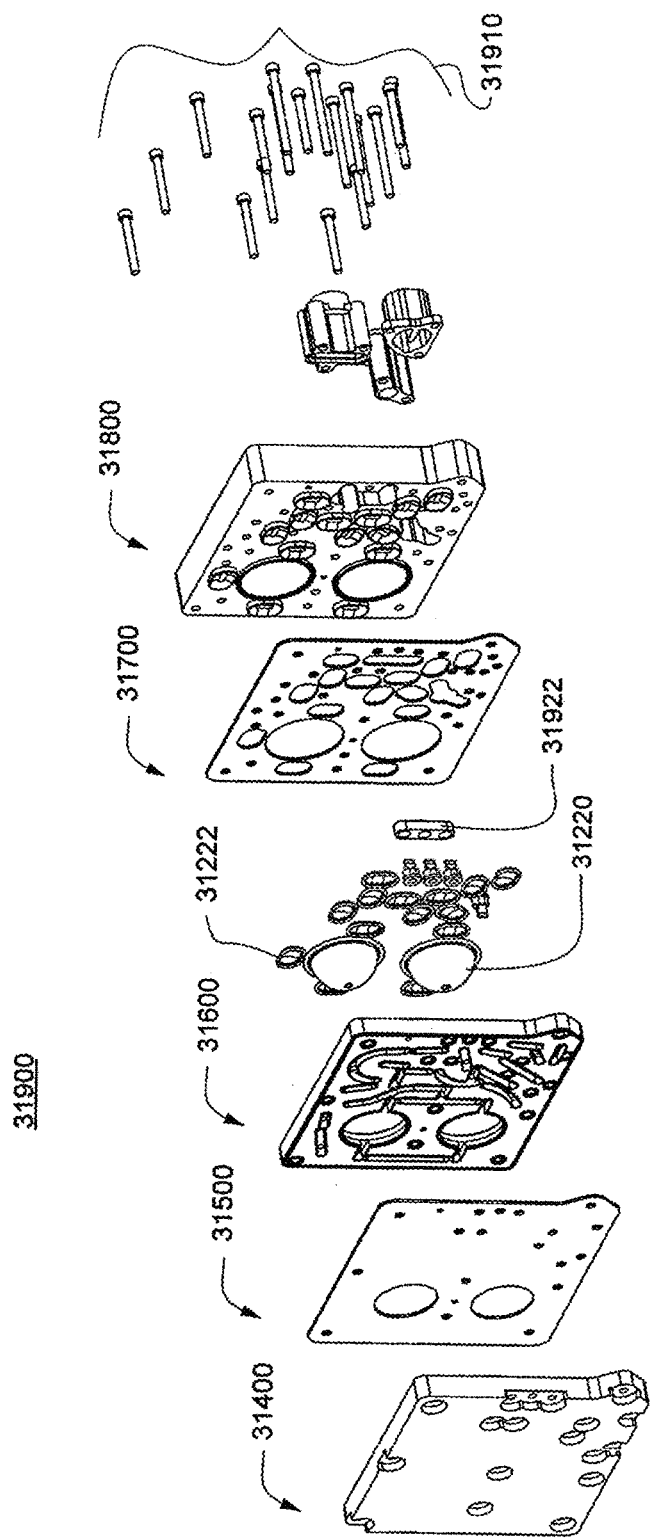
FIG. 33C is an exploded view of the assembled alternate embodiment of the cassette.
Figure 33D:
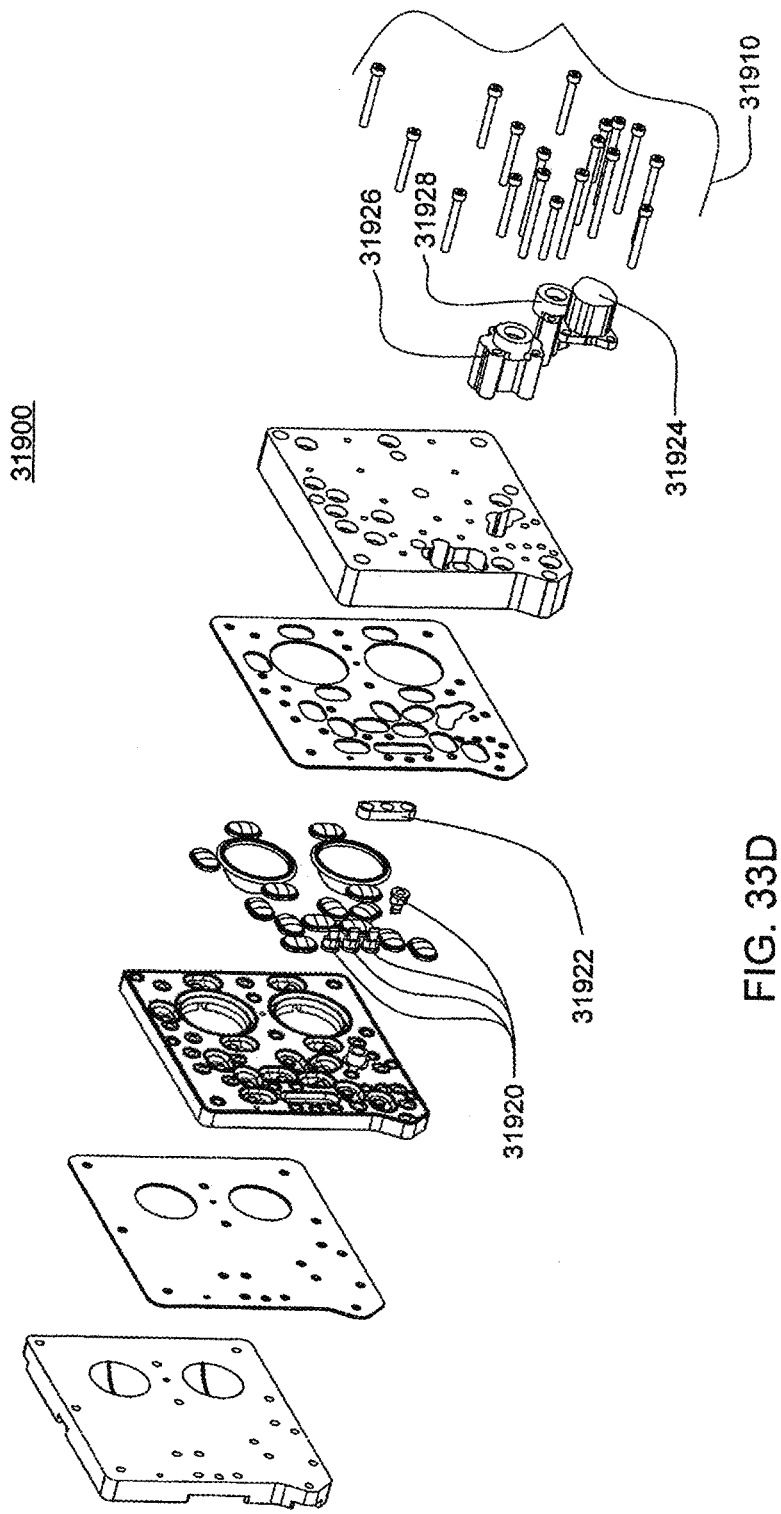
FIG. 33D is an exploded view of the assembled alternate embodiment of the cassette.

Still referring to FIGS. 33C-33D, in this alternate embodiment, the cassette 1900 is assembled with connection hardware 31910. Thus, the cassette 31900 is mechanically assembled and held together by connection hardware 31910. In this embodiment, the connection hardware is screws but in other embodiments, the connection hardware 31910 is metal posts. Any connection hardware may be used in alternate embodiments including, but not limited, to rivets, shoulder bolts, and bolts. In additional alternate embodiments, the plates are held together by an adhesive.

Still referring to FIGS. 33C and 33D, check valves 31920 are shown. In this embodiment, the check valves 31920 are duck-bill check valves, but in other embodiments, the check valves can be any type of check valve. In this embodiment, the check valves are held by a check valve cell 31922. Additionally, in some embodiments, more check valves are used in the cassette. For example, in this embodiment, and in some embodiments of the exemplary embodiment described above that includes check valves, additional check valve holders 31926, 31928 are shown. These provide holders for additional check valves. In still other embodiments, an air trap 31924 may be included as shown in this embodiment. Referring now to FIGS. 35A-35D, one embodiment of the duck-bill check valve is shown. However, in other embodiments, any check valve or alternate embodiments of a duck-bill check valve may be used.

Figure 34A:
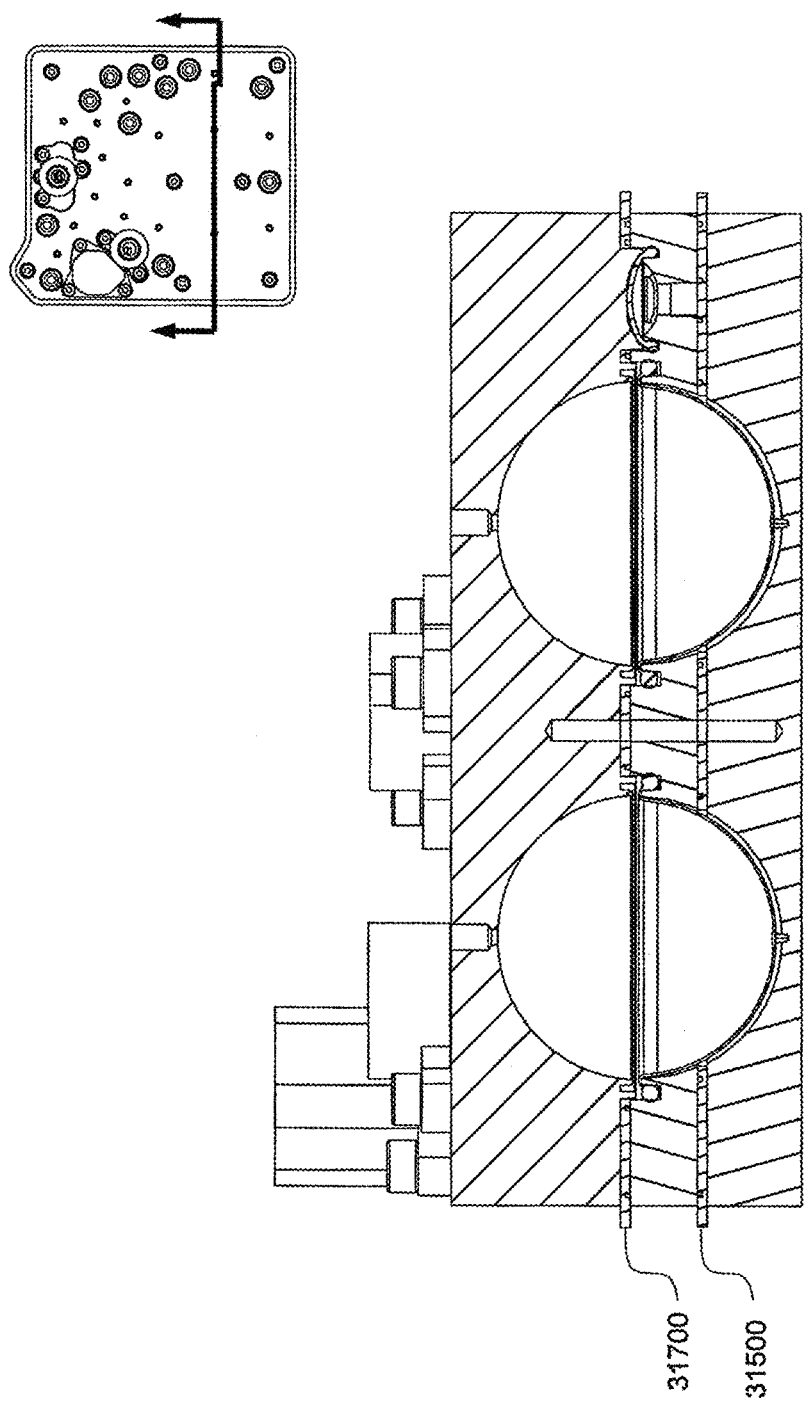
FIGS. 34A-34B show cross sectional views of the assembled alternate embodiment of the cassette.
Figure 34B:
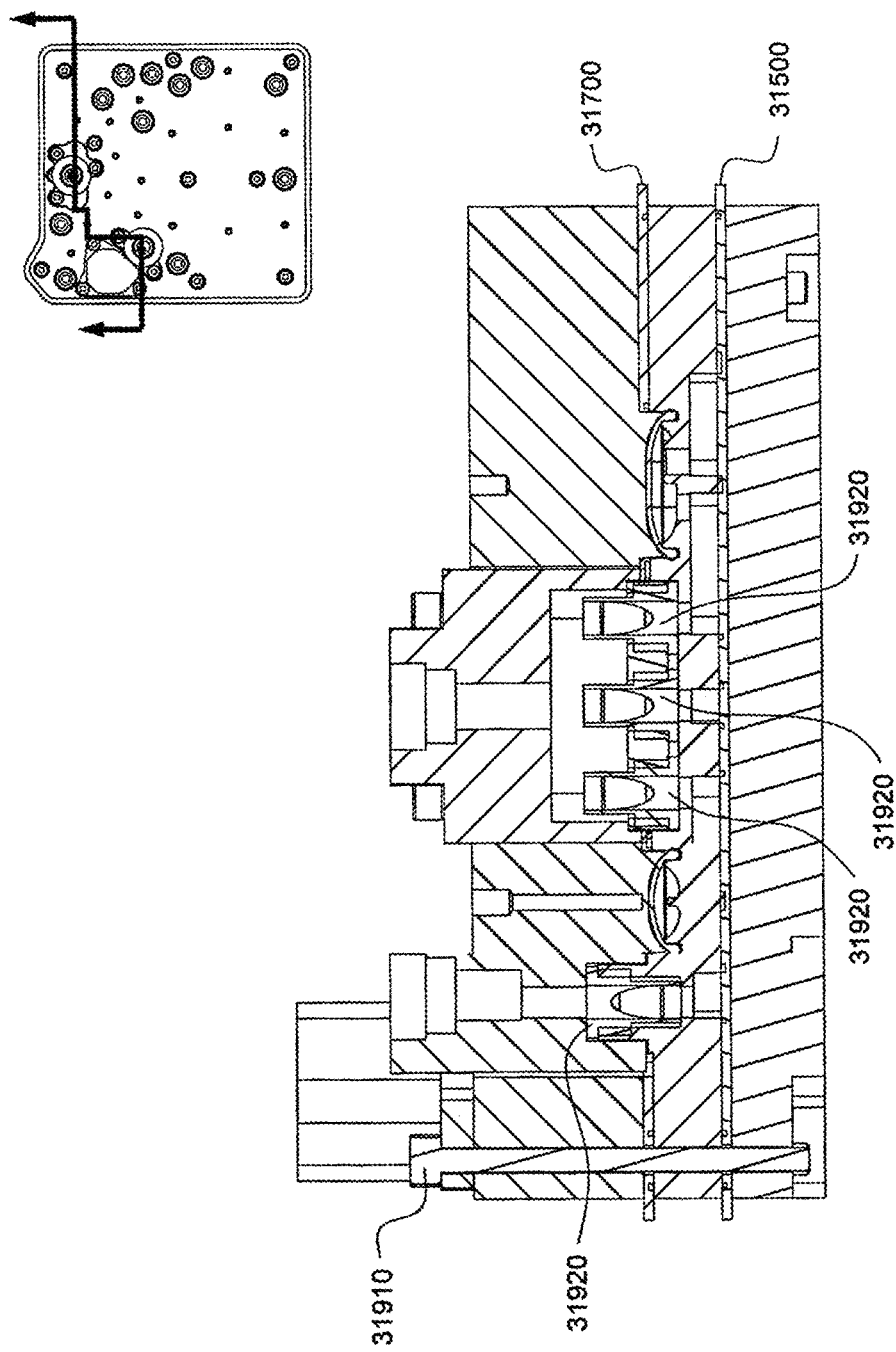

Referring now to FIGS. 34A and 34B, cross sectional views of the assembled cassette and the gaskets' 31500, 31700 relation to the assembled cassette assembly is shown.

In the alternate embodiment, the gaskets 31500, 31700 are made from silicone, but in other embodiments, the gaskets 31500, 31700 may be made from other materials. Still referring to FIGS. 34A and 34B, the connection hardware 31910 is shown. Referring to FIG. 34B, the cross sectional view shows the duck-bill check valves 31920 in the assembled cassette.

6.1 Exemplary Embodiments of the Middle Cassette

In practice, the cassette may be used to pump any type of fluid from any source to any location. The types of fluid include nutritive, nonnutritive, inorganic chemicals, organic chemicals, bodily fluids, or any other type of fluid. Additionally, fluid in some embodiments include a gas, thus, in some embodiments, the cassette is used to pump a gas.

The cassette serves to pump and direct the fluid from and to the desired locations. In some embodiments, outside pumps pump the fluid into the cassette and the cassette pumps the fluid out. However, in some embodiments, the pod pumps serve to pull the fluid into the cassette and pump the fluid out of the cassette.

As discussed above, depending on the valve locations, control of the fluid paths is imparted. Thus, the valves being in different locations or additional valves are alternate embodiments of this cassette. Additionally, the fluid lines and paths shown in the figures described above are mere examples of fluid lines and paths. Other embodiments may have more, less, and/or different fluid paths. In still other embodiments, valves are not present in the cassette.

The number of pod pumps described above may also vary depending on the embodiment. For example, although the exemplary and alternate embodiments shown and described above include two pod pumps, in other embodiments, the cassette includes one. In still other embodiments, the cassette includes more than two pod pumps. The pod pumps can be single pumps or work in tandem to provide a more continuous flow. Either or both may be used in various embodiments of the cassette.

The terms inlet and outlet as well as fluid paths are used for description purposes only. In other embodiments, an inlet can be an outlet. The denotations simply refer to separate entrance areas into the cassette.

The designations given for the fluid inlets (which can also be fluid outlets), for example, first fluid outlet, second fluid outlet, merely indicate that a fluid may travel out of or into the cassette via that inlet/outlet. In some cases, more than one inlet/outlet on the schematic is designated with an identical name. This merely describes that all of the inlet/outlets having that designation are pumped by the same metering pump or set of pod pumps (which in alternate embodiments, can be a single pod pump).

The various ports are provided to impart particular fluid paths onto the cassette. These ports are not necessarily all used all of the time, instead, the variety of ports provide flexibility of use of the cassette in practice.

Referring again to FIG. 21, one embodiment provides for a fluid reservoir to be fluidly attached to the vent port 3830 allowing for the reservoir to vent to atmosphere. Additionally, in some embodiments, an FMS reference chamber is fluidly attached to the reservoir and thus, as fluid is added or removed from the reservoir, the volume may be determined using the FMS. Some embodiments include additional vent ports in the cassette and thus, some embodiments of the cassette may be attached to more than one fluid reservoir.

One embodiment includes a fluid line extending from port 3850 to port 3848 and controlled by valves 3838, 3836. In one embodiment, port 3848 may be fluidly attached to a reservoir. As such, port 3810 may also be attached to the same reservoir. Thus, in one embodiment, port 3850 provides a fluid line to the reservoir, and port 3810 provides a fluid line such that the pod pumps pump fluid from the reservoir into the cassette. In some embodiments, valve 3858 controls a bypass line from the reservoir to another fluid line controlled by valve 3842.

Some embodiments may include an air trap within the fluid lines and/or at least one sensor. The sensor can be any sensor having a capability to determine any fluid or non-fluid sensor data. In one embodiment; three sensor elements are included in a single fluid line. In some embodiments, more than one fluid line includes the three sensor elements. In the three sensor element embodiment, two of the sensor elements are conductivity sensor elements and the third sensor element is a temperature sensor element. The conductivity sensor elements and temperature sensor element can be any conductivity or temperature sensor in the art. In one embodiment, the conductivity sensors are graphite posts. In other embodiments, the conductivity sensor elements are posts made from stainless steel, titanium, platinum, or any other metal coated to be corrosion resistant and still be electrically conductive. The conductivity sensor elements will include an electrical lead that transmits the probe information to a controller or other device. In one embodiment, the temperature sensor is a thermister potted in a stainless steel probe. However, in alternate embodiments, a combination temperature and conductivity sensor elements is used similar to the one described in co-pending U.S. Patent application entitled Sensor Apparatus Systems, Devices and Methods filed Oct. 12, 2007 (U.S. application Ser. No. 11/871,821).

In alternate embodiments, there are either no sensors in the cassette or only a temperature sensor, only one or more conductivity sensors or one or more of another type of sensor.

7. Exemplary Embodiment of the Balancing Cassette

Figure 36:
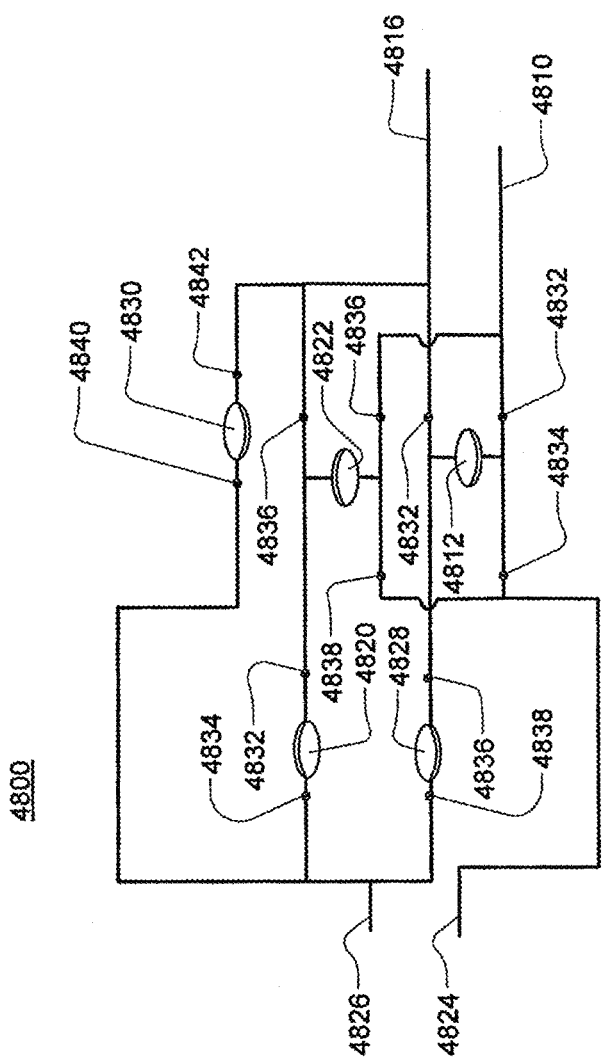
FIG. 36 is one embodiment of the fluid flow-path schematic of the cassette.

Referring now to FIG. 36, an exemplary embodiment of the fluid schematic of the balancing pumping and metering cassette 4800 is shown. Other schematics are readily discernable. The cassette 4800 includes at least one pod pump 4828, 4820 and at least one balancing pod 4822, 4812. The cassette 4800 also includes a first fluid inlet 4810, where a first fluid enters the cassette. The first fluid includes a flow rate provided outside the cassette 4800. The cassette 4800 also includes a first fluid outlet 4824 where the first fluid exits the cassette 4800 having a flow rate provided by one of the at least one pod pumps 4828. The cassette 4800 includes a second fluid inlet 4826 where the second fluid enters the cassette 4800, and a second fluid outlet 4816 where the second fluid exits the cassette.

Balancing pods 4822, 4812 in the cassette 4800 provide for a desired balance of volume of fluid pumped into and out of the cassette 4800, i.e., between the first fluid and the second fluid. The balancing pods 4822, 4812, however, may be bypassed by way of the metering pump 4830. The metering pump 4830 pumps a volume of second fluid (or first fluid in other embodiments) out of the fluid line, bypassing the balancing pod 4822, 4812. Thus, a smaller or reduced volume (i.e., a "new" volume) of the fluid that has been removed by the metering pump 4830 will actually enter the balancing pod 4822, 4812 and thus, the metering pump 4830 functions to provide a "new" volume of second fluid by removing the desired volume from the fluid path before the second fluid reaches the balancing pod 4822, 4812 (or in other embodiments, removing first fluid the desired volume from the fluid path before the second fluid reaches the balancing pod 4822, 4812) resulting in less first fluid (or in other embodiments, second fluid) being pumped for that pump cycle.

The fluid schematic of the cassette 4800 shown in FIG. 36 may be embodied into various cassette apparatus. Thus, the embodiments of the cassette 4800 including the fluid schematic shown in FIG. 36 are not the only cassette embodiments that may incorporate this or an alternate embodiment of this fluid schematic. Additionally, the types of valves, the ganging of the valves, the number of pumps and chambers may vary in various cassette embodiments of this fluid schematic.

Figure 38A:
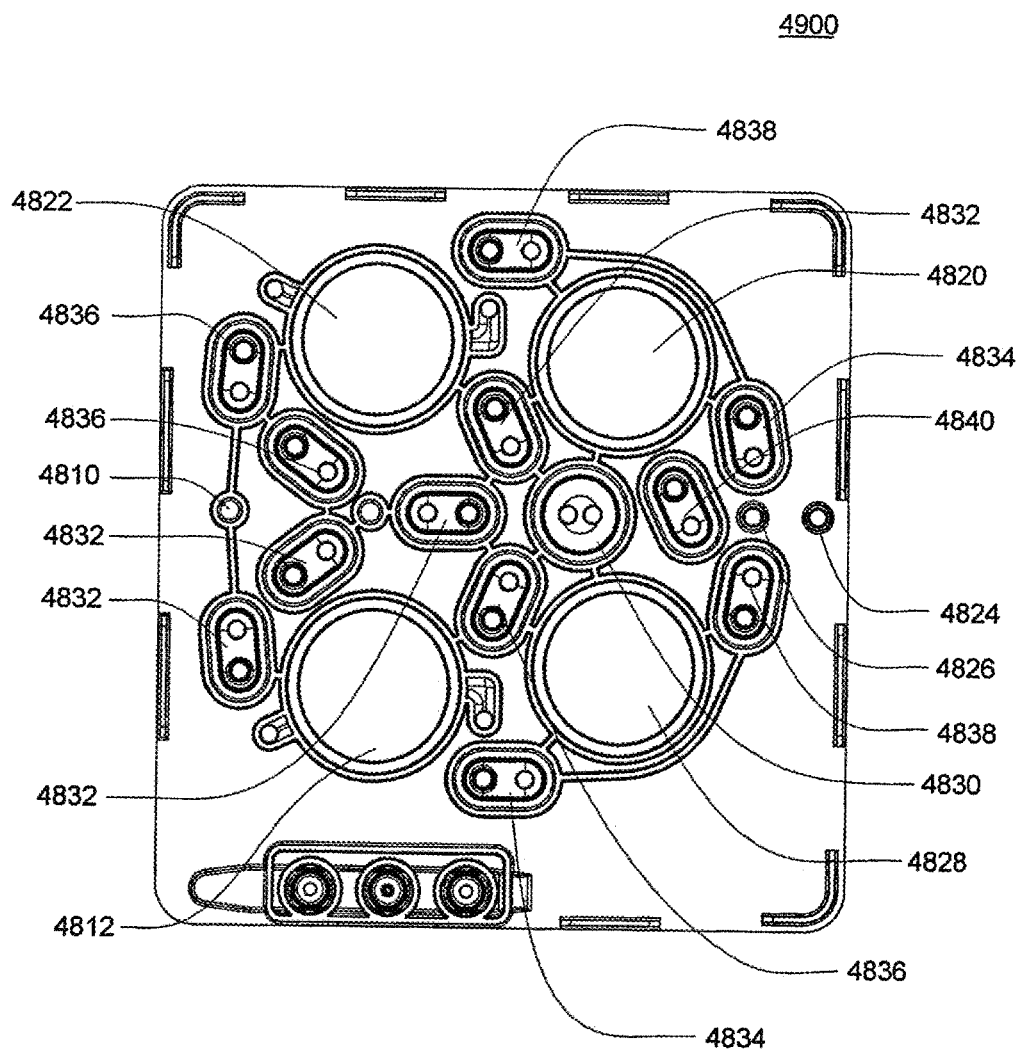
FIG. 38A is an isometric bottom view of the exemplary embodiment of the midplate of the exemplary embodiment of the cassette.
Figure 38B:
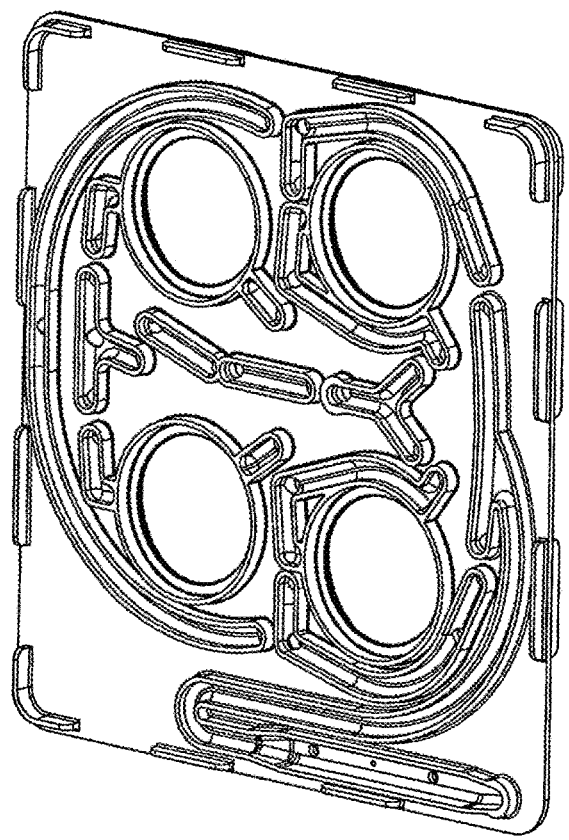
FIG. 38B is an isometric top view of the of the midplate of the exemplary embodiment of the cassette.
Figure 38C:
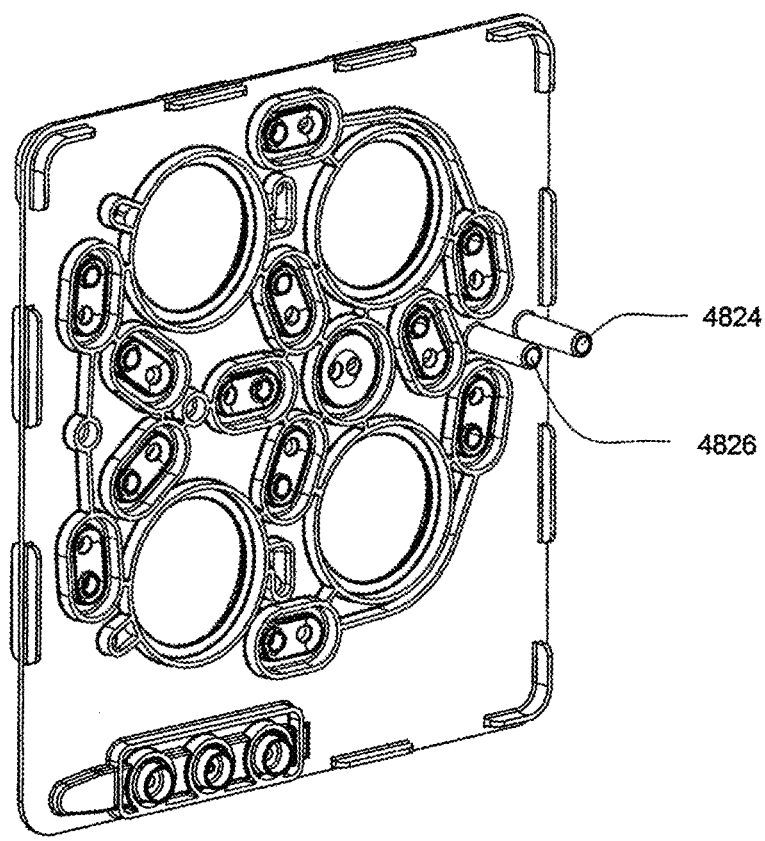
FIG. 38C is an isometric bottom view of the exemplary embodiment of the midplate of the cassette.
Figure 38D:
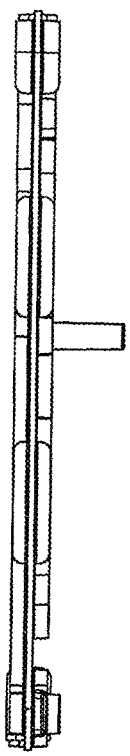
FIG. 38D is a side view of the exemplary embodiment of the midplate of the cassette.

Referring still to FIG. 36, a fluid flow-path schematic 4800 is shown. The fluid flow-path schematic 4800 is described herein corresponding to the flow paths in one embodiment of the cassette. The exemplary embodiment of the midplate 4900 of the cassette is shown in FIG. 38A with the valves corresponding to the fluid flow-path schematic in FIG. 36 indicated. The valving side of the midplate 4900 shown in FIG. 38A corresponds to the fluid side shown in FIG. 38B.

Referring first to FIG. 36 with FIG. 38A, a first fluid enters the cassette at the first fluid inlet 4810. The first fluid flows to balancing pod A 4812. Balancing pod A 4812 is a balancing pod as described above. Balancing pod A 4812 initially contained a first volume of second fluid. When the first fluid flows into the balancing pod A 4812, the membrane forces the second fluid out of balancing pod A 4812. The second fluid flows through the drain path 4814 and out the first fluid outlet 4816.

At the same time, pod pump B 4820 includes a volume of second fluid. The volume of second fluid is pumped to balancing pod B 4822. Balancing pod B 4822 contains a volume of first fluid, and this volume of first fluid is displaced by the volume of second fluid. The volume of first fluid from balancing pod B 4822 flows to the second fluid outlet 4824 and exits the cassette. A volume of a second fluid enters the cassette at fluid inlet two 4826 and flows to pod pump A 4828.

Referring still to FIG. 36 with FIG. 38A, the second fluid is pumped from pod pump A 4828 to balancing pod A 4812. The second fluid displaces the first fluid in balancing pod A 4812. The first fluid from balancing pod A 4812 flows to the second fluid outlet 4824.

First fluid flows into the cassette through the first fluid inlet 4810 and flows to balancing pod B 4822. The first fluid displaces the second fluid in balancing pod B 4822, forcing the second fluid to flow out of the cassette through the first fluid outlet 4816. Second fluid flows into the cassette through the second fluid inlet 4826 and to pod pump B 4820.

The metering pump can be actuated at any time and its function is to remove fluid from the fluid path in order to bypass the balancing pod. Thus, any volume of fluid removed would act to decrease the volume of the other fluid flowing out of the second fluid outlet 4824. The metering pump is independent of the balancing pods 4812, 4822 and the pod pumps 4820, 4828. The fluid enters through fluid inlet two 4826 and is pulled by the metering pump 4830. The metering pump then pumps the volume of fluid through the second fluid outlet 4816.

Although in the embodiment of the fluid schematic shown in FIG. 36, the metering pump is described only with respect to second fluid entering the cassette through fluid inlet two 4826, the metering pump can easily bypass first fluid entering the cassette through fluid inlet one 4810. Thus, depending on whether the desired end result is to have less of the first fluid or less of the second fluid, the metering pump and valves that control the fluid lines in the cassette can perform accordingly to accomplish the result.

In the exemplary fluid flow-path embodiment shown in FIG. 36, and corresponding structure of the cassette shown in FIG. 38A, valves are ganged such that they are actuated at the same time. In the preferred embodiment, there are four gangs of valves 4832, 4834, 4836, 4838. In the preferred embodiment, the ganged valves are actuated by the same air line. However, in other embodiments, each valve has its own air line. Ganging the valves as shown in the exemplary embodiment creates the fluid-flow described above. In some embodiments, ganging the valves also ensures the appropriate valves are opened and closed to dictate the fluid pathways as desired.

In the exemplary embodiment, the fluid valves are volcano valves, as described in more detail in this specification. Although the fluid flow-path schematic has been described with respect to a particular flow path, in various embodiments, the flow paths can change based on the actuation of the valves and the pumps. Additionally, the terms inlet and outlet as well as first fluid and second fluid are used for description purposes only. In other embodiments, an inlet can be an outlet, as well as, a first and second fluid may be different fluids or the same fluid types or composition.

Figure 39A:
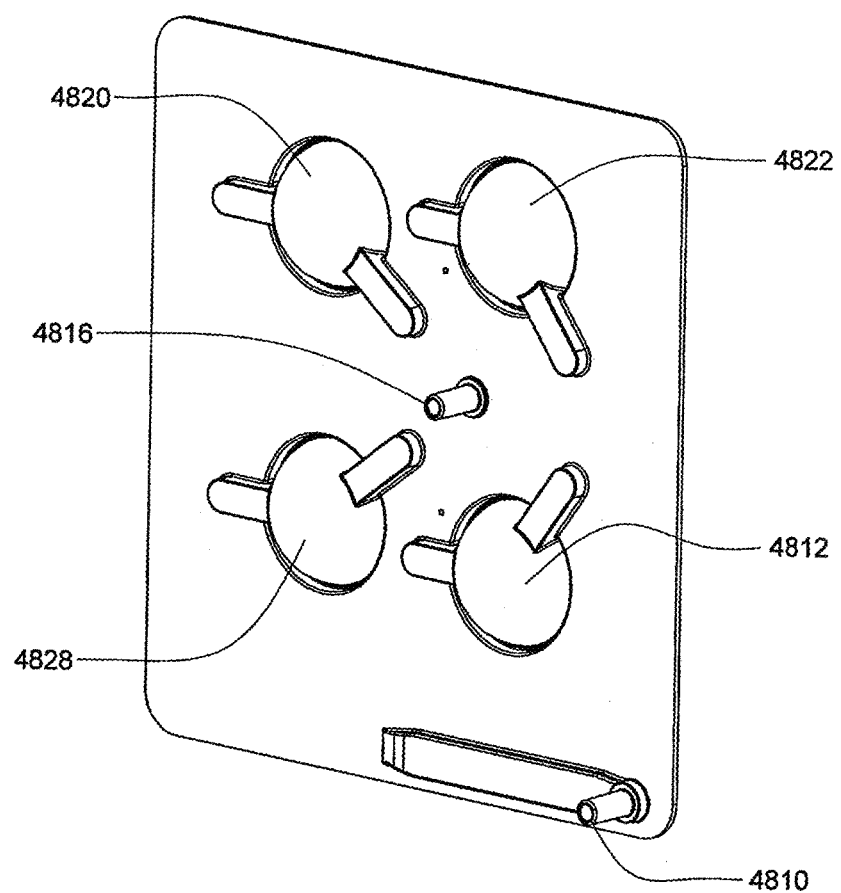
FIGS. 39A-39B are isometric and top views of the exemplary embodiment of the top plate of the exemplary embodiment of the cassette.
Figure 39B:
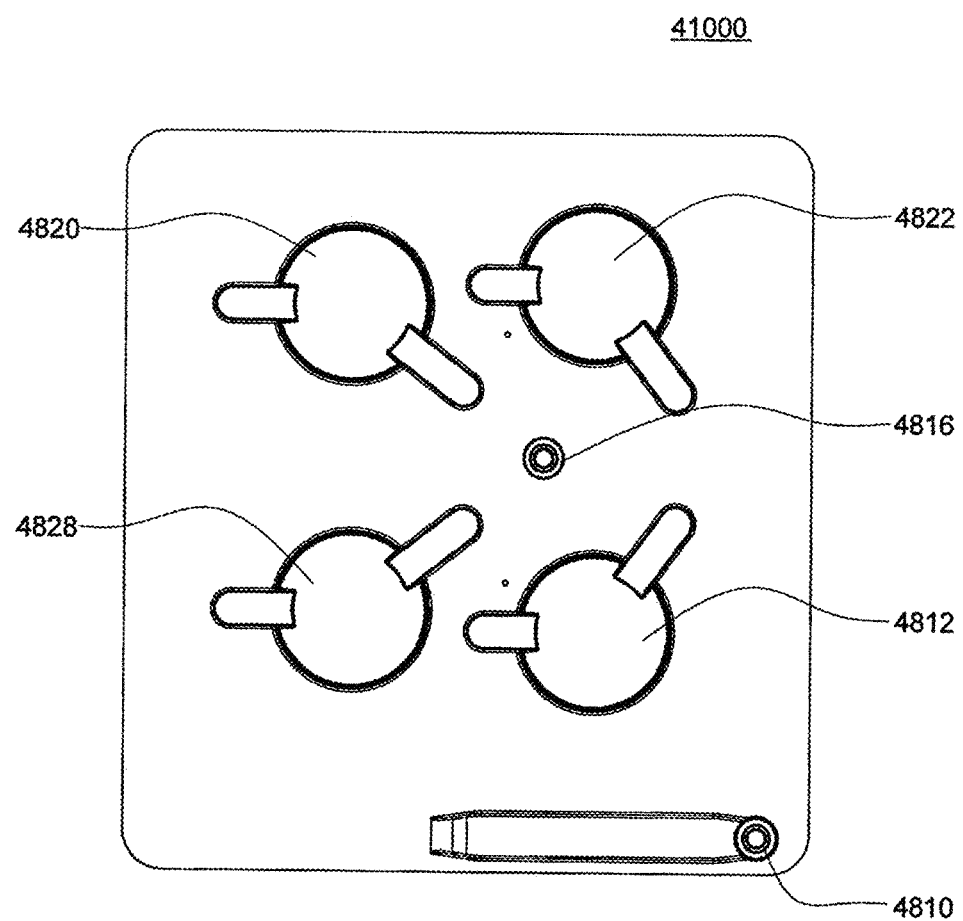

Referring now to FIGS. 39A-39E, the top plate 41000 of the exemplary embodiment of the cassette is shown. Referring first to FIGS. 39A and 39B, the top view of the top plate 41000 is shown. In the exemplary embodiment, the pod pumps 4820, 4828 and the balancing pods 4812, 4822 on the top plate, are formed in a similar fashion. In the exemplary embodiment, the pod pumps 4820, 4828 and balancing pods 4812, 4822, when assembled with the bottom plate, have a total volume of capacity of 38 ml. However, in various embodiments, the total volume capacity can be greater or less than in the exemplary embodiment. The first fluid inlet 4810 and the second fluid outlet 4816 are shown.

Figure 39C:
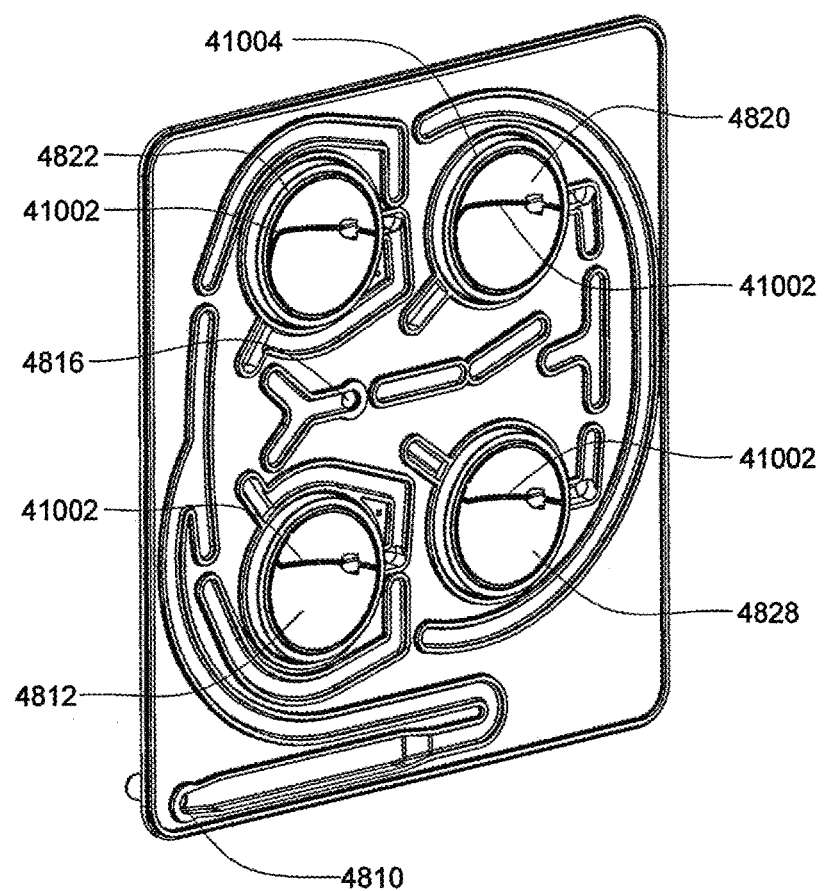
FIGS. 39C-39D are isometric views of the of the exemplary embodiment of the top plate of the exemplary embodiment of the cassette.
Figure 39D:
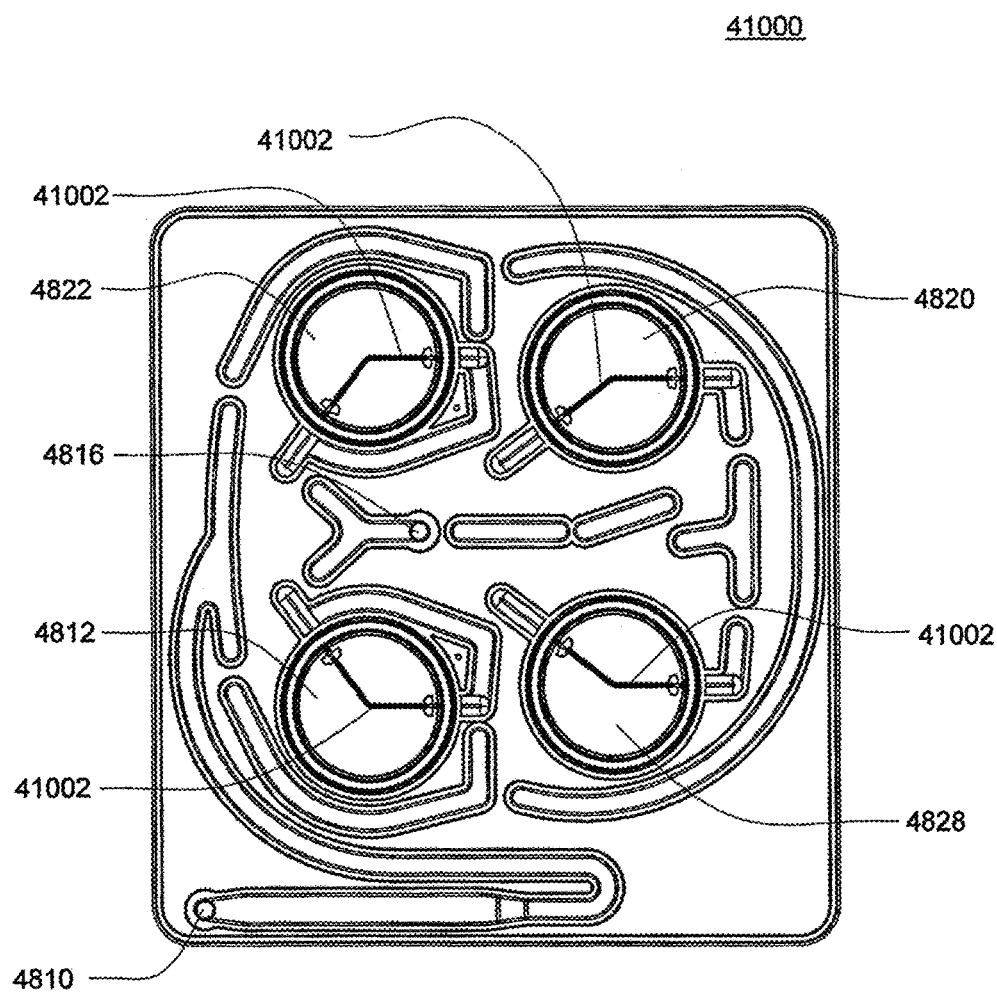

Referring now to FIGS. 39C and 39D, the bottom view of the top plate 41000 is shown. The fluid paths are shown in this view. These fluid paths correspond to the fluid paths shown in FIG. 38B in the midplate 4900. The top plate 41000 and the top of the midplate form the liquid or fluid side of the cassette for the pod pumps 4820, 4828 and for one side of the balancing pods 4812, 4822. Thus, most of the liquid flow paths are on the top and midplates. The other side of the balancing pods' 4812, 4822 flow paths is located on the inner side of the bottom plate, not shown here, shown in FIGS. 40A-41B.

Still referring to FIGS. 39C and 39D, the pod pumps 4820, 4828 and balancing pods 4812, 4822 include a groove 41002. The groove 41002 is shown having a particular shape, however, in other embodiments, the shape of the groove 41002 can be any shape desirable. The shape shown in FIGS. 39C and 39D is the exemplary embodiment. In all embodiments of the groove 41002, the groove forms a path between the fluid inlet side and the fluid outlet side of the pod pumps 4820, 4828 and balancing pods 4812, 4822.

The groove 41002 provides a fluid path whereby when the membrane is at the end of stroke, there is still a fluid path between the inlet and outlet such that the pockets of fluid or air do not get trapped in the pod pump or balancing pod. The groove 41002 is included in both the liquid and air sides of the pod pumps 4820, 4828 and balancing pods 4812, 4822 (see FIGS. 40A-41B with respect to the air side of the pod pumps 4820, 4828 and the opposite side of the balancing pods 4812, 4822).

The liquid side of the pod pumps 4820, 4828 and balancing pods 4812, 4822, in the exemplary embodiment, include a feature whereby the inlet and outlet flow paths are continuous while the outer ring 41004 is also continuous. This feature allows for the seal, formed with the membrane (not shown) to be maintained.

Figure 39E:
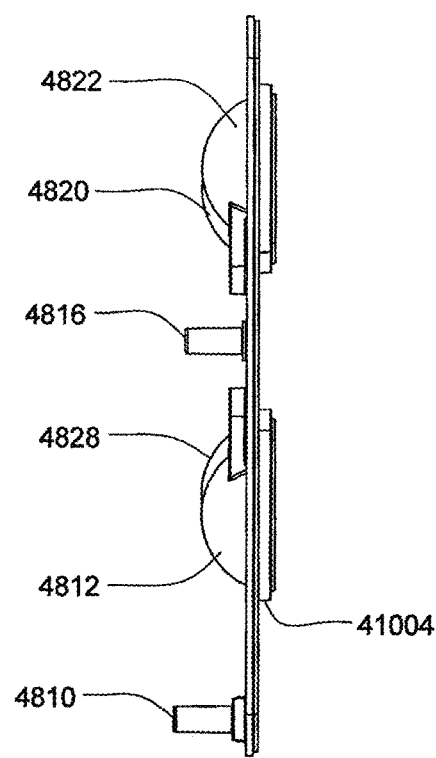
FIG. 39E is a side view of the exemplary embodiment of the top plate of the cassette.

Referring to FIG. 39E, the side view of the exemplary embodiment of the top plate 41000 is shown. The continuous outer ring 41004 of the pod pumps 4820, 4828 and balancing pods 4812, 4822 can be seen.

Figure 40A:
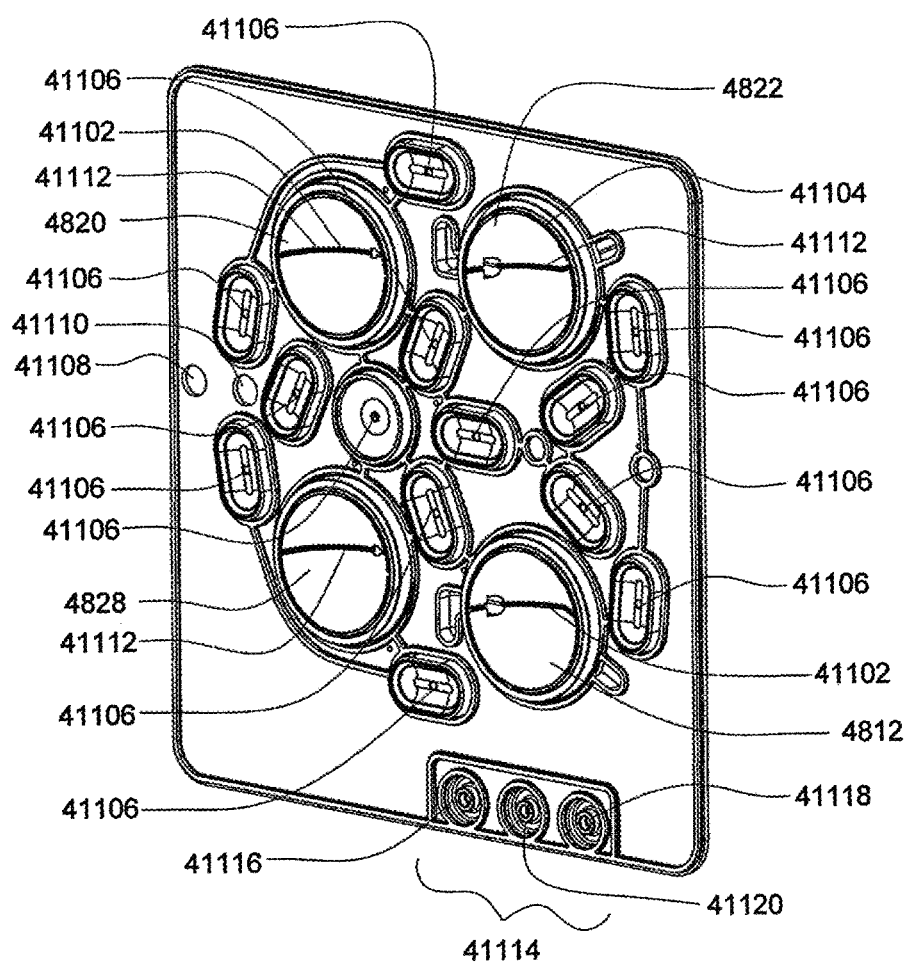

Referring now to FIGS. 40A-41E, the bottom plate 41100 is shown. Referring first to FIGS. 40A and 41B, the inside surface of the bottom plate 41100 is shown. The inside surface is the side that contacts the bottom surface of the midplate (not shown, see FIG. 41B). The bottom plate 41100 attaches to the air lines (not shown). The corresponding entrance holes for the air that actuates the pod pumps 4820, 4828 and valves (not shown, see FIG. 41B) in the midplate can be seen 41106. Holes 41108, 41110 correspond to the second fluid inlet and second fluid outlet shown in FIGS. 41C, 4824, 4826 respectively. The corresponding halves of the pod pumps 4820, 4828 and balancing pods 4812, 4822 are also shown, as are the grooves 41112 for the fluid paths. Unlike the top plate, the bottom plate corresponding halves of the pod pumps 4820, 4828 and balancing pods 4812, 4822 make apparent the difference between the pod pumps 4820, 4828 and balancing pods 4812, 4822. The pod pumps 4820, 4828 include only a air path on the second half in the bottom plate, while the balancing pod 4812, 4822 have identical construction to the half in the top plate. Again, the balancing pods 4812, 4822 balance liquid, thus, both sides of the membrane, not shown, will include a liquid fluid path, while the pod pumps 4820, 4828 are pressure pumps that pump liquid, thus, one side includes a liquid fluid path and the other side, shown in the bottom plate 41100, includes an air actuation chamber or air fluid path.

In the exemplary embodiment of the cassette, sensor elements are incorporated into the cassette so as to discern various properties of the fluid being pumped. In one embodiment, the three sensor elements are included. In the exemplary embodiment, the sensor elements are located in the sensor cell 41114. The cell 41114 accommodates three sensor elements in the sensor element housings 41116, 41118, 41120. In the exemplary embodiment, two of the sensor housings 41116, 41118 accommodate a conductivity sensor element and the third sensor element housing 41120 accommodates a temperature sensor element. The conductivity sensor elements and temperature sensor elements can be any conductivity or temperature sensor elements in the art. In one embodiment, the conductivity sensor elements are graphite posts. In other embodiments, the conductivity sensor elements are posts made from stainless steel, titanium, platinum or any other metal coated to be corrosion resistant and still be electrically conductive. The conductivity sensor elements will include an electrical lead that transmits the probe information to a controller or other device. In one embodiment, the temperature sensor is a thermister potted in a stainless steel probe. However, in alternate embodiments, a combination temperature and conductivity sensor elements is used similar to the one described in co-pending U.S. Patent application entitled Sensor Apparatus Systems, Devices and Methods filed Oct. 12, 2007 (U.S. application Ser. No. 11/871,821).

In this embodiment, the sensor cell 41114 is a single opening to the fluid line or a single connection to the fluid line.

In alternate embodiments, there are either no sensors in the cassette or only a temperature sensor, only one or more conductivity sensors or one or more of another type of sensor.

Figure 41B:
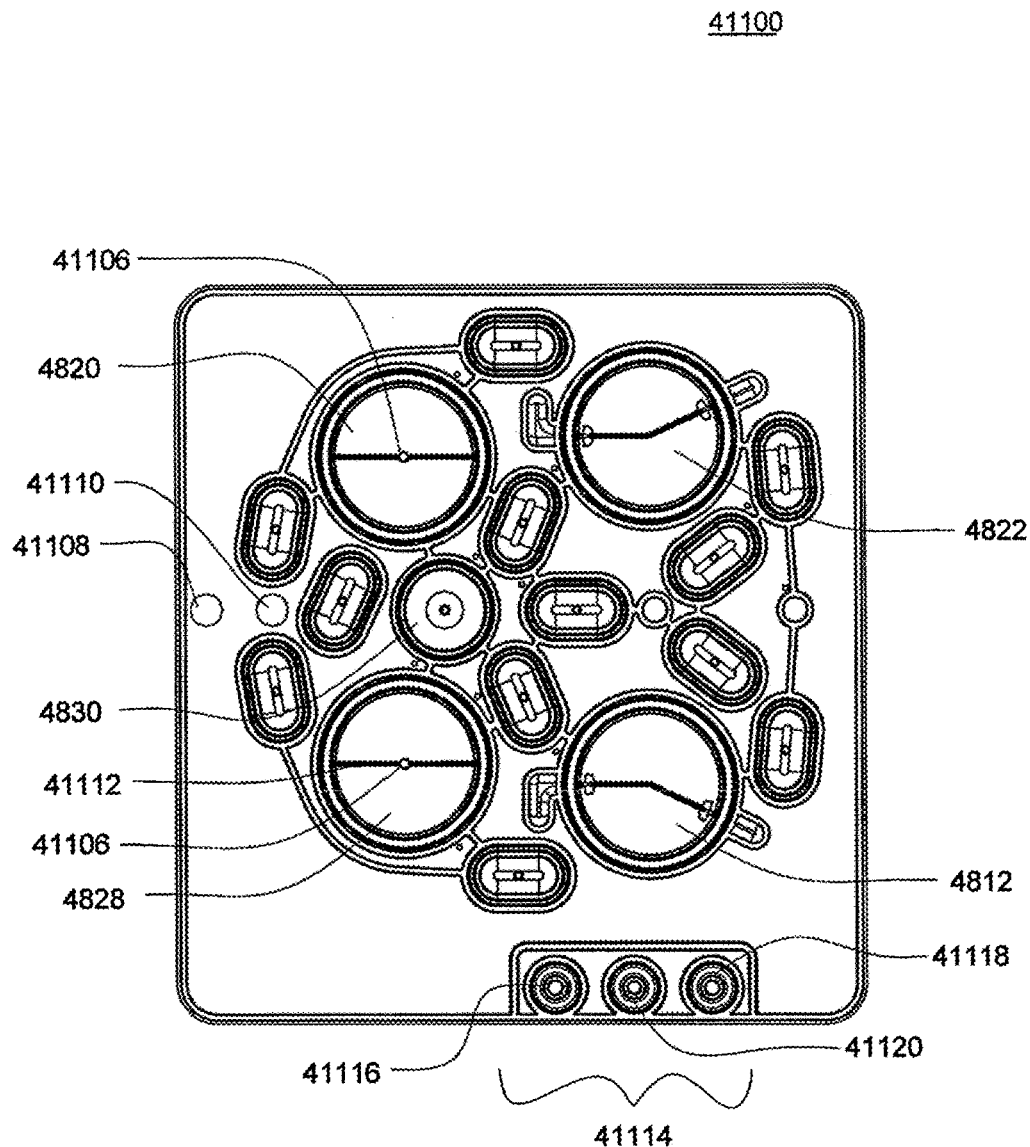

Still referring to FIGS. 40A and 41B, the actuation side of the metering pump 4830 is also shown as well as the corresponding air entrance hole 41106 for the air that actuates the pump.

Figure 41C:
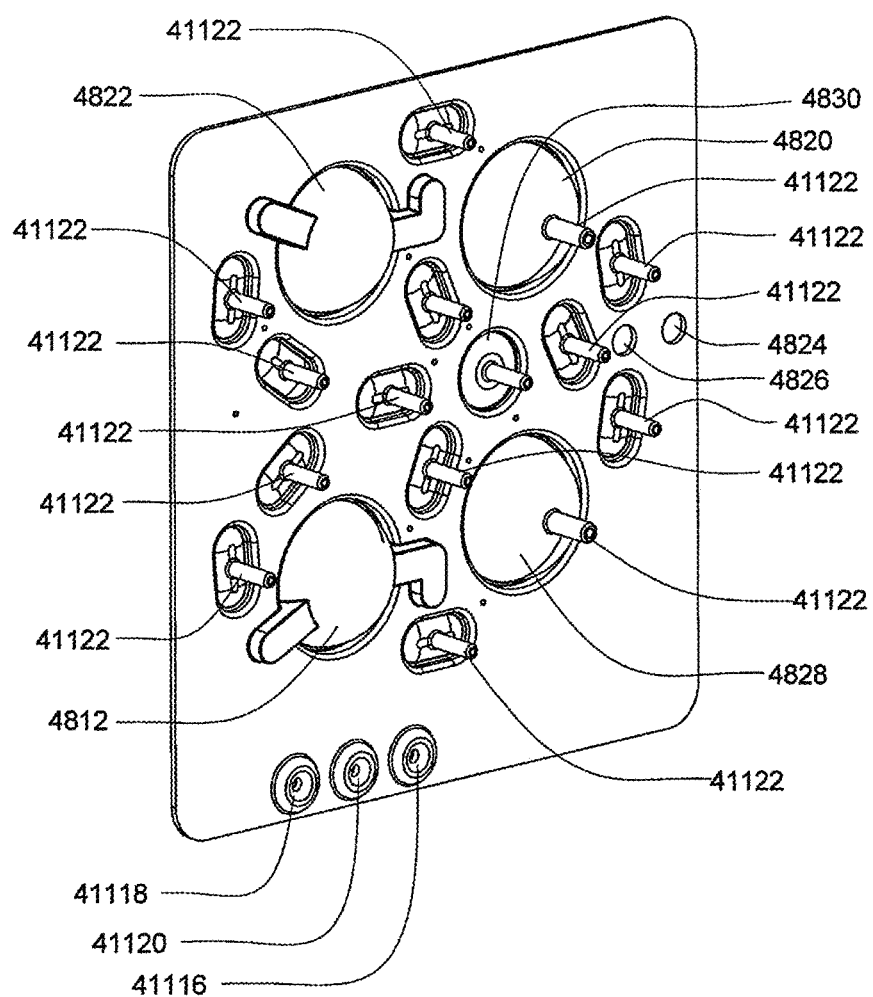
FIGS. 41C-41D are isometric top views of the exemplary embodiment of the bottom plate of the exemplary embodiment of the cassette.
Figure 41D:
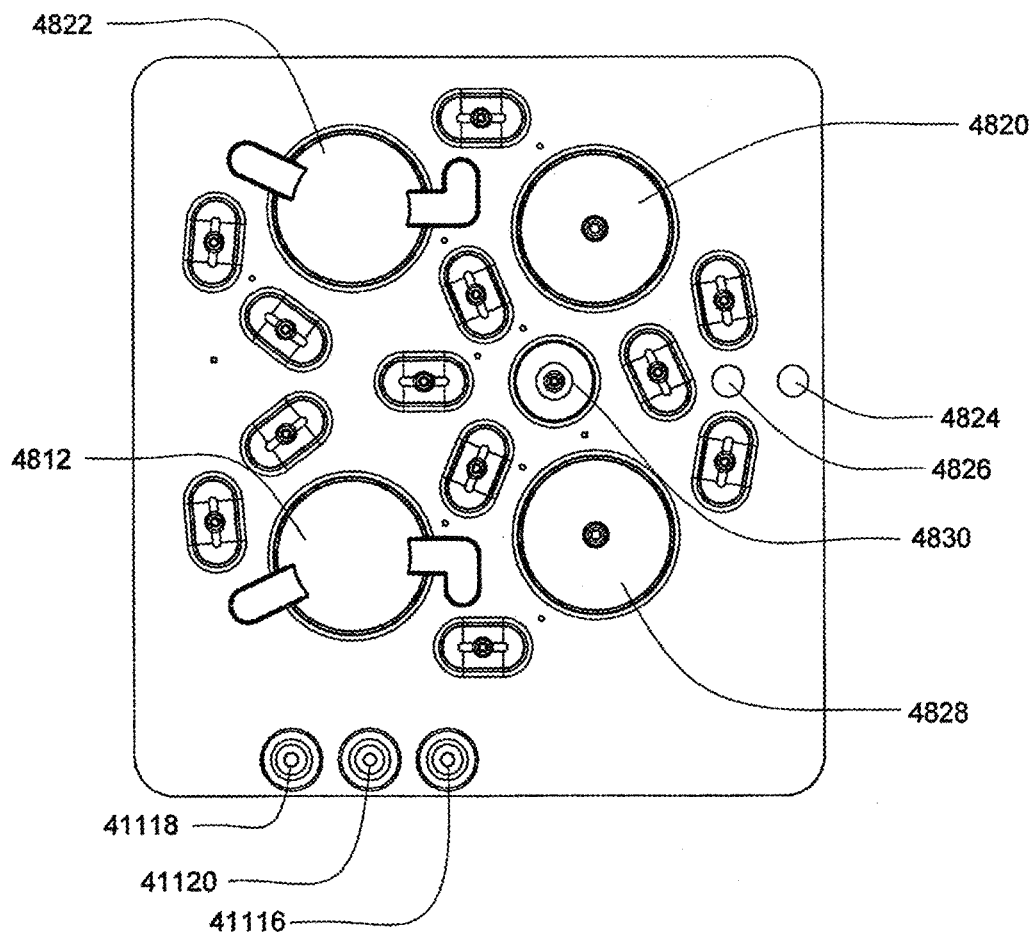

Referring now to FIGS. 41C and 41D, the outer side of the bottom plate 41100 is shown. The valve, pod pumps 4820, 4828 and metering pump 4830 air line connection points 41122 are shown. Again, the balancing pods 4812, 4822 do not have air line connection points as they are not actuated by air. As well, the corresponding openings in the bottom plate 41100 for the second fluid outlet 4824 and second fluid inlet 4826 are shown.

Figure 41E:
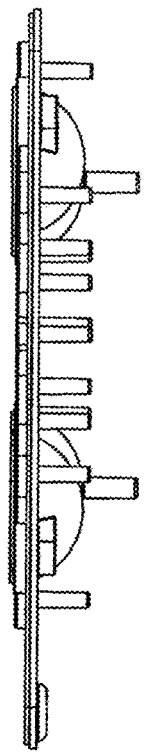
FIG. 41E is a side view of the exemplary embodiment of the bottom plate of the exemplary embodiment of the cassette.

Referring now to FIG. 41E, a side view of the bottom plate 41100 is shown. In the side view, the rim 41124 that surrounds the inner bottom plate 41100 can be seen. The rim 41124 is raised and continuous, providing for a connect point for the membrane (not shown). The membrane rests on this continuous and raised rim 41124 providing for a seal between the half of the pod pumps 4820, 4828 and balancing pods 4812, 4822 in the bottom plate 41100 and the half of the pod pumps 4820, 4828 and balancing pods 4812, 4822 in the top plate (not shown, see FIGS. 39A-39D).

7.1 Membranes

Figure 6A:
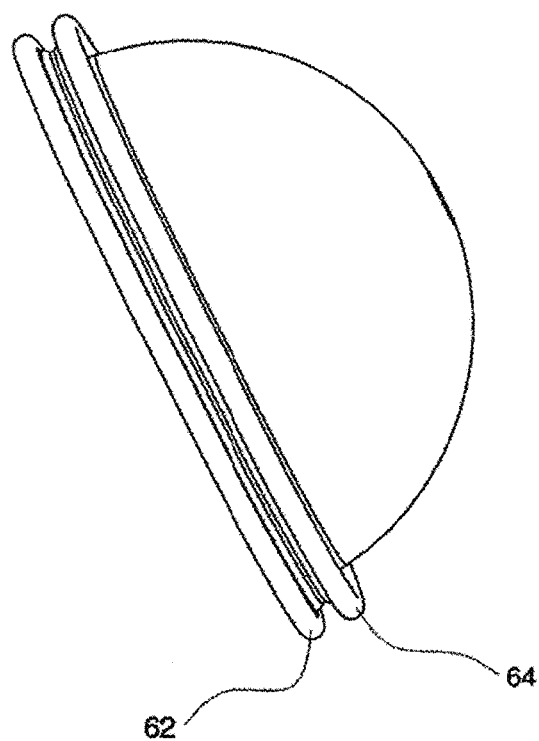
FIGS. 6A and 6B are pictorial views of a double ring membrane with a smooth surface.

In the exemplary embodiment, the membrane is a double o-ring membrane as shown in FIG. 6A. However, in some embodiments, a double o-ring membrane having texture, including, but not limited to, the various embodiments in FIGS. 6B-6F may be used.

Figure 6B:
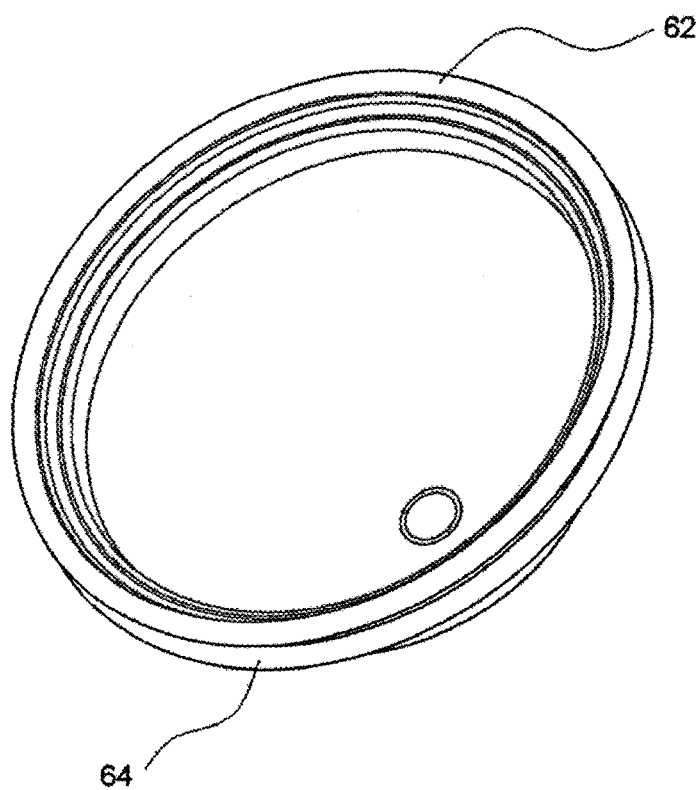
Figure 6C:
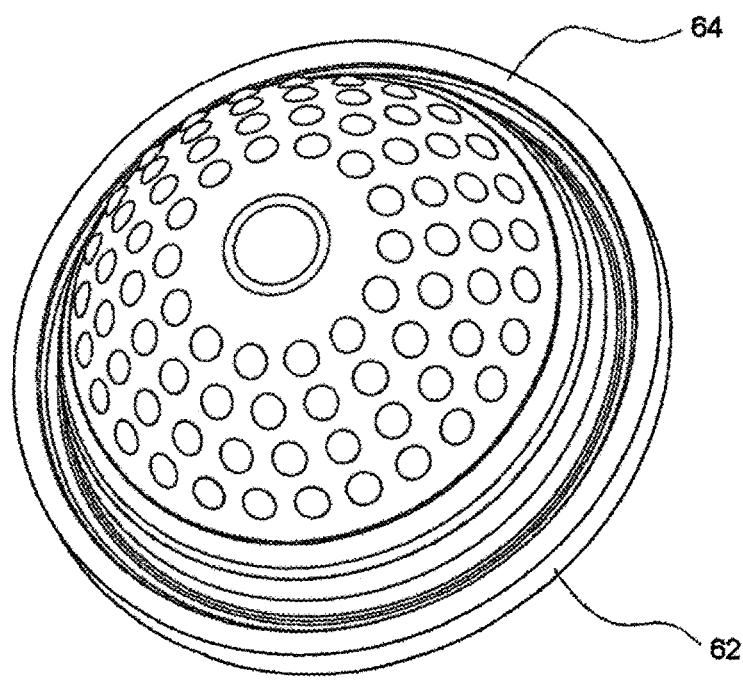
FIGS. 6C and 6D are pictorial views of a double ring membrane with a dimple surface.
Figure 6D:
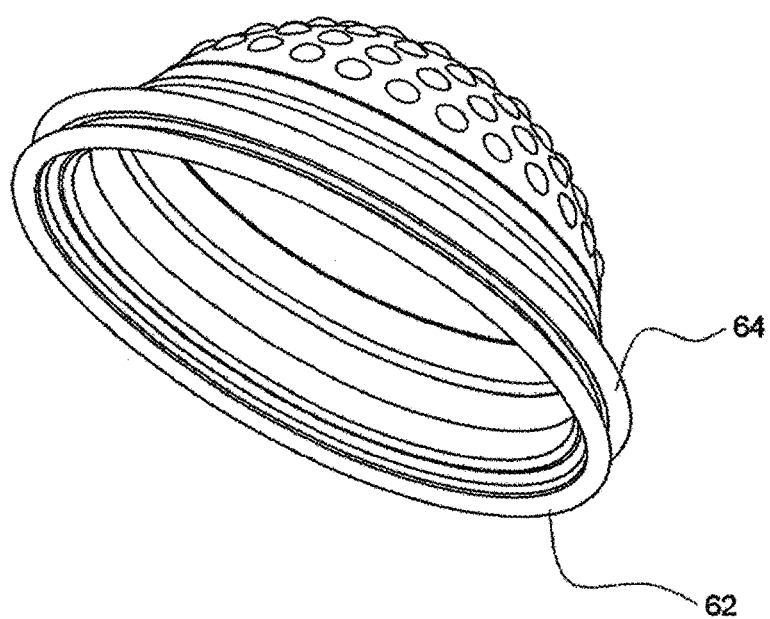
Figure 6E:
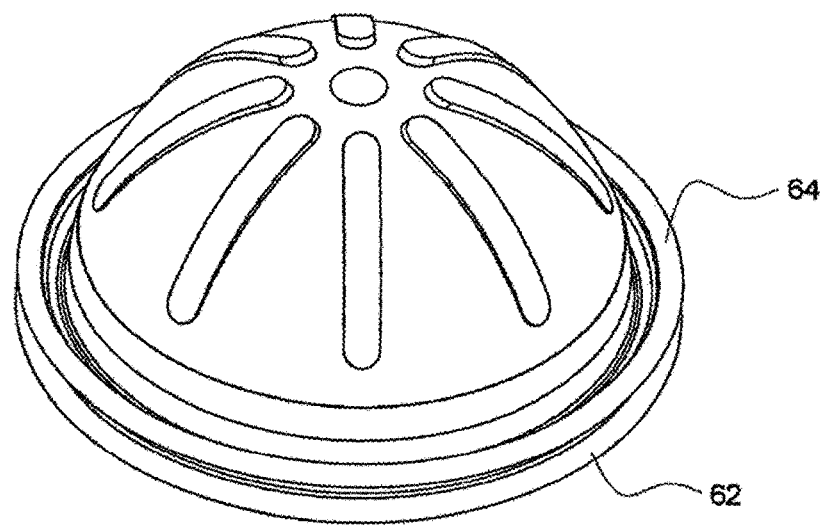
FIGS. 6E and 6F are pictorial views of double ring membranes with variable surfaces.
Figure 6F:
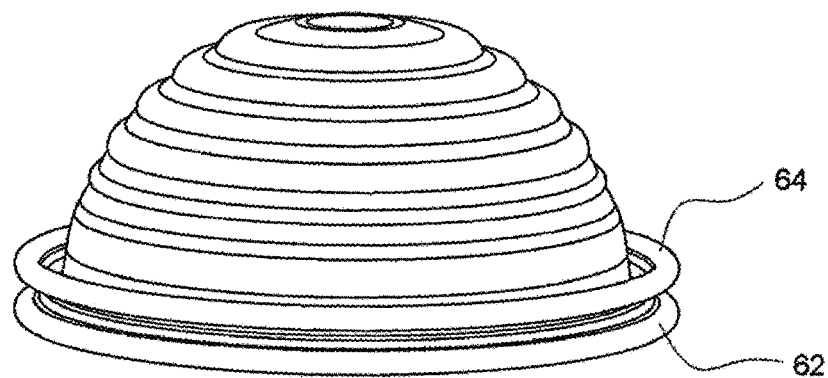
Figure 42A:
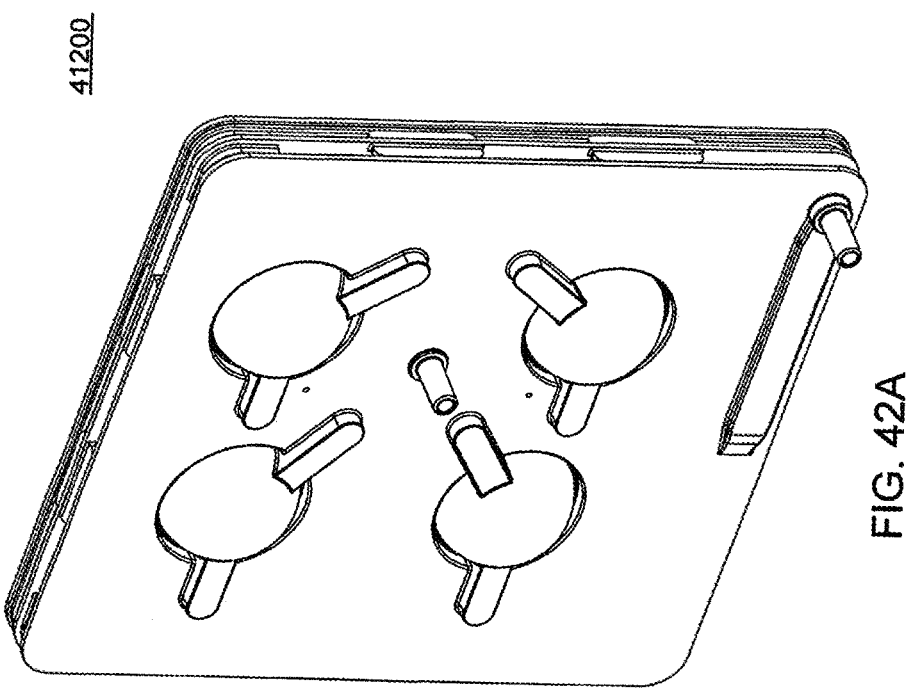
FIG. 42A is an isometric view of the top of the assembled exemplary embodiment of the cassette.
Figure 42B:
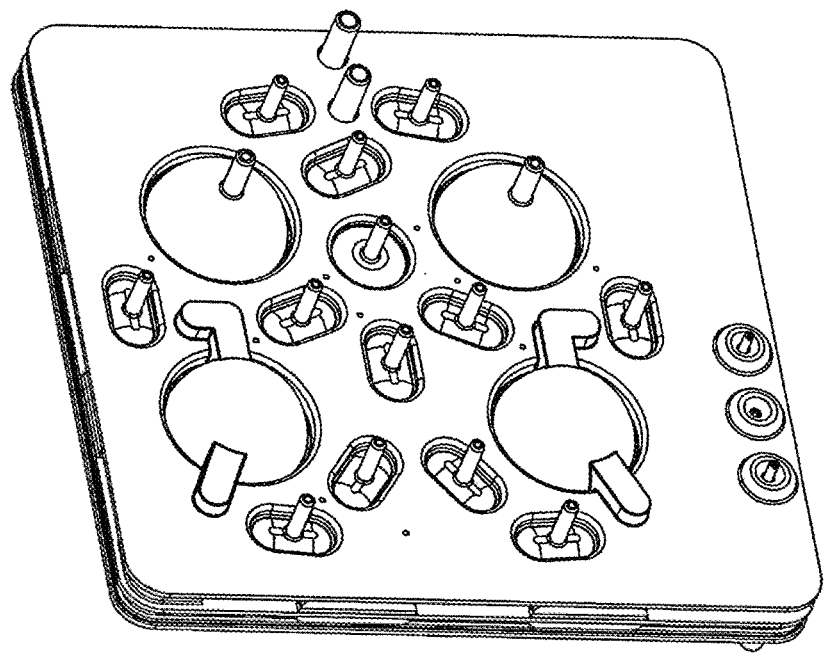
FIG. 42B is an isometric view of the bottom of the assembled exemplary embodiment of the cassette.
Figure 42C:
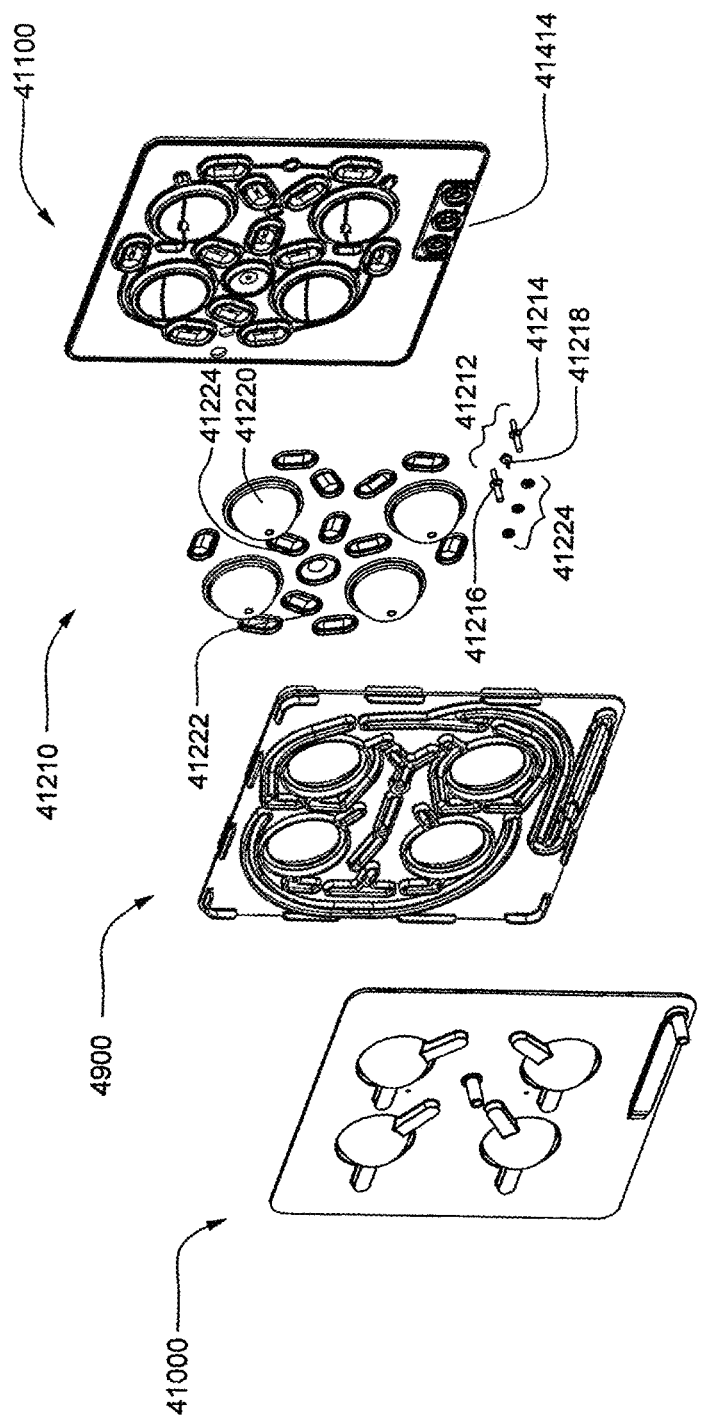
FIG. 42C is an exploded view of the assembled exemplary embodiment of the cassette.
Figure 42D:
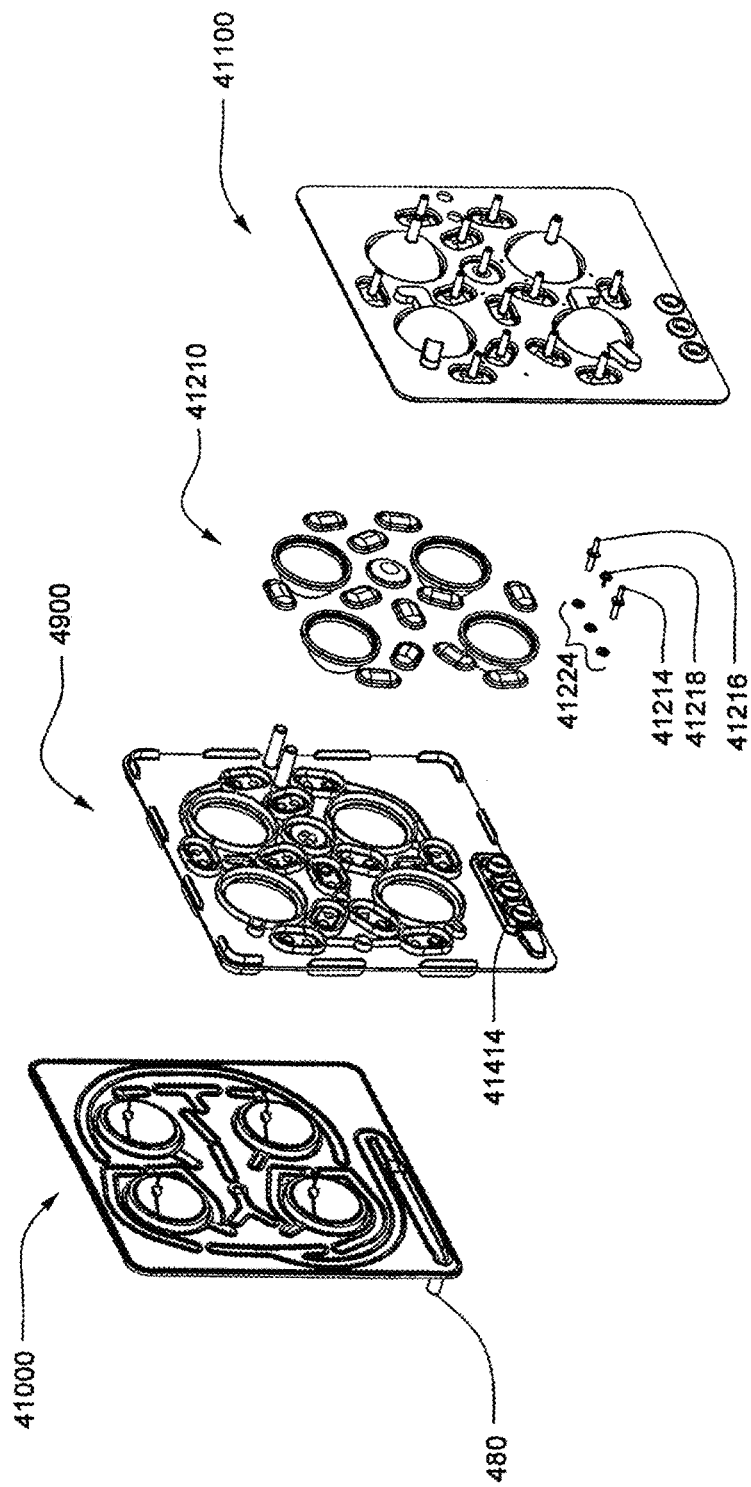
FIG. 42D is an exploded view of the assembled exemplary embodiment of the cassette.

Referring now to FIGS. 42A and 42B, the assembled exemplary embodiment of the cassette 41200 is shown. FIGS. 42C and 42D are exploded views of the exemplary embodiment of the cassette 41200. The membranes 41210 are shown. As can be seen from FIGS. 42C and 42D, there is one membrane 41220 for each of the pods pumps and balancing pods. In the exemplary embodiment, the membrane for the pod pumps and the balancing pods are identical. The membrane in the exemplary embodiment is a double o-ring membrane as shown in FIGS. 6A-6B. However, in alternate embodiments, any double o-ring membrane may be used, including, but not limited to, the various embodiments shown in FIGS. 6C-6F. However, in other embodiments, the double o-ring membrane is used in the balancing pods, but a single o-ring membrane, as shown in FIGS. 4A-4D is used in the pod pumps.

Figure 5E:
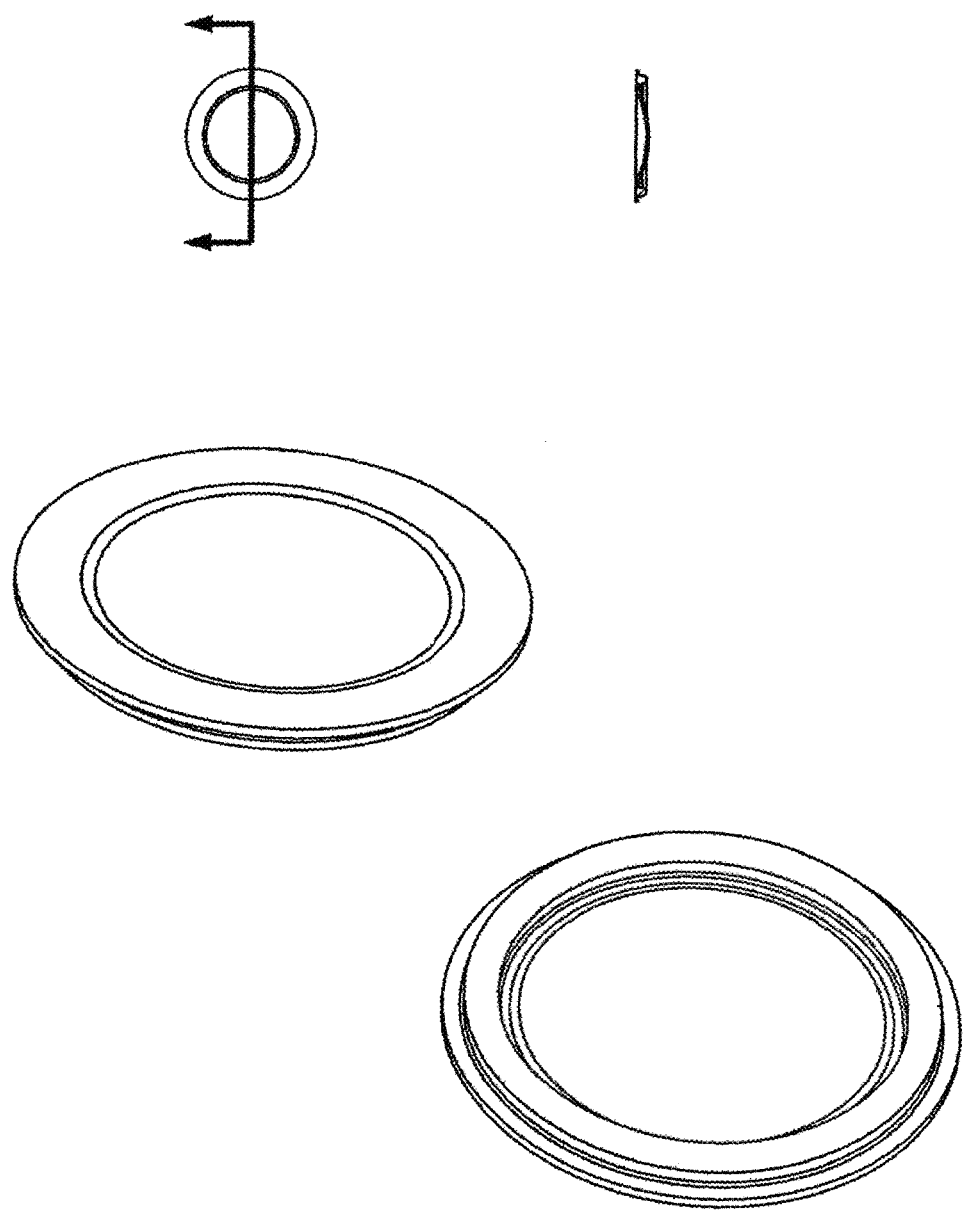
FIGS. 5E-5H are pictorial views of various embodiments of the metering pump membrane.
Figure 5F:
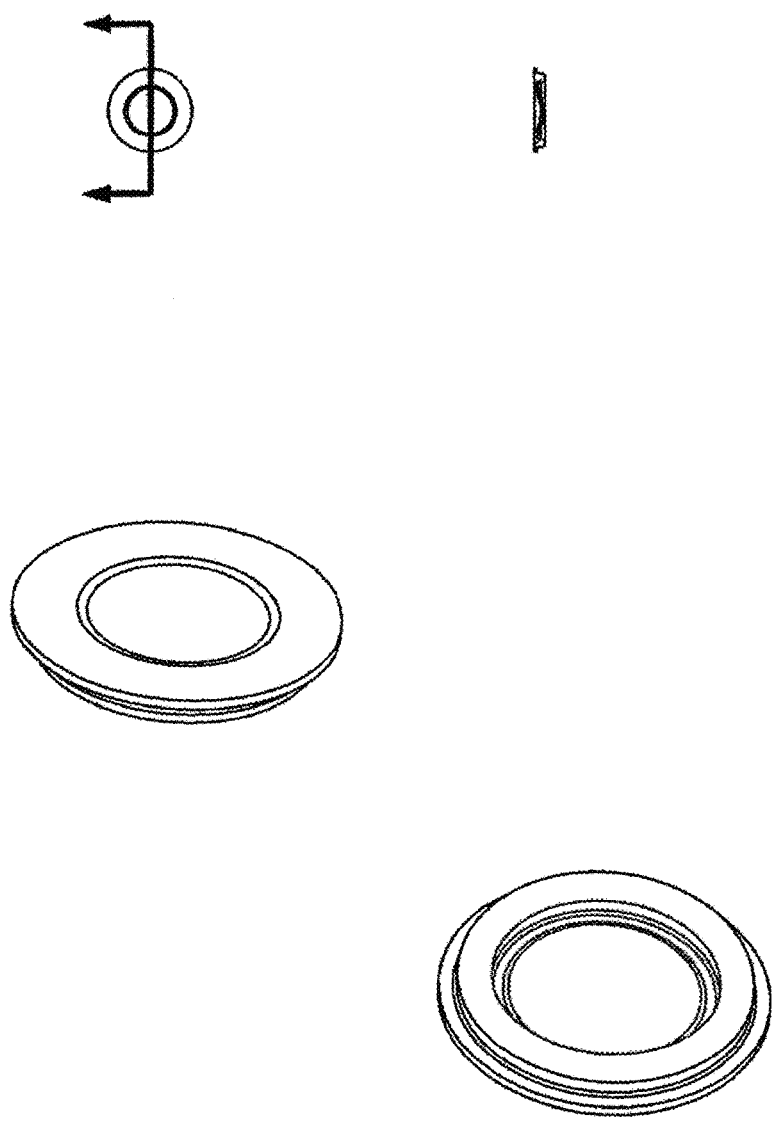
Figure 5G:
Figure 5H:
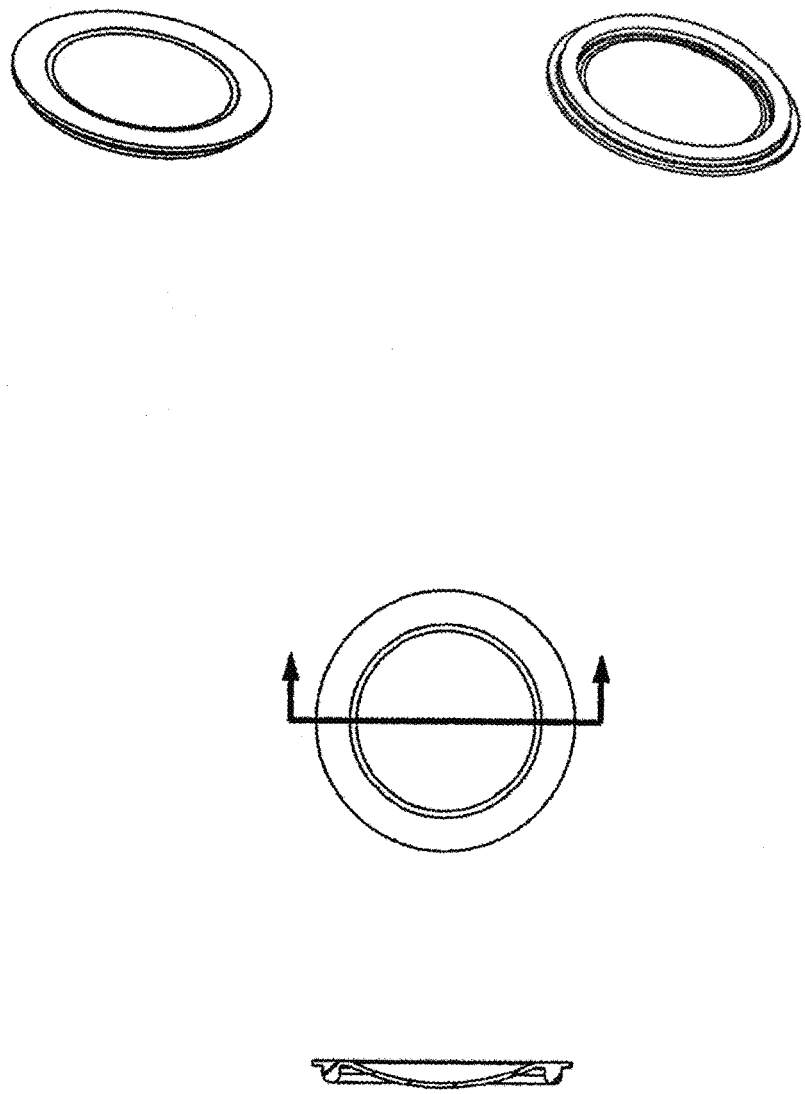

The membrane used in the metering pump 41224, in the preferred embodiment, is shown in more detail in FIG. 5G, with alternate embodiments shown in FIGS. 5E, 5F and 5H. The membrane used in the valves 41222 is shown in more detail in FIG. 2E, with alternate embodiments shown in FIGS. 2F-2G. However, in alternate embodiments, the metering pump membrane as well as the valve membranes may contain textures, for example, but not limited to, the textures shown on the pod pump/balancing pod membranes shown in FIGS. 5A-5D.

One embodiment of the conductivity sensor elements 41214, 41216 and the temperature sensor 41218, which make up the sensor cell 41212, are also shown in FIGS. 42C and 42D. Still referring to FIGS. 42C and 42D, the sensor cell housing 41414 includes areas on the bottom plate 41100 and the midplate 4900. O-rings seal the sensor housing 41414 from the fluid lines located on the upper side of the midplate 4900 shown in FIG. 42C and the inner side of the top plate 41000 shown in FIG. 42D. However, in other embodiments, an o-ring is molded into the sensor cell, or any other method of sealing can be used.

7.2 Cross Sectional Views

Figure 43A:
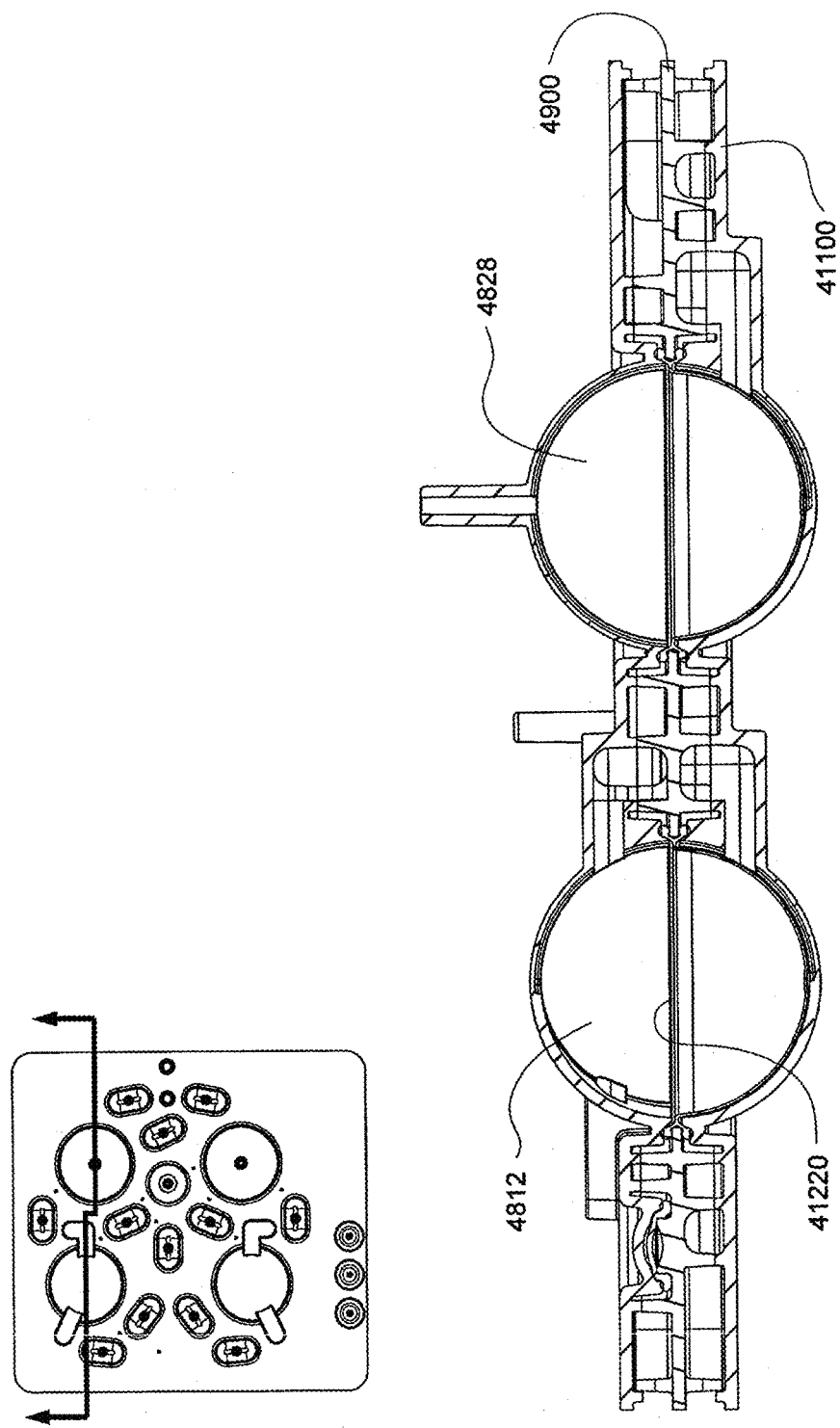
FIGS. 43A-43C show cross sectional views of the exemplary embodiment of the assembled cassette.
Figure 43B:
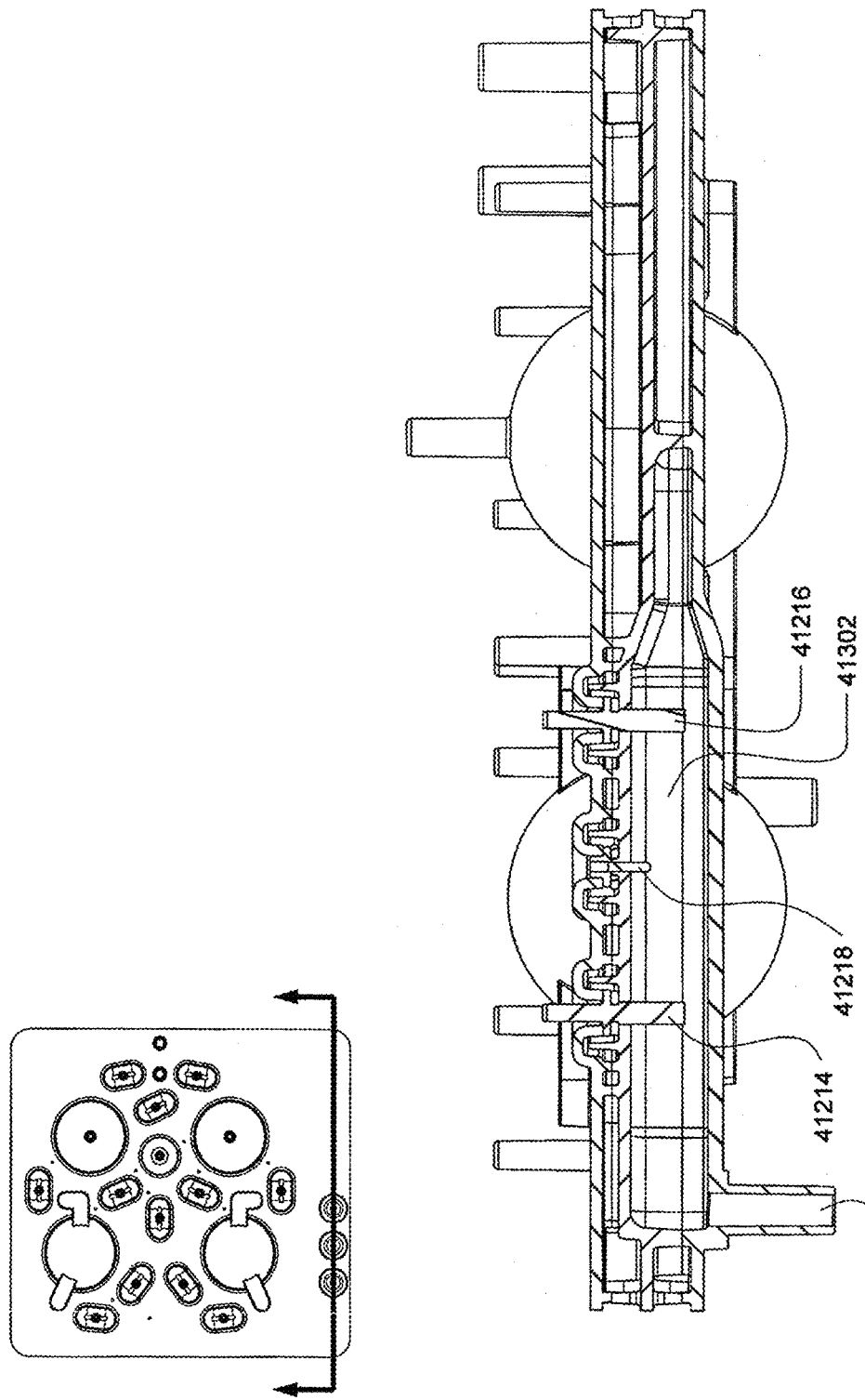
Figure 43C:
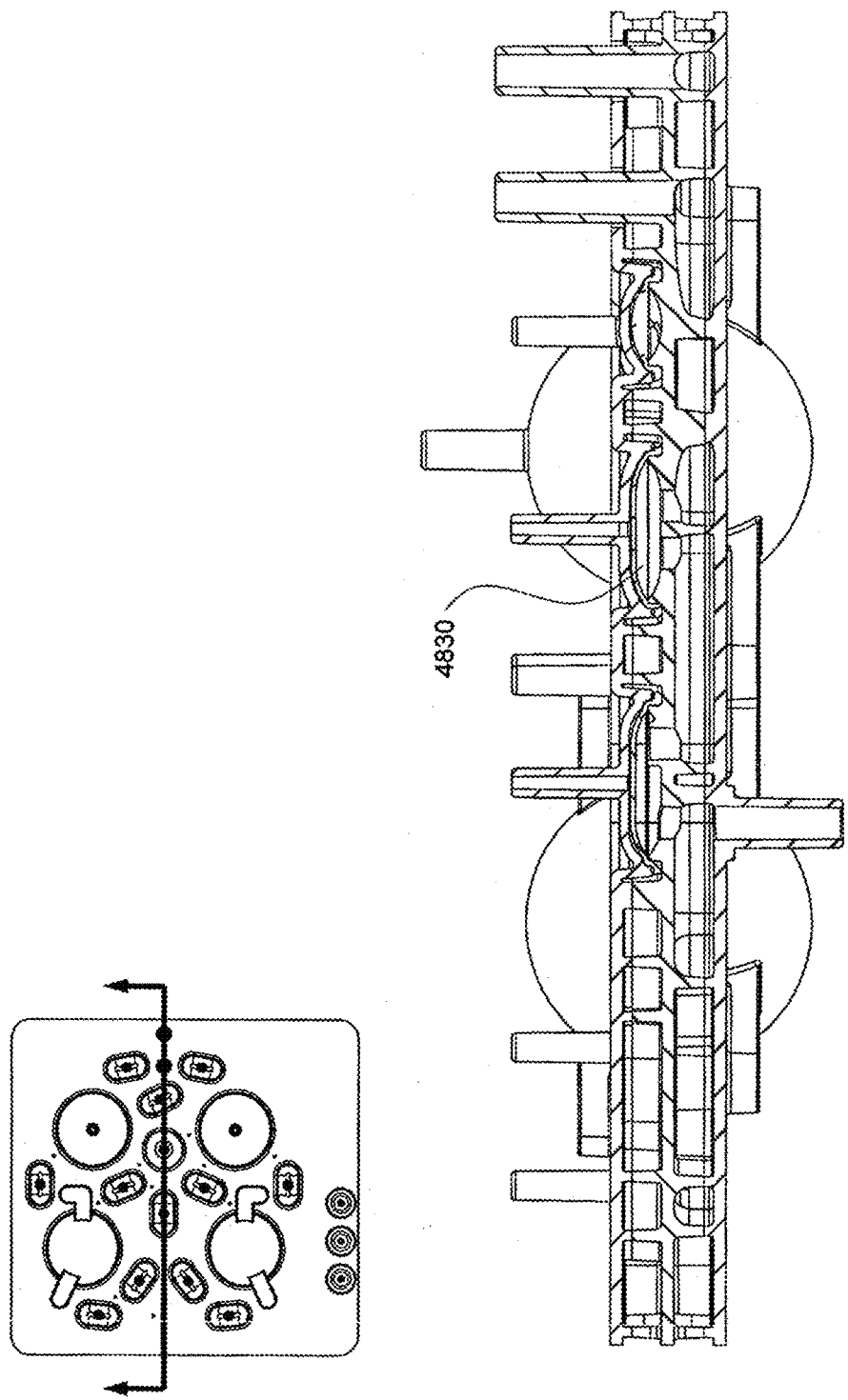
Figure 44A:
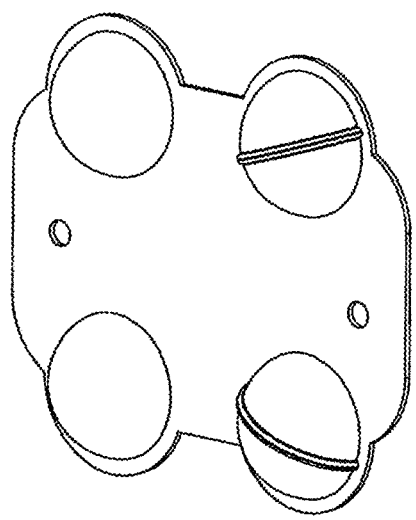
FIGS. 44A-44B show isometric and top views of an alternate embodiment of the top plate according to an alternate embodiment of the cassette.
Figure 44B:
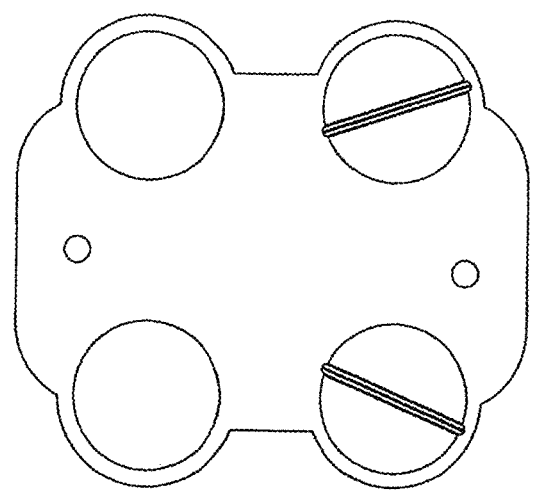
Figure 44C:
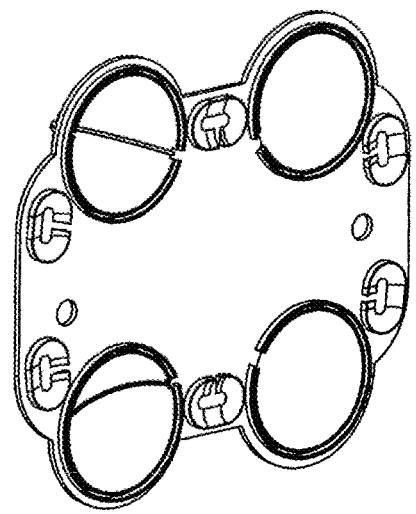
FIGS. 44C-44D show isometric and bottom views of an alternate embodiment of the top plate according to an alternate embodiment of the cassette.
Figure 44D:
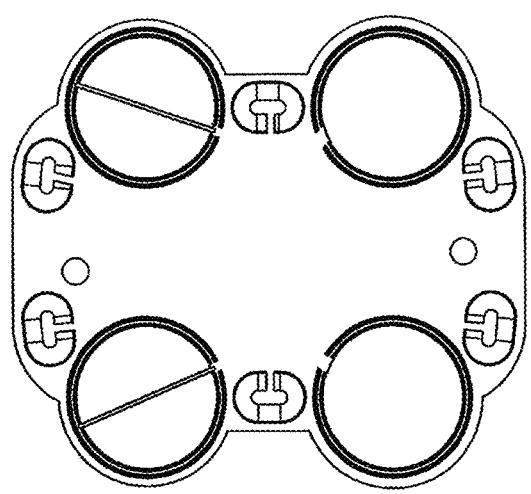
Figure 44E:
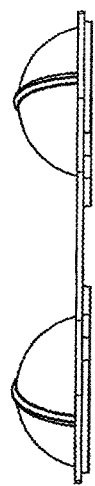
FIG. 44E shows a side view of the alternate embodiment of the top plate.
Figure 45A:
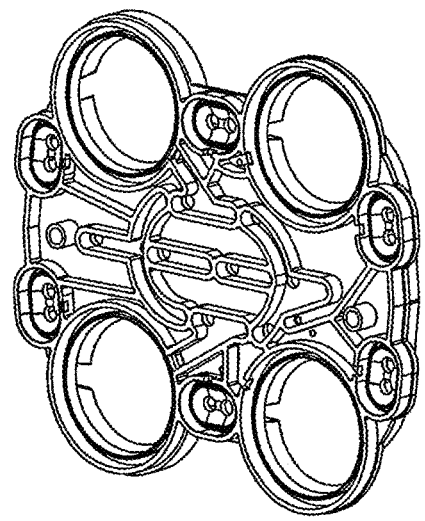
FIGS. 45A-45B show isometric and top views of an alternate embodiment of the midplate according to an alternate embodiment of the cassette.
Figure 45B:
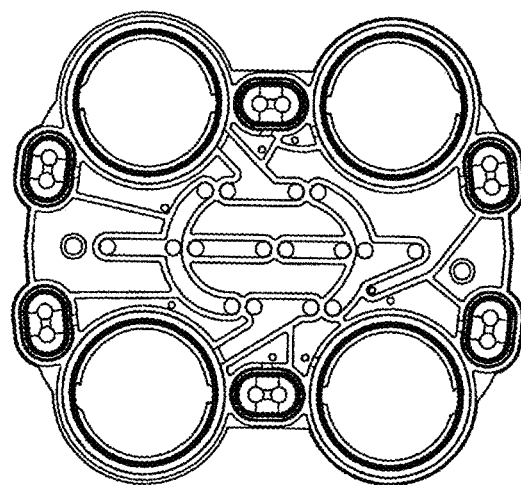
Figure 45C:
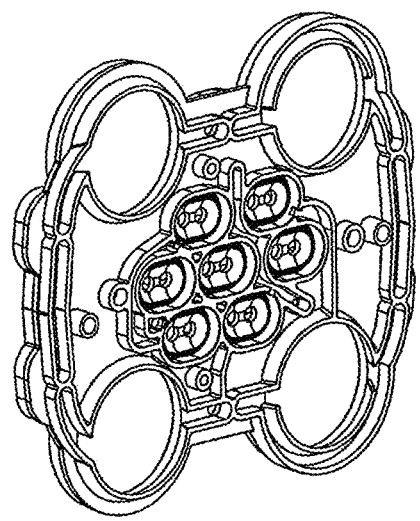
FIGS. 45C-45D show isometric and bottom views of an alternate embodiment of the midplate according to an alternate embodiment of the cassette.
Figure 45D:
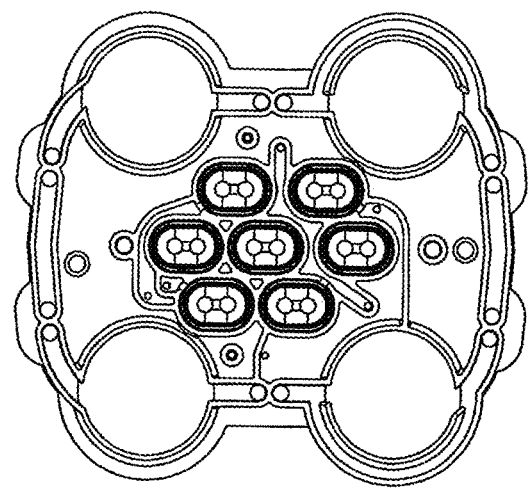
Figure 45E:
FIG. 45E shows a side view of the alternate embodiment of the midplate.
Figure 46A:
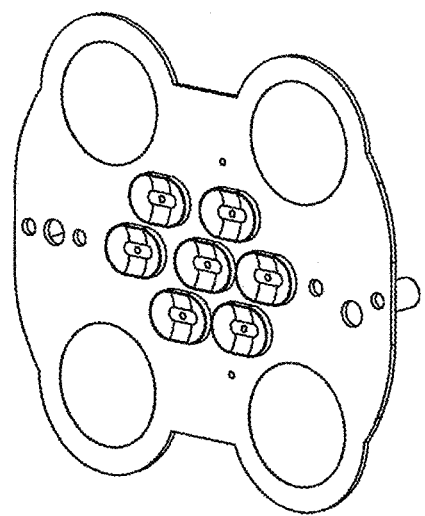
FIGS. 46A-46B show isometric and top views of an alternate embodiment of the bottom plate according to an alternate embodiment of the cassette.
Figure 46B:
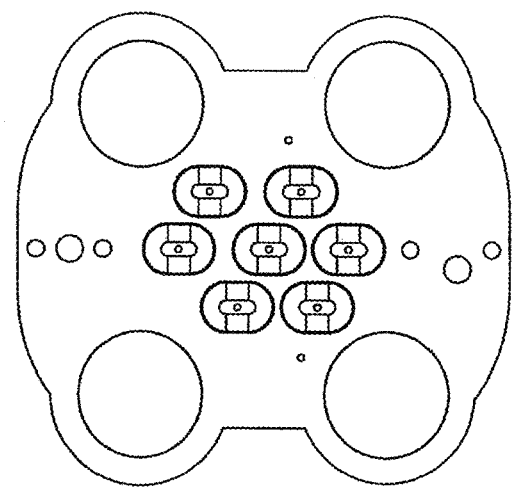
Figure 46C:
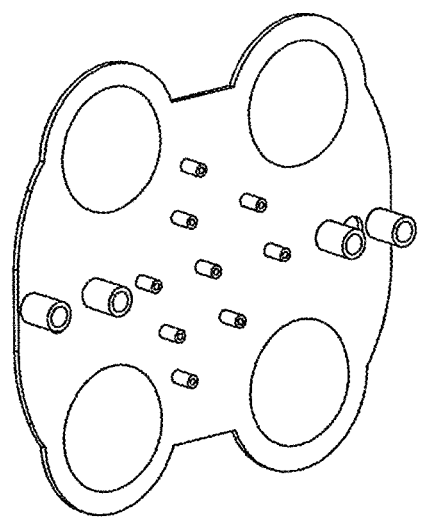
FIGS. 46C-46D show isometric and bottom views of an alternate embodiment of the bottom plate according to an alternate embodiment of the cassette.
Figure 46D:
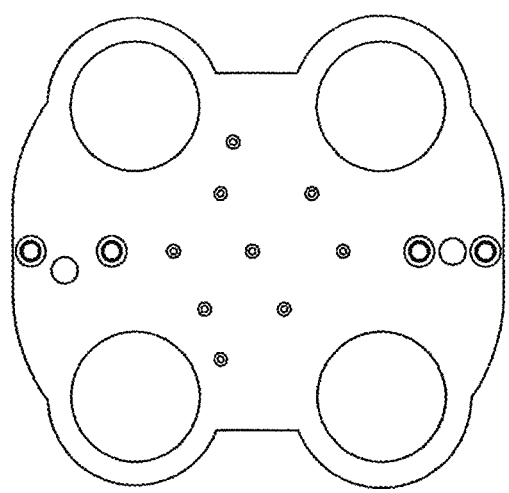
Figure 46E:
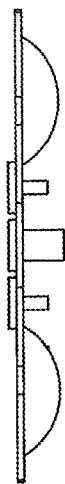
FIG. 46E shows a side view of the alternate embodiment of the bottom plate.

Referring now to FIGS. 43A-43C, various cross sectional views of the assembled cassette are shown. Referring first to FIG. 43A, the membrane 41220 is shown in a balancing pod 4812 and a pod pump 4828. As can be seen from the cross section, the double o-ring of the membrane 41220 is sandwiched by the midplate 4900, the bottom plate 41100 and the top plate 41000.

Referring now to FIG. 43B, the two conductivity sensor elements 41214, 41216 and the temperature sensor element 41218 are shown. As can be seen from the cross section, the sensor elements 41214, 41216, 41218 are in the fluid line 41302. Thus, the sensor elements 41214, 41216, 41218 are in fluid connection with the fluid line and can determine sensor data of the first fluid entering the first fluid inlet 4810. Referring now to FIG. 43C, this cross sectional view shows the metering pump 4830 as well as the structure of the valves.

Figure 37:
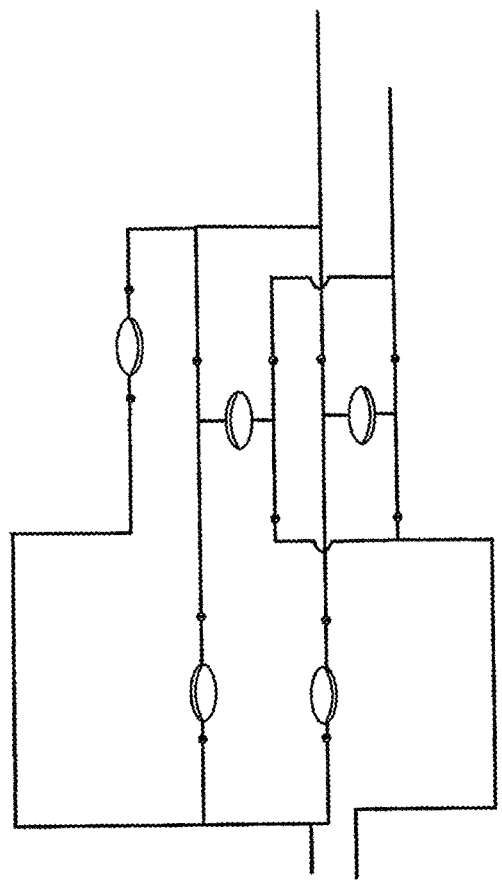
FIG. 37 is an alternate embodiment of the fluid flow-path schematic of the cassette.

As described above, the exemplary embodiment is one cassette embodiment that incorporates the exemplary fluid flow-path schematic shown in FIG. 36. However, there are alternate embodiments of the cassette that incorporate many of the same features of the exemplary embodiment, but in a different structural design. Additionally, there are alternate embodiment fluid flow paths, for example, the fluid flow path schematic shown in FIG. 37. The alternate embodiment cassette structure corresponding to this schematic is shown in FIGS. 44A-48.

Referring now to FIGS. 44A-44E, views of an alternate embodiment of the top plate 41400 are shown. The features of the top plate 41400 are alternate embodiments of corresponding features in the exemplary embodiment.

Referring now to FIGS. 45A-45E, views of an alternate embodiment of the midplate 41500 are shown. FIGS. 46A-46E show views of an alternate embodiment of the bottom plate 41600.

Figure 47A:
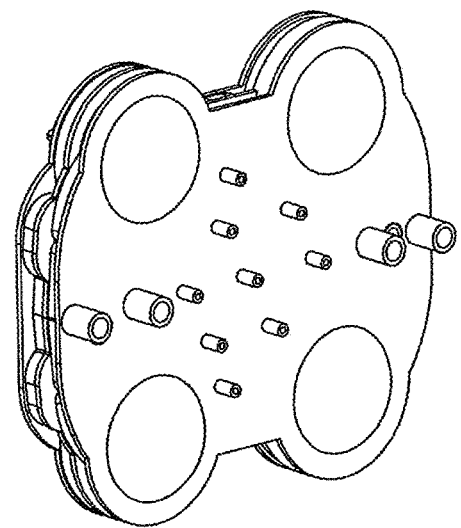
FIG. 47A is an isometric top view of an assembled alternate embodiment of the cassette.
Figure 47B:
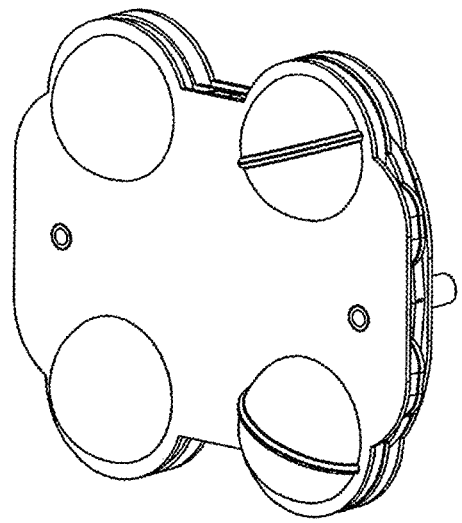
FIG. 47B is an isometric bottom view of an assembled alternate embodiment of the cassette.
Figure 47C:
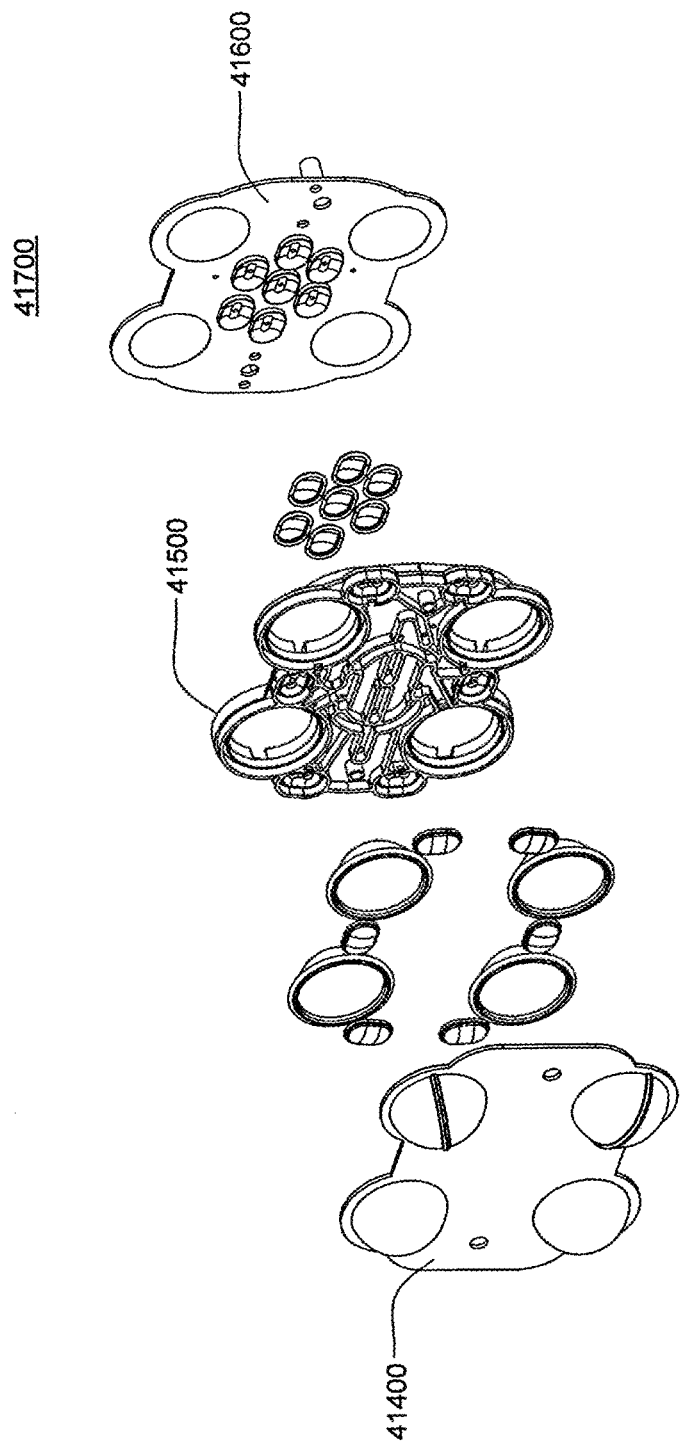
FIG. 47C is an exploded view of the assembled alternate embodiment of the cassette.
Figure 47D:
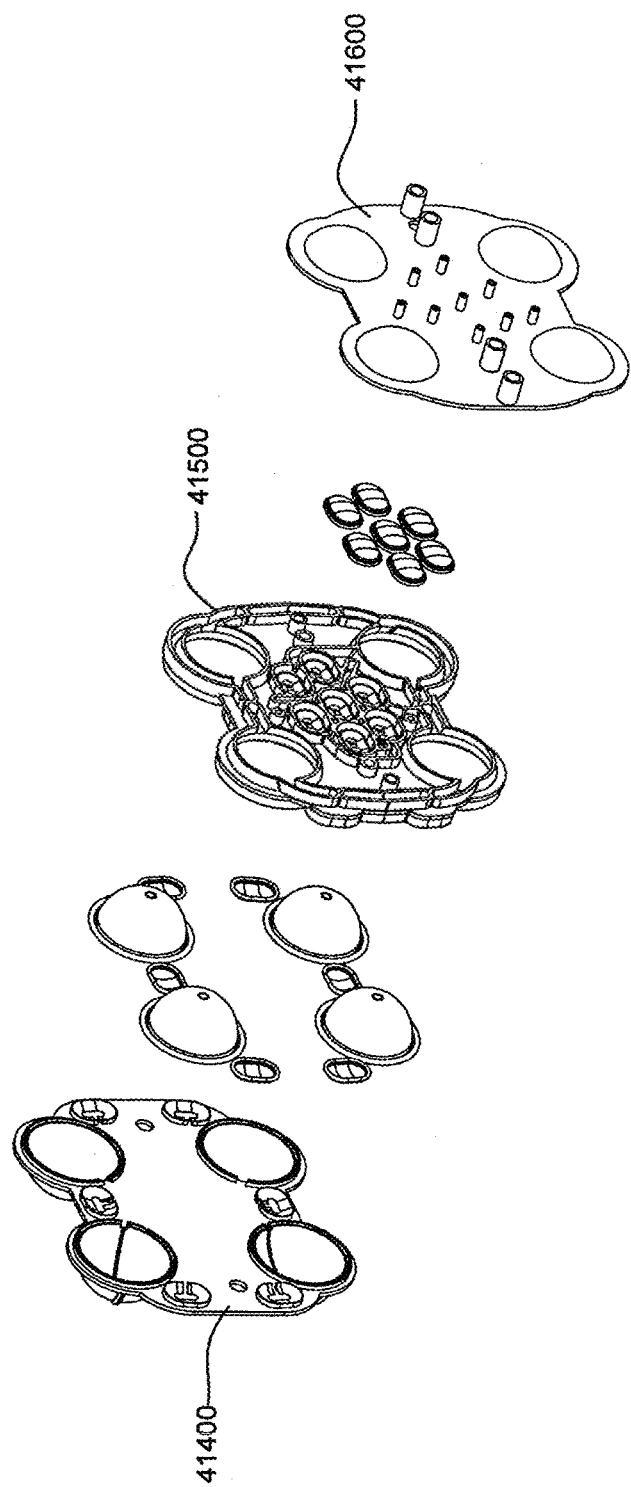
FIG. 47D is an exploded view of the assembled alternate embodiment of the cassette.
Figure 47E:
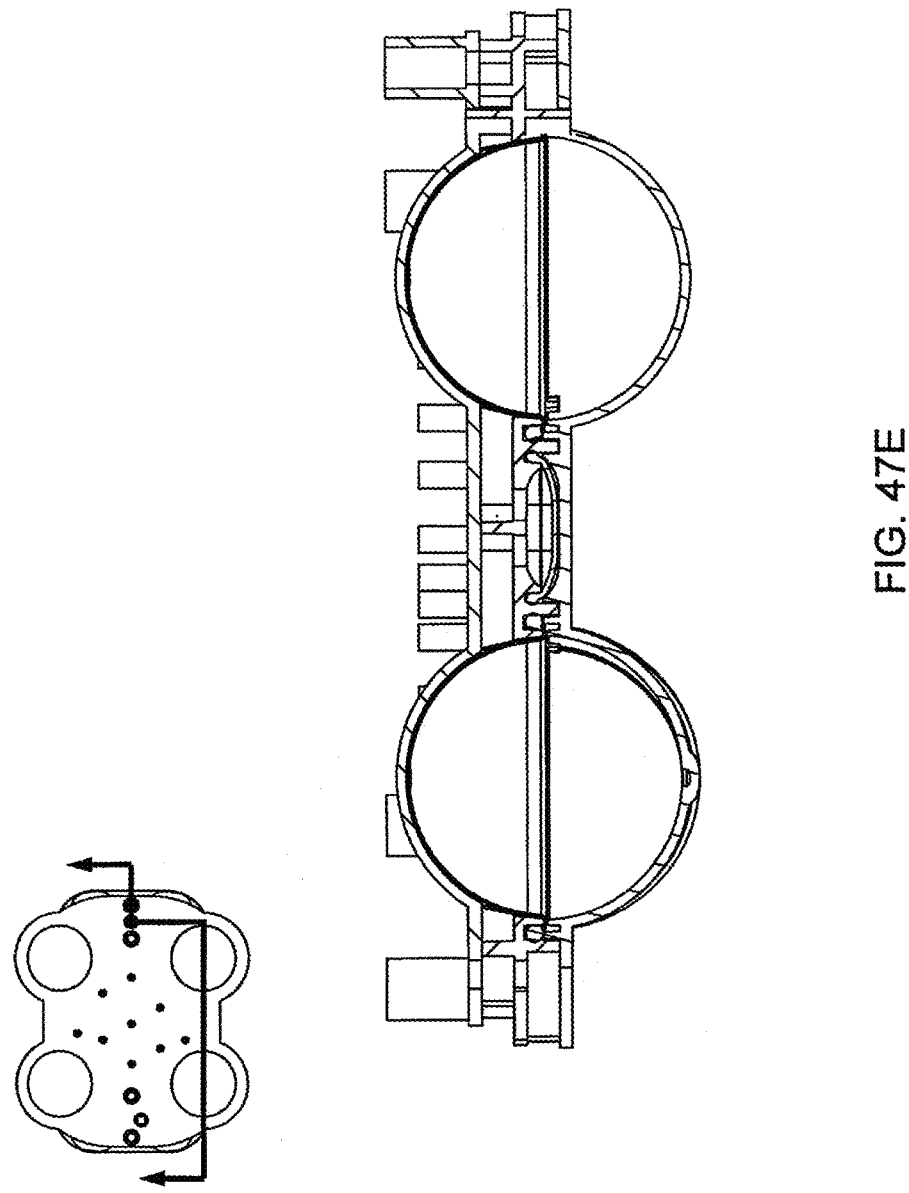
FIG. 47E shows a cross sectional view of the exemplary embodiment of the assembled cassette.
Figure 48A:
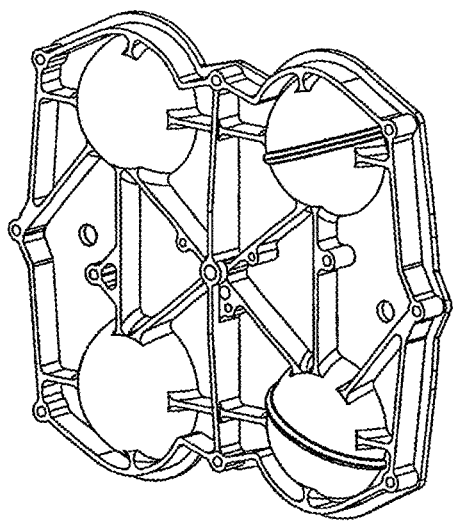
FIGS. 48A-48B show isometric and top views of an alternate embodiment of the top plate according to an alternate embodiment of the cassette.
Figure 48B:
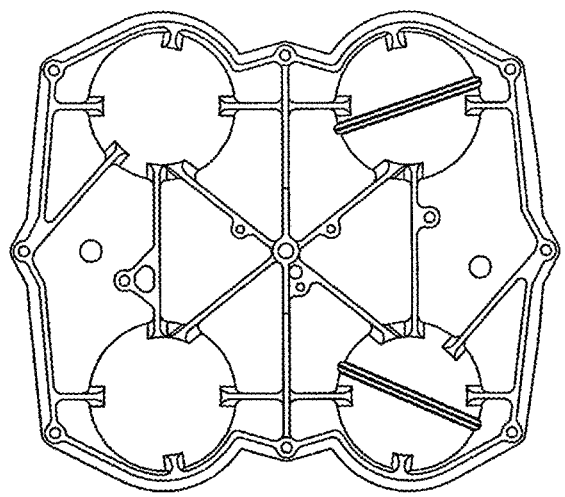
Figure 48C:
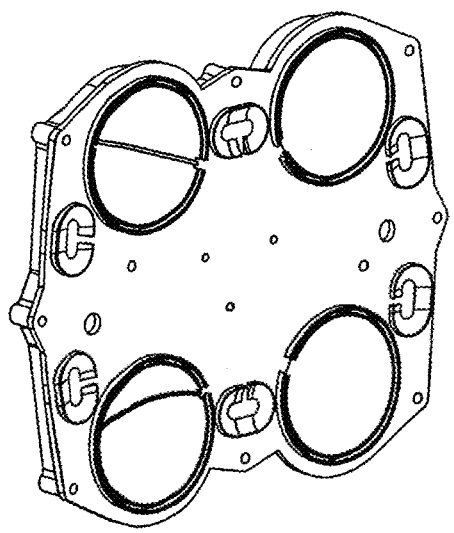
FIGS. 48C-48D show isometric and bottom views of an alternate embodiment of the top plate according to an alternate embodiment of the cassette.
Figure 48D:
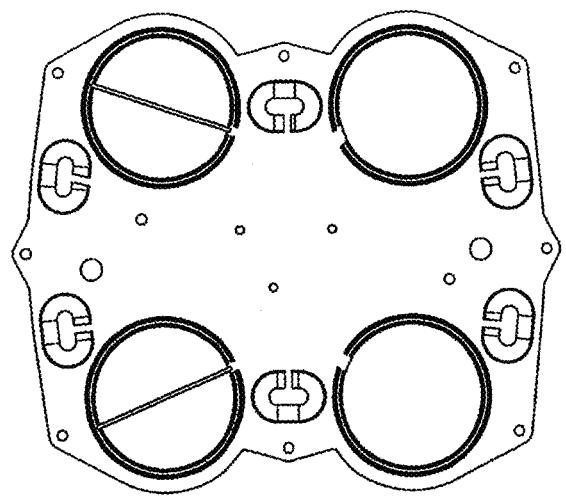
Figure 48E:
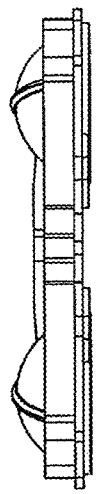
FIG. 48E shows a side view of the alternate embodiment of the top plate.
Figure 49A:
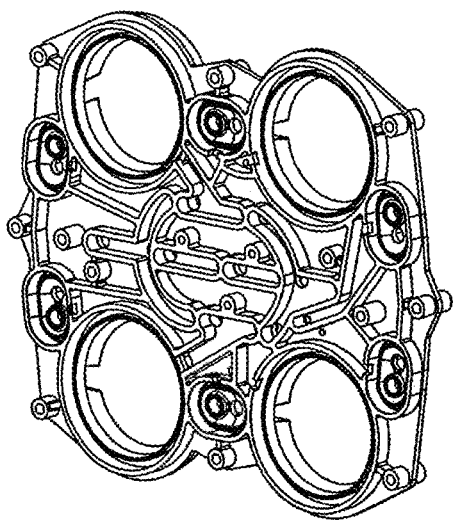
FIGS. 49A-49B show isometric and top views of an alternate embodiment of the midplate according to an alternate embodiment of the cassette.
Figure 49B:
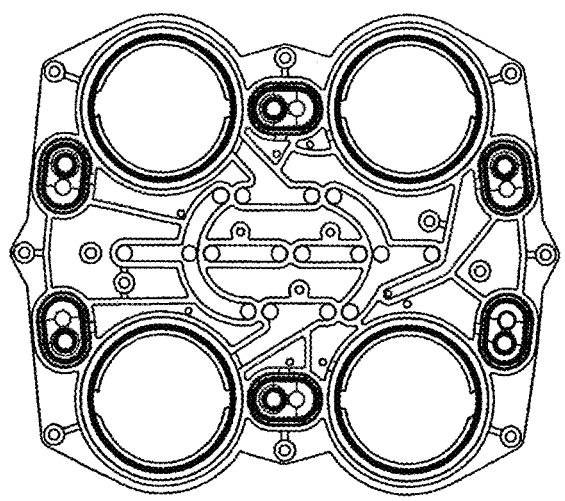
Figure 49C:
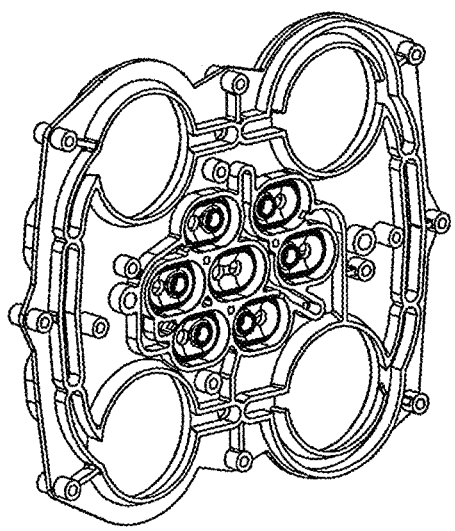
FIGS. 49C-49D show isometric and bottom views of an alternate embodiment of the midplate according to an alternate embodiment of the cassette.
Figure 49D:
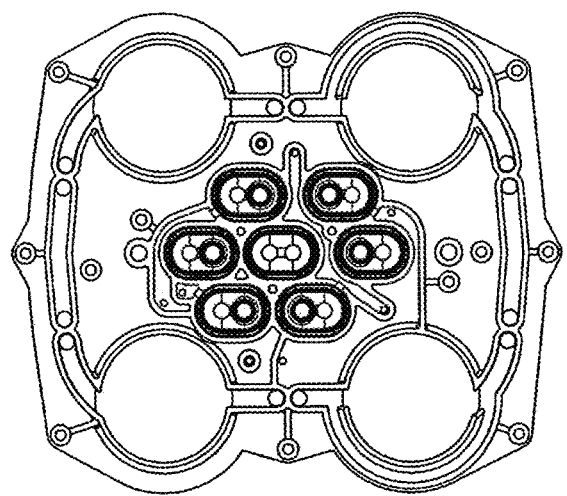
Figure 49E:
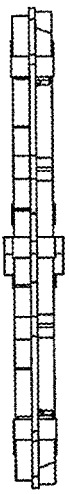
Figure 50A:
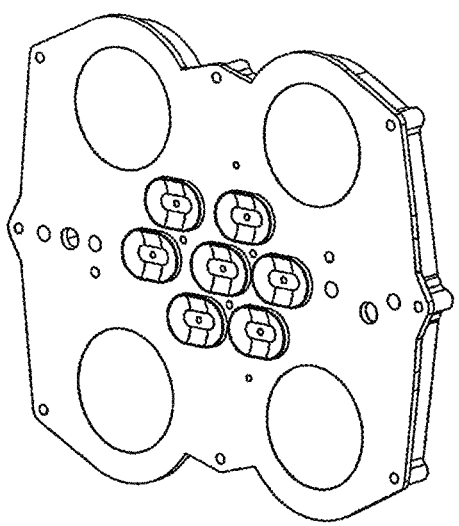
Figure 50B:
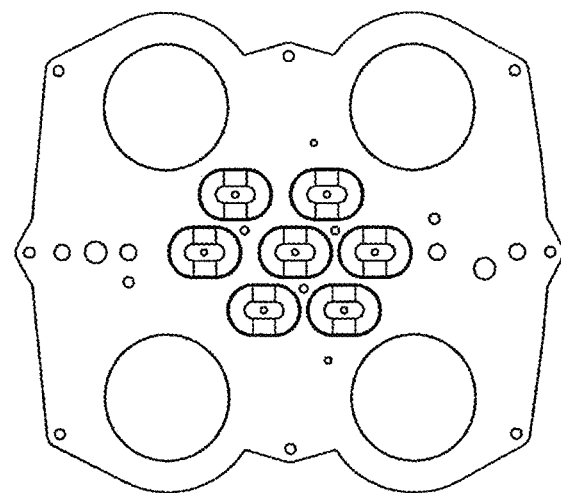
Figure 50C:
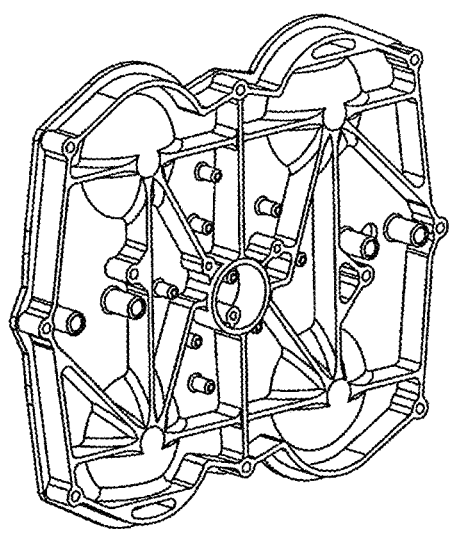
Figure 50D:
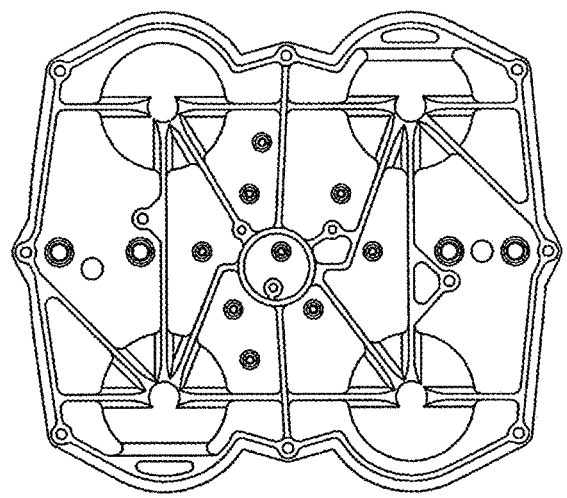
Figure 50E:
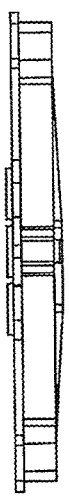
Figure 51A:
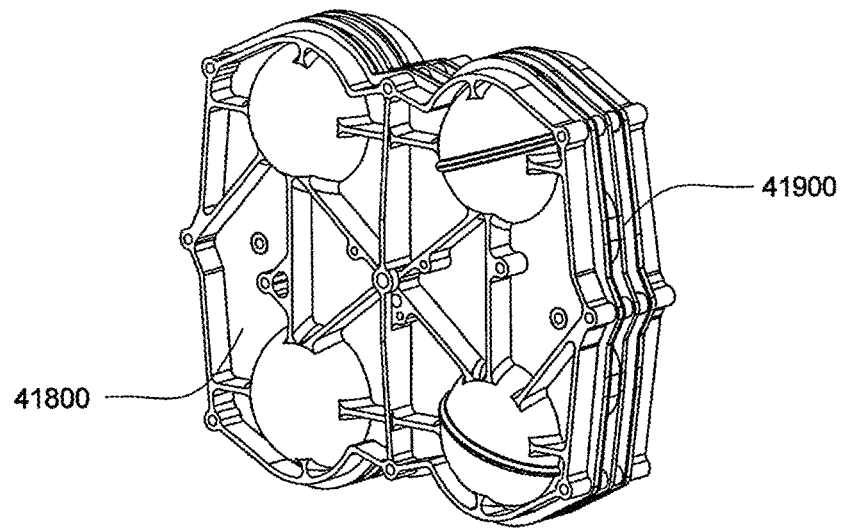
Figure 51B:
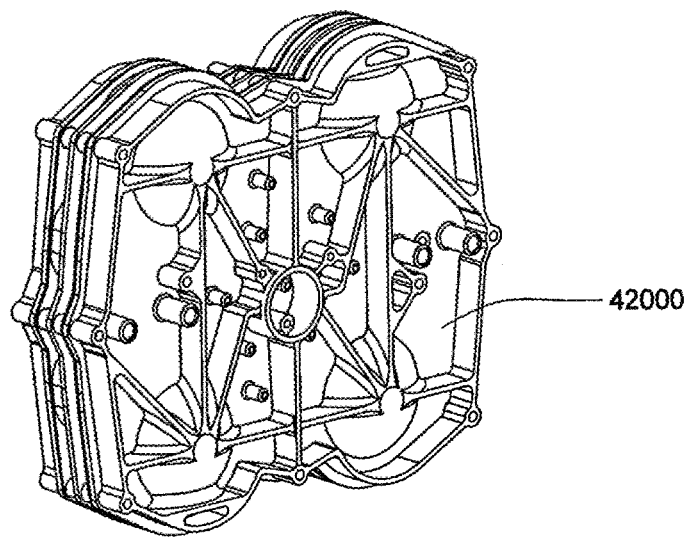
Figure 51C:
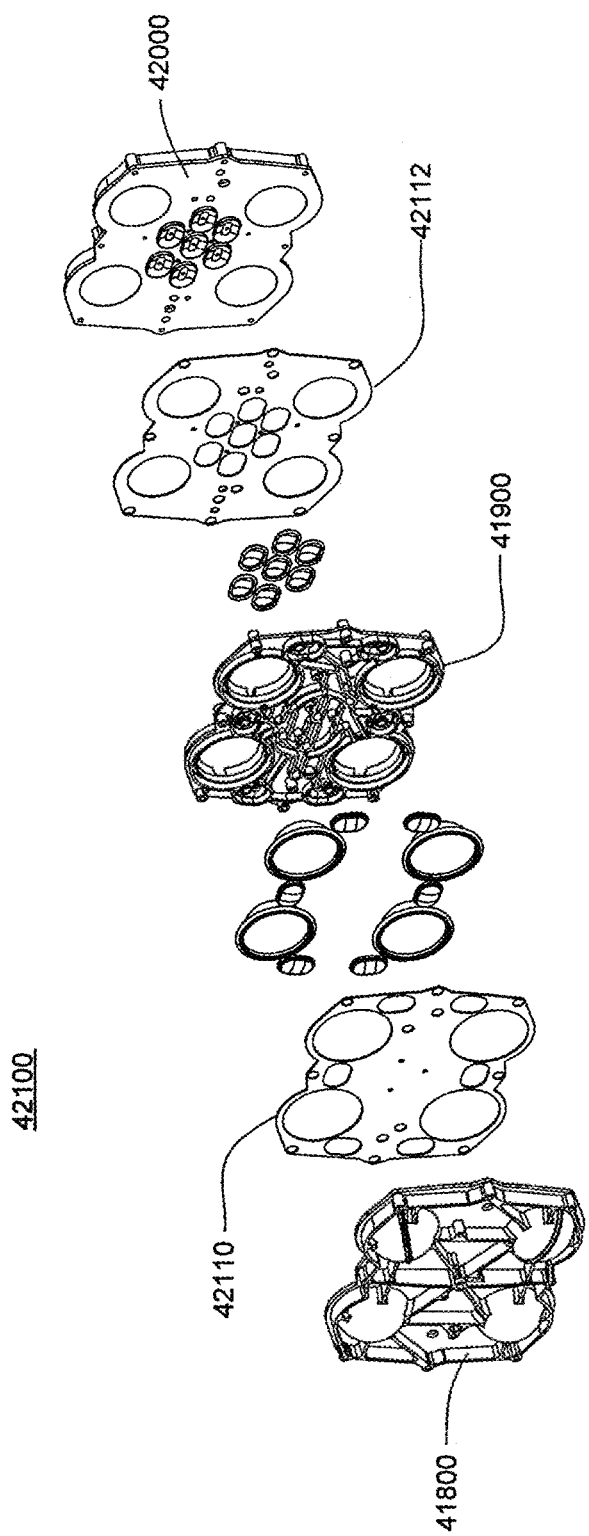
Figure 51D:
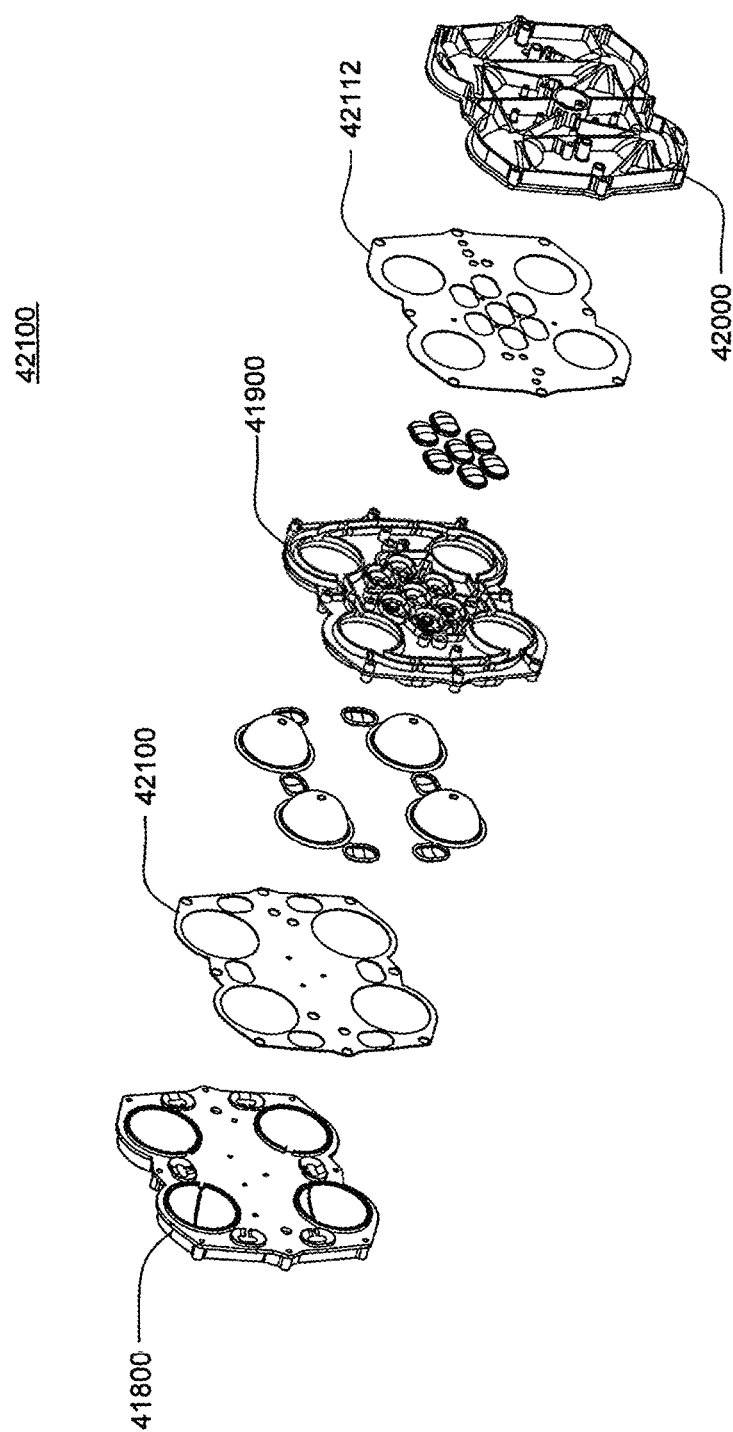

Referring now to FIGS. 47A-47B, an assembled alternate embodiment of the cassette 41700 is shown. FIGS. 47C-47D show exploded views of the cassette 41700. FIG. 47E is a cross sectional view of the assembled cassette 41700.

Referring now to FIGS. 48A-52B, another alternate embodiment of the cassette is shown. In this embodiment, when the cassette is assembled, as shown in FIGS. 51A-51B, the plates 41800, 41900, 42000 are sealed from each other using gaskets. Referring to FIGS. 51C-51D, the gaskets 42110, 42112 are shown. This embodiment additionally includes membranes (not shown). FIG. 52A is a cross sectional view of the assembled cassette, the gaskets 42110, 42112 relation to the assembled cassette assembly is shown.

7.3 Exemplary Embodiments of the Balancing Cassette

The pumping cassette can be used in a myriad of applications. However, in one exemplary embodiment, the pumping cassette is used to balance fluid going into the first fluid inlet and out the first fluid outlet with fluid coming into the cassette through the second fluid inlet and exiting the cassette through the second fluid outlet (or vice versa). The pumping cassette additionally provides a metering pump to remove a volume of fluid prior to that volume affecting the balancing chambers or adds a volume of fluid prior to the fluid affecting the balancing chambers.

The pumping cassette may be used in applications where it is critical that two fluid volumes are balanced. Also, the pumping cassette imparts the extra functionality of metering or bypassing a fluid out of the fluid path, or adding a volume of the same fluid or a different fluid into the fluid path. The flow paths shown in the schematic are bi-directional, and various flow paths may be created by changing the valve locations and or controls, or adding or removing valves. Additionally, more metering pumps, pod pumps and/or balancing pods may be added, as well as, more or less fluid paths and valves. Additionally, inlets and outlets may be added as well, or the number of inlets or outlets may be reduced.

One example is using the pumping cassette as an inner dialysate cassette as part of a hemodialysis system. Clean dialysate would enter the cassette through the first fluid inlet and pass through the sensor elements, checking if the dialysate is at the correct concentration and/or temperature. This dialysate would pass through the balancing chambers and be pumped through the first fluid outlet and into a dialyzer. The second fluid in this case is used or impure dialysate from the dialyzer. This second fluid would enter through the second fluid inlet and balance with the clean dialysate, such that the amount of dialysate that goes into the dialyzer is equal to the amount that comes out.

The metering pump may be used to remove additional used dialysate prior to that volume being accounted for in a balancing chamber, thus, creating a "false" balancing chamber through an ultra filtration ("UF") bypass. The situation is created where less clean dialysate by a volume equaled to the bypassed volume will enter the dialyzer.

In this embodiment, the valves controlling fluid connections to the balancing pods shall be oriented such that the volcano feature of the valve is on the fluid port connected to the balancing pod. This orientation directs most of the fluid displaced by the valve as it is thrown away from the balancing pod.

The valves controlling fluid connections to the UF pump shall be oriented such that the volcano feature of the valve is on the fluid port connected to the pumping chamber. In the exemplary embodiment, the nominal stroke volume of each inside dialysate pump chamber shall be 38 ml. The nominal volume of each balancing pod shall be 38 ml. The stroke volume of the UF pump shall be 1.2 ml+/−0.05 ml. The inner dialysate pump low-pressure pneumatic variable valves shall vent to ambient atmospheric pressure. This architecture feature minimizes the chance that dissolved gas will leave the dialysate while inside of the balancing chambers. Other volumes of pod pumps, balancing pods and metering pumps are easily discernable and would vary depending on the application. Additionally, although the embodiment described discusses venting to ambient, in other applications, negative pressure can be administered.

In various embodiments of the cassette, the valve architecture varies in order to alter the fluid flow path. Additionally, the sizes of the pod pumps, metering pump and balancing pods may also vary, as well as the number of valves, pod pumps, metering pumps and balancing pods. Although in this embodiment, the valves are volcano valves, in other embodiments, the valves are not volcano valves and in some embodiments are smooth surface valves.

8. Exemplary Embodiment of the Cassette System Integrated

As described above, a mixing cassette may be used to mix dialysate, and then send the dialysate to a storing vessel or reservoir. The middle, also called the outer dialysate, cassette provides a vent for a container and a variety of fluid lines and ports, and the balancing cassette provides a system for balancing the volume of fluid that enters a cassette in one direction with the volume that enters the cassette in another direction. Additionally, the balancing cassette provides a metering function, where a volume of fluid from one direction may be pumped such that it bypasses the balancing chambers and does not affect the balancing volumes. In some embodiments, these three cassettes may be combined into a system. Fluid lines can connect the cassettes such that a cassette system integrated is formed. However, various hoses can be difficult to manage and also, get tangled, removed from the ports or the connection may be disrupted in one of a variety of ways.

One embodiment of this would be to simply connect the fluid lines. However, in the exemplary embodiment, the three cassette exemplary fluid flow-path schematics are combined into a cassette device which makes the system more compact and also, there are benefits with respect to manufacture.

In an exemplary embodiment of this the cassette system integrated, the three cassettes are combined in an efficient, stand alone, cassette system. The fluid flow-path schematics shown and described above with respect to the various individual cassettes are combined. Thus, in some cases, fluid lines may be in two different cassettes to save space or efficiency, but in fact, the fluid lines follow many of the same paths as shown in the schematics.

The fluid flow—path for the exemplary embodiment of the cassette system integrated is shown in FIG. 63A. This fluid flow-path is shown with a blood circuit fluid flow-path also included. Thus, in one embodiment, the cassette system integrated may be used in connection with a hemodialysis system. For description purposes, the cassette system integrated is described below with respect to a hemodialysis system, i.e., a system including a cassette system that mixes dialysate, transports dialysate and balances the volume of dialysate before and after flowing through a dialyzer. The cassette system integrated may be used in conjunction with hemodialysis systems and methods, for example, similar to the hemodialysis systems and methods described in U.S. patent application Ser. No. 12/072,908, filed Feb. 27, 2008, now U.S. Pat. No. 8,246,826, and entitled Hemodialysis Systems and Methods and is hereby incorporated by reference in its entirety.

Figure 53B:
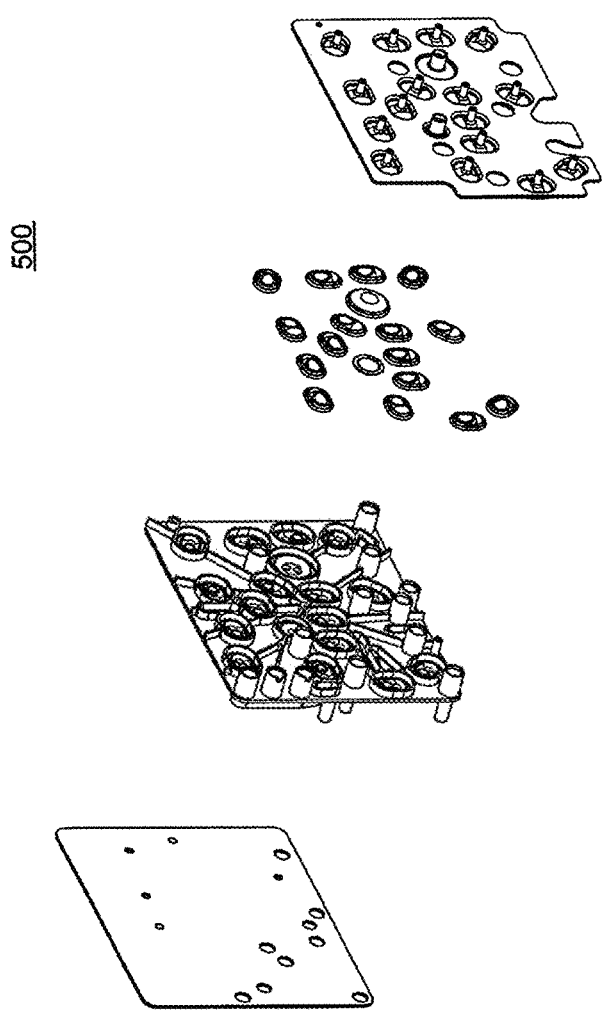

Referring now to FIGS. 53A-53B, one embodiment of the mixing cassette of the cassette system is shown. Referring to FIGS. 54A-54B, one embodiment of the middle cassette for the cassette system is shown. Finally, referring to FIGS. 55A-55B, one embodiment of the balancing cassette for the cassette system is shown.

Referring now to FIG. 56A, the assembled cassette system integrated is shown. The mixing cassette 500, middle cassette 600 and balancing cassette 700 are linked by fluid lines or conduits. The pods are between the cassettes. Referring now to FIGS. 56B and 56C, the various views show the efficiency of the cassette system integrated. The fluid lines or conduits 1200, 1300, 1400 are shown in FIG. 60, FIG. 61 and FIG. 62 respectively. The fluid flows between the cassettes through these fluid lines or conduits. Referring now to FIGS. 60 and 61, these fluid lines or conduits represent larger 1300 and smaller 1200 check valve fluid lines. In the exemplary embodiment, the check valves are duck bill valves, however, in other embodiments, any check valve may be used. Referring to FIG. 62, fluid line or conduit 1400 is a fluid line or conduit that does not contain a check valve. For purposes of this description, the terms "fluid line" and "conduit" are used with respect to 1200, 1300 and 1400 interchangeably.

Referring now to FIGS. 56B and 56C, and FIG. 63A, the following is a description of one embodiment of the fluid flow through the various cassettes. For ease of description, the fluid flow will begin with the mixing cassette 500. Referring now to FIG. 56B and FIG. 63A, the fluid side of the mixing cassette 500 is shown. The fluid side includes a plurality of ports 8000, 8002, 8004, 8006, 8008 and 8010-8026 that are either fluid inlets or fluid outlets. In the various embodiments, the fluid inlets and outlets may include one or more fluid inlets for reverse osmosis ("RO") water 8004, bicarbonate, an acid, and a dialysate 8006. Also, one or more fluid outlets, including a drain, acid 8002 and at least one air vent outlet as the vent for the dialysate tank. In one embodiment, a tube (not shown) hangs off the outlet and is the vent (to prevent contamination). Additional outlets for water, bicarb and water mixture, dialysate mixture (bicarb with acid and water added) are also included.

The dialysate flows out of the mixing cassette 500, to a dialysate tank (not shown, shown as 1502 in FIG. 63A) and then through a conduit to the inner dialysate cassette 700 (pumped by the outer dialysate cassette 600 pod pumps 602 and 604 (604 not shown, shown in FIGS. 56D and 56E). The fluid paths within the cassettes may vary. Thus, the location of the various inlet and outlets may vary with various cassette fluid paths.

Referring now to FIG. 63B, in one embodiment of the cassette system, the condo cells, conductivity and temperature sensors, are included in a separate cassette 1504 outside of the cassette system shown in FIGS. 56A-56C. This outside sensor cassette 1504 may be one of those described in U.S. patent application Ser. No. 12/038,474 entitled Sensor Apparatus Systems, Devices and Methods filed on Feb. 27, 2008, now U.S. Pat. No. 8,491,184, and is hereby incorporated by reference in its entirety.

The fluid flow-path for this embodiment is shown in FIG. 63B. In this embodiment, during the mixing process for the dialysate, the bicarb mixture leaves the mixing cassette 500 and flows to an outside sensor cassette, and then flows back into the mixing cassette 500. If the bicarb mixture meets pre-established thresholds, acid is then added to the bicarb mixture. Next, once the bicarb and acid are mixed in the mixing chamber 506, the dialysate flows out of the cassette into the sensor cassette and then back to the mixing cassette 500.

Referring now to FIG. 56D, the mixing cassette 500 include a pneumatic actuation side. In the block shown as 500, there are a plurality of valves and two pumping chambers 8030, 8032 built into the cassette 500 for pumping or metering the acid or bicarb. In some embodiments, additional metering pumps, or less metering pumps, are included. The metering pumps 8030, 8032 can be any size desired. In some embodiments, the pumps are different sizes with respect to one another, however, in other embodiments; the pumps are the same size with respect to one another. For example, in one embodiment, the acid pump is smaller than the bicarb pump. This may be more efficient and effective when using a higher concentration acid, as it may be desirable to use a smaller pump for accuracy and also, it may be desirable for control schemes to have a smaller pump so as to use full strokes in the control rather than partial strokes.

The conduits 1200, 1300 include a check-valve. These conduits 1200, 1300 allow for one-way flow. In the exemplary embodiment, these conduits 1200, 1300 all lead to drain. Referring to the flow-path schematic FIG. 63A, the locations of these check-valve conduits are apparent. In the embodiment shown, any fluid that is meant for drain flows through the mixing cassette 500. Referring again to FIG. 56B, a fluid drain port 8006 is located on the fluid side of the cassette 500.

Once the dialysate is mixed, and after the dialysate flows to the sensor cassette (1504 in FIG. 63B) and it is determined that the dialysate is not within set parameters/thresholds, then the dialysate will be pumped back into the mixing cassette 500, through a plain conduit 1400 then to the outer dialysate cassette 600, then back through conduit a check valve conduit 1200 and then through the mixing cassette 500 to the drain fluid outlet.

Referring now to FIGS. 56D and 56E, the various pods 502, 504, 506, 602, 604, 702, 704, 706, 708 are shown. Each of the pod housings are constructed identically, however, the inside of the pod housing is different depending on whether the pod is a pod pump 502, 504, 602, 604, 702, 704 a balancing chamber pods 706, 708 or a mixing chamber pod 504.

Referring now to FIGS. 56D and 56E, together with FIGS. 63A and 63B, the various pods are shown both in the fluid flow-path and on the cassette system. Pod 502 is the water pod pump and 504 is the bicarb water pod pump (sends water to the bicarb) of the mixing cassette 500. Pod 506 is the mixing chamber. Once the dialysate is mixed in the mixing chamber 506, and then flows from the mixing cassette 500 to the sensor cassette 1504, and it is determined that the dialysate qualifies as acceptable, then the dialysate flows to the dialysate tank 1502 through the mixing cassette dialysate tank outlet. However, if the dialysate is rendered unacceptable, then the fluid is pumped back into the cassette 500, then through a 1400 conduit, to the outer dialysate cassette 600 and then pumped through a 1200 check valve conduit, through the mixing cassette 500 and out the drain outlet.

Referring to FIGS. 56A-56C, together with FIGS. 63A-63B, the outer dialysate cassette is shown 600 between the mixing cassette 500 and the inner dialysate cassette 700. Pod pumps 602, 604, pump the dialysate from the dialysate tank 1502 and send it to the balancing chambers 706,708 in the inner dialysate cassette 700 (driving force for the dialysate solution). The outer dialysate cassette 600 pushes the dialysate into the inner dialysate cassette (i.e., the pumps in the inner dialysate cassette 700 do not draw the dialysate in). Thus, from the outer dialysate cassette 600, the dialysate is pumped from the dialysate tank 1502, through a heater 1506 and through an ultrafilter 1508, and then into the inner dialysate cassette 700.

Still referring now to FIGS. 56D and 56E, together with FIGS. 63A-63B, the inner dialysate cassette 700 includes a metering pod 8038 (i.e., an ultra filtration metering pod) and includes balancing pods 706, 708 and pod pumps 702, 704. The inner dialysate cassette 700 also includes fluid outlets and inlets. These inlets and outlets include the outlet to the dialyzer 1510, the inlet from the dialyzer 1510, and a dialysate inlet (the ultrafilter 1508 connects to a port of the inner dialysate cassette). Fluid inlets and outlets are also included for the DCA and DCV connections during priming and disinfection. Various conduits (1200,1300,1400) serve as fluid connections between the cassettes 500, 600, 700 and are used for dialysate fluid flow as well as fluid to pass through in order to drain through the mixing cassette 500. The largest check valve 1300 (also shown in FIG. 61) is the largest check-valve, and is used during disinfection. This tube is larger in order to accommodate, in the preferred embodiment, blood clots and other contaminants that flow through the conduits during disinfection.

The valves and pumps of the cassette system are pneumatically actuated in the exemplary embodiment. The pneumatics attach to the cassettes via individual tubes. Thus, each pump, balancing pod, or valve includes an individual tube connection to a pneumatic actuation manifold (not shown). Referring now to FIGS. 64A-64F, the tubes are connected, in the exemplary embodiment, to at least one block, 1600. In some embodiments, more than one block is used to connect the various tubes. The block 1600 is dropped into the manifold and then connected to the pneumatics actuators appropriately. This allows for easy connection of the pneumatic tubes to the manifold.

Referring again to FIG. 56D, the cassette system includes springs 8034, in one embodiment, to aid in holding the system together. The springs 8034 hook onto the mixing cassette 500 and inner dialysate cassette 700 via catches 8036. However, in other embodiments, any other means or apparatus to assist in maintaining the system in appropriate orientation may be used including, but not limited to, latching means or elastic means, for example.

Referring now to FIGS. 57A-57C, the exemplary embodiment of the pod is shown. The pod includes two fluid ports 902, 904 (an inlet and an outlet) and the pod may be constructed differently in the various embodiments. A variety of embodiments of construction are described in pending U.S. patent application Ser. No. 11/787,212, filed Apr. 13, 2007 and entitled Fluid Pumping Systems, Devices and Methods (E78), which is hereby incorporated herein by reference in its entirety.

Referring now to FIGS. 57A, 57D and 57E the groove 906 in the chamber is shown. A groove 906 is included on each half of the pod housing. In other embodiments, a groove is not included and in some embodiments, a groove is only included on one half of the pod.

Referring now to FIGS. 58A and 58B, the exemplary embodiment of the membrane used in the pod pumps 502, 504, 602, 604, 702, 704 is shown. This membrane is shown and described above with respect to FIG. 5A. In other embodiments, any of the membranes shown in FIGS. 5B-5D may be used. An exploded view of a pod pump according to the exemplary embodiment is shown FIG. 59.

The membrane used in the balancing chamber pods 706, 708 in the preferred embodiments is shown and described above with respect to FIGS. 6A-6G. The mixing chamber pod 504 does not include a membrane in the exemplary embodiment. However, in the exemplary embodiment, the mixing chamber pod 504 includes a o-ring to seal the mixing chamber.

In the exemplary embodiment, the membrane valve membrane is shown in FIG. 2E, however, alternate embodiments as shown in FIGS. 2F and 2G may also be used. The metering pumps, in the exemplary embodiment, may use any of the membranes shown in FIGS. 5E-5H.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A fluid balancing cassette comprising:
   a first fluid flowpath and a separate, second fluid flowpath, each said first fluid flowpath and second fluid flowpath having a separate inlet to the cassette and a separate outlet from the cassette;
   a first fluid balancing pod having a fixed first total fluid volume and comprising a flexible membrane separating a first chamber from a second chamber, the sum of a first chamber volume plus a second chamber volume equal to the fixed first total fluid volume;
   the first chamber connected to the first fluid flowpath between a first fluid flowpath inlet valve and a first fluid flowpath outlet valve, and the second chamber connected to the second fluid flowpath between a second fluid flowpath inlet valve and a second fluid flowpath outlet valve;
   wherein said valves are pneumatically actuated membrane valves, and the first fluid flowpath inlet valve and the second fluid flowpath outlet valve are ganged together by being connected via a common actuation port or pneumatic line at a single pneumatic pressure to a pneumatic supply source able to controllably pressurize the common actuation port or pneumatic line to the single pneumatic pressure to actuate both the first fluid flowpath inlet valve and the second fluid flowpath outlet valve at the same time.

2. The fluid balancing cassette of claim 1, further comprising a second fluid balancing pod having a fixed second total fluid volume and comprising a flexible membrane separating a first chamber from a second chamber, the sum of a first chamber volume plus a second chamber volume equal to the fixed second total fluid volume;
   wherein the first fluid flowpath inlet valve is a first fluid flowpath first branch inlet valve, the first fluid flowpath outlet valve is a first fluid flowpath first branch outlet valve, the second fluid flowpath inlet valve is a second fluid flowpath first branch inlet valve, and the second fluid flowpath outlet valve is a second fluid flowpath first branch outlet valve;
   wherein the first chamber of the second fluid balancing pod is connected to a second branch of the first fluid flowpath between a first fluid flowpath second branch inlet valve and a first fluid flowpath second branch outlet valve, and the second chamber of the second fluid balancing pod is connected to a second branch of the second fluid flowpath between a second fluid flowpath second branch inlet valve and a second fluid flowpath second branch outlet valve; and wherein all said valves are pneumatically actuated membrane valves, and the second fluid flowpath second branch inlet valve has a pneumatic connection that is ganged or interconnected with the pneumatic connections of the first fluid flowpath first branch inlet valve and the second fluid flowpath first branch outlet valve.

3. The fluid balancing cassette of claim 2, wherein the second fluid flowpath second branch outlet valve, the first fluid flowpath second branch inlet valve, and the second fluid flowpath first branch inlet valve have pneumatic connections that are ganged or interconnected to the source of pneumatic pressure.

4. The fluid balancing cassette of claim 1, further comprising a pump with a fluid pumping chamber connected to the second fluid flowpath between a second fluid flowpath pump inlet valve and the second fluid flowpath inlet valve that serves as a pump outlet valve.

5. The fluid balancing cassette of claim 3, further comprising:
- a first pump with a fluid pumping chamber connected to a second fluid flowpath first branch between a second fluid flowpath first branch pump inlet valve and the second fluid flowpath first branch inlet valve that serves as a first branch pump outlet valve;
- a second pump with a fluid pumping chamber connected to the second fluid flowpath second branch between a second fluid flowpath second branch pump inlet valve and the second fluid flowpath second branch inlet valve that serves as a second branch pump outlet valve;

wherein the second fluid flowpath first branch pump inlet valve and the second fluid flowpath second branch pump inlet valve are pneumatically actuated membrane valves; and wherein the first branch pump inlet valve has a pneumatic connection that is ganged or interconnected with the first fluid flowpath second branch outlet valve to the source of pneumatic pressure, and the second branch pump inlet valve has a pneumatic connection that is ganged or interconnected with the first fluid flowpath first branch outlet valve.

6. The fluid balancing cassette of claim 2, wherein the second fluid flowpath has a branch flowpath that bypasses the first or second fluid balancing pod to move fluid through the second fluid flowpath via a bypass pump connected to the branch flowpath.

7. The fluid balancing cassette of claim 1, wherein the fluid balancing cassette is connected to a dialyzer so that the outlet of the first fluid flowpath is configured for connection to a dialysate inlet of the dialyzer, the inlet of the second fluid flowpath is configured for connection to a dialysate outlet of the dialyzer, the inlet of the first fluid flowpath is configured for connection to a source of fresh dialysate solution, and the outlet of the second fluid flowpath is configured for connection to a drain.

* * * * *